US012247229B2

(12) United States Patent
Fukuda et al.

(10) Patent No.: US 12,247,229 B2
(45) Date of Patent: Mar. 11, 2025

(54) BACTERIOPHAGE AND THERAPEUTIC AGENT FOR BACTERIAL ENDOPHTHALMITIS

(71) Applicant: NATIONAL UNIVERSITY CORPORATION KOCHI UNIVERSITY, Kochi (JP)

(72) Inventors: Ken Fukuda, Kochi (JP); Shigenobu Matsuzaki, Kochi (JP); Atsuki Fukushima, Kochi (JP); Masanori Daibata, Kochi (JP); Jumpei Uchiyama, Kanagawa (JP)

(73) Assignee: NATIONAL UNIVERSITY CORPORATION KOCHI UNIVERSITY, Kochi (JP)

( * ) Notice: Subject to any disclaimer, the term of this patent is extended or adjusted under 35 U.S.C. 154(b) by 0 days.

(21) Appl. No.: 18/463,731

(22) Filed: Sep. 8, 2023

(65) Prior Publication Data

US 2024/0026308 A1 Jan. 25, 2024

Related U.S. Application Data

(62) Division of application No. 16/979,371, filed as application No. PCT/JP2019/009112 on Mar. 7, 2019, now abandoned.

(30) Foreign Application Priority Data

Mar. 12, 2018 (JP) ................................ 2018-044407

(51) Int. Cl.
*C12N 7/00* (2006.01)
*A61K 35/76* (2015.01)
*A61P 31/04* (2006.01)

(52) U.S. Cl.
CPC ................ *C12N 7/00* (2013.01); *A61K 35/76* (2013.01); *A61P 31/04* (2018.01); *C12N 2795/10121* (2013.01); *C12N 2795/10132* (2013.01)

(58) Field of Classification Search
CPC . C12N 7/00; C12N 2795/10121; A61P 31/04; A61K 35/76
See application file for complete search history.

(56) References Cited

U.S. PATENT DOCUMENTS

2009/0054406 A1 2/2009 Ward et al.
2011/0166126 A1 7/2011 Ward et al.

FOREIGN PATENT DOCUMENTS

JP 2010-536860 12/2010
JP 2018-99080 6/2018
KR 10-1587113 1/2016

OTHER PUBLICATIONS

International Search Report issued Jun. 4, 2019 in International (PCT) Application No. PCT/JP2019/009112.
Fukuda et al., "Development of novel treatment by using bacteriophage for ocular diseases induced by bacterial infection", Kaken, 2015 Fiscal Year Research-status Report, 2 pages, partial English translation, cited in ISR.
Fukuda et al., "Treatment of old and new infections: Treatment of eye infections with phage", Journal of the Eye, vol. 30, No. 9, 2013, pp. 1267-1269, partial English translation, cited in ISR.
Uchiyama et al., "Improved Adsorption of an *Enterococcus faecalis* Bacteriophage ΦEF24C with a Spontaneous Point Mutation", PLOS one, Oct. 2011, vol. 6. Issue 10, e26648, pp. 1-13.
Uchiyama et al., "Potential Application of Bacteriophages in Enrichment Culture for Improved Prenatal *Streptococcus agalactiae* Screening", Viruses, 2018, vol. 10, No. 552, pp. 1-12.
Extended European Search Report issued Nov. 22, 2021 in corresponding European Patent Application No. 19766897.3, 11 pages.
Kang et al., "Isolation and characterization of an *Enterococcus faecalis* bacteriophage", Misainmurhag Hoiji—The Korean Journal of Microbiology, vol. 51, No. 3, 2015, pp. 194-198, 5 pages.
Uchiyama et al., "Isolation and characterization of a novel *Enterococcus faecalis* bacteriophage ϕEF24C as a therapeutic candidate", FEMS Microbiology Letters, vol. 278, No. 2, 2008, pp. 200-206, 7 pages.
Fukuda et al., "Pseudomonas aeruginosa keratitis in mice: effects of topical bacteriophage KPP12 administration", PLOS ONE, Public Library of Science, US, vol. 7, No. 10, 2012, pp. e37742-1, 8 pages.
Kishimoto et al.: In Vitro and In Vivo Evaluation of Three Newly Bacteriophage Candidates, phiEF7H, phiEF14H1, phiEF19G, for Treatment of Enterococcus faecalis Endophthalmitis. Microorganisms. Jan. 20, 2021;9(2):212. (Year: 2021).
Office Action issued May 5, 2023 in corresponding Taiwanese Patent Application No. 108108129, with English-language translation, 10 pages.

*Primary Examiner* — Janet L Andres
*Assistant Examiner* — Ruixue Wang
(74) *Attorney, Agent, or Firm* — Wenderoth, Lind & Ponack, L.L.P.

(57) ABSTRACT

The objective of the present invention is to provide a novel bacteriophage useful for treating bacterial endophthalmitis and a therapeutic agent for bacterial endophthalmitis comprising the novel bacteriophage. The therapeutic agent for bacterial endophthalmitis according to the present invention is characterized in comprising 1 or more bacteriophages selected from the group essentially consisting of Myoviridae Spounavirinae phiEF7H (accession number: NITE BP-02886), Myoviridae Spounavirinae phiEF19G (accession number: NITE BP-02887), Myoviridae Spounavirinae phiEF14H1 (accession number: NITE BP-02888), and mutants thereof.

3 Claims, 9 Drawing Sheets

Specification includes a Sequence Listing.

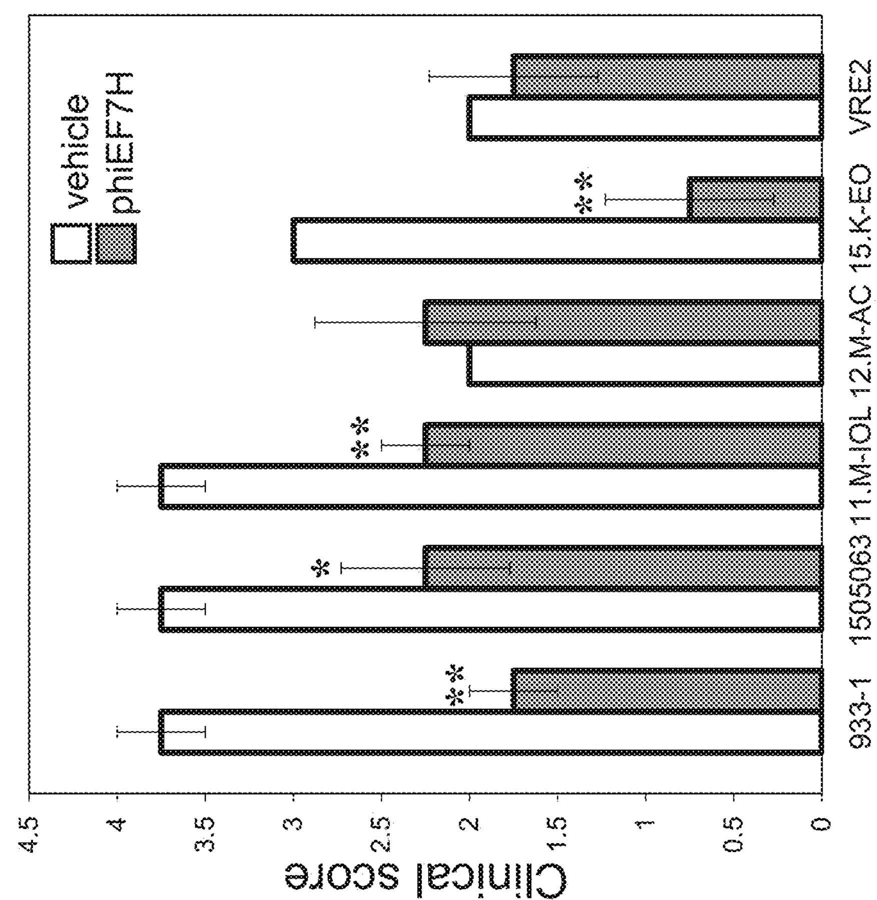
[Figure. 1]

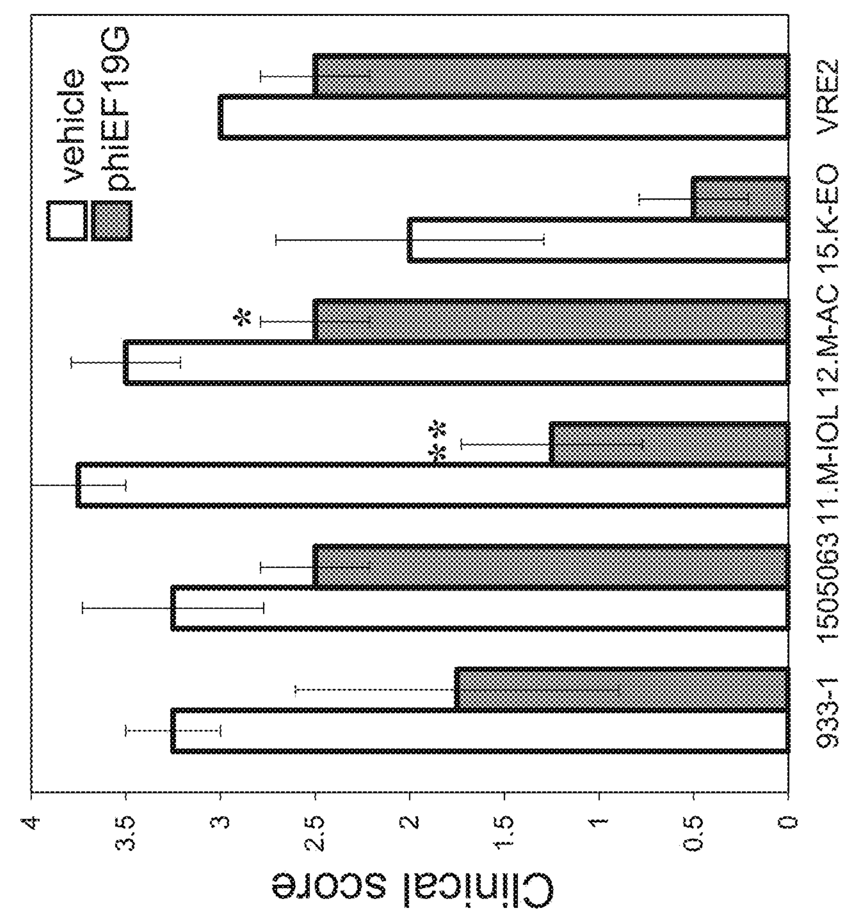
[Figure. 2]

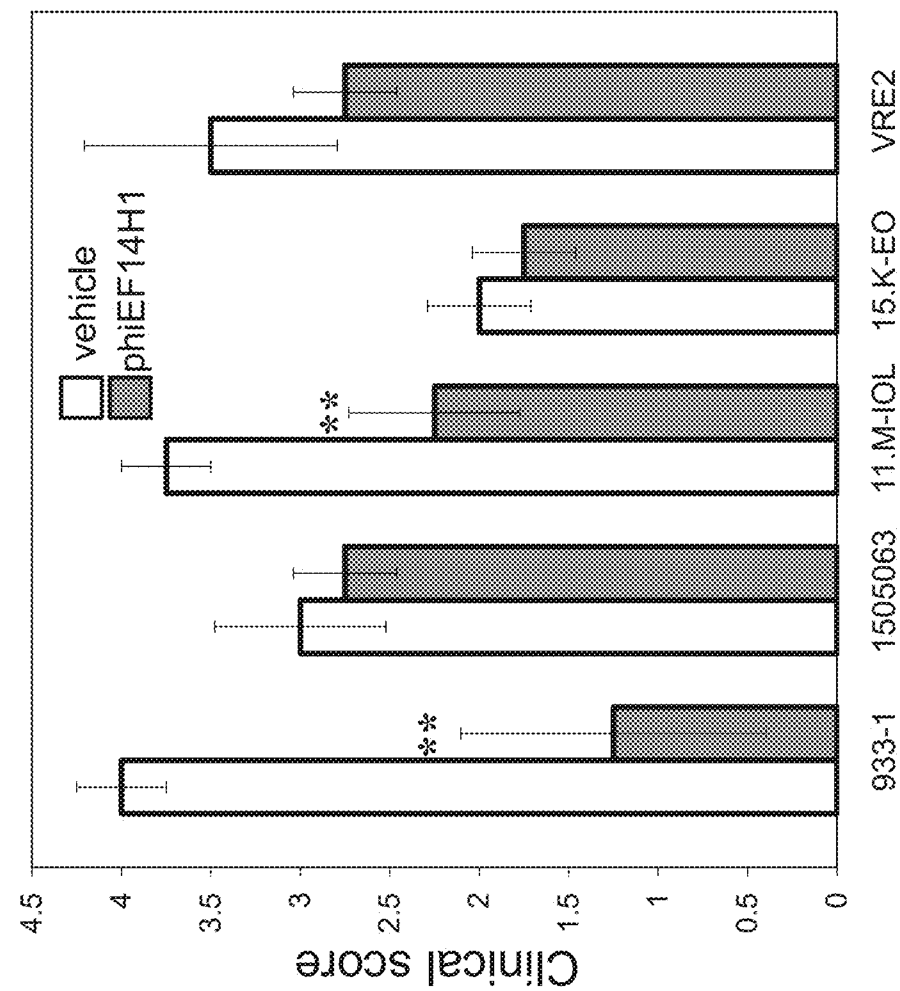
[Figure. 3]

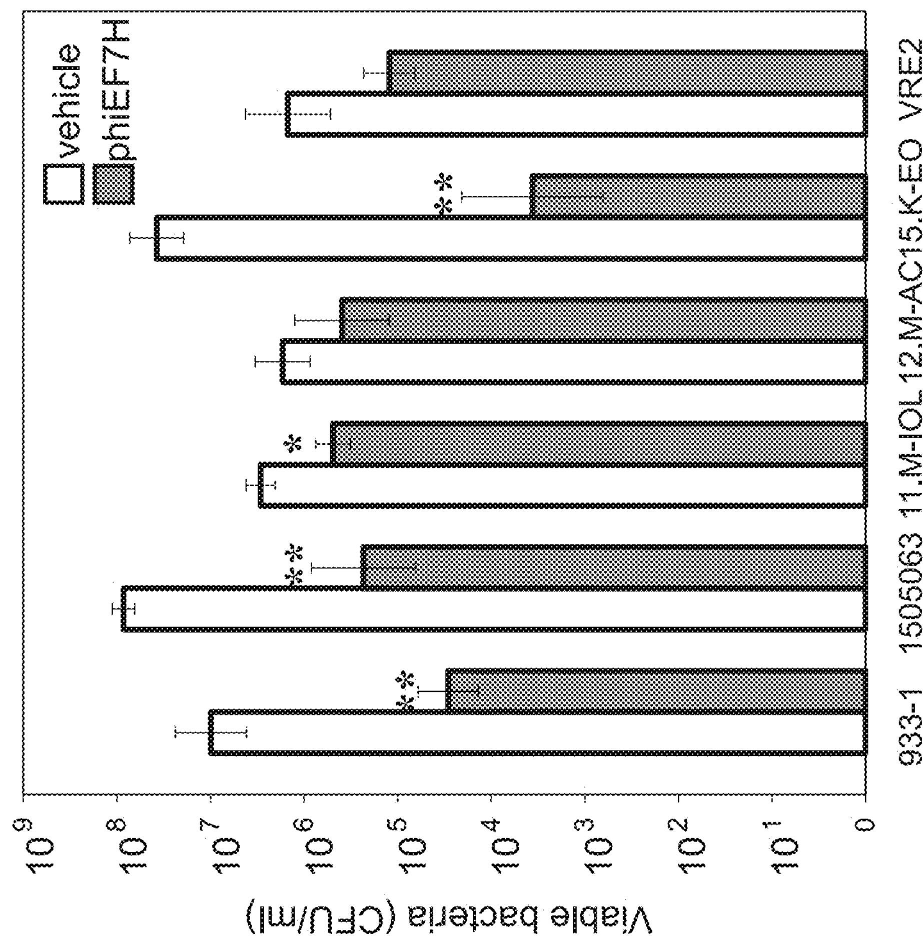
[Figure. 4]

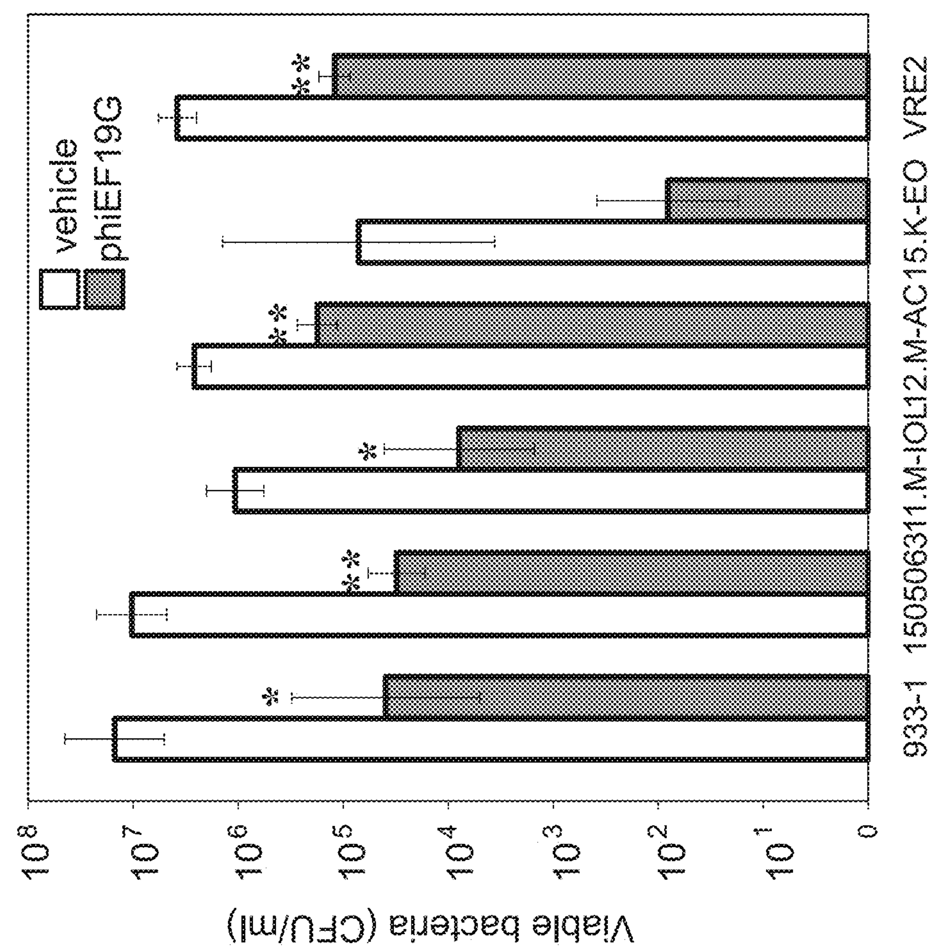
[Figure. 5]

[Figure. 6]
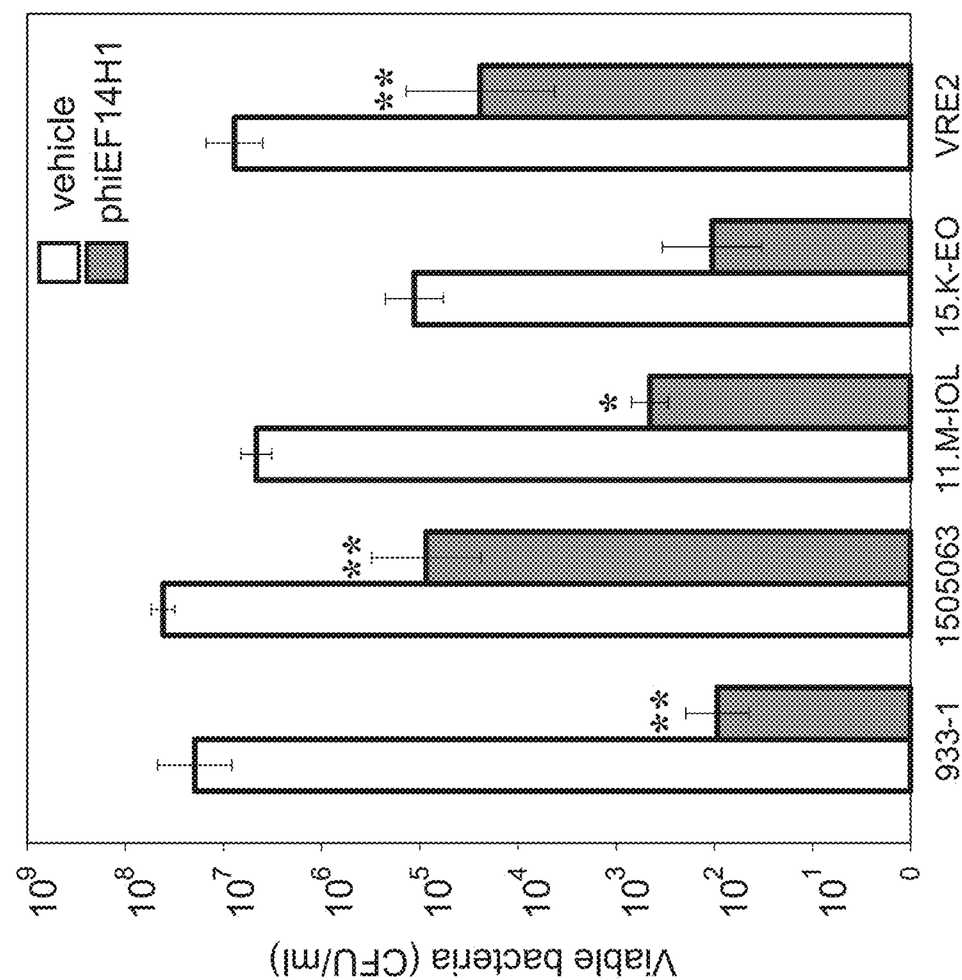

[Figure. 7]
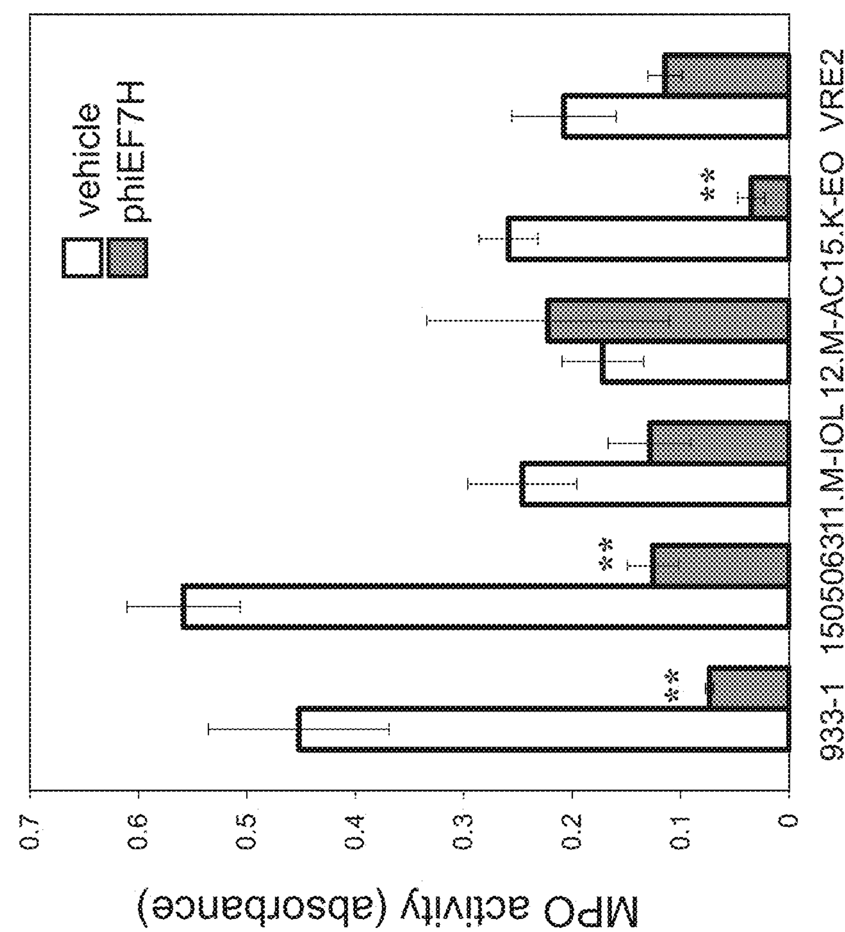

[Figure. 8]
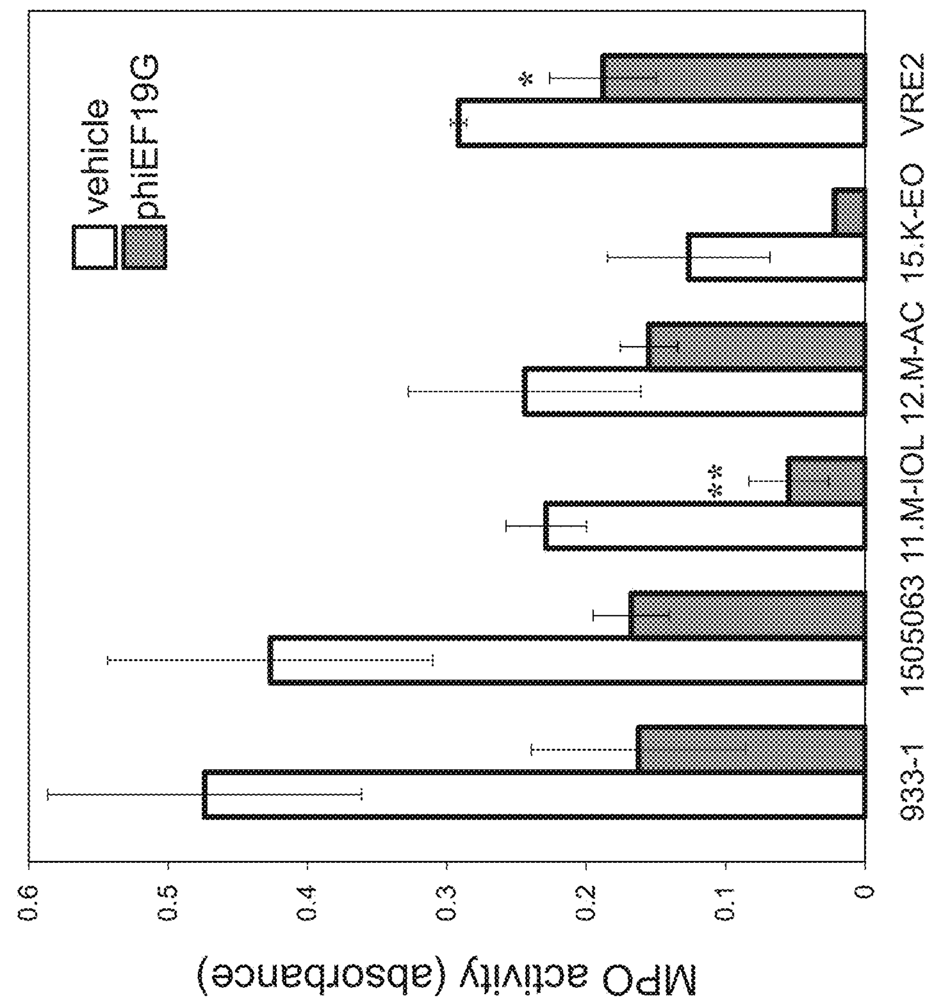

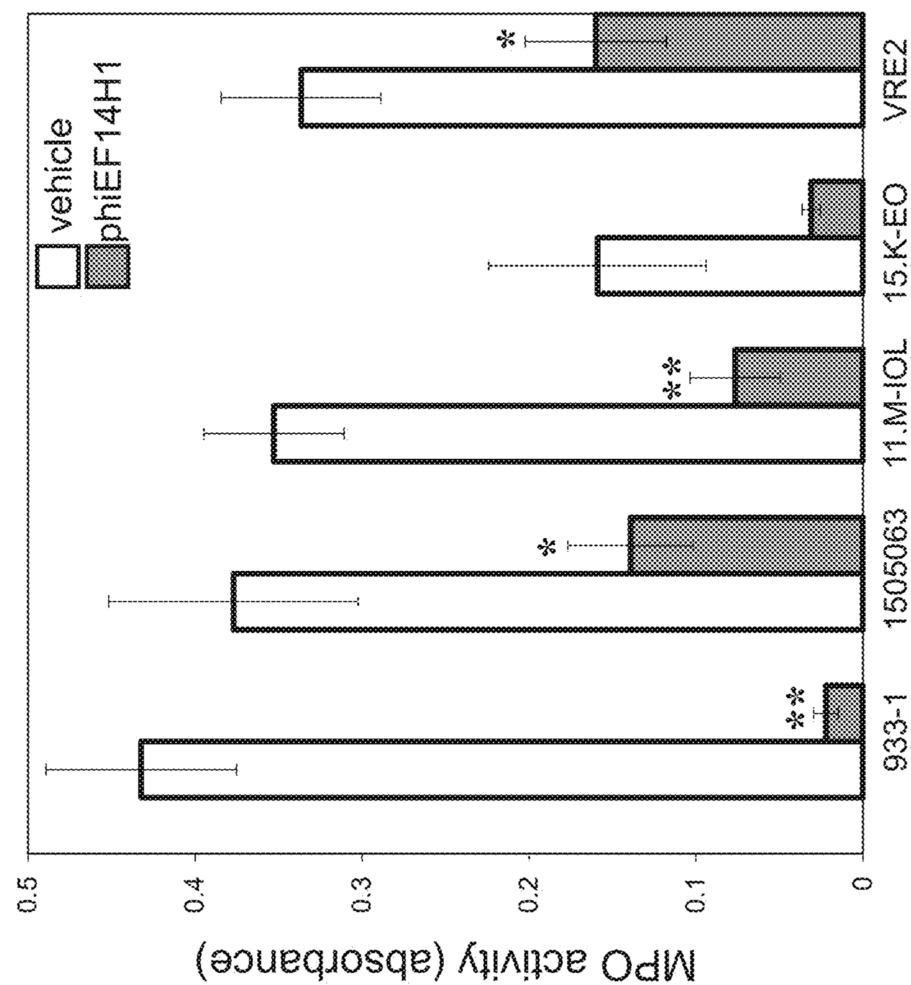
[Figure. 9]

BACTERIOPHAGE AND THERAPEUTIC AGENT FOR BACTERIAL ENDOPHTHALMITIS

REFERENCE TO AN ELECTRONIC SEQUENCE LISTING

The contents of the electronic sequence listing (AttachB1_SeqListing-1424.xml; Size: 434,846 bytes; and Date of Creation: Sep. 8, 2023) is herein incorporated by reference in its entirety.

TECHNICAL FIELD

The present invention relates to a novel bacteriophage useful for treating bacterial endophthalmitis and a therapeutic agent for bacterial endophthalmitis comprising the novel bacteriophage.

BACKGROUND ART

Uveitis is a disease that causes inflammation in the eyes, and endophthalmitis is a kind of uveitis. Infectious endophthalmitis among endophthalmitis is caused by bacteria, fungus, virus, parasites or the like. In particular, bacterial endophthalmitis after an ophthalmic surgery is a social problem, since such bacterial endophthalmitis is iatrogenic. In addition, postoperative bacterial endophthalmitis quickly develops in many cases and may possibly cause blindness in a few days. If there remains corneal opacity or scarring of retina due to bacterial infection, visual function does not recover even after bacterial eradication, since eye tissue plays a role as an optical system. It is therefore very important to rapidly eliminate bacteria the germs and minimize eye tissue destruction for treating bacterial endophthalmitis.

Bacterial infection has been mainly treated by drug therapy using antibiotics since penicillin was discovered. For example, Patent document 1 discloses a method for treating endophthalmitis by using fluoroquinolone, which is a kind of synthetic antibiotics. But drug-resistant bacteria began to emerge from the 1980s due to abuse of antibiotics, and new development of antibiotics and emergence of drug-resistant bacteria have alternately appeared. There is an urgent need to develop a therapeutic agent having a mechanism different from conventional antibiotics in the present day, since multidrug-resistant organisms showing high resistance to many drugs have emerged and there are some cases difficult to be treated but the number of newly developed antibiotics has been decreased year by year.

A phage therapy using a bacteriophage has been known as a method for treating bacterial infection without using antibiotics. Since a bacteriophage has higher specificity than antibiotics and does not exhibit a bacteriolytic action to bacteria other than a specific bacterium in many cases, it is possible in theory to select a bacteriophage to be used which bacteriophage is harmless to not only a patient but also the other bacteria which is not pathogenic and which prevents opportunistic infection disease, such as good bacteria in intestinal flora. Thus, a phage therapy is hardly considered to cause an adverse reaction. In addition, a dosage amount and a frequency of administration may be small, since a bacteriophage infects a host bacterium to grow proliferously.

A phage therapy was clinically applied mainly in Eastern Europe and Russia. In recent years, a phage therapy has attracted attention as a therapeutic measure against drug-resistant bacteria also in Western European countries. The possibility of a phage therapy is specified in national action plans relating drug resistance in Japan.

PRIOR ART DOCUMENT

Patent Document

Patent Document 1: JP 2010-536860 T

DISCLOSURE OF THE INVENTION

Problems to be Solved by the Invention

As described above, if bacteria germs cannot be rapidly eliminated in bacterial endophthalmitis, a destruction and a scarring in an eye tissue progress and visual functions cannot be expected to be recovered. A phage is the only therapeutic agent that increases in a lesion of disease, since a phage infects a bacterium to grow proliferously. Also, a phage is considered to have low toxicity due to high host specificity. In addition, a phage may effectively inhibit a destruction of an eye tissue, since a phage can kill a bacterium more rapidly than an antimicrobial agent. Furthermore, a phage can be expected to be effective against drug-resistant bacteria, since the mechanism of action is different between a phage and an antimicrobial agent.

Accordingly, the objective of the present invention is to provide a novel bacteriophage useful for treating bacterial endophthalmitis and a therapeutic agent for bacterial endophthalmitis comprising the novel bacteriophage.

Means for Solving the Problems

The inventors of the present invention conducted extensive studies to solve the above problems. As a result, the inventors completed the present invention by finding novel bacteriophages which exhibit a bacteriolytic action to a plurality of *Enterococcus* strains derived from bacterial endophthalmitis. The *Enterococcus* is one of four major responsible bacteria to cause bacterial endophthalmitis.

Hereinafter, the present invention is described.

[1] Myoviridae Spounavirinae phiEF7H (accession number: NITE BP-02886).

[2] Myoviridae Spounavirinae phiEF19G (accession number: NITE BP-02887).

[3] Myoviridae Spounavirinae phiEF14H1 (accession number: NITE BP-02888).

[4] A therapeutic agent for bacterial endophthalmitis, comprising 1 or more bacteriophages selected from the group essentially consisting of Myoviridae Spounavirinae phiEF7H (accession number: NITE BP-02886), Myoviridae Spounavirinae phiEF19G (accession number: NITE BP-02887), Myoviridae Spounavirinae phiEF14H1 (accession number: NITE BP-02888), and mutants thereof.

[5] The therapeutic agent for bacterial endophthalmitis according to the above [4], wherein the mutant comprises any one of the following nucleotide sequences:

(1) a nucleotide sequence of SEQ ID NO: 1, SEQ ID NO: 2 or SEQ ID NO: 3 having deletion, substitution and/or addition of 1 or more and 1500 or less of bases, wherein the mutant having the nucleotide sequence exhibits a bacteriolytic action against a bacterium causing bacterial endophthalmitis;

(2) a nucleotide sequence having a sequence identity of 99.9% or more to SEQ ID NO: 1, SEQ ID NO: 2 or SEQ ID NO: 3, wherein the mutant having the nucleotide sequence exhibits a bacteriolytic action against a bacterium causing bacterial endophthalmitis.

[6] The therapeutic agent for bacterial endophthalmitis according to the above [4] or [5], further comprising 1 or more bacteriophages selected from the group essentially consisting of Myoviridae Spounavirinae phiEF24C, Myoviridae Spounavirinae phiEF24C-P2, and mutants thereof.

[7] The therapeutic agent for bacterial endophthalmitis according to any one of the above [4] to [6], wherein the therapeutic agent is a liquid medicine.

Effect of the Invention

A general bacteriophage has very high specificity and exhibits a bacteriolytic action against only one strain in many cases. On the one hand, a phage therapy for bacterial endophthalmitis caused by various strains of bacteria becomes possible according to the present invention. Thus, the present invention is very useful as a therapeutic measure for endophthalmitis without using antibiotics.

BRIEF DESCRIPTION OF THE DRAWINGS

FIG. 1 is a graph to show each clinical score of endophthalmitis model mice to which bacteriophage phiEF7H according to the present invention was administered.

FIG. 2 is a graph to show each clinical score of endophthalmitis model mice to which bacteriophage phiEF19G according to the present invention was administered.

FIG. 3 is a graph to show each clinical score of endophthalmitis model mice to which bacteriophage phiEF14H1 according to the present invention was administered.

FIG. 4 is a graph to show the numbers of viable enterococci in the eye of endophthalmitis model mice to which bacteriophage phiEF7H according to the present invention was administered.

FIG. 5 is a graph to show the numbers of viable enterococci in the eye of endophthalmitis model mice to which bacteriophage phiEF19G according to the present invention was administered.

FIG. 6 is a graph to show the numbers of viable enterococci in the eye of endophthalmitis model mice to which bacteriophage phiEF14H1 according to the present invention was administered.

FIG. 7 is a graph to show a myeloperoxidase activity in the eye of endophthalmitis model mice to which bacteriophage phiEF7H according to the present invention was administered.

FIG. 8 is a graph to show a myeloperoxidase activity in the eye of endophthalmitis model mice to which bacteriophage phiEF19G according to the present invention was administered.

FIG. 9 is a graph to show a myeloperoxidase activity in the eye of endophthalmitis model mice to which bacteriophage phiEF14H1 according to the present invention was administered.

MODE FOR CARRYING OUT THE INVENTION

The bacteriophage Myoviridae Spounavirinae phiEF7H, hereinafter abbreviated as "phiEF7H strain", of the present invention has been internationally deposited to Authority Depository as follows. The genome nucleotide sequence of the phiEF7H strain is shown as SEQ ID NO: 1.

(i) Name and address of Authority Depository

Name: NITE Patent Microorganisms Depositary (NPMD), Biological Resource Center, National Institute of Technology and Evaluation Address: #122, 2-5-8 Kazusakamatari, Kisarazu-shi, Chiba 2920818, Japan (ii) Date of the original deposit: Feb. 14, 2019

(iii) Accession number: NITE BP-02886

The bacteriophage Myoviridae Spounavirinae phiEF19G, hereinafter abbreviated as "phiEF19G strain", of the present invention has been internationally deposited to Authority Depository as follows. The genome nucleotide sequence of the phiEF19G strain is shown as SEQ ID NO: 2.

(i) Name and address of Authority Depository

Name: NITE Patent Microorganisms Depositary (NPMD), Biological Resource Center, National Institute of Technology and Evaluation Address: #122, 2-5-8 Kazusakamatari, Kisarazu-shi, Chiba 2920818, Japan (ii) Date of the original deposit: Feb. 14, 2019

(iii) Accession number: NITE BP-02887

The bacteriophage Myoviridae Spounavirinae phiEF14H1, hereinafter abbreviated as "phiEF14H1 strain", of the present invention has been internationally deposited to Authority Depository as follows. The genome nucleotide sequence of the phiEF14H1 strain is shown as SEQ ID NO: 3.

(i) Name and address of Authority Depository

Name: NITE Patent Microorganisms Depositary (NPMD), Biological Resource Center, National Institute of Technology and Evaluation Address: #122, 2-5-8 Kazusakamatari, Kisarazu-shi, Chiba 2920818, Japan (ii) Date of the original deposit: Feb. 14, 2019

(iii) Accession number: NITE BP-02888

Myoviridae Spounavirinae phiEF7H, Myoviridae Spounavirinae phiEF19G, and Myoviridae Spounavirinae phiEF14H1 respectively means phiEF7H, phiEF19G, and phiEF14H1 belonging to Myoviridae Spounavirinae. The description of the other phage strain has the same meaning.

Myoviridae Spounavirinae phiEF24C, hereinafter abbreviated as "phiEF24C strain", is a publically known bacteriophage and described in, for example, Uchiyama J., et al., FEMS Microbiol Lett., 2008, 278(2), pp. 200-206.

Myoviridae Spounavirinae phiEF24C-P2, hereinafter abbreviated as "phiEF24C-P2 strain", is a publically known bacteriophage and for example, the accession number thereof is AB609718.

The therapeutic agent for bacterial endophthalmitis according to the present invention comprises 1 or more bacteriophages selected from the group essentially consisting of the phiEF7H strain, the phiEF19G strain, the phiEF14H1 strain, and the mutants thereof. Hereinafter, the above bacteriophages are conveniently described as "bacteriophage 1" in some cases.

The genome of the above-described mutant corresponds to the genome of the phiEF7H strain, the phiEF19G strain or the phiEF14H1 strain having one or more mutations and exhibits the bacteriolytic action against a bacterium responsible for bacterial endophthalmitis. The bacterium responsible for bacterial endophthalmitis is not particularly restricted and is exemplified by *Enterococcus* such as *Enterococcus faecalis.*

For example, the above-described mutant has the genome having any one of the following nucleotide sequences.

(1) a nucleotide sequence of SEQ ID NO: 1, SEQ ID NO: 2, or SEQ ID NO: 3 having 1 or more and 1500 or less of deletion, substitution and/or addition, wherein the mutant having the nucleotide sequence exhibits a bacteriolytic action against a bacterium causing bacterial endophthalmitis;

(2) a nucleotide sequence having an identity of 99.9% or more with the nucleotide sequence of SEQ ID NO: 1, SEQ ID NO: 2, or SEQ ID NO: 3, wherein the mutant having the nucleotide sequence exhibits a bacteriolytic action against a bacterium causing bacterial endophthalmitis.

The number of the mutation in the above-described nucleotide sequence (1) is preferably 1200 or less, more preferably 1000 or less, and even more preferably 800 or less, 500 or less, 200 or less, or 100 or less.

The identity in the above-described nucleotide sequence (2) is preferably 99.92% or more, more preferably 99.95% or more, and even more preferably 99.98% or more, or 99.99% or more.

A person skilled in the art can determine an identity between nucleotide sequences by an ordinary method such as a method using Clustal (clustal.org), which is a program for multiple alignment of amino acid sequence. In addition, a position of the mutation in the above-described nucleotide sequences (1) and (2) can be similarly determined by an ordinary method.

It can be determined by an ordinary method whether a mutant exhibits a bacteriolytic action against a bacterium causing bacterial endophthalmitis or not. For example, a bacterium is isolated from an affected area of a bacterial endophthalmitis patient, the bacterium is cultivated, a mutant is added to the culture medium, the bacterium is further cultivated, and then the bacterium is observed. The bacteriolytic action may be evaluated depending on a change of bacterial morphology and an existence or non-existence of plaque. Also, the bacteriolytic action of the phiEF7H strain, the phiEF19G strain and the phiEF14H1 strain according to the present invention, and the phiEF24C strain and the phiEF24C-P2 strain against a bacterium causing bacterial endophthalmitis may be preliminarily tested in a similar manner.

The therapeutic agent for bacterial endophthalmitis according to the present invention may comprise the 1 or more bacteriophages 2 selected from the group essentially consisting of the phiEF24C strain, the phiEF24C-P2 strain, and the mutants thereof in addition to the bacteriophage 1 selected from the group essentially consisting of the phiEF7H strain, the phiEF19G strain, the phiEF14H1 strain, and the mutants thereof. The bacteriophage 2 may supplementally exhibit a bacteriolytic action against a bacterium causing bacterial endophthalmitis to which the bacteriophage 1 does not exhibit a bacteriolytic action.

The therapeutic agent for bacterial endophthalmitis may be orally administered but is preferably administered through an intravenous drip infusion into the blood or by injection into the eye, since bacterial endophthalmitis must be immediately treated.

The therapeutic agent for bacterial endophthalmitis is produced from a suspension of the above-described bacteriophage. Such a suspension of the bacteriophage can be prepared by an ordinary method. For example, a bacterium to which the objective bacteriophage exhibits a bacteriolytic action is cultivated in a liquid culture medium, and then the objective bacteriophage is added to the culture medium in order to transmit the bacteriophage to the bacterium. Next, the bacterium is subjected to lysis by continuing the cultivation. As a result, the bacteriophage is increased in the culture medium. After a concentration of the bacteriophage in the culture medium becomes appropriate, for example, becomes included in the range of $10^2$ phages/mL or more and $10^{12}$ phages/mL or less, a solid component other than the bacteriophage is removed by centrifugation, filtration or the like to obtain a suspension of the bacteriophage.

A stabilizing agent is preferably added to the above liquid culture medium and the suspension to stably preserve the bacteriophage. An example of such a stabilizing agent includes a pH adjuster and a buffer to maintain the pH in the range of 6 or more and 8 or less, preferably 6.5 or more and 7.5 or less; an amino acid such as glycine, arginine and lysine; and a salt such as sodium chloride and calcium chloride.

A final concentration of the bacteriophage in the liquid therapeutic agent for bacterial endophthalmitis is preferably $10^3$ pfu/mL or more and $10^{14}$ pfu/mL or less. Also, the liquid therapeutic agent for bacterial endophthalmitis is preferably isotonic or nearly isotonic with a body fluid such as blood. In addition, the solid therapeutic agent for bacterial endophthalmitis for oral administration can be produced by, for example, adding an excipient or the like to the above bacteriophage suspension to be granulated.

A dosage amount of the therapeutic agent for bacterial endophthalmitis according to the present invention is not particularly restricted and may be appropriately adjusted depending on age, sex, weight, symptomatic state, severity or the like of a patient. For example, the titer of the bacteriophage 1 to be administered to a human or an animal per one time can be adjusted to about $10^2$ pfu or more and about $10^8$ pfu or less. A frequency of administration per one day can be adjusted to about 0.5 or more and about 6 or less.

The present application claims the benefit of the priority date of Japanese patent application No. 2018-44407 filed on Mar. 12, 2018. All of the contents of the Japanese patent application No. 2018-44407 filed on Mar. 12, 2018, are incorporated by reference herein.

EXAMPLES

Hereinafter, the examples are described to demonstrate the present invention more specifically, but the present invention is in no way restricted by the examples, and the examples can be appropriately modified to be carried out within a range which adapts to the contents of this specification. Such a modified example is also included in the range of the present invention.

Example 1: In Vitro Experiment

Each strain of *Enterococcus faecalis* causing bacterial endophthalmitis was cultivated overnight. An agar was added to Tryptic Soy Broth manufactured by Bacto in a concentration of 0.5% to prepare a soft agar. The temperature of the soft agar was maintained to be 55° C. On a Tryptic Soy Broth agar medium containing 1.5% agar, 0.2 mL of a preliminary liquid culture was inoculated and the soft agar was further poured to be mixed. The double layered agar medium was left at room temperature until the upper soft agar became solidified.

Streaks of one loop amount of the each bacteriophage liquid were drawn on the double layered agar medium using a 10 μL inoculation loop and subjected to cultivation at 37° C. overnight. Then, whether plaque was formed or not and the morphology of the bacteria were evaluated. The result was shown in Tables 1 and 2. In Tables 1 and 2, “Excellent” demonstrated that plaque was clearly formed, “Good” demonstrates that plaque was not formed but bacteriolysis was slightly observed, and "Poor" demonstrates that bacteriolysis was not observed.

TABLE 1

| *E. faecalis* strain | phiEF7H | phiEF17H | phiEF18H | phiEF19G | phiEF28H | phiM1EF28 |
|---|---|---|---|---|---|---|
| 933-1 | Excellent | Excellent | Good | Excellent | Excellent | Poor |
| 1505063 | Excellent | Excellent | Excellent | Excellent | Excellent | Good |
| 11. M-IOL | Excellent | Good | Excellent | Excellent | Excellent | Poor |
| 12. M-AC | Excellent | Poor | Poor | Excellent | Good | Poor |
| 15. K-EO | Excellent | Excellent | Excellent | Excellent | Excellent | Poor |

TABLE 2

| *E. faecalis* strain | phiEF24C | phiEF24C-P2 | phiM1EF2 | phiM2EF28 | phiEF14H1 |
|---|---|---|---|---|---|
| 933-1 | Good | Good | Good | Poor | Excellent |
| 1505063 | Good | Good | Excellent | Excellent | Excellent |
| 11. M-IOL | Excellent | Excellent | Poor | Poor | Excellent |
| 12. M-AC | Poor | Poor | Poor | Poor | Excellent |
| 15. K-EO | Poor | Poor | Good | Poor | Excellent |

It was experimentally demonstrated as the result shown in Tables 1 and 2 that the bacteriophages phiEF7H, phiEF19G and phiEF14H1 exhibit the bacteriolytic action against all of tested 5 enterococci derived from endophthalmitis and broad antimicrobial spectrum against *E. faecalis* as one of bacteria causing endophthalmitis. Among the above-described enterococci, 11. M-IOL was isolated from the intraocular lens of an endophthalmitis patient and 12. M-AC was separated from the anterior chamber of the same patient.

Example 2: Identification of Novel Bacteriophage

The genus and species of bacteriophages phiEF7H, phiEF19G and phiEF14H1, of which effects on bacteria causing bacterial endophthalmitis were particularly demonstrated in the above-described Example 1, were determined. Specifically, the DNA of each bacteriophage was purified and the nucleotide sequence thereof was determined. The genome nucleotide sequence of phiEF7H is shown as SEQ ID NO: 1, the genome nucleotide sequence of phiEF19G is shown as SEQ ID NO: 2, and the genome nucleotide sequence of phiEF14H1 is shown as SEQ ID NO: 3.

Then, the obtained genome nucleotide sequence was analyzed using BLASTn; as a result, the genome nucleotide sequences had a high homology with that of phiEF24C-P2 as 89% of Query cover, 0.0 of E-value and 98% of Identity, but no same publically known genome nucleotide sequence was found. Since the phiEF24C-P2 is a publically known bacteriophage disclosed in Uchiyama, J., et al., 2008, Appl. Environ. Microbiol., 74, pp. 4149-4163 and belongs to Myoviridae Spounavirinae, it was clarified that phiEF7H, phiEF19G and phiEF14H1 are novel bacteriophages belonging to Myoviridae Spounavirinae.

Example 3: In Vivo Experiment

To the right eye vitreous body of four mice, $1\times10^3$ cells of *Enterococcus* 933-1 strain, 1505063 strain, 11. M-IOL and 15. K-EO strain separated from an endophthalmitis patient, and vancomycin resistant *Enterococcus* VRE2 were respectively administered to induce endophthalmitis. Phages phiEF7H, phiEF19G or phiEF14H1, or normal saline solution as control was administered to the vitreous body 6 hours after the infection. Clinical score was evaluated 24 hours after the infection, and then the eye was enucleated to count the number of the viable *Enterococcus* and evaluate myeloperoxidase (MPO) activity to estimate the number of inflammatory cell infiltrate. The average value of clinical score is shown in FIGS. 1 to 3, the average value of the number of viable *Enterococcus* is shown in FIGS. 4 to 6, and the average value of MPO activity is shown in FIGS. 7 to 9. The clinical score of endophthalmitis was determined in accordance with the following criteria. In FIGS. 1 to 9, * demonstrates that there is a significant difference ($p<0.05$, independent 2 group Student's t-test), and ** demonstrates that there is a significant difference ($p<0.01$).

Score 0: anterior chamber and vitreous body are transparent, and clear view of the retina Score 1: there are a mild degree of anterior chamber flare and a mild degree of opacified vitreous haze, and slightly obscured view of the retina Score 2: there are moderately severe anterior chamber flare, dense vitreous haze, and moderately obscured view of the retina Score 3: there are intense anterior chamber flare, opaque vitreous, and completely obscured view of the retina Score 4: there is anterior chamber hemorrhage in addition to the findings of Score 3

In the normal saline solution-administered group, endophthalmitis was developed, the ocular fundus was not visible as a result of fibrin precipitation and bleeding in the anterior chamber, the number of viable bacteria in the eye was increased to about $1\times10^8$, and MPO activity was increased 24 hours after the infection of *Enterococcus*.

On the one hand, when the bacteriophage of the present invention was administered after the infection of *Enterococcus*, clinical score was increased and MPO activity tended to be increased in the case where phage phiEF7H was administered against the endophthalmitis caused by *Enterococcus* 12M-AC, but all of the clinical score, the number of viable bacteria and MPO activity tended to be reduced and often significantly reduced in the other cases as the result shown in FIGS. 1 to 9.

It is clear from the above results that all of phages phiEF7H, phiEF19G and phiEF14H1 have effect on endophthalmitis, and endophthalmitis may be treated more effectively by combining two or more of the phages.

The invention claimed is:

1. A method for treating bacterial endophthalmitis comprising the step of administrating one or more bacteriophages selected from the group consisting of Myoviridae Spounavirinae phiEF7H (accession number: NITE BP-02886), Myoviridae Spounavirinae phiEF19G (accession number: NITE BP-02887) and Myoviridae Spounavirinae phiEF14H1 (accession number: NITE BP-02888), wherein the one or more bacteriophages are in a therapeutic composition.

2. The method according to claim 1, further comprising administering one or more bacteriophages selected from the group consisting of Myoviridae Spounavirinae phiEF24C and Myoviridae Spounavirinae phiEF24C-P2.

3. The method according to claim 1, wherein the treatment composition is a liquid medicine.

* * * * *

UNITED STATES PATENT AND TRADEMARK OFFICE

CERTIFICATE OF CORRECTION

PATENT NO. : 12,247,229 B2
APPLICATION NO. : 18/463731
DATED : March 11, 2025
INVENTOR(S) : Ken Fukuda et al.

It is certified that error appears in the above-identified patent and that said Letters Patent is hereby corrected as shown below:

On the Title Page

Item (54), and in the Specification, Column 1, Lines 1-3 change the title from "BACTERIOPHAGE AND THERAPEUTIC AGENT FOR BACTERIAL ENDOPHTHALMITIS" to --NOVEL BACTERIOPHAGE AND THERAPEUTIC AGENT FOR BACTERIAL ENDOPHTHALMITIS--

Signed and Sealed this
Twenty-ninth Day of April, 2025

Coke Morgan Stewart
*Acting Director of the United States Patent and Trademark Office*

SEQUENCE LISTING

```
Sequence total quantity: 3
SEQ ID NO: 1             moltype = DNA  length = 143399
FEATURE                  Location/Qualifiers
misc_feature             1..143399
                         note = Bacteriophage Myoviridae Spounavirinae strain phiEF7H
source                   1..143399
                         mol_type = other DNA
                         organism = synthetic construct
SEQUENCE: 1
gttgttccct cctctccctt agagctacta ttaatatagt acactgagct gttagcaaac  60
aggtgtgcta aattaatata gagactaaaa atgtagacgg gagagtggta aaaatggata  120
atagcaaacg aattattaaa aaaattattt ttattaccat ctctgcatta gtcatggtta  180
ctttaagtaa gctgttctct aaatatgtta ttgtagaaca aaatgcccca tttcaggcat  240
tagttggcgg tgcctcatgt gcactgttat ctagtattct gtttgactgg tatactaata  300
aaaagaaaaa agagaacgta gagaatcaac ttaaagaagc aatcagtgac ttgcagaaga  360
ttaaagctat cataaaaaga tagcctatta ggaggtggga tggtgtcta ttaccaataa  420
agacattaag gataaacgta gatatatttt tagtcaatct agtaaaacaa caactataaa  480
aagaggggac aaacgcataa gtagtgcaac aagaatatgt gcagtttgtg gaagaccgct  540
atctaagctc gtattaagaa caggcgtacc aacagtagta gtagaccata ttagctgtaa  600
gatttcagac attgttagac taaatgtctg tgaggatata aggtcttgtt atgcgtattc  660
tagtaagaaa ggggaaagct agctaatggg tatggcagat agacttaaag ataatgcaaa  720
acaaaaaaag ttagaaagaa caccagagca acaactaaga gacacattta atcaagcttc  780
aataaagctt atcaatcaat ttatggctaa cgttacatca ggtgctatag aagttgatga  840
tattgcagat ttaacaaggc tatttcagat ttatttacag gttaataata taaatgatgg  900
aatgcaagaa ggtacaggaa ctctacctgc acttacatct gagcataaag acatcatatc  960
tgaaaaggtt agcacagaaa agattattaa ggacggtgaa gaagaggagc taatttctct  1020
tgatgagtta gccagtcttc cagatgacca acttgaggaa gtcttagtta acagagagct  1080
acagatgaac agagagaacg aggcgacctt ctaatgacga caaaagcaca acatatagct  1140
aaaatggcta aagagatgta tggtacagat aaaattacaa cggagcagtt agcttatata  1200
acagatatgc tgaccccatc aacgtaccta ttgagaaatc actctgtgcg taatcaccca  1260
ataactttta ttatatcagg aagggatgca acaaaagcac aggcacatag accataaacc  1320
aacaaagctg tggtctttaa actctactaa acgggcatag taaaataata tacacgtaaa  1380
caatatactg gtaagagaga ctaaatccta gtgtataagg acagggttga cctaccgtgc  1440
taaatcagtt atactataac tgtaaaagcc taacgactaa atttctaggt agctaactaa  1500
aaggagttag tgagaactag ataaaaggca aataaactat gcaagctcaa taaaaataat  1560
aatatacagg aggtgattaa gatagctaag gacagaaaag aaattttcat agaaaagctc  1620
aaaagtgtaa aaggaactga ctttgaactt ataggtgagt ttacaaagca acgagaaaag  1680
actctatttc gtcataacgt gtgtgggcat gtttgggaaa ccactccggt tgtcctactt  1740
aactcaaaaa aaggcggagg gtgccctcat tgtcaataca gaaacaaagc aacttcacca  1800
aaagaatacg aaaaaagagt aacagacaca tttaaaggag aatacgttgt actcaatatt  1860
aatgagtata aaaacaatag tactaaactt aaattcttgc attctaaatg tggtacagaa  1920
ttttatctgc gaccagcaag tttattcatt aatgcaacta gttgtcctaa ctgctctaaa  1980
aataaccgtt gctcaactaa gagaactact aatgagttta gagagttgct tcttaaaaca  2040
aaaggatact cctatgagct aacggaagat gcagagtaca ccggagctaa caaaaaaatt  2100
aaggttaggc atacaacttg tggttatgtt tgggaggcta gagctaacca cctgctacag  2160
ggttcgggtt gtcctagatg taacgaatca aaaggagagc tattagtagc tactattctt  2220
aagctaagca acacctcttt tttgagagag cacacctttg acgattgtag aagtactaga  2280
cccttacctt ttgactttgc attaattagt aataacaaag tgcgtggttt aattgaatat  2340
gatggagaac agcacacgaa accagtaagt tgtttcggag gggaacagaa gtttaaaagt  2400
acagtaagaa atgataacac taagaatgat tattgtactc ataaaaaaat acccttactc  2460
agagtatcat acactaatag tcctgaacag attgagcacc tagttcagca gtttttaaaa  2520
agcatagatt tgttgtaacg tagagcaacc taaaccaaaa agtaggttga tgatatagtc  2580
tagtccccta ataaatatcg ggaaaccgag ggtaaccaaa tgggcaacca aagataataa  2640
atgaccaaca tagagacaag gcaataatta aatcaagaca attagggtta agattagccc  2700
ctttataaag caatttgtaa agaaaactct gttaaacggg catagctgaa taaccaataa  2760
gctgataaga gaacctaagt cctgaaaagg atagaggtaa tcccgtgcta aatcagtgca  2820
aagcactgta aatgcctaac gactaaattt ctaggtagct aaccaaatgg ggttagtgag  2880
aactagataa gaaaacctct taagaggaag taaagcagag caacctaaac caaaaattag  2940
gttgatgata tagtctagtc ccctaataaa tatcgggaaa ccgagggtat aacgtaagtg  3000
agatgggtgt tggttctatg ctacagtttg cagacacgca tagttatgat gctgttaaat  3060
gtctttatac attcccaacg aatgagcaaa tgactaaatt tgtacagaca aggttagacc  3120
ctgttttaca gaatgggtac tacagcacaa ttgtagacca agaagttaac tcattaaaag  3180
ctaaaaaaat aagaaatagt tttttgtatt ttcgttcaag ttcaaaaccg ggcgctgtgg  3240
aaggtgtcga tattgactat ctatctatgg acgagtatga ccgtgtacct gcattagcag  3300
aggcttctgc gttggaatcc atgtcttcct caccttataa gatagttaac agatggagca  3360
ctccatcagc acccgatatg ggaatacatg ggctctttaa agggtcagac caacattggt  3420
atttacataa atgtgagaaa tgtaattatt acaacgaaat gagttatgat gcatataccc  3480
cagaggctcc tgtagagagt agaggtaaca ttctttgtgt taacccaaaa ggggtcgatg  3540
ttgttgctaa aacagtagtt gacggctcat tccagtttgt ttgtcaaaag tgcggagaac  3600
cgttagacag atggtacaac ggtgtatggg tacctaaata tcctgataga acaaaaaatg  3660
gtctaggtac tagaggatat atgatttccc aaatgaacgc agtatgggta actgccgacc  3720
agttaaagac caaagaactt caatcattgt ctaaacaagc cttttataac tatactctgg  3780
gtgaataacg ccccttcaac tggaaacagt tgtcgaaaac tctgttaaac gggcaaagct  3840
gaataaccaa taagctgata agagacccta aaccctaaaa tagggcagtg ggaatcccgt  3900
gctaaatcaa gcgtaagctt gtaaatgcct aacgactaaa tttctaggta gctaaccaaa  3960
tggggttagt gagaactaga taagaaaacc tcttaggggg aagtaaagca gagcaaccta  4020
aaccaaaaat taggttgatg atatagtcta gtccgactgc caagagcagt aacaaaatac  4080
tacgaaagta gcggtagctc gtatccttac gcagacttga aattaactgt taacgactct  4140
```

-continued

```
gacgttgata gccataagag aaactattta atagaacctg ctaaagacag aggtgattat  4200
aaatttatat ctgttggtat tgactggggt aacagacatt gggtatctat acatggtgtt  4260
aaaacaaatg gtacggtaga tttgataaaa ctttttctg taggtaagtc caacccgcta  4320
gaccctaatg caatagatgt agacatacag tctataaaat tacagctagc tccttacaat  4380
ccagatataa tcgtagctga cgtaggagac tcaggggata aagttgctaa acttatgcaa  4440
atttatggaa aagaacgagt ttttgggtgc gtttacccat caacccctaa atctacaggt  4500
aacttagtac ctacttggag cccacaagca aataaagtat ccgctgacaa gttaatgcag  4560
aataaacgtt acattaacaa gatgaaagaa ggagaaatag gttactactc aaaaccagat  4620
acagagctta atttatataa agagcactgg aagaatgttg ttatacgtga tattgaggac  4680
gaaaagacat cgacaggttt tagacaaatt atcggcagaa aaggtgatga ccactactca  4740
caagcaagcg tttattccat gttagggtat gagtacctaa tgaatgtatt tacaggagta  4800
aaagagtatg gatttgactc tgattgggtg tcaactcaat tagcacctac gaaacctgat  4860
atatttacag aatttgtata ggtagattgc cttatttagt tttagtcaag ctgaataagg  4920
cattttgtat tgtttgatat atatttttgt ggtataataa atatagttag gggatagtt  4980
atggtagaca acaatgtaaa aataagtaaa agtacaattg aaggactaat aaataagtct  5040
ttaagttatg agtacgttat aaaaaataac gaattgctga caaacgaata tcaacatatt  5100
gtaaaagcgt atgggtttga caatttttat gacatgtatc tatatgcaga tagctgtgat  5160
tctaaagata tgtatttagt aaaaggtggt caaaaagact tgtctaagct gaaacccgtt  5220
aaaagaaaag ttgttagaaa tggtaaaact atgactacaa ctatttatga agatacaggc  5280
agttcagaca gtaataacag taacccttta gacaaagaga gtaaaaagaa aaaagagtta  5340
gaaccagtta atgctaagga actacgtaag gtcagcttag gtagtgatga agaagagaag  5400
ttagacccta aaaagatagc aaaattgcta gcagacacta aaaaatttgg aaataatttt  5460
gatacgcagt gtactgatta tcttattctt gaacaagact ctgttacacg aggagtggta  5520
gggtttacta gagaaggttc ttatttaaaa atgtctttct caatgtcaga tgaggctgtt  5580
gaaggtatga agatgttagc tttttcacag ctcacattaa aggcttggaa attgggtcta  5640
ggggctaaga taagcacaga taatgcacct gatgtagagg aactaattag cttatatgga  5700
tacaaaagaa ataatacaga gtatattgtg tcaatgagct cactgcgtag tcttctaggg  5760
gagccttagt cataagtgct acgttagtca ttatactagt attttcaact attattttt  5820
taatttttaa tttactagta agtaaggtag ttaaagaatt ttataactta aagatgctag  5880
caaaagaggg actaacagat aaagtaacag atataacaaa tgatataatg catatattga  5940
aaggagaaat aaataatatg gaattaatta tgaataataa gaaactagat gaattaacta  6000
ataaggtagc cactgatgag gactacgata tttttgtaga gaagatgggt aagctagtta  6060
aagatttgta tgagaactac cagtttttac aacaaaaccc accagaagga gactacacat  6120
caggttattt tttagggttc caagtaatca gagcagaata cccagttgag tatgagaatt  6180
tatttagatt agctgtagat aaaaatttaa atgaactaga gataaacaag agatttgtcg  6240
aagctgttaa ggatggtaaa gttttaccac taggtgaggc tatcattgat gaattacaaa  6300
cagggtgtag ctctatacta caggcacaag aagtacgtgt aaatattgta tttggtacaa  6360
aagaatatat ggctaagcaa gaagaagagc gtaaagaacg tcaagctaag ttagaagaag  6420
aacgagaaag agctatggaa gtactaaaaa caaaagatga cgtgcttaac acattaagag  6480
taactgaggc tttggctaat gaattaacag atgaagtcgc agaaaaatat gatttaatgg  6540
agctagttaa cagtatgaga gaggggctga aagctcataa tggaaattaa aaattctttg  6600
gggaaagctc ttataaaaaa tttaagattg cttaaagaaa aaagagatgc aatgcccgat  6660
aacttagaat atacaagtca agttatgatt cctgtgccct actatctaat aaaaaaaggg  6720
gataatgcag tagaatcatt ccttatgtgt gcggggatga taaataggga taaagattta  6780
ggtctgccta tttctttaga gaaaggtaag caacaagtta agcttaacaa tggagaactg  6840
acaactattg tagaatgtgt tgctacttac tcagataaaa ctgatattga cggtgtagag  6900
agattcttag ttgaacatct ataaaaatta aattaacgag ttctattttg tgctatatta  6960
gatatgcatg aaatagaact cgtttctttt tttatgacta actaaggagg tttaatagat  7020
ggcaggagaa gtatttagta gcttgattac aagcgtaaat cctaacccaa tgaacgcagg  7080
tagccgtaat ggtatctcta ttgaccgtat tattctacat cataatgcaa caacaaataa  7140
agatgttgct atgaacacgt ggctattagg tggtggtgca ggtacgtctg cgcactatga  7200
agtcacacca acagaaatta tagggtgtgt tggtgagcag tattcagcat tccatgccgg  7260
aggcacaggt ggtatagatg tccctaagat tgctaaccct aatcaacgct caatcggtat  7320
cgaaaatgta aactcgtcag gagcacctaa ctgggatgta gaccctagaa caattacaaa  7380
ttgtgcccgt ttagtggcag atatttgtaa acgttatggt attccatgtg accgacaaca  7440
cgtgttagga cataacgaag taactgcaac agcatgtccc ggaggtatgg atgtagacga  7500
agttgtacgt caagctcaac aatttatggt agggggctct aacaacgcag ttaaaccaga  7560
gccaagtaaa cctacaccaa gcaaaccaag taacaataaa aataaagaag gagtggcaac  7620
tatgtattgt ttatacgaaa gacctattaa ctcaaaaaca ggagtgttag agtggaatgg  7680
tgatgcatgg acagttatgt tttgtaatgg agtaaattgt cgtagagtat cccacccaga  7740
tgaaatgaaa gtaattgagg atatttacag aaaaaacaac ggaaaagaca tcccgttcta  7800
cagccaaaaa gagtggaata aaaatgcacc atggtataac agattagaga cagtatgtcc  7860
agtaataggt attactaaaa aatcttaata ctagatttaa gaccatctta gggtggtctt  7920
ttttctttct ttgtaatatt cgtaataata tgtaatggct atgtaaccgc ttgttatttt  7980
ggctgtaaca attacatgtt atattagttc ttgtaagcaa cacaaataaa gaaaacattg  8040
aggagaattt tattttgaag aaaactagta ttttaggttt aagtttatta agtttaggtt  8100
tagtagtagg tttaggaacc gaagctaagg cagaagaagt aacagagaat ggtaagacat  8160
attggaaggt agagtcagga gacacactat cagaaattgg agctaagtac aacttagatt  8220
tcactaatat ccacaaagtt aataaaggtg ttgtagctga ccctaatgtt attttcgtag  8280
gtgacaaatt gttattacct ttagatgaaa atggcaagct agtggaacaa gtgaatacca  8340
ctgaaccaga tattgaagta caatataacg aaccagtaac acctgaacaa cctgtagttg  8400
tagaacaaga agttgtagag caacctgtag ttgtagcaga agcccctgcc cctgtagtag  8460
aggtacctgc tgacagtagc tcagcaaaag agtggattgc acaacgtgaa tctagtggtt  8520
cttatgatgc aacaaatggt cagtatattg gtcgttacca actatctgcc tcttatttaa  8580
atggtgacta ttcacctgcc aaccaagaac gagtagctga tgagtatgta gcaggtcgct  8640
atggctcatg ggagaacgca aaatctttct ggttagcaaa tggttggtac taaaattaaa  8700
tagcaataaa gacctcttta ttaaggggtc tttttttat gctatattaa tatatagtaa  8760
atagtaatat aaaatggtta tgattagtta tgtggtataa tagacttatg ttaaaaccat  8820
ttaaggaggg gaaacatggg ttatattcaa gatgagacat ggcagatggt taaaaaagtt  8880
```

-continued

```
gctaaaaaga atgggtttgt tggtgactgg attttaatta tccactcata ctatgagtat  8940
ggtggaaatc acgtccagat acatacaaca ataaacggag aaagctatag aattttaaga  9000
ttgttagata gcagagagat acttttatta gatagaaaag gtaaccctgt aatttatgac  9060
tatgaaacag ttaacgatgg tcaaaaaagc ttcttttata atgatatgga agagaaagaa  9120
atcgaaatac ctaatggaag atgcttaaac gataagacaa ggataaaaat ttatgtataa  9180
ggtaggtgta acagttgcca aaatggttag ataaagcact gggtatagaa aaatcgtcca  9240
tagaagaaac taggaatatg gaaaattata agatgcattt aagggaaata gacaccaatg  9300
tggtcaataa cgagccgtac agtatggaaa gtattgaaaa aggtatgaat ggtaagacca  9360
ctgcatatat gcaaccaatt attggagaga tgtcagtaaa ccccgggtat aaaactaaac  9420
cgtctatacg taactctcag gacttacata agacacttaa aaagtttggt aataacataa  9480
tattaaatgc tattattaat acacggtcaa accaagtatc gatgtattgt aagcccgcaa  9540
gaaattctga gacaggtgtt ggttacgaga tacgtttaaa agatattgaa gcagaaccta  9600
cttcacatga cattgctaat attaagcgta ttgaaagttt tttagaaaac acagcacaat  9660
ttagagaccc taatagagat aattttacaa ctttttgtaa aaaacttgtt cgggcaacat  9720
acatgtatga ccaagtaaac tttgaaaagg tatttgataa agatggtaac tttatcaaat  9780
ttgatactgt agacccaact acaattttct tagcaacaaa tggtgaaggg aaactaatta  9840
aaaacggtga aagatttgtt caggttgttg ataacagaat tgttgctaaa tttaatgaga  9900
gagaactagc attcgcagta cgtaacccaa gagcagacat cgaagtaggt cagtatggtt  9960
acccagagtt agaaattgcg ttgaagcagt ttattgccca tgaaaataca gaggtattta  10020
acgatagatt cttctcacat ggaggaacta ccagaggtat cttacatgta aaaacagggc  10080
aacagcagtc tcaacaagca ctagacattt tccgtagaga gtggagaagc tcactagcag  10140
ggataaatgg ctcatggcaa atacctgtag tttcagcaga agatgtcaaa ttcgtcaata  10200
tgacaccctc tgccaatgat atgcaatttg aaaaatggct taactactta attaatgtta  10260
tatctgcttt gtatggaatt gaccccgcag agataaactt ccctaacaat ggtggtgcaa  10320
caggctctaa aggaggctcc ctaaatgagg gaaactcaaa agagaaaatg caagcttctc  10380
agaataaagg gctacaaccc cttttaagat ttatagagga caccgttaac acatatattg  10440
ttgcggaatt tggagaaaaa taccaattcc aatttagagg gggagaccta agtgctcaac  10500
tagataagct taaaataatt gagcaagaag gtaaagtatt cagaacagtt aacgagataa  10560
gacatgataa aggtttagaa ccgattaaag gcggagacgt tatactaaat ggtgttcaca  10620
tacaagctat tgggcaagcg ttacaagaag aacagctaga ataccaaaga agccaagacc  10680
gcttaaacag actattagag ctatctggtg gagatgtaga acaaccagaa ccagaagagc  10740
ctaaagacag tcaaaatgat acagatgttt catttcagga tgaacaacaa ggtttaaacg  10800
gtaagtctaa gaaagttaat ggtaaggtag acgacaatgt tggcaaggac ggtcagttaa  10860
aatcggaaga aaacaccaac tcaactaagc atggtactga tggtataaaa aaagaataaa  10920
agataatgga gggggctagc tccccctcaa ctttgtttgt gttactagat agtacatgtt  10980
ctgctatatt aaatacagta aaacgtttag gtggtgaaaa gcaaattgtc agaagttaga  11040
gaaaaatata gtattttcgt accactggat attgaaaatt ctatacagaa gtctgaatct  11100
gtgaatgatg gtgaatggta tgttcaagga tatgcaacta ccccagattt agatttacaa  11160
ggagatatta ttttaccaca gggcattgat atttcttatt ttattgaaaa tggttggata  11220
aactatgagc ataaaaatga tgctgagttt attataggtg ccccaactag caattgttat  11280
gttgatgtgg acaaagggtt attcgtagag gctaagctat taaaggataa caagtacgca  11340
cagtctatgt ggaagctagc taatacaatc cagaaatcag gaatatctcg tcagttaggt  11400
ttttctattg agggtgcagt agttagtaga aatgcacaag ataacagaat catagaaggt  11460
gttaaaatac ataatgttgc attaacgaca catccggcta acccaagagc tacatgggag  11520
acactagtta aatcttggac tacaggatat ggcacagcac cagatgcaca agtagatgca  11580
ggcgcactta gaagagagat gtttaaagag gacatttcta atttgacgta tgcagtaaga  11640
actattgcag gactatataa taaaaaacct gcagagaaag agtttatttt acgtgaagtg  11700
gctaaggata tagaagtaga cacttccgaa aatgaattat ctaaatttat gttacaatta  11760
agtagaggga tttccttgaa agaagcaaca aactttattg aaaaaagaaa ggggtaagaa  11820
atagtggcta aaacattaaa cgatattata gaagatttg atgcacagtt aaatgaaaaa  11880
gtaaaaccta ctacagatga ggaaattaca aagtctgtag aagaacctac tgaaccagaa  11940
aaagttgaag aaggtgctga ggttgagccg gaagaaaagc ctaatgaatc tgaggagact  12000
acaggcaatg acggagaaga atccggagtt actgaaacag ttgaagcaga acaggaagaa  12060
ccagaaactg ttgaagaagt agcagttgag gaacctgttg aggaacctgt tgaagaatca  12120
gcggaaactg ttgaaaaatc tgataaaact aaagaaaaata aagatgaaga agaggaggaa  12180
gacgaagaca aaaagaaaga aaaagacaaa aaagacaaag ataaagaaga caaagaagac  12240
atcgagaagt ctaccgaagt cgaacaagtt atcaaatctt ctgaaatctt aggagctatg  12300
gaagctatct ttaaaaatat gttaggtcta agtgaaaagt tagacgaaat tcatagagag  12360
tttaaagaag ctaaagaagc taaagaaaaa gacgaagcgg agtctgttga gaaatcttta  12420
cttgataacc ctgaaattaa aacaggaaaa gaggactcag aaggcaaggc tgttgggttt  12480
gttaataagt ctgtagcagt tgaggaagag gtggctaccg aagaaccaac tgtagaagta  12540
gttgttgatg gtgaacaaga cacagcagaa cctgaaaaag aagtaccgtt ccgtgataga  12600
gtacaggcta ttagaccaga ctttatggaa acatataaac gtgtgtctgt tagcggagta  12660
gctcaacgtg gtgaattaga atcagttaga cacacttggg gaactgctag aacaaatgat  12720
gacctagcta aaattgaagg gtttattaat aaatataaat aaatttacta tatagtgaac  12780
gatttttaat tgtactgcta tattaatagc agaaacaata aaagacctga cattccctcc  12840
tgaacctcca cagggtcagg tcttatattg agaggaatat aaagaaaggt gatttataca  12900
taatgacaga gaaaaagaat acagaacgac aattaacttc cgtacaggaa gaagtaatta  12960
aaggcttcac tacaggatat ggtattacac cagaatctca aactgatgcc gccgctttaa  13020
gacgagagtt tttagacgac caaatcacaa tgctaacttg ggcagacgga gacttatcat  13080
tttaccgtga catcactaaa cgtccggcaa cttcaactgt agctaaatat gacgtatatc  13140
tagcacatgg acgtgtaggt catactcgtt ttactcgtga aatcggtgta gcaccaattt  13200
cagaccctaa cttacgtcaa aaaacagtta acatgaaata cgtttctgat actaaaaata  13260
tgagtatcgc aacaggttta gttaacaaca ttgaagaccc aatgcgtatc ttgacagacg  13320
atgctatctc agttgttgct aaaacaattg aatgggcttc tttctacggt gactctgact  13380
tatcagaaaa cccagatgca ggttcaggtt tagagttcga tggtttagct aaactaattg  13440
acaaacacaa tgtactagat gctaaaggtg ctagcttaac agaggcttta cttaaccaag  13500
catcagtatt agttggtaaa ggttatggta caccaacaga tgcttatatg cctatcggtg  13560
ttcaagcaga cttcgttaac caacaattag accgccaagt tcaagtaatt agcgacaacg  13620
```

-continued

```
gtcaaaacgc tacaatggga ttcaacgtta aaggttttaa ctctgcacgt ggtttcattc  13680
gtttacatgg ttcaactgta atggaattag aacaaatttt agatgaaaat agaatgcaac  13740
ttcctaatgc tcctcaaaaa gcaactgtta aagctacttt agaagcagga acaaaaggta  13800
aattccgtga tgaagattta acaatcgaca cagaatacaa agttgtagta gtatctgacg  13860
atgcagaatc tgcaccatct gatgttgcat ctgtagtaat tgacgacaag aaaaaacaag  13920
ttaaattaga aatcactatt aataacatgt atcaagctcg tccacaatat gttgcaattt  13980
accgtaaagg tttggaaaca ggattgttct accaaatcgc tagagtacct gcaagtaaag  14040
cagttgaagg agttatcaca tttatcgatg tgaacgatga aattcctgaa acagcggacg  14100
tattcgttgg agaattaact ccatcagtag ttcacttgtt cgagttacta ccaatgatgc  14160
gcttaccatt agcacaagtt aatgcttctg tgacattcgc agtattatgg tatggagctt  14220
tagcattacg tgcacctaag aaatgggctc gcattaagaa cgttaaatat atcgcaacag  14280
gtaacgtgtt taactaacgc taatctttaa aagactaagc aaaattgaat aaaaatggaa  14340
taggggacgg ttaatactgt tccctatttt tattataaaa tacatgtatg gaggaaataa  14400
tatgttaaaa tcagaaatct taataaataa aacagtaaca acagcttttg gtgaggcaac  14460
atttgaccat aatggggaaa ccacagacct aacagtagaa cagcaagaac atttagggac  14520
taaagttcca tatatacaat atataccaga tgcacctaaa gctaaagaaa aagaagctac  14580
tgcagaaaaa gcagacgagg cacctaaaaa ggctaagaaa gcgcctgcta agaaaactac  14640
aaaatctaaa aaagaggaag actaaggagg tatttatatg tacccagact acggatacga  14700
ggaacaaggg gacaatacat accaatacca accatatgca catgggaacc ctaagcatat  14760
agatttagac aaaattgatg atatacagcc tgctgattat ggttggacac ctgctacgct  14820
gaaacaatac atgtttggtg tagaagttgt taaccctgaa acaggggagc ctttaggaga  14880
tactttctat gaacatatca tagattcagc aatagctaaa gcagagaaac gactagatat  14940
tgctattatg cctagactta taagaggaga acaccatgat taccaccaat cagatttcaa  15000
ctcttacatg tatactcatg tgtttaaaag acctattatt caagcagaaa agcttcaatt  15060
agaagttaat ggtagagggc tatacagata cccgtctaat tggtggaaag tgtatgcact  15120
agcaggtcat atacaaatgt acccaacatc cctcatgcag actggaacac agtttggtta  15180
tgaaatgacg ttctcagggt acccacaatt agcaggaatg cctccatcag gaggacaagt  15240
tgatgctcct caaatgattc atattgacta tgtggcagga atgctaccta ggaaaaatag  15300
aggatacaat gaagactggg agtgccctgc ggacttagaa cagcttgtaa taaaatatgc  15360
gttaaaagag atattccaac aatggggtag acttataatt ggtgcaggta ttgctagtaa  15420
gtcactaaca gtagatggta ttagtgaaag tatacaaaca acacagtctg ctatgtatgg  15480
tggagcttct gcagatattc gacaaattga cgaagacata caagaattag aaaaatcatt  15540
ggtatcttac tttggaatga acttaggtat tatttaaaaa aggggggttaa caaatgggtg  15600
aaaaaccaat tagatttggt ggagcaggtg aaacaggtaa ccctaacaag caattaaata  15660
ctagtagggt tgaatttgaa acaaaaggta tggctagctt cattgaaaat agaggtattg  15720
acgttttgtg ggaaagagca tggctatgta catgccgtaa cccaatgacc ctctcaccta  15780
agtcggattg ccccatctgt aggggaagag ggattgctta ccaacctgca gtaaaattaa  15840
gaatggctat acagagtcaa gagaaaggta tctctaatca agatttagga ctactagaca  15900
caggaaccgc tattggaacg actgagctag attctaagat aacctttagg gacagaataa  15960
cagtccccga agttaaaata tatcaaagct ttatttttaa tgtaaataaa agaagagtag  16020
ctaatggact atttttaagc tatgatgtga acagtataga agatatttat ggtaaagacg  16080
gacgtatctt agttgatgga gtcgatttta gaatggacta tgacacaaat actatttatc  16140
caaatgaatc tttaatagat actaatatat ccataaatat gtctgttaca cttagatata  16200
ttgttataga cctgttaaaa gaaagtagat accagtatac cacattcggt gttaaacaaa  16260
cacaatttga atcactacct aaaaagctct tattgaagcg tgaggacgtg tttattgata  16320
gtgaaccatt ttcattagac atagatacag caagccgtat ggaagagcta gagggcaaaa  16380
aagatacaag tgaagctatg gtagacccta agcgtaaagc tacaaaatca ggaggcttct  16440
ttggaggtaa gttaaatggc tagaaaagga cagagacccg tattatttac tgattcaaaa  16500
gcaatacttg gcaatctgac tcgtgcagtg gttgatgaag tactaagtga tgcgcaagat  16560
gttgctctac gtaatgggtc ttctgtacag agaatgccta gctatttgat agtaacagag  16620
tctaggatgg caaaaaatgg ggttatagat ttgaaacctt tctttgcacg ttctaataaa  16680
aagaaatata ataaaaaagg ggaatggtac ctatacatcc ctattagtat gaaaacacgc  16740
aacatgtcaa gacgattata cgatgagctg agagcagttc cagtaggcac aaaacctgta  16800
actgttaaaa tggactatct gtatgataga cggaagcaga gcccatcagt gtctagtatt  16860
aactataaac ctaaatctac taatgtaact gttataccac agagttgggg taaaggtaca  16920
cgtaacacct atgtagcttt ccgtacagtt aacgctaatt ctcctgcgaa tagttggata  16980
ataaatcgta gaaacgttaa tgatgatgat atgagtaaga caatgctaag aaacatagac  17040
aggctcatga agtggaaact aaagaattta ggaggatagt gtatgatacc aagtttagac  17100
acttacttgt ataaagaatt tgaagaaagg ctaaggataa ttctatcaga gtgctatatt  17160
atagacgaag ctttaaaggg aatggacaaa gaagctttag aatcttttaa aaacacttat  17220
tgctctatag atggtaagcc acctaagaga gaagtagaga tgtcctattc attcccacaa  17280
gaacatctgg attcatttgc tcgatttgta gtaactctcg gtagtagcga agaagatagc  17340
aagtctattg gaggaatcca aggaggctac gagtatcgag aaggtaatgt aattagtgag  17400
gaagccacta ttattagaga aggtgacaag ctgattataa atacatcaaa accagtagcg  17460
gactatctaa acagctcaga cataagtttt gcagaaagcg accattttag gattgaagat  17520
aataaacctg tatttgattt ttcatacaat gaggagttag aaggtatatc cattaatgtg  17580
tcgtatataa gcaaaatatc agatgatgat gttgcaggtg tatacaaagg ataccaatct  17640
aacgataatg ttagtataat tggaataagt tctaatatag atactgctag gtgtttagat  17700
gcaattgcta gaattatact aatcaccatg agagacagtt tagatgaaaa aacagggtat  17760
atgttgcaaa cactacattt tggtgatatg caagttgtca tagaatcagg tgaaacactt  17820
gtgtttggta gaccttgtac tgtaaactac agagttacta attctattgg atttgattta  17880
caacaaagaa tcacagagat tattacaaaa aggaggatga aatcctagtg gctaaagaaa  17940
cagagaaagt agtaaaaaaa gaagttaaaa aggagcaacc taaaaaacct aaaggttatg  18000
tccatgtcga tacattttta gattatgcaa aagtattata tggactaaat aaatatcagg  18060
tagcgggttt cagagcacta atggcaggta gagaatacca acacgaggat gctgattttg  18120
ttccattttt agaaaagtat ataggaaagg aagttaaata ataaatggct gtagaacaat  18180
tcccaagaaa aaaagtatca cgtccacata ctgagattac cgtagacaca agcggtattg  18240
gtgggtcatc aagtagctct gacaaaacat taatgttagt tggctctgct aaaggcggta  18300
aaccagatac tgtttatcgt ttccgtaatt atcaacaagc taaacaagta ctacgtagtg  18360
```

```
gagatttgct agatgctatc gagttagcat ggaatgcatc tgacgttaat accgcatcag  18420
caggagacat tttagcagtt cgtgttgaag atgctaaaaa cgcaactctt acaaaaggtg  18480
gtttaacatt tgcttcaaca atttatgggg tagatgcaaa tgaaattcaa gtagcattag  18540
aagacaacaa tttaacacac acaaaaagat taactgttgc attttctaaa gatggttata  18600
agaaagtttt cgataactta ggtaaaattt tctctatcca atataaaggt agtgaagctc  18660
aagccaactt tacaattgca caagatagca ttagtaagaa agcaacaaca ttaactttaa  18720
atgtaggttc tgaaccagaa agtacgacag aagtaatgaa atatgagtta ggtcaagggg  18780
tttactctga gacaaatgtt ttagttagtg caatcaatag tttaccagat tgggaggcta  18840
aattcttccc tataggtgac aaaaacttac ctactgatgc tttagaggca gtaaccaaag  18900
tagatgttaa gacagaggct gtattcgtag gagctttagc aggagatatt gctaaacagc  18960
tagaatacaa tgactatgta actgtagctg tagatgctac aaaacctgta gaagactttg  19020
aattaacaaa cctaacaggt ggttctgacg gaactgctcc tgagtcttgg gctaataaat  19080
tcccattact agctaatgaa ggtggttact acttagtacc attaacagat aaacaagcag  19140
ttcactctga ggctttagct tttgttaaag accgtacaga caatggtgac ccaatgcgta  19200
ttatcgttgg tggaggcact aatgaaacag tagaggaaag cattactcgt gcaacaaact  19260
tacgtgaccc tagagcttct ttagtaggct tctctggaac tcgtaaaatg gatgacggac  19320
gtttgcttaa attaccgggt tacatgatgg cttcacaaat tgcaggtatt gcaagtggtt  19380
tagaagttgg tgaagcaatc actttcaaac acttcaacgt aacatctgta gaccgtgtat  19440
ttgaaagtag ccagttagac atgttaaacg aaagtggagt aatctctatc gagtttgtac  19500
gtaaccgtac tttaactgca ttccgtgtag tacaagacgt aactacttac aatgacaaat  19560
ctgacccagt taaaaatgaa atgtctgttg gtgaagcaaa cgacttctta gtttcagaat  19620
tgaaaattga actagataac aacttcatcg gaactaaagt gattgacaca agcgcaagct  19680
taatcaaaaa ctttatccaa tcattcttag ataacaaaaa acgtgctcgt gaaatccaag  19740
attacacacc ggaagaagta caagttgtct tagaaggtga cgtggcatca atcagtatga  19800
ctgtaatgcc tatccgtagc ttgaataaga ttaccgttca gttagtatac aaacaacaaa  19860
tcttaacagc atagagtgta ggggcagttg cccctcctct tacataatga ataaaatata  19920
ggagtgatat atacatggct agtgttggaa atcaaacagt ccacacaggt aacacagttt  19980
acctaatgat tggtaataaa attatcggtc gtgcgcaatc tgcatcaggt gagcgccaat  20040
acggtacaca aggtatctat gaaatcggta gtattatgcc acaagaacac gtatacttga  20100
aatatgaagg tacaattact ttagaacgta tgcgtatgaa aaaagaagac ttagcaagtt  20160
taggaattac agcgttaggt gaagacatct tacaacgtga cattattgac atcgtaatga  20220
tggataattt aactaaagaa atcgtagtag cttatcgtgg ttgctctgca atttcttact  20280
cagagtcatt cacagctaac gaagttacat cagaaagtac gcagtgagat tataaataca  20340
aaatttatat agctgtgcta gttcgtaaag agctagtatc gagagttaat tgctttgaat  20400
ccctaaagct caacgaccca aacagtaact ggaaacggta agctgagagg tgcgaaagca  20460
gaaaaaatag ttgagatggt ataaggttaa atcctaagta ctgatacaat gggtctttag  20520
cagggacagc cctaagtcaa ttgatacggg acaccttcaa cgactatcct ctgacggagg  20580
agtaaagcca caagccaatg gtggaagaaa aattctctac cctaacaagg gtacccatat  20640
agtctgagct aacatgaaag tgttagaggc aaacgcctac ttggaagttg cgttccaagg  20700
taacaaaact gttcacatac ctaacttctg caaaggttaa atagcagacg aactccaccc  20760
agcttgactg ggtggttctt ttacggtaca atacttttat tattgttaga tatttaggag  20820
atacaacatg agaaaaaaat ggacattaca agaaagaaat attcttataa aaaaatgggc  20880
ggagactaac aacgtaaatc tcttaccaga aacagcaacc tttacaggaa ataagagcac  20940
tatatactac gtatggtcag atggggagct tcaaggctta ataggtaaaa cgaactttga  21000
cagtataata tctggaagta aacctacagt taacggtctg acagaagaga gcaaaaaatat  21060
tagggctaaa aaacgctttt tggaatatgg gctcgaatta ctagaggagt atcaaggatt  21120
caatacacca cataaggtga gagtgttgga tggagtatac gcagggtatt atggaaaaac  21180
ctcattagcc acagtcaatc aaaaaagtac cagaggtaaa atagcgcagt taaacataac  21240
tattcttaca gaaagtgaga aaagacgata tttcagagaa tatgcagagt ctcggggata  21300
cacaattatt aactaccctg aaaaattagc tgttcgaggt aagtgtactt tgttatctcc  21360
ccaaggtaat gagtgggaga cagtctggta ccattttgct tatcaggaga actgcaattg  21420
tccgttagat gttaaacgta gtattgggga gcgcatggtt agaagtttgc ttaaagagaa  21480
tggtattaac tttgaagaac agaaaaagat agttattgat ggtagaacat tattttttga  21540
tttttactta cctgatgaca atacctatat tgaatataat gggaaacagc actatgaaga  21600
caccggaggt tactataagg gtaaacttca agatttacag gaacgtgaca aactaaagga  21660
gcagtggtgt aatcaagcag gtgttaatct tgttgttatc ccatacactg caaatagcat  21720
aaacgaagta gctaatgttt tatccgagat agtaccaatt aaaaagagac tagtttcagt  21780
tgtttattct gatagtatac ctaatgagga tattattgat tactataaaa cacatacagg  21840
taaggaaact tgtaggaaat atgatttaac acaacgtaga ctgagcttac tttgtaacag  21900
agtcggcttt aataaaagga ggtacctaaa gtgaaatatc catatttagt agaattgtat  21960
gcaaaacatg taattagaga tgcagggtac atagaaaatg taccaccagt tatttatgaa  22020
gacgttgtga aacgtgttga agaaataaaa agagaagaaa acttaacaat agattaacta  22080
gtataagttt aaatagacct aattcagata taggtctatt ttttttgcca ctataaatac  22140
aaataactag atagtgtggt ataataaaga tagtgctata ttaatttatg agtaaactag  22200
gaggaaataa taatgacaga aaataatgaa aaggtattta cacctacacc aaatttatca  22260
cgtgagcaat taatagaaaa gttgcaacgt ggagaaaact tgacggatga agaagtaaat  22320
attttgaaat attacaatga tgcagaagaa cgtaaacagt tagatagaat tatcccgggt  22380
gttaatgatg tattttctaa gcattacaac ttaaaagaat atggtttaga atttgatatt  22440
aaaataaaag cacctaatat tatcgaaaat ggtaaaattc aggcaagaag agaagcctat  22500
ttagaaggca tgggaatggc agttagcaac tttattttcc aaagttacca aatgttagca  22560
actattcgag tatgtggagt agaggtacca aaagtattag ctgatgatga aaaaatttat  22620
aatttatatg tattaggagt aattgcaaag gactatggtg aatggctaaa ctcctttcga  22680
tactagagtt aaagaactag gcggaataaa agcccttgtt agaaatagct atagtagaaa  22740
tctatgggca ataatgaaaa aatttaaggt actaccgagt gaccctgcgt ggcaaaatct  22800
cacaagtgac caagtagagt ggattttata taacatggaa agagacatag aagaacaaga  22860
acgactagct aagggaatgc agttagaaag tgagttccaa gactatgacg attcatggta  22920
tgataaacca catgatgagt tctctccaat tcgtgaaggt gacgatgagg aagaaattgc  22980
tcgtaaactt agtgaaatca caagtgagga agacatggct aaacttaaag ctcgttggga  23040
ggcaagccaa gaagttgatg ctatccgtgc agaaggtgga acaacaattg aagaagatac  23100
```

-continued

```
gattaacgaa cttattgcta acaatgttaa aaaagcaatg gaagaggcta gacgtattga  23160
gaaacatggt ggaaacaaat ggcaagagaa atcatcaatt gagttagaag aggaacgtaa  23220
gaacctagag tttaactcac agttgaaaca aggagatatt caggaggcta tcgatttgtt  23280
taacaaagat gtcgagccaa catcattaga tgacgaattt caaatttaag ggtagggtat  23340
tccctgccct ttacttgtaa aggaagtgtg gaaatgagca acaattatcg tttttatgtt  23400
gaggcaatga ctggggatgc tgttgcaaaa cttaatgaaa tagacaagtt aatggataaa  23460
attgattcaa agagtgcaaa gggcacccag aattttttcc atacaagtca gaaagacatt  23520
gataaagctg ttgaggaaat gcaaaagctt atcaaggcaa aaaaagaact agatagagct  23580
tttgataatc agaagataaa tgcagaaagc atgggagaca tgacagcata taaacgtgct  23640
gtatcggatg cagaagaact aactagaaga tttaacaagg cacaaaaaga atttcaaaat  23700
catgctagaa tgcaagctaa ccctaattac ataaatgcta gtacactaag gcaacaaaag  23760
gcatttcgtg atgagttaac agaacaagag agagcaataa gaaatatctc tagggcacaa  23820
caggaactaa acagagtgaa ctctagggtt aaccatcgtg caaaccaagc aagcgcaaca  23880
ggaagaatga cttacaatca gtcagagagt atgaagcgtg accttagacg tactggtgta  23940
tttgaaagcc taggttcaga aaataaaagc agacagcaag agctacgaga acgatataaa  24000
cagagacaag aagagctagc agagactaga agtaatacaa atttagatag acaagttcgt  24060
aagaataggg aaactagtat tcaggctgag ataaaagaaa ttgagaaaga aattgaagct  24120
agaaaacgcc tagcagactc tattaaagag actgtagaga acttaaaatc taaggaagct  24180
tcactaaatg catctgacat aaaagtagat gctgatagaa agagtgctcg tggtgttcta  24240
gctgagcgtg caccttctat atcaatggct atgctaggag gtaccgccgc cgccataggt  24300
ggtttatacg caaaaggagc aactgctaac gcaggtatgc gtgatgcatc tatatcttta  24360
ggacaacgta caggtactag tgacttccgt gcattaagaa aaagtatgca agaaatgggt  24420
attgagaaac agttaggcta taaaggtgct gacatgttac aattccaaga agatgcattg  24480
agtaatattg gttttacaag taaagaggac ttagcaggga gtacaagagc cttagcagag  24540
ggctcaagag cagttccagt agacaatgag actttaagtg acttcatgaa tagtcaaatg  24600
aagagcgggg ctattagtgg tagagaccaa attaagaata ttcaagaagg tttcttaggt  24660
gctatccaac gctcagggat ggcaggtcgt gagaaagaac agctagaagc tcttaaaaca  24720
ttaagtgagc aaagctttac tggtcgtaac ggaagtaatc aagagcttaa agaacaaatg  24780
gcaatgttaa caatgctaaa ccaaacaggt aagcgtgctg ttcaaggtga gcaaggggca  24840
cagttaatgt caagtttatc tgcaggtatt caaggtagtg tatggaacaa taaggcatct  24900
ttacttttag gtaaagggac acaattccaa gggctagcag gaatgtacga cttaaaagct  24960
atgcaagaac aaggagcaac accagagaac ttacagaaaa ttattggcag tgtccaacaa  25020
tcagttcccg gtgacgaaaa gtctcagaag tatgctttcg gtagtgcttt acacgaacta  25080
ttcggtacag atgctaagaa tgaccaaata gatgcaattt gggaggctta tgccaacggt  25140
ggtttaagtc aggataacgt agacagaata atgaatgaaa gccaatctac aggaaaaggc  25200
aaatacgata agaacataga agactatgca aactctaaag aaggaaccgc taaccgttca  25260
gaagctgtta cagagaaaca agcttcacag attaatgata tgggggacat cttaagagaa  25320
actaactcta aattaggagc acttcctcct gcgttatatg cgttaggagc aggcttagga  25380
gctatggctg tttcactagc cacatcaggc tctattggtg gtttatctag tttaatcaaa  25440
aaaggaactc gttctacttt tagtacaggt ggaggggtaa ctgcaggggg cggatttta  25500
aaatcagcta aagaagcatt ctctgcaggt aaaggctctg gcggatggtt ccaaggtatt  25560
aaaaatgtag gtagtgtagc taaggactcc gcaatgggtg tcggagctaa ggctgttgaa  25620
ggagcaaaag gactaaaagg tgccggaatg ggcagtaagg ttcttggtgg cttaggaaaa  25680
gcaggtaaat tcctaggcaa agttgcaacc cctctagcga taggttcctc tctactagat  25740
attgcaaccg cagatgataa aacaaaggcg gtaggggaga gtgttggagc tattggtgga  25800
ggtatcggag gagctaagtt aggggcaatg attggtacat ttattgcacc cggtcttggt  25860
acaggtatcg gaggagctat tggtggaggt atcggcgcca taggaggtac tctagcaggt  25920
tctaaactag gcggtaaatt tgttgatggt gttcgtaaat tcttcggagg agaagaagct  25980
catgcggaag aagcagactt aactgcaggg caagatgttg cttctgggca agagagtaaa  26040
tcaggagtac aagaagccag agacacggct aacaaacgag tcctatctga gaaaacacgt  26100
gcagagaata acgcagaaga gtccgccaat ctctctatct attctaagtt attagataga  26160
gcccaacgta tactaaacca agcaaaaaat caaaacggta tattcggtaa ctcaggtagc  26220
tctaaagatt cttctgacgg aatgggttca gatgcttcta gtaaagactt tggaggagac  26280
tgggagaaag ccattagaca agcatctaag aaaatgggag tagatgtttc tgacgatgaa  26340
atagatacaa tacttagatt gattcaggcg gagtctagtg gtgacgagag cgccgttcaa  26400
cagataattg atgagaacaa cttcaatggc aatggtggag ctaaaggttt gctacagtat  26460
gtccaaagta cttttgatgc atacaaagta gacggtcatg acaacataat gagcgggtat  26520
gaccaattgc tagctttctt taataatagt aattggaaaa atgacctaaa ttcttgggat  26580
agccgttatc aaaacggtag tacaggatgg ggtcctactg gtaataaaac tagagcgatg  26640
ggtgggcaca taactagccc agagtatgcg ctactgggag aggtagcagg tcaagatgag  26700
tatgttataa atcctagtca gccaacagct ccacgtttat tagcagaagc tactagaaaa  26760
acagcccaaa acttccgatt aacaggtaat ggttctggtc atgattgggg agcttcaatt  26820
tctaaaataa atgcaacagg aggagctcaa tcaggttcag ctcctacgat gacaaataca  26880
aatgaggtat cagttaatgt caccatacaa ggtggaggaa caagtgatag tatagctaga  26940
gaaattggtg ataagtcagc aggaattatc agcaaaacac tcgatgctac cttcacagat  27000
ttcttcgcaa aagaatacag gagagtgtag aggcttaatg tctctacttt tctctaagga  27060
ggtttataat gtcagtagag ttaagatacc cgagatttga tttaactttt tttacagaga  27120
cagacaacta ccatatagtt tatgatgcaa aagatgggct tactggacgt aataacaata  27180
acggtgaagc agagaaggta agcaataatt ttatggcaga gtctgtaatt agtttaacta  27240
caaaaaatgc tttagaggat gatagtgcag tcttctcatt cgtattagca ggggacgtgt  27300
attgggatag agtactaaat gctaatgatg cagttattct taaaatagac ccagatactt  27360
cctccactaa aaaatcagat aaccctgtac tactagttgg tttaatatct gaggttagac  27420
tagagggtga ctatggggaa aactctaaga tgtacaggat aacaggacag tctttcgcaa  27480
aggcgctaat gcagtttgac ttaggtgtta ttcaggaagt aagtgtagtt ttgacagatt  27540
taggttggtt gcctgacgat gcacaagaag gtataaaaat gtctggtagt agtgcaagtc  27600
aaatagcaga aagcttaatg aaaagatttt tacaatatat gaaatttaat tttaatggtc  27660
aaggtataga taagttctta gagtgggagc tagatagttg gacagaggcg gagagactaa  27720
tagatagtac cccttacata aactatgaag gttctttaaa gcaacttata gatgatgtaa  27780
ccgctaaacc gtttaacgaa ttatatttcg atgcaacacc agagggtaaa tgcagaatga  27840
```

```
ttatgcgtag aaccccattt gataaatctg attgggaaaa attacaaacc tacacagtaa  27900
catctgcaga agtaatatct gaatctgtag cagttaacga tacagaagct tactctatat  27960
ttaacatatc tattaataac ttgtatggga ctgactctat gatgttaggt tctaaaccac  28020
aagtattccc tgatttagtt tctaaatatg gttataagaa actagaagta cctaataggt  28080
atttagaagg agcaattata gataagagta acagtggaga taaagctaac acaaaacccg  28140
aaagtgataa tgatagtaaa gagagcgatg gctcaacagc taaacagatg tttgacagag  28200
agtacgctct tgtcttaaac tatctaaaag ggtatcctgt tgatgtgcta agagttaaaa  28260
aaagtaatgt aagaacatca ataacacagg tagacagacg tataacagat aacgaagcag  28320
ataaaattat agaccactat attacaaatc aagcattaag taaagaagac ttttctaaat  28380
ttacaggaat aaccgaagaa aatatagaag agggtaacgg taaagtagaa cctacatata  28440
ccgcagttag ggacttcctt aatgggttag ataaaaacct aggagtatct agcataaaag  28500
agaaattaat gaactacttc aatttgatac ctaaccaagc cacatctatt gctagtgaat  28560
acaaagcaca aggtaactta ggtaaactaa aatatgaaga aataatggag aataacccaa  28620
gtgatagctc aaccgtcact ggttcagata aacgatttgt ttctgagttc actaaaagac  28680
tagcaaattg gtactgtgaa aacgctaatt tctacagtgg ggatattgta gttaaaggtg  28740
accctaaata tagattaggt aaccgtttgt ttgttcaaga tgagcaaaat ggtgagttgt  28800
gggaatacta catagaatca gtagaacact cgttctccta tacacaaggg tatatcacta  28860
ctcttggggt cactagaggt ttacaaaatg gaggaaacga tagattcact catttatggg  28920
gtaaatctga ggacttctcc ggaggtatgc taggtgagaa aaccttgcaa gcactactag  28980
acgaacaagc agaagcaaac agtaaaaatg atggaggctc tgatagtgga ggtagctcag  29040
gtaaagagta tacagcaggt gcaggaactc agctagcggt attcccatta gacgtaatta  29100
atgtaactca gggagaaaat ggtggataca gccacatggg agcacttgca atagactttt  29160
cagatggtac tcctcataaa ccttactatg caccatttga ctgtgaatgt gtgtacactg  29220
actcttactc aggggttgca tggcaatctc aaaagcctgt taaatgtgta gatggtagcg  29280
ttacttacgt aacactatta tgtgtacacg acaacaactg ggcaagcaac aaagtagggg  29340
ataagaaagc taaaggggaa gtgatagggc actcaggaac tgcaggacaa gcatcaggag  29400
accatgccca cttcgaggtg tctaaaggta aatggcaagg ttggagcaca agcagtgcgg  29460
gagtttactt tataaaaaac ccttctcatt tatacgatgt attttctata aaaaataatg  29520
taactggaaa aacaactaaa attatgaatg gtggagggta caattggcgt agtatagact  29580
gggacgataa atctggctca ggttctggaa agaaaaagac agttggtgct agagccatgg  29640
ctactccatt cggattacgt atgatgcgta gcgctcctgt agaaccagaa gaaccaaaag  29700
ttgttaaaca agtagaaact aaaacagttg ttgaaaagaa accaaaagta gaagttaaaa  29760
agctcccaat actttatggg aataacattg ccacagaagc aactaaatgg ggaagagctc  29820
actcgaaaac agagtccaca ttccaatctg ccttcaattt tggagctaat acagataaag  29880
acccatttga ggaagacatt atagcaacag acagtgcagg atttgtttgg tggtgtttct  29940
accatgcggg catatcacta tctggtggag ctagaatggt taccactcgt tcactactct  30000
atgataacca attacaaact atctctacta gaggtcagaa gtctttagag ctatttgata  30060
agatgaaggt aggagattta gtttggttta acagagctag tcatgtaggg atatattgtg  30120
gtgagggcaa gatggtctct tgtaatggaa aaggtaacat ggatgagtcc ccaaaaacag  30180
gtattgttat tgtcgacatg tctaaaggtt attggtggaa cgcttttgac ggaaatgtac  30240
gtagatataa ataaccctat tttttagggt tatttttttt gtataggtag tttttagtta  30300
ttgtgctata atagataatg aggacacatg atgagaggat gaataaattg gtaaaacgca  30360
gatttcaagc aggtctaggc tcagaaatta aaagagtata taaagaagga caacaaatta  30420
acacgctact attagcacaa gtaattcaag taaactataa atataataca gtagacctac  30480
tagctttaca gcataaagaa gtatttcaaa attcctatgc aaatgaggga cgtttctctg  30540
caagacttcc tatggaattt ggcggtagaa atatcgttgg acagccttat gggcaggtta  30600
acccgatagc agtaggaaca gtagtattag ttggttttat taattccgat aaagacatgc  30660
ctattgtaat tagtgtttat aataataacg atgtaagcaa gcaactttca agaacacaat  30720
tttcaaattc agaccctaaa gatttagagt taattgggga tatgcaccaa aaatttagtt  30780
tataccettc attgacatat gatagcgttg atggagaagg aggacgtgtc gttacttttt  30840
ctggtaaatc atttattgct tttgatacaa aagaagtagc taactcctct acaactgatg  30900
caggttatgg tactaaatat gaggacttag agacatcata ctataataat ggtgacctaa  30960
tagagcctat gaaaggtaga gcaccaaatg tactgtttaa gcatcaaggg gtacttgacg  31020
atgatggcaa accagatttg cacgatttgc taattcatat taacccagat ggtacttata  31080
gaacttctat gatgaacaaa gaagaggatt ggcgcacact atttgaaatg acaccagatg  31140
gcagagttaa attaagaaaa caagactcta ttaatattga tggtggcata gaaataagtg  31200
agctaggaat caacaatgag gggttcgttt atttacgtaa tggggatatg gatttagaag  31260
tacgaaaaga cggtatctat tcacaaggga aactgtttac agccgatgta gacctatccg  31320
atgtatatga caaactaaat gggttgtcta tacagattaa ggaaacaaat ggtcaattag  31380
agattatagc taatggtgta gaagaacaaa atggaaaaat atcagaactt tctacagaaa  31440
taacaattgt agcaggtaaa gttgaatcaa aagtaacaaa gacagaagtt caggatatga  31500
ttgacagttc ttttgtagat atgtctgatg cgattaaaaa agcacaagaa gatgctgaca  31560
aagcaaataa agtgattgca gatatgtcta gtgataatag actgactccg agtgaaaaaa  31620
tagatttatt aaaagaatgg gatattataa aaaatgaata tccaagctat ctcgaacaag  31680
cagaaaccta cgaggttgac agtaaagact acactgctaa gtacaattca ttagagctat  31740
ttgttacccc tatattggct gacatggagt caactagctc ggtagacgga gcaacacttc  31800
gcaaaacgtt taattcttac tatacagcaa gaatagcttt actaaactct attagtaaaa  31860
aactaaaaga cggtatcaca gaggctatga aaaaagcatc ccaagcatca ctagatgcaa  31920
cacaagcaat ggcagatgcc tcacaagcta agattgatgc agataatgct aacaaactta  31980
tatctgatat agcaagtgat aacaagctaa caccttctga aaaataccaa cttaaaaagg  32040
aatgggatgt aattgttaag gaataccta caacaattgc acaagcagag aagtacgcag  32100
tagacacagc agagtataca gctaaatata aagccctaga gctgtttgta gagcctttgt  32160
ttaaagacat ggatgaaact agtatagtag acggagaacg ccttagagcg acattctcgg  32220
actattacgc aagtaagatt gctttactaa aagaagtaac ggactcagct aaaacagagc  32280
tagatgccta tggtaataaa atatctgtaa tggaaacaaa cattactcaa acgtcagaag  32340
ctattacttt actagctact agagtacaaa ctgtagaaga cggtgtacaa tcaaataagg  32400
cacaaatcga aatacaagct gaacaaatta gtcaaaaagt aactgctagt gaggttaaag  32460
gaattgtaga cgattctatt aacaatctaa cattaggtgg aactaactta tttgttataa  32520
agacacagac agcaggtttg ctaaacgaga atgatggaac tgtaggtact gcagtagaca  32580
```

-continued

```
actcagtagt gtcagactac attaaagtta atcaaaaaac accatatatt gctacacttt  32640
acggtaacac tggcacaaac atgattataa cagactggta cgataaaaat agaacattta  32700
tttctgggga agctgtggca gactctgggg attttagtaa aaagtatgtg tcacctgaga  32760
atgcagtcta tgctagggta agttataaga aagcaaactc tgtgaatatc aaattcgagg  32820
caggtacaaa ggctactgat tacagccctt catgggaaga cataaaaggt gaccaaactg  32880
ctttagagga atacattaaa aaagtagaag aacaagccaa gaaagctcaa caagatgctg  32940
aaaatgctaa aaatgatgct gaaaatgcaa ataacgcaat agctgatatg tcaaatgaca  33000
atatgttagc accgaatgag aaaaaacaaa tactcttaca atgggaacag attaaaacag  33060
agtatccaat aaacttagac caagcaacta aatttggggt gtcttctcaa cagtatacaa  33120
cagcgtataa cgcactagac gagtacttaa aaccaatact agctgacatg acaacaactt  33180
ctgtagtagt tggttctact ttaagaaata cgtttaacaa ttactatgac aaaagaacta  33240
ctttactaaa cagaatatct gacgtagcaa aaaatgtagc agacaaggca caagaaactg  33300
cagatactat caatgataat ttacaaaata ttggtgggta caactatgta gggttctctt  33360
ccggagacaa tatgttgcct agactgatga ttaaaaacgt tggttactac acattaggtt  33420
cgtcaaccac agagttcatt gacagcatgg tagctgtaaa aggtgatgca acgacccaac  33480
ctttcgatta tactgtaggt acttctgata aagaaattgc tggtggcggt ttagctgatt  33540
atcgtatgaa agaaataaaa gaaggtcagt ggctaacagc ttctgcgaat gtgcaggtaa  33600
taggtggtgg ctccgctagg ttagctatct acactttaga aggggataac tgggtaggtt  33660
ctaacagtac acctatacaa gtaagtgatg gtttgaaacg tgttgtggct caaagaaaag  33720
taacaggctt aacaaaaggt gtgttaatac gtattgagtc agccgacact aatgttaaag  33780
agtttcgatt tggtaatgtt caactagaag tgggtatcat cccaactcct tggaaaaagt  33840
ctgatataga tattcaagag gacataaaca atgttgttca gaatatcaaa acatacactg  33900
cttgggctaa cgatttacag ggtcttgatt ttacaagaga aaaggttgaa ggaaaaactt  33960
acatgtatgt aggtacctct atgaaagata gtgataacta ttcagattat acatggaggc  34020
taactgatga acatatagaa ggtcagatta atggtaagga aggcgcatgg atttactctc  34080
caacagcccc tgctaaccca tcgcaaggac ttatatgggt agacttgtca aaagtcccca  34140
accaacctaa gcgttgggta gattcagaaa ctgggtgggt tgcattaaca ccagaagagg  34200
ttaaagattt gccttggggt gaagatggca caagcttagc cgactgggtg tcacaggcag  34260
agcaaagaat atcttctgat agcattataa atactgtact aggttctgag gatttcacta  34320
gtgtgttcga tacaaaagct aacacttctg acctaggtaa cttggctacc tatgaagact  34380
tagactcaat aaaagaggac tataaccggc taatcaaaga aggcataaat ggtattgatt  34440
ttactcctta tgtgactaac tccgaactac aacagcttaa agacagcttt aacttctctg  34500
ttcaacaagc cggaggggtt aacatgctta aaaactcttt aggattctct gggttagact  34560
tctggaatgg tacagtaggg aagaacttac tacctaactc tacttggaat ttaggttttg  34620
gtagatgggg tggtacttca atcactagtt ttgaaatatt accaccagaa gatgacaagc  34680
ctacgagtaa catattagcc tcaatgccac ttcgctcttc tactaaagaa ataggtaaca  34740
gacctcaccc attaaaagtt aactcgggtg aaacgtacac agtaagcttc gactataaag  34800
aagaagcatt atcttacaac aaggacagac ctatccttgt tgtaagaaac taccctgata  34860
agaacacaga ccaatggatg gagtactcaa tagaaggttg ggcagtaatg gctaacggaa  34920
gcactactga cttaactgtt tggagacgtt ttacaaaaac atttacaata ggtactagtg  34980
gctacttaga tattttaccg aaaaccataa tagaatcgtg ggaacacagg tctttttgga  35040
gagagctaaa aatagagaaa gggacacaag ccactacttg ggtacctaac aaggaagacg  35100
gggcgtttac tggtgatatt gttgagacta ttcaaacaga agaattagcc aacctcgggt  35160
ttggttccgg atttattagt tctaaaagac ctagctcttc attaacacaa tctgtagaac  35220
tacctgaaat aggtgctaac cttgagtatt cactatcttt ttatatgaag gtaactacag  35280
ataaccctgt agctgacttt aaatgcggta ttcgggttta tgatggaggt actctaactt  35340
atacattagg catagaagat gcaacacagc caataccact agggttccaa caatacaagc  35400
ttgtgttcac tcccacaagt acctctacta aaatagaaat gtttgtagaa aatgggcaag  35460
aggcatctgt tattatatca ggtattatgt ataatatcgg gagtatacct cttaaatggc  35520
aaccatatcc aagtgagata tacaatacga atgttaagat tgatattaat ggggtaaccg  35580
ttaaaaacaa tcaaacagat gggtatacaa tgattactcc ccaagagttt tcaggatact  35640
ctcgtattga tggtaacata gaacgtattt tcactttaaa tggacaggta acagaagtta  35700
aaatgctaaa ggctgaaaaa cgtataacta tggaaccagt atctgtattc gctatgaaca  35760
cagtaacgga tacaaaaaga attagaggtt gggcatttgt gccatcattt gaataaataa  35820
ttcaactttt taaccgaaaa cctcacttac aagttgtttt cggttaattt gtgttatact  35880
atatagagaa ggacacgaaa ggacgatgag actatatggc tttaaacgga acaaagtata  35940
cagcctttgc ccgacataga ttagttttag agtggcgcgc aaatcaaaac attgcaggga  36000
actactcaac aatcagcgta tggctatatc tacaatctat ggataaatgg gggagacttg  36060
atgctcccgc tattggtgat gccaaagtta ccgtagaagg aactacacag acagaaaaag  36120
cttcctctat gttaaatgct ttccaaaaga aactattact agctaaagag tggagagtta  36180
accataataa tgacggttct aaaagaataa ctattggggg tagctacttt gtaaacgtta  36240
cttttactga taatggtgta ccaacatatt acggtacgat aactatacct aacttttcag  36300
tagacctgaa tagaatacct agaagaagtt cattaaaccc tgtccctaca ttaaatttac  36360
cggggaactt accaataaca ataaataggc agagctccac attcaaacat aatctaactg  36420
cttgggtggc taacagagat aaccccacat taagtaatga tgcccattgg acgtacttga  36480
caaatcttaa taatgtagac actagtgggt catttagttt tacagtagca aataacaaaa  36540
ctatttttac tgcattaaac aataggacta gttggcaagg caaggttaaa ctatggacta  36600
tagggttaga tgatgtagtt agtcaggaga gaacatacaa gattgtcccc ccaatgaatg  36660
cacaagcatc gggaggtaag ataaccttaa atgtgggaga gaaaatcaat gtatcactaa  36720
gtaactatcg gtctgatgca aactttactt atgatggggt atttaacatt agtgggctca  36780
acatacccat tgctacaaat tcagcaggga acacaatgtc gtatacacta actcaaacag  36840
atgtagacaa tatattgaag aaaataccaa atgcggattc ctcgtggggt caagtaactg  36900
taacaagtaa gtatagtgga gtacaataca ggactccatg gacaggacag agaatagata  36960
taactatacc taaaaacaag tatgtaccaa gcattaatgg taccccctact tatgaagata  37020
caagtagtgt ctctgtcggg cttacaggtg acaatcaggt agctcttcaa ggtaagtcta  37080
atatcaaagt gactatccct gctaactttg caacggctaa tggttactct actttgaaaa  37140
caattgatgt gtctttaggc ggtacatcaa aaacagtcaa ctattcaaat gcagaaacag  37200
ttgtagagtt aggggctccc gctaaccata catcagacac cttaatagtc acagtaactg  37260
acagtcgtgg gtttaagtct aactggacaa agcatgtaga catttacccc tacgaaaacc  37320
```

-continued

```
caaatatgta ctttacagtc acacgtagaa ataactttga gacaactaca gatattaatg  37380
ttaatagtac atggtctcct atcactatag gtggtgtaaa caaaaatgct gtccaatcag  37440
taacctacgc aacaaaagta gcaggtgttg gtacttatgg agcagaaact gctttaaatt  37500
ttacagctaa tggtagtatg gtaacagtaa aaaatacacc aatagaatta gataatacca  37560
atacatacga agttaggttg agtgtaactg ataagtttag tacgtttact agaacagcta  37620
ctgttaaacc gggtaaccct atcatgttta ttgatgccga taatcgaagt ctgtttttag  37680
gtaatgcctt tgttgacaat aacaataatg agctaagagg cttattagag atagaaagag  37740
ataagtggca ggagaatggt ttagtaggaa tatccttaaa caacagtgat atatcagcag  37800
tcaatggcat atggttctcg acagatacat caaataacgg aggtgaaggg ctccacttta  37860
ttaaatcagg taaatcaaga aattcattga cttgggatga ctatgattac ttttatatga  37920
gggacaatgg attctatgtt aacaatgact ctaaccctat atttactgtg actgatggtg  37980
gggatttaag gttccctaaa ctggataact tatgggatgg ggcggcttac atgcacaaag  38040
accagataat agtaccacgt aaaaaactca gtgaatgtag aaatggttgg gctttaacgt  38100
tcagttctta cgataaaagt acaggtaagc tgtccttatg ggatataatt acattcttta  38160
ttcacaagac cgcaccggat tctcctttaa gtggtacagg tcacaggttc ttcttaccag  38220
atggtaggga tgctacatct caaaagacaa aatatatata cgtcaatgac tatcagttaa  38280
ggggtcacga agaaaatgat gacaaaggcg gaacagctag cacaaataac agaaataagg  38340
ttcttatgag ggtggatgaa tggtaaatat gagaacaata tacgtagaag taaatgatga  38400
aggttatgta gaaggttggg gcagtaacct gtcaggtaat aataacattc atagtgtaac  38460
aatagaggat aacgaccagt ttttttataa aaactcctta aattttaagt attcaaatgg  38520
ctctctagta ttcgatgaag ataaggcact gcacagtgct aaactagcca aaaaagatga  38580
aatgttaact gcatgtaact atgaaaaaaa tctacctttg acttttaaac tagacaacga  38640
aaattacttt gctcaaccgt taactgcgga agaacttaat gaaacaatat tgcctctgtt  38700
gtcaggttta acagagactg ttcctcttga attagttaaa gtaagtgacg atgtacaagt  38760
aacattacaa gttggataca gtgtaattaa aaatttatat gattatacaa atctaataaa  38820
tgaatactta aataaaaagt tagaagtaga tgtgtttaag atgatagatg aggctactac  38880
ttttgaagaa gttgaggaag tatcatggaa aactacaact agtgatgagt tacctaatca  38940
acctaaaata gaagacctcc ctataaataa caaccaagaa atcgtagata agttaaaaca  39000
agagaataaa gagctaaaac aaagagtaga atttaacgaa ctagctttaa tggatgcaat  39060
aaacatgttt tctgaaatga acaagtaagt tattattaac taaaggaggt gatatttcta  39120
tgtacccata cttatcaatg ttatatgcat cttatgtaat caaagaccct gagaactatc  39180
ctttagagaa ggttccggca ctaattagag aagatgtgga gaaaatcgtg gaagagatgg  39240
caaaaaagaa cgaaaaacaa ggatagttaa tttagtaatt ggagtaacaa taggtttaat  39300
catagggcta ctaatttaaa ctaatataaa tgagggtagt ttgtgctacc ctctttttta  39360
tactatattg tactatatta aggaacgaaa ggagcggtta ctatgggaca atcagatggt  39420
atgggcggta cattaaaacg tattgcgatt caagtaggta acgacccgaa taaaggttgg  39480
tatcgatttc aagtaaaccc aactcaatat aaatataata agccacatcg tgttactata  39540
tttaaaacta aatcaaacat tataacagaa gactttggta aagatataga aactatccaa  39600
ttttctggta caacaggatt cagggtagat agcagaggta aaaatggggc ggacagacta  39660
aaagaattag aagaaataat agataattac gcaaaacagg gcggtaatgg taataggtct  39720
agtgtagaga tgaaatttta taatttcaca gacgataaat attttgttgt tcatttagca  39780
ccagaagggc tatccattga acgttctgca gaacagccat tattatttaa ttacacctta  39840
agtttagtcg tgttaagaga ggcaggacag ccctctgaga gagctcaagt aagccctcag  39900
ataggtaatg taagtcctag cattggacgg acatacaatg cacaacagga cactagaaca  39960
cctgctcaaa tacttcatga tgaatatagg agaagtgtta tgctaaatac agcagtaaat  40020
cctgcagtaa catcgggagc ctataactat ggtgtaaatg agttaaaaaa aataatcgga  40080
tatggagggt agctcatgga aaaagtagaa caatcagcag atttgctaag atttttttaga  40140
tatttaaatg tcgatattaa cggtgaagtt gtagccaatg ttattgacga ccaaccaaac  40200
tttatatcaa ggttctacac ccctcataca cgagttaata aaatatctag tacactatta  40260
gatattgttc gagataatga tataggggaa acaaataagg ctttgtctaa agactcctta  40320
acttataaat ttttaaaaag tggacttaag ctttcatctc cacgtattta cgagctagca  40380
caaattgtag tactagaatc ttttgctctt atatatgcta tcgaagaaga accagagatg  40440
tttaaaatga ttaacgaatc agatgtaaag cagactagag agaatgttaa atacttaatt  40500
gattgtttag gaggagcaaa agattataca gacatagtga tggacttaca atctatggat  40560
gtcgctctag gatatattca ggagcaagtt cctctaatac aaggaggttt accagtaaat  40620
ggcacgatat aaaaaacatt taattgtata tggggataca atgcaatcca tagcacaaaa  40680
agaaacaggc tctgtagata attgggtaaa aattgcggag tacaatgact tagtttaccc  40740
ttacatagta gatactatgc aagaaaaaat gagcaactta gaacatctag ctacacttgg  40800
ggacaccctt tttatacctg atgaaggtaa cttattggac attaatacaa gctcattaaa  40860
ccaaagagat atggatttct tattaggctt agctttaggt aaagacttgg atatgacaag  40920
tgatacagat tactacgaga atcatggaac aagtgatgaa gtgtttgcaa taacacataa  40980
tgggcatggg gacttgaaga tagctagtgg ggcagacaat attaagcaag ccactatatc  41040
aagattgatg acagctaagg ggtctcttat gttgcaccca gagtatggta gtgacttgca  41100
cttaatgttc ggtaaaacaa caattgaaca aatgaagata attagtatag aagtatgcga  41160
tacagtactt aaagatacac gagtagcaga atgcgttcta gtgaaccatt atattgaaga  41220
agaccgatat gttggtaact atagagcaac cttaaagtct actagagagc aatttgagtt  41280
tgttgttcaa aacgataact caggggctct aattattgta tagaaaggat aaggtttaat  41340
gagactaaag aaaatttcag agatactagg tagactaatt gatgtaacta tgataaacac  41400
acatgagata aacgattttt cagttggttc tactattcgt tctatttatg aagctgtttc  41460
tatggagtta gaacagtact atattttagg tagagagaat attttatggg gaattgaaca  41520
aggagtccta aatgcttttg actttaggaa aagagaagca aaaagagcgt atggtatggt  41580
aacactagag ttccatacgg ttactcagac ccctgtgtat gtgccaacag gaacaacatt  41640
cgactctagc ttgtctggtg cccctagcac gttaacattc caaacgatgc aagactacat  41700
aattccagaa ggtgttataa cagcaaaggt agaagtttat tgtacaactg taggtacaaa  41760
agggaacata cctaaaggaa gaatcaatcg ggtaattaac aatatatcaa acttaaaaac  41820
cgtgtataat gagtttgatt ttttaacagg tactgatgag gaaagtatag aatccgttaa  41880
aaaaagattt catgcatttg tggaatcacg tggtagagca acgataaaag ccttagatta  41940
cggtacacgt caagtagagg aagttgcagg agtttatatc aaagaagaag taggctacgt  42000
tagaatatat gcacatgact taaacggtga tttaaaacaa gaaacactag ataaaataaa  42060
```

```
agtagctatt gaggactaca gacctgcagg cattaaactg gatgtattcc ctgtaataaa  42120
atccaatgta caagtgagtg caactgttac tataagtgac aaatcgagaa taaatagtaa  42180
attagaagaa agagtggagc ttacaataag aaactactta aatagtcaag ttgtttcaca  42240
accattaatc ttagctgacc taattcaggt tataatgaat attgacgatg ttttaatcta  42300
tgactgtaaa attaacaaca tggaagggaa catggctgtt agggacgaag agataattcg  42360
tgcaggagag gttattgtag aactgatata aattaggagg aatataatgt gagtaacttt  42420
tataaaaata tccaccctct gttgagacgt ggtaagaaac ctaacaagta tgatgatact  42480
aactttgcag tgcttaatgc gttgaactat gaattaactc aggcagagca ggagaccatt  42540
gctagtaaga ttcattcttc attagaaaca gctacaggtg agtacctaga tacttggggg  42600
gactggtttg gtgtatatcg taaagatgat tggaatgacg aatattatag aaaaagaatt  42660
ataagagaac ttttactaaa aagagccaca attcctgcta tcattgatgc gttattggat  42720
ttccttaacg acaatgatgc agtcatccaa atatatgaac cttggagaaa cattttctat  42780
acaaataagt caaaattaaa cggtgacgac catttaatgg gttactacta ccgttttgca  42840
attatcgata tttcaattga tagaccgttt cctcctgaaa ttgtagagat tattaaggct  42900
ttcaaacctg cgggagttct attttatcta aggctagaca caagcttaaa taagaataaa  42960
acaactgtag aaagcccata tgtataccta gacgtgacga ataagacaga attagagttc  43020
cttaacggtt tatactatga cctacgaggt aacattaacc tgtctgacca acgtacacaa  43080
gtagtagaga gtaatatctt ccatacgaat aactctatgc taaacgggga agatgtgctt  43140
gcaggagcat ttgaccacgg aagaggctac attcacttag caagtacaac attgcttgat  43200
tacacaccaa aacctactga ctctatgagt gacttaaaaa cagctctagg agaatcaggt  43260
gctgatatgt ataatcaaac aaaagaaaag gacggaagaa cagcttctat tcaagtacct  43320
gcaacaaaga atgttcacac cttgtactca aacagcattg actttggtgg ctatgattat  43380
tcggggaatc cgaatgttat gactaagcct tatattgctg acaatataac cggcggtaca  43440
acaggagtag ttgtaacacc aattgatgat ggcgcaagac tagaaaaaac acgagttgat  43500
atatctggaa cgtttaactt agcattgggt aatcttttga ataatacaga ttatataatt  43560
tcatatgatg tacttgtgga aaatggatat gtaggagatt taaaaacttg taatgttgca  43620
ttagaaggac agtttgaagg aaagcctaac tattttggta ttttttatat gaatagtgta  43680
acatcaacag atgtatggca aaaggtttct gtaaaattca atagtggtgc caacatggaa  43740
aaattaagtg gttttaagtt tagagtatat ttatctcaac gtgttcaagc agcattaaaa  43800
ataaaaaatg tgaaaattga acgtggttca acagccaccc cataccagcc aaatttactc  43860
gatgcaccat attatctggg taaggtggct ttgggtgaga atattgctaa taagtccgtt  43920
gagtttccaa taaaatctag caattatctc ttatataacg ctagaatggt agagcctttt  43980
gttgtaggag aaccttatac aattaccata aaagcaataa aaccagccag tcaaacgttt  44040
atggtatata acattgggga aggaactact tattacggaa aactaaatcc agttgaggga  44100
ttgacagacg tatggtcact aacattcaca ccaagaaatg tttcgtcaac taatcctagc  44160
gatttacgta tttttcagta cccatcatca acattaggca catgtcaaat tgattggtta  44220
aaaattgaaa aaggtgacac cagaactcct aacattgatt cctacgacta cgtaggttct  44280
ctgatagaag atacagaaac acctacgtta gacccgacta agtatacatg gacagtaaat  44340
ggggatataa caaataaaaa ggcatatatg gtgtttgata ttaagacatt tatcgaagaa  44400
aattatgcta tagaatttga aaaacttatt actgacctag gagaagacca agcattaaat  44460
accgtgtttg aaaactttaa catctctaca acacttaagg ctctagtaag tccaagttca  44520
ccaatcagtt tctcggttga actatacgat ttttctacga gtgcatggca caagttaaac  44580
acggatagct tagacttacg tatgcgtaca ttcaacttag tagcaaaccg tatcacagac  44640
tatctaaatg attacaagct attatttgtt cgttacgtgt ttgataacga aacagataaa  44700
gatgtaacag ttgaactaga catgctaaat gtactattca agtatcgttt aggtgagggg  44760
tacagtatag gactacaatc atctgtggaa tcactaacgg aactcgttcc tatagaaggg  44820
taatagcaaa taatatgtta taatataaat agggcaccta gttgtgtcct attttttaat  44880
aaacatgcta tattaacaat tgaatgataa agaaaagagg taaataatgt ggctattgca  44940
actaacaatt cacgagtgta tgcctcactc caattaaaaa ataaacaaga cagtatgtac  45000
ctagcaattg gtaaaaccac tccttggact aatgaagatg cccccccctgc accagaccct  45060
actacggcta ctctaacaga ggttatcggt tataaaaagg tagcaagagt atctttatgt  45120
agagaatatc taccaagtga cgattctaaa taccctgtgg tgtcctatgg ttcaagaaaa  45180
tttacgctaa ttccagatga ggacggctat aaagagcaag cgtggatggt gtatgtagaa  45240
gcagaaatta caggagatga actaccaata ggaacattta ggcaagtagg tattcatact  45300
gacttagtgt ctaaggcaag ttcagaaaag aaagctttgt tacctacaga tgtaacagat  45360
gcaggtattt tgcaattttt tgaaaataga cagcaacaaa atagaacaag tgatgtaatt  45420
ttaaaagaga agtttattat tacaatggaa aataagaagt cagttaaaca ataggaaggg  45480
tgacatagat ggctaaaaat attacaaatg atgatttagg taaagagcct tataacaata  45540
gatattacca aggcaaacga ttttcaggtt tactatttaa accagataag ccgttacaac  45600
aagccgagtt aaacgagtta cagtcaatta ttcaaggaga tttaggcaat gtggctgaat  45660
ccatatttag tgacggtgac atccagactg gtatggaata tgtactacaa gataagaagc  45720
ttactattaa aaaaggtaaa gtattcttag gcggtaaaat gcgtaacttt gacgaacaga  45780
gtatcgatat taccggagag ggtacggagt atgtaggtgt taaacttgta caaaaagtta  45840
ttacagcaga agacgaccca tcactgttag accaaacaag tggtgttcct agccatttct  45900
cagaaggggc tgaccgatta gacgaagatg tagtactagc agttaatgat gattctgcat  45960
caaacattta ccactttgtt aacggtgagt tatacattaa cccagatact cctgagatgg  46020
ataagattaa taaaatacta gcagaaagaa cttatgatga atctggttca tatcgtgttc  46080
gtggttttga tatgtacaca gaagttcacc caacagaccc taacaataaa attcagttag  46140
ttgtcgattc aggtcgggca tatgttttag gttttaaagt agataaacct acaactactc  46200
gtattgatat tgaaaaatca agagagttag aaacaatcaa taacgaaggt ttctactata  46260
gcaatgcaac tcgtaaaaat aaattaggta attccccagt atcttctgta gaccgtgtaa  46320
ctgcacaagt tgaagttgct aaagaacagg tttctcgtgg ggtcgtaggt ggaggtaccg  46380
attaccttaa aaacacctct gtaacaaaag ttattcgtgt atggactgag ggttcaggag  46440
cacaggagta caaacaaggt gaagacttcc aattagtaaa cggtcaagca atatcttggg  46500
cacctacagg gcaagaacct cctgcagggg gaacctactt cgttcaatat gtttataata  46560
aaacaatgat tgaaaataca gattacaaag ttgtaattac tggtgaaggt gatgctaggg  46620
aatggtatat cgactttaac gagatgacag gttctaaacc agtcgatgaa tcacttgtta  46680
acgtagacta taaatacttc ttagctcgta aagacctaat tgtattagac cataacggga  46740
atttcactgt ccataaagga caacctaacg ctttaagact agtagaggca cctaaccatg  46800
```

-continued

```
tagacccatt agttttagct attggtacag tagtagttta cccagactca aatactgctg  46860
atgctaaaca atggacaatc acacgtctaa caatggaaga gctacagaag ttatctgttc  46920
gtgtggaaaa catggagtat aaccaagcag tgttctactt agaccaaccg gcaatggcag  46980
gagaaaaccc tatctatcta cgtggagtat tctcggatgc gtttatctca ctagataaat  47040
atgacgttag tcacccagat gccacaattg cttttgactt tgacacagca gaaataacat  47100
taccttatgc agaaattaat aaaacagttc caacaattat cgaaggttct agtgaagcac  47160
atgtgtgggg cagactagta acagcaccgt ttaccgaaga agtgggtatt agacaaccat  47220
ttgctacgga agcaatgaac gttaacccat acaacacctt taacaaacag ggtgccttaa  47280
agctaaaccc ttctgcagat aactggattg aagatgagcg tatcacagtt accaaagaag  47340
aaacatctac tatgactgtt cgtcaatggt ggagacatgg tggagcatct tggacaaacg  47400
atgagatgaa catggtatct aacatcacgc ttgaccccgg acaatcgtgg ggaggtgcct  47460
ctggtacaga agaccaacgt aaacaagggc tatccggttc tactttaacc agtggtggtc  47520
agcaaaccaa agaatcaatg attgagttta tgagacaaat tgatgttgag gtttacgcag  47580
agaacttgca acctaatgct aacaacttat acgtaacatt cgatggcttg agagtacctg  47640
ttaccccatc ttctggttac cgtaaaggtg ccacagaagg cactggtatg gcaaatgcag  47700
acggaacatt taaaggggta tttaaaatac ctgcaggagt tcgttgtggt actcgtgaag  47760
tatctgttag aaacgataca aacttagcaa gtactacgtt cactgcgcaa ggtacgctaa  47820
aaacaactga ggatattatc ataaaaaccc atgttactat taacttggtt gaccctctgg  47880
cacaatcatt cagttttaac actaacagag ttgcaacaag ttttgacgta ttctttgcat  47940
ctaaggataa cagtacaaat attatttgtc aagtacgtgg aatatcagaa ggtgggcaac  48000
ctaataaaac tgtgtatgct gaaagagtgt taaaaccttc tgaaatcaaa gtatcagatg  48060
atgcaagtgt tcctacgaaa atcagctttg atgacccact aatgtgtaaa gcaggtcaag  48120
aatactgttt agtattcatt actgactctg ataaatacac aatgtggatt gcaactatgg  48180
gtcaaaatag agtagacgaa ccaacacaaa cagtaacatc aaatccttac ttggaaggtg  48240
tcctatatag ttcatctaac gcaagtgcat ggtctattca ccaactgtct gatttgaagt  48300
tcactgtata cacggctaaa tttaacgaag aagctgtact tgagttcgat gttatgaaga  48360
acgttaatgt agaccgcata gtgttaatgt ctacctacct aacacctgca aacactggtt  48420
gtagatggga tatgaaacta gtccttgata atgagcctgc aggtacaaca gtagatgaca  48480
aaccttggtt acctattgct aactacgtag acttagatgt taaccagtta gctcgtgagg  48540
ctaagcttag agcaacattt aaagctaacc aatacatctc accaatgcta tccttggacg  48600
acattatgtt cgcaggattt ttaacagcat tgaaaggtag ctatgtatct cgtacaatag  48660
atttaacaga ggctccatac aacacggtta aaatgtcata tgaacaattt acacctgccg  48720
gaactgttgt gactgctaaa tatagtacag atgaaggtaa aacatggaag acatttacag  48780
tacagcctac aacaacacaa cgtacacaag actttgttcg tgtagactat gttgaaaaga  48840
ttaatacggg tgggacattt aagtccatta aattccgtct tgatatgacg acccagaatt  48900
catttttgcg cccgcgcgta agacgcttac tcactaatat gaccgacaaa tagaagatgt  48960
aactgtaatg taacatttct atgcctccta ctgtggtata cttactgtat acaaaatagt  49020
aggaggtttt ttaatgggta aagcattaca attagcaggt actacatttg gtaaatggta  49080
cgtaaaagag cgagatactt ctaagaaagg tagagcatac tggatttgtg agtgctcttg  49140
tggaagaaca gttcaatcta ttccgagcgg tactcttact acaggctcat ctgtgatgtg  49200
taaacaatgt gcaaatgaga aatctttagt gggtaagact tttggtaggt tgaccgtcat  49260
taaggattca ggtgaacgag caactaatgg tagtatcctt tgggagtgta aatgttcctg  49320
tgggaaaaca agccttgtca ggggttcaga gttgacaggg ggtcgcacaa agagttgtgg  49380
ttgttactcc acggatgtac tcaaaaaagt agccactaag catggattgt ctaaagtgaa  49440
cggaaaaccc acaaaattat tccgggcatg ggcttcgatg aaacaacggt gttacaacaa  49500
gaaccatgcg agttataaag attacggtgg aagaggtata accatatgtt ctgaatggcg  49560
tgaagacttt gaaactttcc atgattggtc tatagctaac ggattttccg atgacttgtc  49620
tattgataga attgacaatg acaaaggcta ttcaccagac aattgtcgat gggtagatgc  49680
taaaacccag attcgaaata gacgaaatac cattacttac aactggaagg gttcagagta  49740
caccttagct gaactgggag aactaacagg tataaacaag atgactataa aatctaggct  49800
gaactccgga gccactcttg aagaagcact agacccaaaa gtgaatacgt cagttttgac  49860
tatgagttac aagggagaaa ctaagcctgt caaacaatgg tgtaaagaac tgggattgaa  49920
ttacgcaact gtacgtagca gacactataa aggttggact gatgaagaag ccttaactgg  49980
tatacgtaac aaatagcaac agaataagta taatagactc tatatgttat aatagacata  50040
tagagtctat ttttttgtt aggaggaata aaattgccag aaacacacag acaaacaagc  50100
tcaggtgcgc ttatatttaa accaactata gctgaacaag agcataaaaa tgctatggaa  50160
tctataaaac aagagagaac agagctagag aaagaactag ctaatgttaa agctatcaaa  50220
gatgagttgt caaaagagct agcagatatt aaacaactga aagatgaatt atcaaaatag  50280
tttctaaatt gtcttattta ggatttctgg ttcccttata ctattaacta atatatttaa  50340
ataactatat ataaaatata taatatataa ataatatata ataagactac gaaaaatata  50400
aaataggaca aatcaactct gtatacacct tgacaattac ctactatgtg atataatgaa  50460
tatattgatt atactaaggt gggtatgtca aggagcatgt atactaatct aacttaaagg  50520
agatttatta ataaatgaga ctagtagtag atattatgca tactcagata aggtatgaag  50580
attcggaaaa ttatcttaga ccagaaattc ataaggtaat gcattcagaa ttaggagtta  50640
aagcagatgg ttatcaattt agtcctgcat ataaagcagg ttactgggat ggtattattg  50700
atttttcga taaagaaaat gacacgttcc ccacagggtt actacctcat gtagaaacaa  50760
tactagggaa ccttcaatca actttatcaa agtcaggtta catttttcag tttgagataa  50820
ttgatgatag acctgatgag ttcatgtcag tagatgacat ggataaggag atagtgctta  50880
atggggataa caatgacaag ataacattaa gagactatca atatgaatct gtggagcaag  50940
ttattaagaa cagaataggt attgtaaacg ttagtactgg tgggggtaaa tgcgtagtag  51000
catctacgaa cctactgact tacgataaag ggtacaaaac atttgaacaa ctgttcaagg  51060
aacacaacat tgatttaaca caatcagagg caactatccc taacacattt ggggttacat  51120
tagtgaatga aaagggagaa ccagaaacgc ctagtcattt aactattaat ggagttagac  51180
atgtaaacaa ggtaacaact gagcatggat ggactgaaac aattactgac aaccatccat  51240
tactaactgt atcagaatct ggtagcttta aatgggtaga agctaaagac ttgaatgtag  51300
gtgattggat tgttggacgt aaaggtgata atttatttgg aacgaatact acatgtaccg  51360
tggagagcgc atatagctta ggtttattaa cagcagacgg ctattgtggg caaccaaccc  51420
agattacatt aaccaataac caaccggaga tactagcgga cattcaagat ttctttacta  51480
aagaagggct gtccactaag gtagacccta acaaagactc taaagatagt aagatagtta  51540
```

```
ggggtaccgc aggagctaga gaactttata ataaatatgg cttatcacaa ggattagcca  51600
aggataagtc aatcccagag tgtatcatgg aagcaccgaa ggaagtacag ttagcttata  51660
taagtgggta tttagagtgt gaactgagta tggaggtacc taaatgttca atagaggtaa  51720
tttctgcctc cgagaagtta cttcaccaat tacaactctt attaggaaac atgggagttt  51780
cctcaagatt agctaagaag gtagttaaag ggtacgaggc taattggtat ggtagattaa  51840
ctatcggagt gactgactca gtttacctac taaaacaatt aacatttaaa acagcacaac  51900
ggaacgaaag aagagcctta tttattgaaa cagcagagtc ccgtaatagt aaccaccaag  51960
gacaacctgt accttttggt aaggagttag ttaaacgata ctgcgataac tacctagggg  52020
acactaaagg acttagtaag gcattcaaag taccaagaac aattagctta catcggctta  52080
aaaatttaat tcatgagttc cctaatggaa acccgacaga ttttgctaac ctgacaagat  52140
taactgatgg tagatatgtc tattcacaag taacaagtat tgaagatatg ggatatgaac  52200
caacttatga tttacacatg cccgaaacac atagttttat tgcaaatggt atgataaacc  52260
ataacactga aatagcatca ggacttatac agcaaataac cccttactta gagtcaggag  52320
aacgtattgc atttttacg aatagttctt ctatttttc acagtcaatt gaccgtattg  52380
agaaaagact tggaataaaa gtaggtgctt ttggtgcagg taagaaggac attcagcaag  52440
ttacttttgt aatgatacct acgattgtat ctgcaatatc tgcagaccca gaggctaagc  52500
ttaagctgac tgctaaagaa agaatgtaca agaaaattgc taaggatata gctccaaaat  52560
ttgaaagagg gtttaaccaa aggagtttgc ttgaaggata cctaaataac tttcaagtta  52620
agacaaaagc agacctgcag ttgaaacatg aactagaaga aattttttat tcatgtggta  52680
cgaacaaaca ggttattatg aaaatgaaag ggtatcaagc agaataccaa aagattgttg  52740
aaaagaaaaa tggtaaagtt cttaagaagt acaacgaggc tatggagttt ttagattcca  52800
tatctgtaat gattgtggat gaggctcacc atacaagttc agatacttgg tataaagtgc  52860
taacatcttg taataacgct cagtatagaa tggcacttac tggttcgatt gaccgtacaa  52920
atcatgtgct ttggcaaaga cttcaagcta tattcgggga gattacgact aaggtgtcta  52980
acaacacact tattgagtta ggtcactcag ccaaacctaa aataacaata ttccctatta  53040
tagctcctgt agatattcaa accactacgt atatggatgc ctatcaaaaa ggtatagtag  53100
acaatgaata tagaaattct cttattgcaa agttgactaa gaagatgtat gataaaggta  53160
atgggatttt aattataatt aatcgtatag agcacggaga ggctattagt aacttactaa  53220
aagaagaggg agtagctcac tactttatca atggacaact tgaaaatgat ttaagggatg  53280
aaaaaattca ggacatgcgt gatggagcac ttaaagtaat gatttcttct acgattatag  53340
atgaaggtgt cgacatttca gggattgaca cattaattct tggtgcagga ggtaagtcct  53400
taaggcagac actacaacgt gttggtcggg gcttacgtaa gaaaaaaaca ggagaaaaca  53460
aagtagaagt attcgatttt tatgatttaa caaacaaaca tttgaaaaaa cattcagagc  53520
agagaagaaa aatatatgaa gatgagcaat ttgaaattgt tgatattcct attcctaaat  53580
aactataata aagaaagggt ggcatacaat tgcaaagtcc atgcctaaat attgaattaa  53640
aagaaaaatt taaattaaac aaaggtataa cagacttttt agagagagtt gcagataaat  53700
ctcagagatg gggtgaaaca gtagcctccc ctatccgtaa aacggatatg gcaaaagaga  53760
ctggaaaaaa ccctagaaca attacaagat atattaatca attagaggaa ctaggtttaa  53820
taaaaaccga aacaaaaaga ggaatgaatg gagggacttt agtcgtgttt aacacagata  53880
tgcttaattt tgagccaaag gaaaacccta tcacgtctga tactaaacaa gcaaaggaga  53940
ttagagaaca agttttccct aaagccccaa ccaaagtacc aaaacgcaga tacagaacaa  54000
aagcggagat agctgaggca cgtatactta gtgaaaaact taaaaaacgt gaagacattt  54060
taaatgataa aattgagttt aacgttgtta ctagaagttt tttcgatagt tttgacgaac  54120
cagaagcgta ctttaaaggc tatttaattt caagaatgta taatgcttat gtgacaatca  54180
ttccttatga aaaatataat agactgaaaa atttagatga gaaaaaggct aaacaacaac  54240
tacgagcata cgaaagctct tacaattacg atgtgttgcc tagaagattt gttgggacac  54300
ctcagtacaa aaaatttgta gagctagcta aatattgtga agagaacaat atcaatcctt  54360
tagtttattt aacagtgcaa tttgatagaa cagagttttt gatttctgta ggtaaagcac  54420
gagtaggggc tacaccctat gtaaatactt tgttatgtgc agaggctaaa gaggcttaca  54480
caaatagaaa actgttctac agaatgttac agaaccaata tggattgtat acgtctatca  54540
attcagaagc tacttattat ggtgcaactt atccaattat ttcaggacta ttgaatgctt  54600
acaatatgcc acagaaagac ttgtcacagt tagatactgt gatttgtgac ttagaatata  54660
aaaaagatat tgacaaaaaa gcaggtacgt tgtactctta ttatacagca acacttaaat  54720
cgttaggtga atctgacgta tctagtgaag ctaaagaaag tattgctaac ttcttgaaag  54780
aacaagttgc aaactttttct agtaaacgtg ggctaacttc aacacagtat gccttagcgt  54840
tccctattca gataaactct gcacgcagtt tattaatgaa tgaggaagac gaagaactac  54900
tttatttatt gttaggtaac cagtcacgat tatctaatgt aacaaatgat gaagctgaaa  54960
tgtttattaa acaaggtaga aaattaagta tgtcttggtg gggctcacag aacttctcaa  55020
gaacaatgtt catgttagcg gactactatg ggtttaaaac aaatatatct aagttaggta  55080
tgtacattaa agaatttggt gaggagaaaa ttcctttaga ttctgtaggt atgttagatg  55140
taaatagaat ctatgatgtc ttaatgactg aacaagagat tttagagatt gacaaaagta  55200
actgggagaa ccaaaaagat atgcgtgacg acaaataaga aatataaatg ggagagggac  55260
ggatagtaag atgagtcaaa ttcaaaaaca agttatttat agagcattaa gtgagccatt  55320
ctttgcaaag gaaatcctaa gtaaaattcc aatggatgag tttaaagatt ctggatatga  55380
gatgattgtt tctacaatca acttatatta cagaacacat gatgagagct tagaggaaca  55440
gagtttatta acactagtag aagataagat gttaaaacaa aacaaaagtt tggaagctca  55500
aaacaaagtc tttgaggtag ttagcgactt atacgaacta gagaacgaag atgtagactc  55560
agaagttatc agtgagaaca ttcagaacta cgttcgtaag gtactaacac gagaagcaat  55620
catgaaatct gtaacaaatg aaggcacact aggctctgat agtaatattc aacagctaat  55680
ggatgacttg agagacattc ttactatcga gacagcaggc aataattcag aattgctaga  55740
cttcttcgat gacgtagata aaaagatgga gttacttgca aacttgcaac aaaacaaata  55800
cccaactggt ttcacagcta tcgatgctat ttccgatggt gggctagctc gtggagaagt  55860
cgggatggtt gttgcaccta ctggtggtgg taaaactact tgggcagtta accaagctag  55920
aaactatgtt gtacgtggtt taaatgttct ttatgttcct ttagaggaaa aagtagaccg  55980
tatgattgtt cgttttgaac aattattatc acaacaaagt aagaagaaca tcttagttga  56040
tggtgaattg aataaagact tgtataccca aatccaacaa gcgtatggag cgggtaaaga  56100
acagatgaat tggggtaacc tttggattcg taaatataaa cccacaagagc taacacctag  56160
cggtttatct cagttaatct ccgatgtaat gattcgtaaa ggacagcaaa ttgatgttgt  56220
cattattgac tacccagatt taatgaaaaa tcctcatgca agtggaagta atggtgaatc  56280
```

```
agatgcagga ggtaaactgt atgaagatat tcgtgcgatt gcacaagaat atgattttgt  56340
ttgttggacg ttatctcagt tgaaccgagc aagctatggt caagatatta aaaatgcagg  56400
agctatcgaa ggctctaaac gtaaaatgaa cgcagtagag cttattttta cattaaacca  56460
aacatcagag gagtttagta acggatattt gagagcttac gtagataagt tacgtaataa  56520
tagtgggatt gcctatgata aaatgttgta ttttaaagta ctcccagaaa ctatgactat  56580
tagagatgaa acaccagaag aacgagcaga acatgaagca ctgttagcag ataatgcgat  56640
gaatagagca agtagccact ctgatgagaa taactacaca gcaaacgatg ttaataaaaa  56700
gataagtaat ttgaataata ccctttcagg aggttggaat taatgaaaca tattattaat  56760
ttttcagatt ttcatatgca ctttttttaaa gatttttcaa aaccagaccc agagtatgga  56820
actgataggg caaaagagca aattactata ttagacaact tgatgaacta tgcacgaaac  56880
aaaaatgggg atgttttatt taatggagac atgttccata aacgagtatc tattgatgtt  56940
agaatattca atatgttatt tcaagtaatt agtagctacc ctgatgttga tgttatcatg  57000
gtcagtggta atcatgataa ggtaactaac tctctatatt cagatagtgc tttagcacca  57060
tttagtgctt taccaaatgt tacagtttgt tctacgttaa acaagattgt taaagatgat  57120
tatacgttgt atgctgttag ttatggggaa gaggtcgaag agatgaaagc ttggataaaa  57180
gaacaagctg acaatttaga ccatgaaaca gttaatattc taagtgcaca cattggtgta  57240
gatggttcat ctactgggaa gtactcccat acacttggtg gtgcttttaa agtagctgat  57300
ttataccctg acaagtttga catagttaca ttgggtcact atcataaacg acaattttta  57360
ggaaacctat ctaatgtgtt ttatgtgggc aataccttac agacttcttt tgcggatgaa  57420
ggtcaagaaa aaggttttta tgatattact atagagggta agaagtggga acaaaaattt  57480
attaaaactg actatactcc gtttgaaaca gtaacagctg ataacccatc aacaacaggt  57540
tctatggaga aatcttatat ccagtttatc ggtaatgtgg atgaggttga ggctgtaaag  57600
agaataaaag aagagaataa cttaagcaat attagaataa aagttcagaa ggactaccat  57660
gttgagccac gtataaacat aacagcaggt tcgacaccta atgaagttgt caatgcattt  57720
attagtaaaa agtaccctaa cgcaaaaata attaaagaaa aagctctcga ctgtttgaga  57780
gaagcaatgg aagtataata attgtttagc ctagatatat ctaggctttt ttgcgttgta  57840
ctattgactt tattagtatt ttgaagtata atatgtttat tgaaataatt aatattttgg  57900
gaggaaaaga tgttaaagtt taaacgagtt agcgcagaga actatatgtc cattggctct  57960
gtatctattg atttagacaa ccaaggactc gtacttatcg aaggtataaa tgatacaaac  58020
gaaacatttc agagtaatgg ctcaggtaaa agtactttac tgtctaccgt tacttatgca  58080
ttgtatggag ctacccctag tggtttgaaa gctgatgctg taattaataa acaagcaaag  58140
aaaaatatgt cagtgatttt agaatttgaa aaagatgggg taccatatcg tatcgaacgt  58200
tatcgtaaac actctaaaca taaaaatact actagatttt tccaaggaac aaatgatata  58260
actcagaaat ctgtagcaga cactgataaa aagattcaag atgtgttcgg tattgattac  58320
ctgacttatg ctaatagtat catgtatggt caaggtaacg tagaaatatt tgctacagca  58380
actgataagg gtaagaaaca aatcttagag aatttagccg atattggtgt ttaccgatat  58440
gcacaggatg ttgctaaaga aagagcacaa aaagcactag ctcttgcaga agagctgaac  58500
agacagtaca ttgctaagac atatgaaaaa gatgggttaa ctcaatctta caatagtgct  58560
ttacaacaat atgagaatac agaaaagctg attcaacaaa aagagagtga gttagctaat  58620
gcagaattag ctattaaaca aagtgagaag aatctgtcag agggaagagc gctacgtgaa  58680
cccgaattag aaaagctaag agagcagatg gcacaactaa cttcccctgc agacgttcgt  58740
gaaattgatg tagaagttga aacacagtat tctaacgtta gtagattatc tagtgcaaaa  58800
acacagaatg atactgctat tgagaaatta aaaaaagaac tagaagatgt taaaacaaat  58860
acaaattgct acctatgtgg tgctttattg agcccacagc atagagaaca agaaattcaa  58920
cgcattcaaa gagaaatagc ggataaagaa gcgtttatcg aaaagcttaa tagtgcatta  58980
gcagtgtatt ctcctctgtt agagcaagca agagctaaac aagaggaagc aagaaaagct  59040
attcaagaac atactaatat ttatcataaa cttaatggtg aaatgaatgc gttgtatcat  59100
gagatagata cattagagaa cacattgaac acatctatta ataataggga cagcattaag  59160
gatatgttag caagactaca agaaatacct aaacctcaat atgactatga caaagaccgg  59220
gaaatagaag atgagctaaa taaaattaac caattaaaat tagatgccga agaagaagct  59280
agtcaatata aaactattgc acaagaaatt ttctctaata aaggcatacg ctctgaggta  59340
cttgacctag ttacaccttt cttaaatgaa agagcaaacc attacttatc taccctttca  59400
ggttcagata ttgaaataaa ctttagtacc caaacagaga aagcagatgg tagtttagct  59460
gataagtttg acttagaggt agtgaatggc tccggtggaa acacatatca agcaaactcc  59520
gagggagaga agaagagaat tgatttagca atatcttttg ctattcaaga tttagttcag  59580
tcaaaagcaa acattgctgt taatttaggt ttgtatgatg agtgttttga tggtttagat  59640
gcaattggtt gtgagaacgt tattaaaata ttgaaagaac gccaaaagaa cattagtagt  59700
attttcgtaa taactcactc ggagaacttg aagccattgt ttgagaacgt aatcactatg  59760
aaaaaagttc aaggtcgttc ttaccttgaa gaaagtaaat aggtgattac atgaagattt  59820
atacattaag tagagagtta aacgaaggta ctatatttgt acctacaagt agtagtaatg  59880
aagggagact atttagcttc ccgctagaga cactattcga ttggtaccct tgttgcccaa  59940
gatatgagta tcagtacagc acttctcgaa aaaaactata tttgagattg ttagactcag  60000
acaaaacatt agtagctaga tacggtgttg gggataataa aaagagagtt atttcaaaaa  60060
tagcttgctt taatgagaat gaatggtata atgaagaagt ggcaaatgag aatgcagagt  60120
tgtttaactt tgctaaacaa tatgacattg ttacaccttt aaaagaagat tacaccttaa  60180
aagaagtaga taatagtatc tctaaagtac tggacattct tgatttactt tacacaaatc  60240
aaaaagttaa agtagaagaa gagcttataa ataaagtgga tactctacaa ttgagtaaac  60300
cagactcgga tgaacttaaa caagcgtata aggatatatc tgagtatatg aggttagaca  60360
gagaggaaaa agctacttat gtattaagca ggtcactaga ctctttaaat agtgtttatg  60420
aaaaatttgg taatgtgtat acaatgttaa atattatgag gaaagtagtg gcttaaatgt  60480
ttacagactt gttatctaac gaattaggtt cacctaaata tgcagtaagg gactacaggt  60540
ataattgccc tttttgcgac tacgatacta agtataagtt ttatgttagg gtagaagaag  60600
gacacccaaa gaataactta tggcattgtt ttaagtgtgg tagttcaggt aacccagtat  60660
cttttgtaat gaagtattac aacgtgtctt ttaaagaagc gctagagata ttagaagaat  60720
acggctatag gtttaataat aaaaattatg tgcctaaatc agataagtta actgatgagg  60780
aatacttatt acttcttcta ggttcgttag gtaagccaaa agaagaaact aaacaagcta  60840
aaaaagagtt agtagcaccc ccattgccag atggttttaa actactaagt cagaacctga  60900
gagagccaga agcgtaccct ttcttattat actgtaataa gagggggttt acattgaatg  60960
atatttatat gcacaatatt ggatatgtaa aagattcttg ggtaccctta gaaaatggta  61020
```

-continued

```
agtcagttag actcaaagac cacttagttt ttttaactca tggaaaagat ggtaagtatc  61080
aatattggaa tactagggct attggggaaa gctttattaa gtctttgaac gccccaagta  61140
aagagggtga gcattcaaaa aaggatacta tatttaatat taatagagct agtcaaaccc  61200
ctcagatagt tataacagaa ggtgttccag atgcattaac agttggtgag tctggtgtag  61260
gtacttttgg taaacaagtg actgacgagc aagttgaact tattttagat agtgtgaatg  61320
aagagcaaaa aatatttatc tatttagata aagatgctaa aaaagaaatt aagaagttag  61380
cagagaaact atataagaga cataacgaga cttatgtagt tataagccca acaactcaag  61440
atgcaaatag tctagggaga gaagaggctt ggaatattat aaataactac tctgtaaaag  61500
cagatggagt agggttaata aaattaatgt tatagatagg agagggaaaa aaatgaagta  61560
tacactagaa gatttacatg caggtatgaa attacgttgc acggacaata aaaactacag  61620
tttttggact acgaataaaa tctatgaagt aactaaaaaa gagtcaggtt cactatgtat  61680
ttttgatgat tatggaattg agagcctaga tgaggacatc ttagtacgtt taaatggtaa  61740
tacagggaac gcagaatttg aggttgtttc taaggtgatg aaggatgcag attacacaga  61800
agaagacctt gaagaaggga tgttacttca ctgcaaagat gatatgagct ttccatggtg  61860
ggctacagga caaacctatg aaatctataa gggtgaaaaa ggaattttat ttaccaagtc  61920
aggagacggt aaccaatact gtgctaaaga aatagtagct cgattaaatg gtagtgcaag  61980
cgggtctttt gaattactag aaagaccaca taaaacagag ttagaaaaga aagtagaagc  62040
aagaattaag gaactaaaag gaaagaaact ttgtttattc tacaagcaac aacaaattaa  62100
gatagaagaa aacgaaatat ctatagaaat cagtaagcta agtgaagcat taaaagcgat  62160
tgacgtatta agagaatttg aataagaata actataggag gacaacaaac aagatggaaa  62220
gagtatcagt atactttcta aatagcagaa atattatgga tgaggatgag acaaagcgta  62280
cttatcatgg aacatttaat tcaatgaaag aagcagagca gtcagttcgt gactggtgga  62340
aagcaaatga ctttaagtgt ggtaccctta gaattattga aggtactgag gatgggattg  62400
ttcgttggga ctacggaaac catactgggt tctatctatt tgtaccagaa ggtgctgtag  62460
taaaatacac aatccgtgaa ggcgctaaga aaccaaaacg aggaagagaa aatgatgtag  62520
cacatgactt gttcacagca gacgatggag tagttattcc cgggagatta ggttcaaatg  62580
ttatttctac tggaataaaa acatcgtttg accccaaaca atatggttta ttcattaacc  62640
ctcgaggtgg tatgatgaaa tacccaatca ctttaggaaa cacacaaggt gtagtggaag  62700
gggaatatcg tggagaggtt ggtttaccac ttaaaaatac gttctcttta caattagatg  62760
caagagctgt ttctaagaac gttttaacaa tcaatgaaga aggtaaactt attaacatcc  62820
cagtaacagt agctcggtca atgtatccaa gctttaatgc tctttatgaa aaacagctag  62880
agaagctaag tgaggagcta cagctagtct atggaggaga agttagaata tctaatgctg  62940
atgagtatgt ggttgcggga acactattta tcccaaaagg cactcgttta tgtcaagctt  63000
tcttactacc acgatacgac acacagtttg ttgaagtatc agcgttaggt acaactgaac  63060
gaggagaagg cgcatatggc tcatctgggg tggtatagct atgctcatcc cagaatttaa  63120
gccaccatta ttgtacgtta tgggtagctt ttctgttatg ttagaaaaac accagtgcag  63180
tgtaactttt gatttaagag agccttattt aggtacctct tacgataaaa tagtgaagct  63240
tattaaaatg acttacccaa actatagctt aacttatgta gggatgacag ataataaata  63300
taagttcaca ttaaagaata aggaggacta gcatgtacac caagaaagag gaagtagtga  63360
cagttaaaca cctagttgat aaagagcaaa ttagagtagg ggacatagta ggttacaaaa  63420
agactattag agggttcgat gcaaaaagag taaaagacac actctcagta acaaatcaaa  63480
taggtgtagt ttctcgtgta tgtgacgagt acattactgt tcatgacttt tttgataagt  63540
gctcacgaga aatatgggca aagacatttg aaaatttaga agttcgcaaa atagaggatg  63600
gtaacagcct actacggagg tatgaaaatg aatttcgttg attattttaa tcagatgcag  63660
aatttagtga ttgaagaaaa aacagatgag tatgttttac tagagaaaga acatggtcaa  63720
aagtatgtga catatcaaga gctagaagga gcgttaagta cagtagcacg caacactgca  63780
tttatggtag aaaattataa ccttatgcaa gatattaatt taaaaattgt attgaaaaaa  63840
ttaaaagaca gtggtacaat tacagaagag cttgaaaaag agattcttaa agagttcaaa  63900
aatattgaaa gtttaatgga ggacgaaaca tatgagtaaa gagagtaaac gcaacaaacg  63960
tatcggggag ttatcggaag cagacatgag agtgtgggct gagtggttag ccacagggca  64020
ggttcatgat aaaaaccacc aaaaacagtt agaacgctta agtaaacgtt cagtatcatt  64080
atctgatgta actactattg tcgaatttat gggcaaacgg aatgatggtt atatttcttc  64140
tttaattgaa cagcaggctg tatttgacaa tttattaaca aaactaggtg taacggaaga  64200
gaaccgctta gaggctaaag cagagtacga aaaagagtta agccttattc aagaaaaaat  64260
ccaaaaagag ttagagtcta ttaaagaaaa taaagaaaaa taatatgaaa gaggttagct  64320
gaatgacaga ctacagcgca gtaggcaaga aaagtcgtaa caaaggcgga cgtttttgaac  64380
gtcaaatggc taaagaactc acagagtggt ggggatatga gtttaaccga gtacctgctt  64440
ctggggggct tcactgggct tctagtaata acgttgccgg ggacattgta gtccctagcg  64500
atgctaactt cccatttgtt atagaatgta aaaatcgtga agactggacg attgagaact  64560
tattcttaaa taacaaagaa attaagaact ggtgggcaca agttgtgggg gatgcaaaag  64620
aaacgaaaaa tatcccacta cttatattta ctagaaacag agcaaagaat tttgttacta  64680
tggcatataa tgaaaaactt gttaatgaga ttgaaaaaag aggttaccct ttgatggtct  64740
ctaacataac atatgtagac gactacaagg atactcattg ttacaagaca tttactacag  64800
ttttagatgc aataactagc tttaagcctt atggtagcaa agataaagac tactttttat  64860
tttattttcc tagtgactat gactgggaag atagcctagt ttatgaaaca accataatgg  64920
atgatgctaa acaaatggat gcagaggatt cactagatgc actagttaat tcttatttag  64980
gaggagaata gtatggctaa aacatatcag gaagctctag caacggtaca gtcgtatctc  65040
gaatcagata gtgtaatgaa agaaacctca agtatatctg ttagtttctc agctaactgg  65100
acaggtgagc gggaagacta cgttattgat acattgacat acgacattga tttacgagta  65160
ttcagcttag aaactgcaca tgttgtagct atagggaaga aactacctca agatagcaat  65220
gagcatgctg aactccttaa aaaacttaaa aaagaattta aacaagcttc taaaaaacta  65280
cgggaggact agagtagatg atagacaacg ttaatagtcc tagtcattat acgcaaggag  65340
aaatagaggt aatagaggtt atagaatata ttactgctaa gtaccctgcg gaaattagat  65400
accatttagg aaatgttatt aagtatattt gtcgagcacc tttcaaggga aagctacaag  65460
aagaccttaa caaaagttct tggtacttga aacgagcaca actggtttta acacagtcac  65520
caagtagcta tataggtaaa tgtaagaaat ttttagagaa tttcctattt aagaatagcc  65580
atatcagaga tgctcagcta atagaaattc cagaagaacc tattattgag aaatttttat  65640
ttcaaacagc acagagttac aataaagaac agcaaaacta tattatttca gccttaatgg  65700
aactaaacag tagttcaggt gatgtgaaaa ctgttcttga aaatacagaa aactatttaa  65760
```

```
aatttattac aacttagtac aatataatgc tctttctacg aaaagctatc ttttatattt  65820
atggtataat agagataggg aaattaaaaa gtagaaggag cattttataa tgacaaaagc  65880
acccagagtg aaaagactta atatttataa cactgaccgg tactttaata ttaatttaat  65940
gaaaaaagaa gatatagcaa aaaaaattaa agttaaccga ttgaatgaag aagagataga  66000
gagggaaatg gacgaactag caagcaaccc attgaagacc cctataggct acatggatag  66060
aacaaatgaa aaatcttata tactttatca agagaagtat acgaacgaca gacttattca  66120
gaaattattt aaacatgcag ggtctgtgtc ttattacaca gatacaattg taccatacta  66180
cataattgag caaatatcta agaatttaac aagtgaagta atctatccta caaaaaatag  66240
ctatgagaac agagagattg aaaatgttca actagctttc actgcttgcc ctgtaacgat  66300
tgactgccca gtagtactac ctgatgttag cccgtatgat gtgttatttg cactacatcc  66360
tctaaaaaca aatgtagaca agattcaaat atcgttccct tgtcttacag aagaagagtt  66420
cgatactaga catgaagaat actatcataa agtaggtagc cactatgagg ttaaatcaga  66480
gtacaaatat aaattcttta agtatgtaca aacttcctta tctatttggg ctatgaacat  66540
ttggctagtg tgtgatagtg atgaggacta caataaaata gacagatata ttcagaaaga  66600
aaaaattaaa cgtaatgcta acagagagcg tgcattaaag agaaagggta atcaggatga  66660
gtaaagataa aacgattaac cgaacagaca tagctcgaac aatctctcac catactggtt  66720
atcgaatgaa agatatattg aagattttag aagtagaaga tgaagtagta gctcaagcag  66780
tatcacaagg tatttctgta aagaatcaca aattatggaa actaaacatt aaaaaaaagc  66840
cagagaaggt agcatgggat ggtataaact ctaaaagttt tatacaacct gaaaaatatg  66900
tagttaaatt tgtaccatta tctaagttga aagagtcaat agacacttat aataaagaga  66960
gcaaataaag ctctcttttt tgctctttct atattgacaa ataacataat acaaagtata  67020
ctagtgtcat agagcaacag agaggagaaa agtgtaattg aaaattctat tcttacaaga  67080
gtacattaga gaaaatcatg tccataatgg aaagaacgga caaacagttg attttaaaag  67140
aacagaaatg ggtaaaaaac ttacaggtct gttaaataca ataggactga caggtaggga  67200
ctatgctgta gactatgtgt acgacatgat tccggaagta cagaaagtca accctagaac  67260
aggtaaacca attaagtata agacacctac gttaagacag cgtaaagaac cagaggaacg  67320
gttactcaga cgtttaatga aatacaaacc agatattatc atcccaatgg gggagatggg  67380
ttgtaaaaat ttattaggaa gtacttctat cacaaagaat agaggagtac caactaagaa  67440
aacaattacg aatgagaaca tactgagaac ggctgatgag caagggcttg aggtagacga  67500
agtagtagac tcttttgaaa cttgggtact acctatgttt agtatggaat actggacagc  67560
taacccaaac attgagaact ttatcatggc ggatattgat acattgggta agtttgttca  67620
agaaggggaa caagcattta tccctaaaaa agtagattac gaatttgttg ataacattga  67680
acgtgtaaga caaatttttg gtttttaga caaaacgaag ccagtaactg catgggactt  67740
ggagacaaat agtttacgtg gtgacttatt aggggctaag cctcttgtaa tgtctatgag  67800
ttggctagag ggacaaggtg tgactatacc gttagaacac catgaagcta aatggagccc  67860
agaagaactt aacgaaatat atgacttatt tgagaagttt ttagcggaca gacagcaacc  67920
aaaagtagga caaaatatcc agttcgatat tagattctta atgaacacaa aaggatttac  67980
agagtttgaa gacaacagag atacaaaaat tgcttactat ctaattgttt ctcagaaagt  68040
agacacttca aaacggctat ccgatattgc atatgaatta acagatatgg gaggctatga  68100
cgaaccgtta gagcagtata aaaaacaata taaagaggac tatattgctc gtaagaaagc  68160
agagattgat gctttcaaag aagctgaaaa agaacgagta gagtgtgagt tcaagatagc  68220
aatggataga tataagcaag aagttaaaga agctaagctt attggtaaac ctactaagtc  68280
cattattaaa ccagtaaaag aaaaagttgt agtacctaag aaatcagata ttaaacttat  68340
taatgagatt gacggtggta actttaacta cgactggatt ccattagaga ttatgcaccc  68400
atatgctagt ggagatgtcg attgctgtct acgtatctat aacgttctat ataaacgaat  68460
tgaggaacat cctaagatgt tggaattatg gttgggcttt tatcctagac taacagcaac  68520
attagcacac atcgaggctt ctggtgttct attagactct gaatacgcag aattagtaga  68580
gaacatctat acagaagaag aacatcggtt gcttaatgaa attagaaagc taccagaagt  68640
aaaagaagta gaggatgaac atatgatgtt ctacaaagag gggcttaaag aaatgacaaa  68700
gcctgtcaaa gatagagatg cctctgttgc cagactacga gataaatata aaattactga  68760
tagtgagaac aaagtacatt ttaaaccaag ttcgtctgaa cataaaggta gactgctatt  68820
taaagtaatg ggacttacac taccttatga taaagaatct attaaaaaag aaacttttga  68880
caatggggta ccagaacatc agctaacatg gagagattat aaaacagata aacatgcact  68940
agcttatatt gcagaaaatt atccagaggc taaacatgtt gctgaacttt tgctagagta  69000
ttctaaagta aacacactaa aaaataactt tgctcaaaag ttacctaaat tagcatctaa  69060
caaggatggc atgattcatg gttcatataa cagtacaggt acagaatcta cacgattgag  69120
tgcaaacaac ccgaatatgc aacaattaag tagtaaggtt ggagacccta gacgttttga  69180
ctataaatat ccaattaaac gtttatttag aacaagattt gagggaggtg gaatgctaca  69240
actagactac tccgccctag aaatgcgtat tttaggtttg attgcaaaag ataaagcaat  69300
gacacaagca tttattaatg gtgaagatat gcatgaggca actgcatctc ttgtatggaa  69360
gttacctaaa gataatgtac caaaagatat gcgacaacgt gcgaagagtg tcaacttcgg  69420
catcgcttac ggtaagcaca attgccgtct tgtagcgtaa gctactcgat taaacttacc  69480
taaacgggca tagctgaata accaataagc tgataagaga acctaagtcc tgaaaaggat  69540
agaggcaatc ccgtagtaaa gacgatttaa taaactccac taaaggagtg gtattatgga  69600
aattggaaca agaacagaca acaacccttt atatagaaaa ttaagaactg tgcataaaga  69660
catgcgcaga cgatgtctca ataaaaatgc taaatcatat gagttatacg gaggtagagg  69720
tgtaactatt agtaaggagt gggagacctt aaatgggttc ctagcaactg tagatttagt  69780
agatggttgg gacaaagata cattcctcac aacagggcta tccttagata aagacttaaa  69840
aggaggagcc gagtatagta tagctaactg tacatggatg ccacttaatg ataacaaaag  69900
cctactatca atgaactaca agaatgtctg tgctattgac ccaaatggtc aatattatgt  69960
tatagacaac attgacaagt tttgcagaga gcacaacctt aatcattcca atatagttca  70020
agtaattaat ggtagataca agcatcataa gctatgggta ttctggtatg aaggtgataa  70080
acctaagaaa gggatacaac cacacatagc gattagccca ttgggtgaca cctactattt  70140
ctataaagct cctgacatgg aaaagtatgg gctaaattct aaatgtgtag ctagatgctt  70200
aagaggagag agaacaaaac ataaagggtg gaagtttatt aaatctgaaa acctctaacg  70260
actatcgaaa agtgagtagc tgtcgagagg acacctacaa tataactgag tagagtacac  70320
caacaggtgg aaatggtaag gctcctagag taacgactag gagcgtgata tagtctaagc  70380
ccctaataaa tatcgggaaa ccgagggtat aactggaaag tccttttca attgcaccta  70440
agttaggtgt aactgtagaa gaagcagagc gtatttttga agagtacttt gcaagtaagc  70500
```

```
caagtattaa acaatttatt gaagagacac atcaatttgc tcaacgttat ggctacgtag  70560
aaacactaca aggacatcgt agactattgc gtgactcatt ctctaaagat aagaaagtat  70620
ttaatggagc aatgcgtaag tcagtaaata caatcattca aggaactggt gcctacttaa  70680
ctaacctatc aatggtatac attgacgagt atatcagaaa acacaataag cgttcacgta  70740
ttgttatcac tgtacatgac tcacttgtta tcgattgccc acgtgatgaa gtggacgaga  70800
tggcaaaagt ggctaaatat attatggaga acttgccaat tgatttctta atgattgagt  70860
gggaaggtaa agagatgcgt taccctattg tggcagatgt agagattggg gagaattaca  70920
atgatatggt tgattatgat gcagaaatta tcaacgagtt tgcttcttac cgaggatacg  70980
taaaatactt caaagaccaa gctaagatta aagattacta tgataacaaa cttatctcag  71040
aagagcaaaa agaccaaggt atcaaagtta tccaagatgc aatagagtca tataaacaaa  71100
tgacaattta ataaaaaaat gttaaaaata gcttgactat tgacgtatag tatgttatta  71160
taatatggca gacaagtttt ctgtattaat acaagaaggg ggagttagag agtgtgctta  71220
atttacgagt agacgattta gagttcaaaa caattaaaat tattgatgat aacggagaag  71280
ttgtgacaca tgatttacaa acagagttac aagtcaatga atttaatgtg agaacagcat  71340
ttttagagca acctgctaag tatacttatt ggacttcgat actagagcgc ttgcgcatgt  71400
atcaagaaaa ctatgagtta aaagcagaga agaagaaagc agaactatat gagccttctc  71460
gggttgcctt aatcaatcaa ggagtagcta aacctacaaa agaccagatt gaggcacaga  71520
ttatgttaga tgaagactat tacaaactta gacagagtat agttaaccta tcatttaacg  71580
tgagacaact gcaatatata gttaaagctt ttgaacaaag aaaagatatg cttattcagt  71640
atggagcaga ccttcgtagg gaatatgagt atagccaaaa ggttagtatg ccagacccaa  71700
tgaaaaataa ggtaaataat ggtttctcag actttcaatg gaatttagaa cagtaaaatt  71760
agtgataaaa aaaataatat aatataaaaa aaatagaaat ggagaaattt aaatgaattt  71820
tcaagaacaa ttacaacaac aattaaaaca acaaaatatt ggagaacgtg aagcggtaga  71880
ctacccatca aatcatttaa aacataaaga attatacttc cctaaagcag aaaatggtca  71940
gccatcaact ctatatgtac gtgtgttacc tcctgcagta ccgggagaaa actataatgt  72000
tagcgctcgt gaggcattct taacaactcg taatcgtaat ggtaaagatt taaagagcaa  72060
ctttatcttt tcagaacacc ctaatgcaga agacatctta gaacaagcta tgattcgttg  72120
gaacgcagaa aatcgtgtac caaaccctta tagccgtaat acaaaacctc gtcaacgtta  72180
ctacgttaat gtagtgcagt taattattaa ccaacaaaca ggggaagtta gctatgaaac  72240
agattctaat ggtcagctaa tggttcgttt acttaagtta cccacaaacag cttgcatggc  72300
tattaatgag agcttaagta acccaatgtt acgcccacag ttttcacctg atgtaccaga  72360
agaagtagcg caatacagct ttatttcttc tgcagatgca ttccctattt caattacaaa  72420
accaccacgt agtaacaaac ctacttcgta caatgtacaa gtgattagta atcgtagttt  72480
aggtgcatta ccacaaggtt gggaaaactt attagaagac ttgaaatacc aagctacacc  72540
ttctgtagag tacaatcgtg agtttattga gtactttatt gatgtagtag acgggaaaga  72600
acctgtgcat caaggagcac aaagtcaagg aacccaagct ccacaattta atcagcaacc  72660
agtacagcct caatttaatc aacagcctgt acaaccacaa tttaaccaac aacctgtaca  72720
accaatgcaa caaaatactg gttggtcgcc acagcaaagc caaccacaac agcctgctac  72780
aggttttaat gcaacgaaca tgggaacacc tccaaacatt aatggagggt ttagccaaca  72840
acctgtacaa caacctgtac aacagcaaca accgatgggt tctttcaatg aacaaccagt  72900
gacagaccct tctaccattt ctgatgcgga tatgcctttc aatatgcagt ccatgcctga  72960
tgtatcacca caacaaaatg ccgtacctga gcaacctgtg actaatacac cagagccagt  73020
aagccaacca gttgttaacc aacagccaaa taacacacct agtgtagacg acctattagc  73080
aggtatggta ggcaacgttt aacaataatg aaacagttag gaggggcata ctgccccttt  73140
taattctgtg ttaactatcc aaaatattta gtaggagtga ataatattgg caagaaaaag  73200
aaaaagtgaa gaaatagatt ttggaactat tgatttgaca aaagaggtag gactaactac  73260
atttacggac acaaagttct ctaatgtatc agacagacta ccaacaatga ttccacagct  73320
tgattacatt ttaggtggag gattgccatt tggacgtatg gtcgaggtct ttggtaagaa  73380
ctctagtggt aagtccactt tagcagtcca tctgacaaag gtagcgcaaa tgctagatgt  73440
accaactgta tggattgacg ttgaaggtac cgcagaccca gaacgcttag cagaactagg  73500
ggtagacttt agtgcaggcg gagtattcat ggtagagcct aaacagaaca aagacggtag  73560
taaagataca atcacggtag aacgtgtagc agaagagtta caacgactct taccagtatt  73620
tagtaagctt ggaaaacctg tattaattat ttgggactct gtagcgcaaa cagcttctga  73680
gaaagagtta gaaaaaggtg taggtaacca acaaccgggt ttgtaataaa gctccgttag  73740
gtagtaatat ctaaaagaaa cctatcttta tcatgggaaa cctctaggag gcaatcatga  73800
gtgaagctgt agaaatacag aacatgcaac gactatcgaa aggggagttc ttgtcgagag  73860
gacatgaatg agaaccgagt agagtacacc caagtgggtg gaaatggtag ggctcctaga  73920
gtaacgacta ggagtaagat atagtctgta ctacatggtg acatgtagca gttcataaga  73980
gaacgctata agcttaacga acttatagga acataataga ttaaggcaaa agcaatggca  74040
cagtttgctc aaatcattgc acctttaatg acaaattcaa aagcattatt tattgctatt  74100
aaccaagcac gtgacgagct aggtagtatg tttggtggag tagactctcc cggaggacac  74160
gctttacacc actgggctag cttacgatta gaagtagtta aagcaagtca gattaagaat  74220
aaagagctaa atgcattcgg tgcagaggaa gagacctatg taggacatat cctgcgtgtt  74280
aaaacagcaa aatcaaaagt gtcccgtcct aaccaaaaag cggaaatgta cttaatgtcc  74340
gacacaggac tgaacttaga ggaaaacatt tatcgttcat gttttgcaac taataagcag  74400
tatgccttga ttagtggagg cacgtggaag tcttatacaa cggatgcagg gcaagagatt  74460
aaatttaatt cagataaagc ttgggtagct tatttacgtt cagaagaggg aagacctgtt  74520
cgagacgaac tatttgctaa aatgatggta cgctcattcc cacatcgtta tgctccattt  74580
aataatgagg acgtggatgt atgcaaaatt ccattatatg aatttactaa agaatatatg  74640
gaaaatcata aggaacaacc taaccaagct actaaagaag aagtccccga aacaggaaca  74700
gatgtttcag atttacttaa acaggtagac taatagataa gggggcattt agccccttta  74760
ttagctataa aggagaggaa cttattttgc gcaaaggact agcacctaac ccatttttttg  74820
aaatattaga aaaacatcaa gactcctcta aacgtactat gactatgaac agcagtggta  74880
cacctagttc actacaacca ataagagaca tgttcttaaa ggcaatgaga gaaggtaaga  74940
aagtcctaat agagaactct gacttaagta gtgcgaactc tgttgttata gagatagaat  75000
atgtaggtaa tcgttggtgt ttaggttatc aacgagtctt attttatggt atggagttaa  75060
aaataccaca cactatccac ttctgtgatg tatatggagc ctatgggcac gatgctcaga  75120
aggttaagag acaagttaag gtagtgtttg agggggacaa ccctttttgag tagagatgtt  75180
caaaaagagg aaaaagaaat acgtaatggt aatcggttta ttacagagac tcatggcaaa  75240
```

```
ggagtgtttc ctagagatgt agaccgattg taccataagt atagtaatct tagatataaa 75300
gtctataaca ctcataaaga ctcgttcaat agtgaggctt cacgtaagga gctcaagagc 75360
tatattgatg agcaatttat aaagttaaca aaagagtatg atataaatgg agaggtagac 75420
tttccgggat atattaaaaa agctctgaat ttacgagtaa ggcacagcta tgtaaaagga 75480
cggttccgag ataccgctag agaacgtcta ggcacccaag ataacgaagt agagttattg 75540
ttagggattg acgatagctc tcaggcagat attgaggatg cagaacttat tgaatcgtta 75600
ttatcaaaag ccaatttttc agaaattgaa ttagcagtat ttcagcagtt aattcaagga 75660
acagtaaggg atgctcgtat tattactgaa ttgtcagaaa actacggggt gtccaagaaa 75720
gccgtaaaag atgctataaa aaatgttcgt gagtttgtct taataaattt aacagattag 75780
agtaatacct cctttatgtc tgctatatta gcagtagaaa cataaaggag gtattttta 75840
gtggaacaaa acaacactgg caagtatgca ccatttattc gtttaattgt gatgggaatc 75900
tcatttgtgg caactggttt gactacaata tttggttggg aacctttacc attcacagac 75960
gaacaaatga accaaggttt aatgttagta ctatctgtag gtcttgccat ctacaactgg 76020
tacaaaaaca acgctgtaac ttcttatggt aaagcaaaag aagaagcagg aaaagaagta 76080
gtcggaacta gacaagactt caaaaacaga gactaagtac gaggggtgta acccctcctt 76140
agttaataca aaggagcttc gacatgaaga tagacgagat aagcaaatta gaattgccta 76200
atctatttgg aaaattcctt gtggtagaga ctatttcgga tgggtacact ggaaccgtat 76260
ctggtcacta taactacgag atagaccaaa aatctgagga aacttatatt taccctgtat 76320
tttggaatga taagcttaac aaatttatta ggtcagatga attagttgta tacactaata 76380
aaaataaagt atactatgtt tgtaaaacaa ctatagaccc atataatcat gcagtagtag 76440
atgagctcac ggtagaggaa ggcatggaca aagacaagcg taccccttcaa gcgtttaaac 76500
tttttgtaaa tgacctattc tcatttggta gctacaatat ctttctaaca ggtaacctat 76560
cattagaaaa caaccctgat attgttctag ttagcagtgt atcattagac aaacagaccg 76620
ctaaaatgta cacagaacgg acattagaac taactgctac ggttttacca gagggagcta 76680
caaacaaaaa agttagtttc tcagtagata aaccagagct tttagggtta acagtctctg 76740
acaataaagc aactgtcaca agtaaagata aggcaggtac tgcaattgtt accgtaacta 76800
ctgaggatgg agaacacact gataagtgta cagttcagat agaagagtac ataaaagtta 76860
caggaattaa tgttagtgga gaatctgctt tagaaaaagg taagacatac aaatttactg 76920
ctagtattgt acccgataat gcaacgaatc ctaaatttac ttggtcttct agtagtgata 76980
ccatagctag tgttaatgca agcggtgacg ttgtagcttt agcattaggt gaagcagaca 77040
ttatagcaac aactgaggaa ggtagccatg taggtaaagt acatgttacc gtatcagacc 77100
cagaaccagt agaaccaact gaataacata gaaaagagga aagaaaatgg ctaaagaaat 77160
attaaatatt gaagacctgt taaaaccaga gacactagaa gtagcaatag atggtaaata 77220
ccttattgta ccaacattgt cggatgggtt tacaggtaca gtagcaggcg gatatgcata 77280
tgctgttaca aaaaaaggaa cagactacac agttaatgaa ttaatctata atcaaaagga 77340
taacacattt aaaccttctg atgaaccaat tattataact gatgataatg aaatattctt 77400
cattactcgt acattagaag acccatataa ctaccctgta gttgctacag agaaacttaa 77460
aactaaagat gtaaaagaaa aacaagtttt acaagcgttc ttagcatttg ctgatgacag 77520
atttaagcta ggtgtttaca atgtgttcct agcagatgaa ccatttgtat atggggacaa 77580
aacagaatag tttcattata agagacccgt taaggtctct tttttttgt atatagtgtt 77640
gacaatgttg tagtttagtt atatactata cttatactgt ataaggaggt aaccacatga 77700
acgacaataa ggaaaaatgt attaaacaag gaatacgaga tacttataaa gggtacgata 77760
ttttattaga tgaagagaat ggatttttct atgttagcgt acttgaccca gatggcaaag 77820
aaatcattag tgggtttgta gaggcggata aacctattga agaatactat aaagagctcc 77880
taggtaaatg cgaccaagat atatcgttta aagacctttt agggttctta aatggacgta 77940
gagacactga acgtacagac atacgttttt taaagagaga cagtggggta taattaaatg 78000
acaaagataa aacttattac aaaaaagaac acccaaggct atgtcatgaa caccctgcta 78060
cgtagatttt ataaaaataa tgtagacgta gaatttctta ataaattcaa tctacctgat 78120
attcataacc acatagggga gcatgatgct gttatcatag tagggtttcc tttctttgaa 78180
agccaacgag gtgcgttaga cacggcactg tcatctatgg acaacccgtt tagcaaggtg 78240
taccatttag caacatttgg ggacacctat cgtaatgaag gtagctttcg ttcatttgta 78300
gacgaggtta taagccccgt tggtcatttt gtagaactaa taattgacct aactaagttc 78360
actaacacag gtacaaaaga ggatgaacaa aatgtagtgg ctcttgctaa agaggcatta 78420
gtgtttgcca aagatattat agaagagaca gacaactaca atcgttatga agttacagac 78480
agaactatct cttgggttct tcttgtagat ttgcttggag agaacctata taaggtgaca 78540
gagcctagta aagagctaga caccattttg aaagaacaag aagtacttgt agatgccttg 78600
aacataaata tgcaggacta tgtgctaaga acaataggga agatgtctgc aaacgtcatt 78660
aatggaacag tggtttgttt cggttatgca gaacagcatg tcaacgaagt agcccataaa 78720
ttaattaatt tttataagtc acataactat caaaaagtta ttgtctttat tggtaggcac 78780
acaaaaggtg acgacatgtt tagtgtaagg agctatggtg tgaatgccgg agaggttgtc 78840
tataaagttc ataatggtaa agggaaagac acaacggcaa ccgtcttctt aggtaaacct 78900
agtgaagctg taaataacac actgctaagt gtgctttctg aaattttata gtttaacttt 78960
gtggtataat aaagatagat aaattttgat aggagtgtaa atttttgaaa aacaacgaac 79020
ctttagagaa gttattagac aaattagatg aaccaagaat tttacaaaca attattatag 79080
gtagtttaca acggagcttt aatcgagtac acgttggtaa atttaataaa ctagcacagg 79140
agtttgactt agataaggag aacctgtata gcttaaaggc actagttaag gaaattgaag 79200
aagataaaga gttacacgaa ctttacgaag ctagtatggc aggcaaaatt acgctagagg 79260
ctgttcgtaa agtattgtta caagatgata agtcatcgtt tgatgtactg tcttcttacg 79320
tagtagaaaa tcaagcagtg ctagcccgta accgagagtt cggtaagtta caacgtgagg 79380
gagcttatct tgaccatcta attagtggtt tgaagacata cttattaact gaactaaaag 79440
acatgtctag tttaaaatat atcaataaaa atttaaaggc accgaaagta tcctcagacc 79500
gagagcttat tctgtgccta tctgattggc atattggtgc ttttgttaat aacattgaca 79560
caggtggata caactttgaa atctttaaag aacgacttga aaagttatta gaagaagtat 79620
tccaagtggc tatggagcag gatattaaga aaattcatgt ttaccatatt ggggatatta 79680
ttgaacacat taatatgcgt aatgttaacc aagcatttga agcagagttt cctgctacgg 79740
agcagattgc taaaggaatt agagttcttg ctgatacact caatttacta gctaaggcag 79800
aatttgaagt gtctttcggt atggttggtg gtaaccacga ccgtttccaa ggtaacaaga 79860
atgataaaat tcataatgat aatgtggctt atcttgtagt agaccaactt catttcttac 79920
aagaattagg ggcattaaac aaagatatta aacttgtaga caacagaagt gacgtttata 79980
```

-continued

```
gttttaaaga tacagttgca ggtaaacgta ttaaagtaac tcatggtgac actgagggca  80040
aaaaagtgga tgttaaaatc cctaaacata tcaaagatga agttattgac tatttaatca  80100
tggggcatat ccatacaaca cgtattattc aagaagactt ttcaagattc catgtgtatg  80160
tcggctctcc tatgggggca aacaactact cagcagagaa taacttgcca acaacaagtc  80220
ctgcacagct aattatggta ttagaccctg agcgtgatac accgcagttc atgccagtat  80280
tcttatagga ggtactcgta tggaaggtaa tttagtttat attttattgg ctattgcata  80340
tgtaggtgaa ggtataactg cctttactaa tactaagcgt aaagaaagat acatgattga  80400
agaaggagag gctcctttgc cacgtagttc ttatgtattt ttaggcatta actacctttt  80460
aagaatagct atagcaattt ctcttatctt catcatacca actagcttgc aacttaacgt  80520
aacaggtatt gctttgttca cactaatggt atttgtagtt ccttttatag caagaattat  80580
cgaagttgtt attagaactg caattgttcg ttatgttcaa aaacaatata ttaagcagtt  80640
agaagaacga aaaggtaaaa gagagactaa ctagtctctt ttttgctata ttgaataatg  80700
aggtgactaa gtatgaattt tacagaagta ataagcccta atggggagac atcattaata  80760
gatgtaaaca acccaccaac attaatcaga cgtggggtct tatctattaa aacaaaggtt  80820
aataatgaag tgaaggaaac tcctgtttat attgttgaac tagccgagga gctaacaggt  80880
actgatgtag tatctgtcta taaagtaaaa gagattggag attctatcca aaaagactac  80940
attgaagaaa aagtgacccc taggttcaaa agcacaacat atctgggtga gttagcacaa  81000
aagattaaag gacggtcgat aaaggaacaa cgaagagttg aaacaaaacc accattattc  81060
ctagccccag tagttaatgg aatcgataca ttcacaggaa tcgaaggtaa aggtttctac  81120
gaacgtgaag aggacagaca tattctatta cctgatggaa aaccgggcat agcctatgga  81180
gataatacag ggtttttat cggtttgagc tcgattaagt gggacaaggc atatgtagac  81240
gtggagtcta taacaaaggg ttatttgtca cagaaacaga tatggtttaa cctagatggt  81300
caaagaccac aatttagaag tgagacacta taatgacaga taaacaattt tatgaggcag  81360
atattcaaga gttaatttta aataagcaaa gaatattcgg ggatatagga aagagcgcta  81420
ttgtttttga gaaagcaatc atgcaaggta acacaatatg tgattgccta gtcttcacag  81480
aaaaacgagg gctcattggc atagaaataa aaactgaacg tgactcgaca aaaagattaa  81540
ataaacaatt atctgattat gaaaaggtgt gcgactacgt atatgtatta tgccacgata  81600
accatgtacc taaagtagag caaatacttg ctagacataa tcataaacac gtaggtatcc  81660
tagcttacac agagttcatg ggagaggcaa tgttaggtga gtataaacaa cctagccgtt  81720
cccctaaaaa atcagcttat catatgttaa atatcttgtg gaaagaagat ttaataagaa  81780
tgcttggtac attcagacgg tatggtgata gactagaagc taatggagct aaggttatga  81840
aaacaaacag ccgttctggt ggagtatctg gactttatgt taaatctaca actgctagaa  81900
gaatgactaa acctgaactc attaataatt taataaatag agtaggcggt accgaagagg  81960
ctacgagagt gttctgtgat gtgtttatcc ataataggaa tcacccagag aaagcaatta  82020
agttaagaca ttttaaagca aaagagaata ggggtgacct agatggggtt taaaggtgca  82080
aaatatggtt cttggaatac tgtagttggt aagaactatg tgggtactgg gggcagaaca  82140
agtggtagta acacaaaacg gctgtccaca aaaggctact accaagtagg atttgttaaa  82200
gaatatcaga acttgacaga aaaagatatt atgttaaaat tagagtatgg aaaagactta  82260
gtgtctagct acactggtgt acctgcagat atgattaagc tacgtaaaaa gaaagaggag  82320
caaactctag catctttaga cacagtttat tatgttagca ttggtaagga acctgtaggt  82380
aagctgtcta tacgagctca gagacgtttt agagaggtag ggttaacatt tatataccta  82440
gagaagaact acgtacagag gaagcttaga ggcggtaatg tacgtagtgt aggatatact  82500
aacgcaacca aatctcagaa acgtaaagca gatagacgga agggcaataa gtctaaaaca  82560
actagataga tggaggacta ctatgagtat ttatgatgag ctaattggta aaagtgttat  82620
agccctagaa tatgcggagg atgggtgtga ggcaagcctt gtactaaatg atgggtcatg  82680
cttaaaagta tcttgtaacc cagagccaga ctgttgtggg tataatgatt ttgaagttat  82740
tctcccagat ggttttgatt tcacagataa cattattaca aaagttgaag ataatagtga  82800
agaatgttat ggcggttcaa cagttaggat aggcattttt accaatgatg cacggatagt  82860
tattgaaggg gactacggaa gtggttctgg gtggaactat ggagagtatg tagacgtaga  82920
aattgtaaaa taatttacta ttagatggag gtaagctatg cttaaaaaag ggaaagaagt  82980
aacactaaga aaattttata atattatcac agataaggaa tcagtattgc taggggcacg  83040
ctacacaagc tcaataatga ctacagatat tcctattaca acaacttttg aagatgttga  83100
ggtagacctt aagaaagaaa cagttgcagg aactatttca ttcagaccag taggagaaag  83160
acagattaat gcattaagtt tactaaaaga agcaagcaca gcttatgggg gttacggaga  83220
gttcctagat gatactattg agaaaccttt aatcaatagt gattttgcag tagatgttag  83280
cctagcagac tctgctttct ctaacctaca agagattcca tttaacctat atatgtcctc  83340
cccaaaagtt ttttatacag aagtatcaat tagagggcgt aaacatatgc aatatgtatt  83400
agaggatgag tcttctagcg gtgtaacaag tacattagca ctggtattcc gtaaaaaatt  83460
gtatgatggg gaaacattgc taggtgtgca tacttacacc gaagcactag caagagtaga  83520
gggaattaaa gtgttacagt ttatcgcaaa tggctctgta ctagaacaag taatcggtgc  83580
agtgtctgtt ttagggggta gcacaggaac aaccctgttc cctatgtttg acgatatggt  83640
gatgcaattt gtgatgattg agtctgttcc ttgggtgcac atttcttgtg atacaggagc  83700
aattgctttt aaggaagaag acatccgcaa tgtaaccatt aagtcagcta gaccgggaga  83760
atataaggtg actatctact tgctagacga aaaagttaca ttgttaattg gataaaattt  83820
taaaggaagt tgacaatata tgttgacttc ctttttgta tgtgctaaga taactacagt  83880
tggataaaaa aaataaatgg tatagaggga gagatttaac atggactaca aaacaaaggt  83940
atatgtagga gcgcttagtt ggttaggtac tttaggagag aaacgatatt tagggcaaat  84000
gcgtgatgta ttagctgtgt acgagctagg tagtcgatac gcaggttact atacagaaga  84060
tagcgactat gactatatgg ttgtatacat gccggctcct tatgatttaa tgcatcctac  84120
aacaatttat aaacaggaaa cagagattga tggaaataag gtagaggtaa aatatatgtc  84180
tatcgtggaa tatgtttacc gtattgaaaa tggagattta gaggctttac aaatgttaaa  84240
tgccacaagc tcccaaagtt tcttcggaga gcctattgaa ggtattgaca ataagcgtac  84300
tcgtttagtt acgtatatga aagaactaga atacagaaga gaaacattta cttatttagc  84360
accagagaag ttgtttagag gaattaatgg tcgtattaaa gccacaaaaa cacgtatgga  84420
taaggctatt gagaatgacg atatggaagt agcggtaaaa tgtgctatcc ttattcgtta  84480
ttttatggac ttattagttg tgctagcgga cggggaatct attcgtgaag gtctcacgtt  84540
ctctcctatt attgcaaata tcattagaga gtttaggaaa gactgtgagt cagcacaggc  84600
taagacactt atcaatactg cacaagtgct attagaggcg gatagagaag agattttaaa  84660
tagtattaaa gaccatgggt tatcagatgg ttacgctcaa tcagttagac aatatagttt  84720
```

-continued

```
aacaggtcga ttgatagatg tactattagg aggatattat gactaagtta gaacaaaata  84780
aagaaatctt agatatattt aatagaaaag gaaaagtaac agataaagta gaagaatctg  84840
ccaagattat gctagaatta gaccacgatt atgactttgg tacaggggac attgcttata  84900
cagagcgtgg cacagataag aagggacgtt tctatttaga aagtcgtttg tttattcata  84960
aactcatgcc ctatgggttc attttaaacg ctgtagtaag taaagtacac tatggagacc  85020
aagaggagac cttagaacga gaggtatccc gtgtatatga gctagagtac aacctaagag  85080
ataaggtagc tgtgctaatt aagaacggta aaccactaaa cttctcagaa aataacatta  85140
gtaacatgtt ttctgggcac gtagcacaga atattcttga acaattagat acaatgtctg  85200
gttcagatat gtatgtatct gtgtatgaac gagttagtcg agttaaggat gaacaaattg  85260
gtaaagtatc tcggttcttt gatagattga tgaagtacaa caagattgaa ttaatttata  85320
agagtggcgt tcctgaaggc tttgctttgg cttatgctta tcgagtagtt gttgtaggag  85380
aaggcaaagt ccgtaatgaa tggtacgaac ctgtaaagag tgtggactat ttagataagg  85440
aacaaacaaa tccggctaaa cacctaggta ttccaaagtc tatctttaag attatttgtg  85500
aaggtgggtt agagtggaca ttctaccaaa aaatagctag tcgtttccat aaatcattag  85560
ttaacagaag tactaacaaa actcctaaat cccccactgc tatgaagaag atagagaaag  85620
agattgctaa gttacaacaa gcctatgctc gttttggcgg ggtactgtat aacctttatc  85680
agtttactaa agagctagat gaacaatatg gtatctccca tagtaaggat attatcgaaa  85740
cagagtggga atctatatac gaccatatta ttgcaggagt agttaacgat aactataata  85800
gtacaactgc ttatgatatt tctatggttg caaacctaga tttctacaga actgttcgtt  85860
atctatacta tcgagtatat gttgagcaag ggcttacttc acaagcagag gctagataca  85920
catacagaga ctacttgaga gcacaccatt atatgaatgc ggtacctgtt aagtacccta  85980
aagctcttaa gactgctcat gacattatta ttatgaatta ccgaacaatg aaggataagg  86040
tattgaatag taactttgaa agtagtgtag ctaaatataa atatttagaa gaagtatcag  86100
ttagaggtgg ctatattgtt aaggtaccta atagtgtgga agacttaact aaagaaggtt  86160
ctagtttaca ccactgtgtt gctacttatg ctcatcaagt agcagaaggt tctactcgta  86220
tcctgtttat gcgagataag acagagccag atactagctt agttactttt gaggtaaaaa  86280
ataataaact agtacaagca agagggctag ttaaccgtga cttgacaaat aaggagcagg  86340
agttcctaga caaatggtta gttaaagcag aaattggtaa gtattagttt gcctaaaaag  86400
gcggaatatg gagtgtgtat agaccaattc acaatgaaaa aagtacacta aacagttgtt  86460
atttcattat taggtaaaac aacttatttt agatagctga tattgaccaa caaatatttc  86520
ataatgattt agctattaaa gttacaaaaa ccctactaat acgtggggtt tttgcttgtt  86580
tcaattacat atgaaatttt acagatgttc tgctatatta gttacagaag ctaataaaac  86640
aaagggtttc gaccctaaa aatgatattt catataatta aaagttgaag gagtttataa  86700
ctaaaatggc taaaaaagaa gtaaacaaca gctcagtatt actgaatcta tacaataata  86760
aattgcttgt atctaaggta gacgaggcgt tagacgaggg taaaccatac gatttcatta  86820
ttgcttttg taaagagaag ttcgattttg aaattaataa acctgcatta tctaggtaca  86880
aagagaaacg tagagagtct ttagaaacag gagtagactt ggaatcacta cttgacaaac  86940
gtagaaaatc aggtaaaatt attgatatta agtctaaaga ggtaacccca cttcctaatg  87000
aaacatacga taacacattt ggacaagtgg aacagatata caatgatgta gaggtgttag  87060
atacaatcat acaaaaaggt tttaactctc taaaagaggt agactatgtt gaagccccac  87120
ttgctatgaa agcaattgaa gtaaaagcta agataacagc taaccagttc caaggtctaa  87180
gtctaacagg tctaagagag ctaagattaa gacagtctgc taaagaacaa gcaatgactg  87240
agattattct acaatttatt ccagaagaac agcatgaaga agtattcaat gcaattgaat  87300
cagcagagaa agagttctat gaaaacttag atttaacaga ggaagaccaa agaatcacta  87360
aagcgttgca agcatcaggt atggatataa tttaggaggg ctataatggt tgaaaatttg  87420
agagaggtaa attataaaac attaacctta gaagaaagtt tacatgcatt acttgaaggg  87480
aagaccctta ttgtaaaagg gctagaacaa agacgtaagt tagatgtgct agtaaggatt  87540
ttctcagaag gtgttgtacc tgttacgcag ataagttatg atacaacccc tgcggatggt  87600
tattggagaa caggatattg gcagatatac gatttgccaa ttaatgccct tagcacatac  87660
ccatgtttta tctatgatga tttaaatacg gatgaactcc ctaaatttat gataggggac  87720
actgtttact acacaagtaa agaggactct atcaaagatt ccgccattgt aatcagtgtg  87780
tacaaagacg atgttaacaa taagtggtac tacaagttaa gtagagacaa cgaaatatat  87840
gcagagagtg agattagaag agacaggtta taagcctgcc tcttttttt taaatttatt  87900
gttgacaaat atctataact ttgttatagt ataaatatca aggatattga taataaattt  87960
tggaggtgcc atgatggcaa atattttaga cacattaaag tggttagata aaggggacaa  88020
agttactatt gaatttgata aagagcggtc gaagtatgca aaactgactt tgcacgattc  88080
atcagctaag acaaatattg tccgtaacat tgttttttat gatttagaca aaggagtgta  88140
tgcttacact ggtgaataca cccctgtatg ggataactta ttagatgata tgcgtaagac  88200
acaaggcgca ggacctgaaa ttaagactac aaaagtaaat cagttagcta cctatgaaga  88260
tgccttaaag tttattgaaa caaatggtac gttttatgta attggtgagg aagtaattgt  88320
taaggttaaa gatgcaaaag agctagcatt gatgttaatg tactttagag atgctattga  88380
agaactaaga ggagaatacg accctaaaaa acatcatgta gatatgacaa ttgaattatc  88440
aaaagatgtt ttgaaaaaaa tggcagtacc tagacatgaa ttagacttat ctttaggtgg  88500
cttaatgaga gctgtatcac ataatgttgg agaagacctt tttgaaactc ttgggtttga  88560
ctacatgaag caagcttggg aagtcttagt taattgcttg tcactagaca ctatccatga  88620
ggtacctttc cgtgtgctag acgaattaga gaaagtaaca gatagcatgt ctactacaga  88680
ccatattgtt accttgtatg ccggtagaga acttaaaaaa ttctattcag aggaagagta  88740
ctttgatgta atcacacaca atttagctga tgtgattatg gattggtcaa ctatttttac  88800
tacagctgtt cttaataata cagaagatga tgaacacctt aaagagttac agcttaactt  88860
tgagagattc aagctagatg tagcagaggt tctattaggt aacgttgcaa gacatttact  88920
atatgcagga gttaccgata gctttaacga agttaaccat tatgttgtcg gagcaggtaa  88980
cctgattaga acagaaggtt tgattagaat agaagagtta actggaacat tagacaaccc  89040
taaagatgaa gatagttctg aaacagataa taaagagtta ctagatgaca tctttacaaa  89100
tacaggtgat gatggtgttg aagactttac aaaagaagta gacgagcttg ccatgtttga  89160
gaacgaacat gctgaggaac ttttggaagt caataacaaa ttaaaagaca atcaagagtt  89220
attacgtaaa actgtggagg cgatgggtat ggcttcttac tctactattg attcatcatt  89280
tgaacaagag gaagaaacag atagcaacca cacagagact tgtgaggata ccagagcttt  89340
ccaaatgtta agctatgcag tacgttcagg agacaaatta cttgaacgtg tagagaacca  89400
cccacaaact gaaaaagggt tgaaaatggc taaagattct ctaaaagagt ttgaccatac  89460
```

-continued

```
agtgaaacca gaattagaag cttatttaaa agcagaagag ctagcggaag acgttgatag  89520
acatgcaatt gtaactacaa ttatccgtat caaggacact atggaagcag atatggacgg  89580
ctgtaccgac ccaatagagc aaggtttatt ctacgcagga agcctaaata tgttagaaga  89640
aatggaatca ttgttacggg ctagcaatag aggttatggt tgggacgtaa cagctatcta  89700
tcttatcttg tccattgaac tagcttatgg gacttacggg ttgtctgatt tagactttac  89760
aattaaaaat aaagaggaaa ctcgtaaaga agaacaagat gcaattaatg gtattgtaaa  89820
cttcttagcc aatcttttaa atacagtact agaagaagaa tcagaatcag aagaaacacc  89880
tgtagtagtc gaagaggaag aagaggataa ggatgacttc tcactatcta cagaagacac  89940
tgctaagtta ttggcagact ggtcaaatgg tctacctacg tatgtcgtta ctcgtaaata  90000
cggaattagt atgggagctt tatactctat cttatatgca aatggggcag acgttaaatc  90060
ttctaaagta gcagaacgag tggctcatgt ggaaaatgac aaagatatgt taaacgcagt  90120
tattcgagac tacaagaatg gtactcgttt agtagatatt tatactaaat acaaattata  90180
taaaaatggt ttgttctatc ttttagataa atatcgagtg ccacgtagag gacgtacaaa  90240
gaaataacaa tgattaaggt agtggtgctc aactactacc taatctttta ttagggagga  90300
acttaattga ttctttttat atttagcatt attacaatgc tatccatgtt cttactatat  90360
ttgtttggga tggcttctgt ggctgtaatc aaagtagggt ttcttatagg tagtcaaaac  90420
gatatagcta aaggcataca ctctttactt ttcacaggta ttgcacttac tgtagtcacc  90480
ggaataacta gacagtgttt actattattt taaaaaaaat tggaggattt agcatgttgt  90540
tttttattgt tttagcagta tttataggcg ggcttgcttt atggggaatg tatgatagtt  90600
atgggtacct agactggact tcatggttat ttagtattgt ggtaggctct gctgtagcta  90660
ctttttttcac actagcggcg gttggaatta ctttcgatgt tgtaccaagt catggggtaa  90720
cgaaaagtca tgaattacac cctatctatg agaacagtaa agtagttgta gaggctaaaa  90780
aagaccagtt tgagattaac gtagatggcg gtttggtagc tattgatgca gaaggtacta  90840
ctatcctatc tactaaagga gaggttaagc ctaaaattgt gtttacagag aactatataa  90900
acaacaactg gtggactcgt ttcctaggta tagcaggtaa ggtaaaagac acttcatcag  90960
ttctttattt agactcagat accttagtgt acaataagcc ggaaaagaac agtagcgcac  91020
cagatttaaa aattaaataa ataatttaga aaaaggggct tgcataaagt ctctttttat  91080
gttaatgtgt atttatagat aggagggcta ctatggaagg tgaagtagta tacttagatg  91140
agtttatgaa ttttttaact gatagtggaa taaatactga tgatattaac gtagtagatg  91200
atagacagga gggctagtat gtcttataca aaagaagcat tagaagctag aggctatcag  91260
tttgacaata tgtctatgat agataagatg gatgccttgt tagaactgct agaggaacca  91320
gaatttcgag aaaagatgaa agaagagtac gcagagttct ctaagaggca caataacgat  91380
gaagaatgaa aagttagagt cttaccttat gaaagagatt gcacctattt tagatgaaat  91440
agagatgagt gaagaattga taaagggaat ggagaacaac aacccatccg atacggttac  91500
agtctctttt tccaaagaag aagtagacat actcttagca atgttagacc ttgaggtacc  91560
tagattagac agtggttctg aattgtttag ccctaatctg gtaagggaag ctaaactaca  91620
attaattaag aacaagctaa cttcaaaatg atttctcact agaattaatt agtgagaaaa  91680
aaattaaata aagctattga caaataacaa aacatgatgt aaactaagtt tataagataa  91740
agaagaggag agatacacat gaatgaacaa aagaaagtat atgcaaaatt aacagaggac  91800
gaggcagtat ttgcttgtga actaggagat aaaattaaac aaattagaga gagccaagag  91860
ctatctcgat tagaacttgc aaaacgagca aaagtagacc actcaacatt aatcttaatt  91920
gaacaaggta aacgactacc aacattgcgt attatgatga agttgagcaa agcactacac  91980
cgagaattag ctattagctt tacagattaa ggaggaggta tcatgagagg gagcctagat  92040
tattacaact atttgtacca aacaatcgaa aatcgaccta cggaggagct agatgtcctt  92100
tatgacggtc tttataaaaa agccggtgac ctgtttgcaa tagataactt tcaaggagtt  92160
aaagaaggca gactaatttt aaaaatatta aaggctatta gagaagaaat taatagtaga  92220
attgatgaag aaattgacct ttacttgtat aatatctatg acagtatatc agatgaagac  92280
aaacgagtaa attggctata tgaggtgtag gtatgtttag tgttgttaag gctgacagct  92340
atgttaaatc agacatagaa atgtatgaat ttaagaatgt aaaaagtttg gcattgacta  92400
agaaagagaa agaactatgg acaggcaaaa ttgctaaata tgttaatgag tttattgtaa  92460
atgcttatgg agactaccat gggaataaaa tacctgaaat aaatgttgta atcaatggta  92520
agctaagaag aaccctaggt tcttttgtcc aattcactaa cacaaacaaa cactgtatag  92580
agataaatgg taggtttgtt aaagaagtta ttctattaca agaaacaccc ttagctcaaa  92640
gagcgcttga tattttaatg gatgtagcca gacatgaagc tatccactat acactttgtt  92700
atttaaatag tttaagtgga ggagacctac caacgttcaa ctaccatgac ggtggggagg  92760
actttgaaaa agatttatgt ttgacaggaa cttcacctag tggtgctacg aaagaagagt  92820
atatttatag ttcttttaca ctaggagcca tcagatgccg acaccatagt acttgccctg  92880
aatgtgggtt ggaaacatac atgtatacac gaggacggta ctattgctat aatgggtgtg  92940
taggggataa cggtagaaaa attatattta gaccacaagg tgatattgca atttatattg  93000
atgaaccaaa atctaaagct aaaccaaaag tagaggaagc tctaaaagac tataaaggag  93060
cgttaaagct accttataca ggtacggaag aaataaaata aaaaaaatag ttaaatgtat  93120
tgacaaataa caaaacatga tgtaaactaa gtttataaga taaagaagag gagagattta  93180
ttatggcata cgtaacaaat attgatgtag tagcagatgg gttagatttg tataatggga  93240
actatgtggt agaacgaggt caagtagtta cttttaaact acatgtagcg acatggaaca  93300
atgagcctac acccgaaaat gcttatgcga ttattcgtaa taatggggta gattataaga  93360
gtaaagttga tgaatttggc aatgcagagg ttaccttccc agttaatggt cgtcctgacc  93420
aagtaacaac tagcatcttt gcattaactt ctggatatga gggggatatg cctcgtgtaa  93480
tgtcagctat ctttagtgac gaaacagaaa ttaaacaaac tgtaatgaac gttacagcat  93540
ctattaatgg ggagccagtt agtcgtgaag gtgtattttt agaacgagac caagtagtca  93600
ctgtagatgt taaagcaaca ttatctacag gtaagttctg ggaaggtgca caggtaggtg  93660
tgtacaataa caacacggaa tacttaggtg acctagatgc agatggttat ggttcagtaa  93720
ctttccaagt aaaaggaaaa caagggatgg acacatcagc tatctacgta ttcgttaaag  93780
accatgaacg agaagctaca ctaacagttc ctgtgaagtt tactaatact actgttacta  93840
cagaaacttc tacagaagaa tcgtctactg ttgatacgac tacaggaaca gaggagtctt  93900
ctactacgga tacaaccact gtagaaagct ctacaacgga ttctacgtcc tctacagtag  93960
attctacaga aagtacagta gaaagctcta cagagcaaac agtgaccaat gaggacactt  94020
ctactgattc aggagtagtt gaaactacag aaacttccca agtagcaggc tacacagagt  94080
ctacttctag ttctacagag tctaaagaag ttaaggaaac tcatactagc actacagaac  94140
atgctaaaga gttaccatct acaggcacag aggtagacta tgggcttgtt gggttcggtg  94200
```

```
gtgcaacatt aacagttgtg gtggcactag tagttaaaaa attgttgaat aagtaagaaa  94260
cacaatattg cgaccctcat taattggggg ttgcaaatta tattattttt tttaaataaa  94320
cctattgaca tttaacaaac tataaggtaa actaagttca taagataaag gggggaaaca  94380
aatgagtcaa gtaagcaaac atggagaaaa acgtgtacgt gaacgtgtag gagtgaataa  94440
gagctctgta gaccgacaat ttgagttagc tttagaacga ggatacagac aaaaagagct  94500
aacaggtcgt ctaaagaaat gggtagtatc aagagtattt aactctaagt accctcaaac  94560
atgtatttta tataatggta aatgcttcat tgttagcagt gaaggtacac tagttactgt  94620
gttaaacatc ccaagtaatt tactaaaaga ttttgcaaaa ttatctaaga aaagaggaaa  94680
ataaaatgga tattatggat attgagtttt tagaagaaca taaacaatta gtaaaagaac  94740
atgtagaaca agaattaaaa ttaatgcacc ctcttaagaa gttacaagta atgacagact  94800
ggttaggaga tacagaagac aagctttctc aaggagactt agattacttc aatgacttaa  94860
cagaaacaga gctaatagag gcaatggatg ctagtgaaat tgtagagtct tattcagatg  94920
tcttgttaga ttttattgac tactacaata ttgatttaac tggtttagag gaacagctag  94980
gtgtgtaacc atggataagg ctgaaaaggt agataacatt gtaagacagg tcacaggggc  95040
tgttattaag acaactgcaa aagtagcttt tattgttttt gttttaacct ttgcaggtgt  95100
tttagtaggt tattatagtt attcattttt aacaagtgca gggtggtttg ccttacctat  95160
gatattatca gtagatttgc tatatgttgc ggtactgtta ggcgggctag cctttatatt  95220
tgcagaggtc tacaaagtag ttttagaagt gaaaaagata gttaaacgag gagggcaatt  95280
atgagtaata aaacattaga acaaagagta atagatgcta acaaagagat aaacgataag  95340
cttaacgaat catcaattat tcgtaaacaa attgaagaat tagaggaaca ggaagccatc  95400
ttactatcag acgtagagga cttacttgat tacttagaaa atattggagt agacctatag  95460
gagggactta ttatgaataa aaaagtagag gaaatgacaa tggaagaaaa agacaaagca  95520
ctaattgcaa tgggacttat tgatgtaacg caggaggcag actgggtagt attagctact  95580
tgtgaagaat gtagagaaga gtacgaagga gaggagtacg aagaagggga ctgtgcagag  95640
tgtgaacatt gtggaggaga atactttatg attgagacag ctctcgaggg tactcgttgt  95700
ggacgttgtg atgactactt tgatatgtgg gacgactact ttgagtttga gaatgaaggt  95760
aacccatata aagataaaca tatctgtgaa cattgttatg aagaactagt atctatggga  95820
atggaagaga aattttaaga tactactaag aaggagactt aatcatgaac gaattagaag  95880
aacttaaaaa tacactgatt agacaaaaac tttcaatgtt ggagagttac gaaatgagag  95940
aagcatcatt ttggataatg tttaatggga tattacgtgt catcatgtca gtagctgtca  96000
tagcctttgt aaactatgct aagcatgtaa gaccagataa tgtagccaca tggtttctag  96060
ctctgatttg ggttattttc ctagcagaag gtattaaagg tgcttatgat gctgttgcat  96120
ttggtattca ccgcaaaaaa tttgctaaac atattaaaaa tatgcgtggg ataatcgcaa  96180
tcacacaatt acttattgaa gaagacgaag agaaattaaa aggaggcaag ctagatgagt  96240
aaagatgaga aattagttga gtggtttgaa gttgccttaa tggtgattat gtggttgctt  96300
atcacgttca gtatcttata cacaatagtt tccttacctt tcatggtaca cgaaggggac  96360
tggctaggga ttgtgcgaaa cgtactactg gacattgtag tattggcaat tggggttgtc  96420
gctacatggt tgcaattaag atttaaaaaa ggaatggagg aataattaat gggatattta  96480
gagagtgcaa ttgaagaaat tgaacgagta ctactaggaa ataaaagtcg tgacaccgaa  96540
gaagtttatt taaacaatgc aattcggtat atcaaaaaag agttaaagaa aaaagaggta  96600
gagccaacgt ggttaaatga accacagaca ttgttcctta attggtttaa cgaattatac  96660
gcagtaggtg gtttaactca tgtaacagag gcagtaggtt ttttagaatc cacaggaggt  96720
agaatgaagt atccagaagc atattctgct ttcagtaatt taagtgagaa tgaattgctt  96780
gaggtttaca gtaaatttta tacagggtta ttcttaaaag cacaaggggg tgaattagaa  96840
tgaactttca tggtaaagta tttcatgata aagtatttga cattctttct cgtgattacc  96900
ctgattggca gaggtatcag acagagaaac gaccacatcc caatgagctt agaaaagact  96960
ttgccattga tagtacagat agtagatatg aagagtatgt tatgggagag tttaatgtag  97020
aaacggctag cggagatgtt aaagtatacg cagtaggaat tagaagagta gttcataaaa  97080
aagctgagga ggagtaaatc aagtggagta cacagagaaa gacattaaag aaggtatgaa  97140
gttacgttgc acagataata gtaatgtagg ttactgggaa gttgataagg tttacgaggt  97200
aacacgtaat aaagaccttg gcttagttat cgcaggggaa ggtgaaagga gtcacagaac  97260
cgtaaagtat attttagggg tgttaaatgg tgacagcaaa attaaatttg aagttgtaga  97320
ggaaaagcct gtacgatttg ctaaggtaac ttgtgtatac cctcctgata gaggtcttgt  97380
agaggttggg cattgttatg aagtgcttaa agagttccct acaggaagtg tgcgtatcta  97440
ccttaatagt aaactaggga accatgagtt actcccagac cagtttgtct ttgtagatga  97500
accatcaaat gatggagaaa aagacgtaga agagctagat gtagaagcta agatactagc  97560
caagattgaa cagttaacag cagaagcaga acaactgttt gctaaacgtg accgtgtaaa  97620
tgagcaagca cttaacttaa atgcaaaagc tcgtaagtta gaagaatctt tagaggtact  97680
aagggagtac atgtagctaa gtgtttttat gattacatct attaaggaga tgagagaatg  97740
atttattata ttaatttttt agaagatttc gcatcaagtt ggagtgcaga taagcgttat  97800
cgtgttcgta gaattatgac aactggtagc tacgctatta ttgacaacta tggtcatgtc  97860
agattcagca gtgacacagc acgaggtgtc cttaagaata tagagcagga gtatgccact  97920
cataaggttg agcttacact agcagaagaa gaaacaacga ataagcctag gtttaaagta  97980
ggggaacgag tgaaagtgtc taatgattta caggcattcg ggatagaata taagactcac  98040
ataacctcta agatgatggg ctgtgcaggt aatgaggcta ctattacacg tgtttggggg  98100
agtaacgtac gctactttat taacatcgat ggtatacacc aagattggtg ttggacggag  98160
gacatgttag ataagattga agaagaacct acactatcta ttagatgtgt tgaggcagtt  98220
catccctttt ggacaaaagg taaagcctac gagataaacc ttacatctga tggtcgctat  98280
cgggtctggg atgacgagga agatggtagc agtggcaaat ccataaaaga actactggac  98340
gttatcaata gtggcggtaa caaatttgag ctactagatg aaacaccctc agaagcagaa  98400
cctaggctaa accatgctat atctgactta gagaaaatag aagctaagat taccgcttta  98460
tcagaagagt cttttcagct attcaataag agtgaagagt taagtactag agcaattgaa  98520
ctgcaagatg agtcaatagc tttagaagaa gcattgtata ctattaaaca atatttatag  98580
gaggagattt aaatgcgtaa aaatgtaatt tgtagattag aatgtgtttc aaaagacaaa  98640
gacaacttag gtgaatggac tgtagataat atttaccctg tgtttgaatc agaactaggt  98700
aaagtatata tcctcgatga tgaaggtacc acttgttcca gagatagcgt gtctcttatt  98760
atctctagta tggctagctt tggggtaaca tttagggtag caaaagataa agcagaagac  98820
cctatcccta gcaatccaca aagcagtaca tcattagaaa tagttaaagg gtatgaacac  98880
ttagcggagt ttatagactc attaagtagc aaccaacgtg tagtgtctca ctcagtagac  98940
```

-continued

```
cctaactctc aatggcacta tatcatttat gaaactaagt cagctgaatt gggcggagta  99000
accctagagg aattactaga cacactagtg tataatgtac atgttgtagt gatggaacgt  99060
agtaagagaa catatgagcc actagaaaat cacacgttta agtgggaata tggaacaaag  99120
aataccaagg attgggaaaa aattgtacct ttattaggtt gcaaggtgtt taatactaac  99180
ctcaatagta acagagggtt ccatattact attttgaaat aaactgttga caactactat  99240
agtccatgct atagtaggta catagataaa aaacaaacaa tattaggagg tagcatagag  99300
tgaaagaaac agaaaagaag tatagcagag agtataaggg gctagaattt gaaattatta  99360
tcacttatta ccctgaacaa gacatgtatt ttgtaattgt aaggaacgga cagcaccgta  99420
cactaactaa ggttacaggg aaagagtggg gaatgagccc tcatacagag gaagctgtta  99480
ttgaggtagc acttgataca tgctacacct atattgaaaa tcaagaagcg caaaataact  99540
agattaagga gggactatga tggtaggaga cttcatttta tgggttaaac aagcatggaa  99600
agaaacattc tgtattcatg actacacggt taaaggtgta tataaaacat tagatagtca  99660
tgggtactta aagtgtaaaa agtgtggaag aattaaatag gaggacaaca acatgaacca  99720
gagacagaag actagacaag aaaataaatg gtttgaggag catgggtatg atacacagca  99780
accacgagaa tgtattgagt gcggggctcc tttaagttgg aaagatgagt tacagaaaag  99840
tcatggagtg tgtagtgagt attgttatat gagaagtgtt gggctgtcgt tatcagattt  99900
tatttaagga gatgaaacac taatgtttaa aaaagataaa aaagaagaaa agacttatag  99960
agaaggagac ctccttaagg ctgtaggggg ttactaccca gatgctaggt tgagtttagg  100020
aatcacatat ccattgtata aaaccaccaa tgagggttgg tatattatca ataacgaagg  100080
tagtcgggta accttaatcg aaatggatgc tttaggcatt gactacgctg tgatggaaga  100140
acccttatta gaattaaaag aaggagaccc attgctagtc gtgtccgacc ttaagagagg  100200
tgttcgaggc ttagcaggtg cagaagtaca gtgtttaaac attaccggtg aaatggcttc  100260
actagcaggt acagttgttc attatgataa agatatgagc catattgcaa aggggctgtt  100320
cactgttaaa gagaacgatt cttattggtg tgtagcgatt gctattccac taaataaagt  100380
agctgaccct gattttgcat tagagcattt gcttgctacg ttaaataaaa aagcctctac  100440
taaacgtctg gtattgaatg agataaaata tgatttaaac cttcttcacg aagagctaga  100500
cgaggtgtcc aacgaagtag agaagctaac aaaaaacatt gaaacaatct ataataacag  100560
ataggaggta cttagatgag tatgccgagt gatttaggga aaacattaaa gaaacctatt  100620
gcaataaata agaatcctga tttttatgaa ttagcggtag gtggtaaagt tatctacaac  100680
gaagaagtaa tggagattgc taaagctttc tctaataaga agaccaagta ctacctacta  100740
aacacacgaa gtaacaaaca agtatgtgta ccagtgtatc atgtaagacc ttatgatacc  100800
caagtagagg gtcttaaact aggtgatgtc ctagatgcta tgcacattat gacaactgta  100860
acgttaaggg cagtgaacaa gcacgggttt gttgtcgatg aggatattat tgaatgttta  100920
gtagatgaca tcccagaaaa tgcgcttatt gttactagtg aggtatcccg tattcagcca  100980
gaggattttg gtaaggtaac tattgactat tttgtttaga tatgttagga tagacttaag  101040
ataggatagg ataaacttag gatgcgcttt tgtttaggat aggcttagga taagatagga  101100
taaacttagg atagacttag gatagactta ggatgcactt tggtttagga taggatgggg  101160
gatataacta tgagttacgt taacgagttt gaaacaattg gagattggtt agatagagaa  101220
atttatgatg tgttactaag agatgagcat gatattgaag aattagataa ttggggaatg  101280
gctttgtttg cattaagtga aggttacgtt ctaacagatg gacttgacaa accattccta  101340
gagttaacta gagaagacct agtagcaggc tacaaccact ttaaagaaga gctgaatggg  101400
tggttacgag gaggtaaact gctagaagtc tctgataatt tatctacaat tcaggggttc  101460
agttttgacc atgacgatgt tttattctta gaggataaca acaaagctta tgcaatgcta  101520
gtaggtatta tcattgaagc aagagacaca tataaaaatg gtttctgtaa gggtcactat  101580
gtaatacctt accaagattg agttagcctt atggctagct ttttctttta ccctaagtag  101640
caggctacaa aaatcttcta agtagcaggt tgcaaaatct tctaagtagc aggttgcaaa  101700
atcttctaag tagcaggcta caaaaatctt ctaagtagca ggctacaaaa atcttctaag  101760
tagcaggcta caaaaatctt ctaagtagca ggttgcaaaa tcttctaagt agcaggctac  101820
aaaaatcttc taagtagcag gctacaaaaa tcttctaagt agcaggctac aaaaatcttc  101880
taagtagcag gctacaaaaa tcttctaagt agcaggttgc aaaaatcttc taagtagcag  101940
gctacaaaaa tcttctaagt agcaggttgc aaaatccgga tgcgcccggc tagcggtggg  102000
gagtcaagcc atgcgggttc accttaatag ctaccgtccc cagattgtcg gtttttctta  102060
ctatatatag taagaaaaat aatttaaaaa aaactaaact tttctattga caaaaaacaa  102120
aagctagtat aatatagagc gtgtaaggaa caacaataat aaaaaaaata aagataaagg  102180
ggcgctatta aaatgaacaa gtataaattt acctatgcag acattaagaa tttaccagag  102240
gaagaaaaag aaaaagaatt aaaaaatcgg tgtggtgttt tagcggtaga gtgcttaagc  102300
actaaacagc tacaaaagaa aaaacctcga tttatggttt tcttaaatac cgttattttt  102360
gatagtaccg cagaaacagg cggacaatac gcaacggcaa ccgttaaaac cgaaccgata  102420
ggggacggac gttttcgagt gtgtgacggt tggggacagc tttctaatgg aattattgaa  102480
ctgttaaaat aatttataaa aaaaatattg acaaataaca aaagataaac tacaataaac  102540
ttgtcagata aagaagggaa gttatgaaca tgaatgaatt agaagcagtg aaagaatgga  102600
ataataaaat tgaggaacaa caagaagtgc taaacaaggt tattgttgct ttttataaag  102660
aaattgactt aaaggttaaa atggtaaacc gtggcttgct agggcagtta ccagcttttta  102720
acgaactaaa aggaatgcta tcaggtatcg agctaacagc aaaggttatt gcacccgata  102780
acgtgctgcc tattacaacc cacaactttt tagaatattt atttctaggg gataacgaac  102840
aacgagcata cgcaaaagaa tacctagacg gctttttaaa atcagtagaa taaggggagg  102900
aaaattttcc tcctttacat aaaaaaaaga ttgacaagtt aaaagaacca tgataacata  102960
taaatgtaga caagggaggg gctttacatg atgaacggac taaaaaaact tgtgaaagct  103020
aggcaataca agaaagaagt aaaaaaaatt atcactatgc aaaagaaagc aataaacgaa  103080
ctagaaacat taaacaaaaa tttaaaatta attaatcaaa actattgaca aataacaaaa  103140
gataaactat aataggttta taagataaag agaggaagtt attgacatga cagaacaaca  103200
atttaaaaaa gagcatttat tagaaccaac agaatggcgt agtgggggct acttagacac  103260
tagtttaatt gaccaatcac aatcttatta tattgagtca cgtccgagag tctacggcgg  103320
gtgttacgtt taccaatatg ttacaatgaa agatggcacg gtttacgagc tttacagcat  103380
gacggcaagc actaggggaa ttgttgcaca taactgccac gctagaaacg tattgcaaag  103440
agatgtaaaa caatacagag atagcgccat tcattattaa ggaggggagg gctttcctcc  103500
tttacataga aaaaaaattg ttttatctat tgacaaataa caaactatag tgtattataa  103560
atttataaga taaagagagg aagttttaaa tatgaaatta tctaatatta ttctagtggg  103620
gttgcttgtt agcgttgtac tactttgggg ctaccttagc attatgattt gcttacaagt  103680
```

```
ttttagagcg ttaggcggtt gggatattag aacgttaacg gtttgcagtg gtttgctatt  103740
tgcctatgtt ttcggtttaa aaggaatttg ggaacaaggg acagggaaaa acaaataaaa  103800
aaagtttata aaaaactatt gacaaaaaac aaaatataga gtattatagg cttataaaga  103860
taaagagagg gagttataaa catgaaattg aacgttattc atttactatt ttgcttattt  103920
caagaacaag aaagctattc tattttaagt tacgaatcag tagacgaatt ttattctagg  103980
ttaggttatg acttagagag tgagtggcta cttagggact taggtattaa tggaacaagt  104040
gacttggtag agttgctaac agattacaat aatttattag agaatgagat aacaaaagca  104100
gtcttttctg ataaatggtt ataatttaaa taaaactatt gacaaaaaac aaattaagga  104160
ggaagaatag gggaaacggg gagggaggga cttcctccct ttacatagac taggagggct  104220
taaaatgaca acagaggaga aagcactaaa cattgcagag aatagaggta taacagatta  104280
taaggttagg gggaacgtat taagctatta tactagctac ccgatggaaa aatgcacata  104340
ccttgtaact attgacattg aaacgctaga agaagaaaga aaagaactca aaaaatatta  104400
taaaaaaggc ttgcaaaatg cttgcttata gactataata taaagagggg tggcggttgt  104460
tattaataag agaataaaaa aattacaata tgaaagaatc agaaagctag aaaagagaaa  104520
aagaggtgaa ccacctgaat ttattttcaa cggtaactat tcattggaag aaatagagct  104580
atttttacat tttagaaaaa aaagtgaggg caaaaaatga gcgtggtggc tttgcttggt  104640
ttacttgtaa aaattacatt tatttttaaa ttgttagcag ataaaaaaag ttaatcaaaa  104700
ctattgacaa ataacaaaag ataaactata ataagtctat cagataaaga gaggaatggt  104760
aaacatgaca aaagcagaac tacaatataa aaaagcaata ggagttgcag tctttgcaac  104820
aagtggaaag gataaaaagc aactaggaaa cgtggcaccg tttagcattt atgagatttt  104880
agaaattgac ttaaataaaa atcgggtata ttatgcttta aattgtgggg aacgacatgc  104940
agtatgcttt actaaactac gcaaagaaga agaaacaggg aacgatttta ttttaatcaa  105000
taaacaacca tttttcttaa aagatatgca caaaggttta agttggtcaa aaagtttata  105060
aaaaaactat tgacaaataa caataactaa tatacaatag gtttataaaa taaagagagg  105120
aagtttttaa catgacaaaa gaaaacaacg tatttttaaa tgaaaaagag ctaatgaaag  105180
aagttattga cactttagaa aatggctttg atggttatta ttgcgactta catggtgaga  105240
tttttaatca tggagcaaat gctgacatta aagacttgga agaatatgga atttttaacg  105300
caattggaga aatacaagaa tacgaagaag aaaatttttgg ggaggttttg acagacctag  105360
gaaacccgac ggaggttacc aatacgcttt actatattaa aggtcacgag tttttatatg  105420
gtagattaga ctttaatgat gttttagcag atgttgcaga ggggctaaaa ttagataaag  105480
acttatggaa cgaggaagcc accgaggaag tgaacaaggc tattattgag tgtttaaaaa  105540
aagaagtgcc ttatttaata gattagaaaa acagggagga gtttcctccc tttacataga  105600
aaaaaaatat aaaataaggg aagtgctaaa catggaaaca ttagaaaaat tcggttatac  105660
atggcaagga atgaaagaag ttacaaaaga agaagcagag aaaaacatta agaacggggt  105720
cggcactttt ctattatatc cagataacaa caattgaagc agtgaaagaa agaaagcaat  105780
gcaatattag ataaagtatt gagagcttgc aacttgttac caactgaaaa gaacgtgcaa  105840
acagctaaaa actttttaga agaacaaggc tttaaagtag aagctagtaa agagttagcg  105900
ggaaaatacc ttgtaaaatt ttcaatttaa taataaagaa tgaagagggg aagttataaa  105960
aatgaaacta acagaaaagg aactaaacac aattttaaga gatgatgaaa cagggaacgg  106020
gggaacggct ttcttaggtg aaacactagc cgacttctta gaagaatcag gtattgactt  106080
tacaaaccta actattttag aagtaaatga attactagaa aataatggaa ttgaaccaat  106140
tgaggtagtg ccatgttaaa aaatatcaaa aaatcagata aactcactag aaaagatata  106200
caaggttttt ggggagatga aacaaaaaca ttagaagaat ggtataagtc aatttcaaaa  106260
gaatcagaca ccgaaaaagt agaaactgct aaaatgatta atacattgaa agaatatgca  106320
aataacaacg aatttcattt cgtaaaagga gagcaaggac aatgacaaac acaaacacaa  106380
acaaccaaca atggaatcag aagtttaatg atggtactat gaaccagaac aaccaacaaa  106440
aggaagttat cactttacaa gtcgcagaaa gtttcgtcag tcagatttta acaaaagaat  106500
attcggtgat tggtttagtt attctaatgt tttattttat gtttggcatg tttggcattt  106560
tcgggggtgc aatctatatt gctttcactc acacaaaccg taaaatcggg gcatggcaac  106620
aagtaagaag cgtatacact attaaggagg aacaagaaga atggaacaat taaaagggct  106680
aacaattaga gaattgatta agaaactaga agaagtgcca gaagaaaata aggacttgcc  106740
tatttatact tttgaaaatg aaaactcttt gcctattaaa gatatttcat tatatgatga  106800
aaatgctaaa cactcacaag aaaacccgtt aagttttgat gtaatcagat aaggaggggc  106860
aaagatgaat agttttatga ataaacaagc taaacaggta aaaagaagta aagaaataaa  106920
actagtagaa gaagtaagaa gaaaaaacgt aaagaaacgt ttttcagagg aagttagaaa  106980
gtacctagaa aaagggtata taatcaggtt agaaaaataa gtttttccat ttgctttaat  107040
atctattgac ctagaaaaag gggaaaaggt cataagtctt attcttgtga acgaatatga  107100
tggaatagca aactatacag caatgaaaaa ggttacctta agagaaaaag ggaatagagc  107160
tatcctaaaa agaacgttaa cggataaaga tataaaagta gtgagtatgt ggaaaggaat  107220
ataaaagaat gagtgtatac agtttaaaat tactagcaat cttagggata gtattattct  107280
tttcagttat cgggatagtg tacgataata aacaggacga aaagaaataa acatataaag  107340
aggtaaagag ataaggaact atagagctat ataaatgtgt acacttatag gaataagaag  107400
aaaaggaact atatacctat acactcatac actcatattc agatagacac ataataagta  107460
agggtaaagg agagaggagg agggagagaa agaggaaaga ggaaaaaagt tgtttacctg  107520
agattttaaa gaatcgactc catcaaaaac ccgacaaggg ggcgcataag tctatttcaa  107580
aataatctga aataagtata gttattactg tttatagatg gttatcctta aatatctgaa  107640
aatagggggcg tttatctgat tatatagtta gctatcttat actattaacc atctagccta  107700
ttactgcatt cattgctatt atattctata tagggggcgc ttatatcgtt tatagtgtaa  107760
ttatgagggg aacgactagg aacgcttata cggggcttata gggggcttta aatgcatagg  107820
ctatttatac atatattaga atacacaagg aggaggggcg gaaagttagt agattagact  107880
gttaaaaaca aacgggggat agatgcacat tgttatttta ctgattgggc taggttaact  107940
agctaaaata agaatgctat tgtagcaacg tttataagaa atagggggtgt acttttcccc  108000
tagggaggtt ttaaaagggt ataaaattct tttgttattt aataaaaaag tccatcttag  108060
ctattgacaa ataacaacaa ctttggtatt ctatatttgt aagataaaga aagggagtta  108120
tagacatgga atatacatta gacgaattgc tagaagagga atatagcaca ctagacgaat  108180
tgctagacag tagagaattt aaaaaacaaa tggacaacct taatcacgtc ccacaaatgc  108240
aaccgcaaag ccataacagc aatacgctag cagatacggg acgttatcct gaaaaataaa  108300
attgaaaaaa ggggttgaca agttcagccc ctagtggtat tctatatttg taagataaag  108360
aaagggagtt tttattatga atcattataa attatatgta gatatgaaag agggaactca  108420
```

```
cgattatgtt tcggcaactg tctataatat acttgatgaa aaagttttag ggttgccaga  108480
tattaaaaaa cctgagaacg tagcttacta tactgatgaa tggaaaaacg ggctatattc  108540
ttactatgaa aaactcgcaa tatcagagtt aaacgactac aacgctactt tttcacattt  108600
ataaaaaatt aaaaaaaact attgacaaaa aacaacaact agtgtatttt attaagtgta  108660
aggaggaaca aacctcctta caccacacaa caggaaggaa gtttttacta tgacagaatt  108720
tgctaatatg aataaagaag aggtattgga gctacttaat gattggtttg gtgttagtga  108780
ctatgataca gtgatggaag agttaggaga gatgaaacaa gttaccttta caggtagcac  108840
aaaccaacct ctattaggtg gtaacggtaa cttaattagt ttacctcaat tctttaaaaa  108900
taacgaagca gaatcagagt tcccaactta tggagagcta ctagaggaac tagagaaaga  108960
tacatggaat ctcgaagcag aggacaacac ttacaattat agtggctttt tagaaagtga  109020
atcagatttt aaagttattc aggcagaaaa ttcagacacg actattgcat tctttgcaat  109080
ccatacgggt atagacataa gagcgggcta ctcaaaagca atcccagtta tttttgaaac  109140
ttactatgat ttttatgaat ttctaggtaa ctacttttgt agtcaaggtt actatgcttt  109200
taaacacgac aacaaggaat acacaatcag tttagacgtt tcggctacct cagaatatgt  109260
acgaatttat atagctgatg aaaacaacga ggaactacag caaggctatg aacaagaaac  109320
ttgtatggac ttagacatag aaagcgtaga aggatacttg aaagaggaag gaattgagtt  109380
tactgactta aaacccgcat tgtaaccata taaggcacta gggagcttat acaatagagc  109440
tacaagcctc ctagtgtaat tataaggtaa ataactagaa acgcttatac gaaagaatag  109500
ggggctttaa aatgacaacg gatgaattaa aagagtttta ctatgaaaac gggattgact  109560
tgtggaatga taacctatat tttgaacaag ttgtttctag tggtggatgg tactacgaca  109620
atgaacgcgg tttatggttt aattatgagg attaaaaatt taaacttttc tattgacaaa  109680
aaacaaaaac tttggtattc tatacttgta agataaatag agaggggaac taataaaaat  109740
gaaactaaaa gactttatca aactagcaga atccaagggc gctacattag aagcatacaa  109800
cgagctagga ggttatgaac taactagagg ggacacagta gacccgaatc cggttttgat  109860
tgcttacatg caaggggctt acagcgtaga aataccaaac aaggaactag aaaacaagga  109920
gttaacagaa ctagcgtttg tctataaaaa tgtaagtctt atttatccaa atgaaaaaga  109980
actattgtca ggactaggac tatagcacaa cggcatataa agcccgtagc gaggttttag  110040
cgggctttat atataaatac cttaaggagg aaacaaggtg cttacagtgg aaaataaggg  110100
cgttaggtgg ctagtgagta aagaagcatg gaaagcaggc tttgctatgg aggtgctagg  110160
cttgccagat tgtaaaatta gtacagtatt aaaatcggtc tataaaatta ttatctaact  110220
atttaaacta atctattgac aaataacaaa aactttggta ttctatacat gtaagataaa  110280
taaaacaaaa gaaagagagt gacaagaatg gaaacgaaca aagcatatga aagactattg  110340
aaagaagtag aaaacttaca gaatgattta atggatatcg aggactattc agaagaagta  110400
tatcaagcct ttcaaagatt aatcgaagaa ctcgaagagg taaccgaata gggctagacc  110460
agtcctatag gtatatacca gttgacccgc ccccgtggtt ttttgaccgt actttggggg  110520
tggggctatt tgcctacccc gaccctgggg tataaatttt tttgtagcta gaaaattttt  110580
atatatttat aaagtcaaca ccccacatat aaagtcaaca taagggctca ccctagggct  110640
cctatatagg ctcacctaaa tactcccata taaaaaagac ccctccccgt tgataaggat  110700
aggtcttttt tatttagccg tctgccctat gattggttat taggttcagg ttccgccata  110760
gtctttgcga agtatgtcca gtatttatgg aagtctgcaa agtccaagaa gtactccccg  110820
acaatctctc ctgcttgatt gcggtaaagt ggtactttcg ttttctcgtc tttatggact  110880
ccatactctg tgccatttaa tgaaatccat acaatatccg gagtcacact agttactgtt  110940
gccttatcac aacctagtat cggtcacga agttctggtt ttgtgaaaac tgtatcccca  111000
accttcaatt tgtctagtcg ctctttgtct attaatgttg tctccatttg ttctccctcc  111060
ttatacatta taaaaaatat ttaacgtcta attactgccc tcaaataaag aacattacta  111120
cccatccaat aagcataaat aacaatgttg atacagtagc ttttgcaaat accatcaaaa  111180
tagaatcttc tgtatttgta gtagtcttag ctgtaataaa actaataaat acatctagcc  111240
caattgcctg cgcccatgta agtgttaaca ccccaaatgt tggggcaatt aacccgttcc  111300
acaagaacat cgtaacatac cctccaatag caagggtcaa caccactaga actaaagtcc  111360
caaaaaattt acctaatgca tttgccaatt cgtcttttgt attcttatcc atcgttttcc  111420
tccttaataa tagctatatt tacctcttat ttttttgtta attctattta ggcttgcaaa  111480
agtaattatg ttcaagatat atgcgccaat tactgatact gcctgcattg tgcaaaacac  111540
gattgttatc cagtagcttg tagtagcttc cccgctagtt agcccccaat aaatgctata  111600
tgtcaccatg agtgtgttta gcagtatagc taccccctcct accaataata gtaggtaacc  111660
agatagtttc atttagttcc cctccattga atgattaagt aagctcttgt tcagttcttt  111720
taagtaatag tcacacctaa cgtgcacaag acccatacgt tcccttgtaa tagggttata  111780
atgtaatcgt gtaggtactg tgtactcatt aggtatagat aagtctaatt gggtagttaa  111840
attgactact ctatccggag ggcacatcca tagaggctta ttacagtgcc aacatgtccc  111900
actttgtagt acctcgtatt ttcgtttaag ttgtttctct tcttctattg ttaattagtc  111960
gtgatagcac tgtgtcattg cgtatggctc cctccgcttt tatatttgtt atagtttagt  112020
gttaaaccag tcctatatcc tctcctagcg tttacaatag ttgtttaagg tgataatagg  112080
tagaatacct atcaccgccc taagaggcat atagggtact tataggactg gtgtttagtt  112140
aactgtttta agtggcataa aaaatatgcg cttaagtcaa cattagttct tttactttag  112200
atgatgtcaa ttgcaatata atgatttgtt ttggatacat tagcaatttc ataatctaag  112260
tatggttcta gtacttcgtt gttacttcct atctttgttc taactgttat ggtagcccct  112320
gccgtgggat aagtaatgag tacgtccact ccgggcttca ttaacttaac taaatctttt  112380
aacttcatct ttatctcctc tttaatagca tatgcttaaa tctattttat gtcaactgct  112440
taatttttgt gctcgtagtt gcacagatat tgtatcaaca atgactgccc actgctcctc  112500
cgtaaaattg aagtcaaact gtgtatagtc ttcctcacct gttgtagtaa ttgcaatgtc  112560
tccataatca tcaactgaga aatagatagt tgcagtcgca ttttcctccg gattttgagg  112620
aagtgtaata gctaactctc cttgctctac tttcatctat tgcccccccct tagctctctt  112680
ccttctcaat catcttgata cctgtaaagg catatacagg gagttcttct gtgtaagtgt  112740
actgattagc tttaaaggta acttcgtagt aactctccat gccacagtgt aacatgtcta  112800
catatctaat ttccttacaa ggcatagcat ttttctcact cccacagaag agccagtctt  112860
ctgtacagta ttctactcta cctgtgtgga tacttctaac tgctacgtat ggtttttcca  112920
tctattcttc ctcctgtgta atctcttcta ggtcacaagg gtgtacatct agtgttcctg  112980
tccttagact ataacgagag tttcctcgta ctgcgtaaac accatctggg tatacttttt  113040
caagatatac agtatcccca attgtaaacc catggtcata acgggtatcc ccaataacct  113100
taaactgtct ttttatcgta tacccataca tgtaagcccg tgctaatacg tattggttac  113160
```

-continued

```
cctcatcaat ccattcaact agcttgtcat ctggtgtttc atcgtatggg tcaaaatact  113220
cattagctaa taagctcaac attgaatcgt actttttgat tgctcgtgca acaaaactag  113280
gtatctctac tttttagcc atctattctt cctcctattt aatcataata catacaaaat  113340
acataaaaaa gctaacatca gcaaaacacc accccatcca gctgttacat atgacatata  113400
gaaaacgtat ataaggtatg ttactgctat aattgttaat aatacaagta tcgtgttaat  113460
gagcttttct aaatcaatca ttatacaacc tcctagtcct cacaagtgcg agtctggttc  113520
ttattatact cttactccta cttatatcca aagaacttta agtaattttc tgcttctttt  113580
tctaagtgct cgtttagttc atctagggta acaactttcc cacagtcctc acaggtgtag  113640
gtctggttct tcttatcttc tagcagttca ccatcacata caaggttgat acaatgggtt  113700
gtccaactcc ctacatcatc aggtaagtgc cccattatac gtcacctact tttacggcaa  113760
atgccatgaa tcgttcatcc attttgcgga tttctttctc tgtaaaggta gggatgtctt  113820
ttaggtagtt tgtaaagtca ggagacccta atcggtcgat atagctatat ccccaaccat  113880
ctttatcttt tgcaataatg atgtagtact cgtcttcttc ttcctctacc gtatgaccta  113940
gtacccatgc tttggcaagt ttctcatggt tttctgggtt attagctaac caaaagtaca  114000
tcttactagg gtagcttcct ttgtcaatca tgttaataaa cgttaagttc tcttctttgc  114060
acttgtcaat atatttccct actttataag gaataacaac tttttcaggt tcgtctaaat  114120
catatgctaa ggagactgct tttgctatcc ctgtattgta gcctagagca tgggggttca  114180
atgtaccgtc acaccctact tgagtaaaaa cctcgtcact tagtctacta ataaattcat  114240
tcttattcat ttagttccct ccttaaaaat caagactgtt ttcaataagt tctgatagtc  114300
ggagcattac ctcatgaggt agctctaatt ttgtactctc ctgtgagtct gcggagctga  114360
cttccaaagt atattttact tctgttttct catttacacg ggaagccttc ttctcaacac  114420
atactttata aagtgctgag ttattgactg cgataatttt ttcttgtgta tttacactag  114480
tattgctatc ataagtaatt tcatagccca ttataaaacc ctcctatttg tatactggta  114540
cagcaaaagc ccagtatctt tcatcaattt cttttatttc ttgttcggta aatttgctct  114600
tacccatgtt gggtttattt gagaagtata cttcattatt gtgggatgtt tcaacccaaa  114660
gataacaatc ttctccttta ttaccaagac cagtaaacac gacatggtaa agtggttctt  114720
tctccacctc atatccatct ttcattcgta ttaaagtttc aatagggtta ttcttacttt  114780
ggtctaacca acaatcgaac tctgattcat gtgggtagct gttgccatct aacattctaa  114840
tttgtgtaaa aatagctagg tctaatgcat gtttattttc ctcgtaccat tccgcaacaa  114900
actttggcac aattactttt ttaggttcgt ctagctgttt tgctaaagag attgcgctaa  114960
taattgatag atttgacact atacgataag gtgttttact agattctttt agttcttcta  115020
atttttaat caattcttgt ttattcattt aatttctttc ctttctttca atagcccact  115080
ggctgaatgc ttgtaagact tgcaactgcg caatttctgt catgtatcta taatttttat  115140
aaacagggct attccgataa tctgtttttg tagaattggc tctcagtctc caaaatagtt  115200
ctataggttc aatatctgtt aacgtatatt tttcttttaa ccaacccaaa acaatttgtt  115260
gattctcact tagttctact tggtctacct tatcatcagt gtatttgaac cagattttct  115320
catatgttgt ttgtccgcct gtgattgtta caaattcggc gcttggttgc tcattttgaa  115380
atttttctag ttgttcttcg taatgtatat ccccaacatc aaattcttta aatttaatca  115440
ttgtactccc cctgttctaa aaaccaatca gtaaatgctt gaataacttg cgcttcctcc  115500
gttactgata aagagtaata tgcctcttct gttttagggt cttcataggt ctccccaata  115560
cgttcgagcg cctcaaataa ggaatcttta ctacagtaac ctacttttaa ccattcaaat  115620
acctgtttct gattttattt cagttctggc tttttaactg cctctactgc agtcttatac  115680
gctattttta aaaggtctcc ttcaaaacta ttagggaaat taatttcacc atttgctttc  115740
atatacatat agcaaactct atcaattatt tcgttatatc tttgtctact cattcactat  115800
ccctcctcgt cctctacgtc accccaacca aagctacagt aggaagagaa cacgtctcta  115860
gctacttcgt ctatctcctc attcgtagca ttatcgggta cttctactgt ctctatttca  115920
ccaatacctg cccaagttgt ctcaatatat acatttattt ttcgcatagt ttaataccta  115980
agactacata gtcgtctttc tgtgcataat cggtgatata agtaacttct actttaataa  116040
actctcctgt atacgaacca catgtgtact catttaataa aagaatatct cccacatggt  116100
attgtctatc atttttacgt atttcaaata gttttctacc ttccttaact gctttaaagt  116160
acgtaggtgc aatcttgagg ttatgagtaa cttctaattt actaactaaa tcaaaaatga  116220
tagtgtttaa tttgttaccc tctacctgat gattcaattt ttgtaaagtt gttgatatta  116280
cagtatgcct accttctcta tcaataactg agtttcttct gttatactta gtaagtcttt  116340
ccttttctgc ttttgcctgt gctagtccat ttattgtttt agatactttt acttctccat  116400
ttacaataac ttgtactagg tatctgtcgt cctttgttgc aaacttatta tccataatta  116460
gtacctctct ttcataatct taattgacca gttatcgttg ttactgaata cccgttctag  116520
gtcattcaat gagttggtat ttacaatttc ttttttagt tttctatctg aattaatatt  116580
accaaatcgt ttaaggaatc tttgtttaaa gtgggcataa cccatatagt cgaaggtaat  116640
aacgtgttct ttaccaaata taccccgctc tcttaactta atctctacac tctcataaga  116700
gctatctact ttcataaaat tatttagaag agtgtgcaaa tcaatacaaa tagatgcccc  116760
tgcactaccg cctataagta tatatttagg gcactttata tcggggtaac aaggggcatc  116820
taattcatac cacatattat ttacgtctac cccataccat acactattta catctactga  116880
ggctctttct gtcttaaatg gttttatgca agtatatttc attgtctctc ctccaaatcg  116940
tctagtacgt cttctaatgt tgtgacaacc ccctgcaaat aaccaagttc atgccaccca  117000
taccctctct tatcttgctc taacaaatta ttaattcttt ttgttttacg tttaatttgc  117060
cggttatatc ttctttttag tccctcttca aaggtcacta cctttttgc ttcctctata  117120
tcttttaata attggtctag cccatctcca ttagtgccat agctatacac tagcgctttc  117180
tcgtccttat aggtagttac ccctaatgat tggtatacat acttcttact ggggacaaat  117240
acaagagtaa tgggtctgta caattgaggt aaaagacaat cttctgacag cccaccaaaa  117300
tctgttttag aagatacctt ctctaccaca tacctcatat cttccatact taacgactta  117360
atacataaaa tatatctgtt aataaccatt ttctttagct ccccctacac ccaaaatagt  117420
tttcgattct ctgttggttt aaaagactcc aattctcgtg aagtattact ttttccatct  117480
gttaaacctt ctttcacttt atatattaaa aaaaataaat ctagctatct acaaatacat  117540
tgtatcatca gctagattaa aagtcaacac tttatattta attattttat attacaatag  117600
ttctttatct aaaattattt tagggatagc ccatattgta gtgtaacgaa ccccttttatg  117660
gttacctgta actaatacga acgttgccgt gtctagctta gtaccgagta cagatgctag  117720
tagttcgtgg tcttctttgc taattggtac ttcaaaatca agttctccaa gctctaccac  117780
aaagttattt gctctaattc ccataaagta ttcatcatta cgttttacat ggaatatatt  117840
cttcgtatga aaactttgca taacaatatt tgcaaaataa ctgttatccc tagctacaat  117900
```

```
aaatctatct acatagatag cctctttact gagtagttct tcaatgcagt tactcataac  117960
atattctcct cctcttctaa tagtagctct gatacgtaaa tttccatcat tagactttgt  118020
tcaatcccgt ctagtaataa atgcatagca cacaagccac acaacatttc atctaaataa  118080
aaatcaccac atgtctcctc taatggtact tgacacatta aacactctat cattgtacag  118140
ccctccttaa tttaagtttt ctctaacttc tgttagcacc tctcctaata gattaagtcc  118200
ttcccattta ctcatatcac gagagcgtgg gtctgattca cgtaacccta ttccccatac  118260
tttatcaaaa ggtgatgcct ctgcaaactt ggttccttta gggatggata gcataaagtt  118320
acgtaaacta tcattttgtg tgaatttata agtatttcca gctaaaacga ttgatttacg  118380
atgctttacc cacaagtctt cttcaaaatt tttaacttgt ctacctaaac gtttagcatc  118440
ttttgggctc tctgttttta aaattctttt tgctgtatcg acatcattaa aaagcattgc  118500
tttacgtacc atcatgtagt gctctgctgt cgggaaaata atagcttccc ctaaaccctt  118560
aataggtgca ctgaactgtg atgggtacca ctgtgacaag cactcttttc ctagtttatt  118620
acgtttgctt ggggtatgtc cccaaaataa aatatattta ctcatttaat gttcctccca  118680
atattcatag tagtttccct tatgttcaaa aacaaaatga gggctaggta actcaccatt  118740
aacttctata tgctctgggt tattataaga atagtagggt tcgttaccag taggactaat  118800
tgctattact ggtttatctt taaaaaatgg tggtatttta tctccatcat ttaagtttaa  118860
tttataggta cttaatggca cgcttctacg atgccctttc agtgttgtat actcctcaag  118920
actaattatt ctaaggaaac ccttagcttt tagaggcgct aaactgtcta tcgaaacgtc  118980
ttcttgctta taagtgacaa gggcgctata aatggttgag gggtttttgt atgccactga  119040
ataattaatt gaagtgtgct tatggtttgc taaaaatttc tctaattcct tagataaacc  119100
ataaggtgta tcactatcaa taacttttac tttaatcatg tgttatcctc cctatatgct  119160
tctctaactg ttcctatact ttggtctggg tctggtttac taaatggtaa gcttgcacgc  119220
tcttccttac tcaatgtttt taagcaagcc acatgtactg caatgacccc tgacttagct  119280
tccatactat ccgggagtgt aagtatatag tcattataca gtttacttaa cactagccaa  119340
taacgattgc tactactttt catattagct aaaatcatca ttttttcata gtaatcttgc  119400
cccatacaag aaagtcctcc tattgcagat tggaggagct catcttcaag agctaagata  119460
gtatttgcgt accctttcag ctccttgtta agcccctcta tagcaatctc aaaacattct  119520
ctttctggag agcctacagt taaatcatta agtggctcat atgctcttac ttctctccca  119580
ctaggggctt gtcttcgttt acctatacga taagagtctt taaactcata ctcggaacga  119640
aaaatttctt cttgactatt tcttccagac cttcctccaa aatagcaatc ttctactact  119700
ccaccaagac cattataatg tcctctagtt gtccctatga ctttagaatg tctaatatgg  119760
gttagctgac agagctcccc tccgttatca gggtcaccta caatagctgt ctcacataca  119820
ggacagatat atccaaaaca catcacttta tctacctcca attaatatac attaagaaaa  119880
agttacaatt ttttcacaag gaatatcata gtatgccttt aaaccataat gttccaacat  119940
gtattcttta gcataatcta caaggtgctc agggcattta aatgtgtaag agccactcat  120000
cattacacca ctattactta actcttctct cgaagcttta gcaaaccact tagcacactc  120060
tacaggataa ccaataacac accctaaaac ttcctcgtca ttaaacccta gcttaattga  120120
ttcattgtat acttctatac tcatcttatc tgatgttact aggtatatac taccatataa  120180
cctcgtttta tagtaagagc gttccagatg gcttagctct tcttccccta atacgattgc  120240
tacacgatga cctaaattaa aatctaaaat aggctttgga aaaacgtatt ctgctttctc  120300
aacaaactcc acttagccac ccctttttctc attccctaaa ttatcttaaa tgctgtatta  120360
gttagaacgg taagtcacta ttgtgttctt cctcttctgg gatatatagg atattttcaa  120420
tcttttcttc aatatgtcca ataatctctg tgtgctcttt aattttctct ttatgatttt  120480
ctctttgctt atttaacttt gcatattgct gtaattcatc tggtgttagc tcttctagtc  120540
ttttttttcat ttgttttctc cttctaatgt aattttctct acgtcatcaa cactaccaaa  120600
agatgggggc tgtgtcaagt tcttatctaa ccagttagcg ataatgtcat gtaactcgtc  120660
tatagcctca tcgcttactt catccgttgg gtagtagtcc tccgctactt ctccatattc  120720
actgtatagc tgttcccccta cagattctaa catacctact acatctacac taataactgc  120780
tttattgaac tgccctactg caaagcttgt tgttcccttt tcaggtaatg ctccaaatat  120840
atcctctacg tgcatcccta agctatctac atatgttttt ccttcattaa tggacaataa  120900
tgcaagtttt cctgcagaca ctgcctcttc tctcgtagag aacgtctcac acgctttcca  120960
tacatctgtg tcttcctcta gtgctaatac atagtcttta tcttccattg tcttgccctc  121020
tctatccttt taatataatc atatttgtat tactgtctag ttgccatcca tcaaattcta  121080
agtagtggtc ataagggtta attggttcac ctacaactat atagtcctct agtgcgtgac  121140
cttggtcttt tagctctagt aattcgtcta ataaatcttg tgctgtcaaa ttattcatgc  121200
catatagtat cctttctctt tagcttcttc ccactcatct acagaaaaca aacgctcatt  121260
ccgagacaaa gagccataac agtttactgt taagtctacc ataaggaagt ccttaccgta  121320
ttgttttgtc caactctctg tatatggtgt tactgagtgc acttctttaa tatattgctc  121380
taacatattc attttatgtt accctttctt ggtttaaatt ttcgtgtttg tgttcggttg  121440
tttctactta cttctttgta tctacggatt cctaatgcct tagattctgg gcgagaacga  121500
cctatctgtc ttacatataa gtctagcgct tcttttactt tatcatcata catcttccct  121560
aattctcgga aatactcaaa ctcacctaaa tacacataag gcatacgcca gtcatctagg  121620
gtagccgtta ccattgttcg tttgtttaaa tcataattat agatatatag aaacactata  121680
taagcacctg tcatcacaga atagcttgtc ctaatttcac ttagagttac gctgtctctt  121740
aatgatgtta aataaccatt ccactttttt ttacgttctt ctgctaaagt ttctatgaag  121800
tagtttacct ctttttcgtc cctcaccact tgctacctcc ttgttgttta tgtctatata  121860
ttatcatcta ctttgttata tgtcaacacc tttgtaataa aaaagaacct agtaatttac  121920
ttacttaggc tctcttgttt atacgtgttt agtaagttac ctttactatc gacaacaaca  121980
gcattaagct gaccaccata tgcacaggca ccatcaatga aaatacttct atcacctaag  122040
aagacatcgt agctgttctc ttttctcaaa ttaattgtgg gtgtgtgacc cattacaatt  122100
gtcttatctg ttttattctt ctgtaacgct agcggtctcg tccaaatcat ttcatcttta  122160
gtggctgttt tccaatcagg ctgacgataa acaggtatcc ctgcgtgtac acataaggtg  122220
tctccatgct catagtatgg ttctaataaa ctaattactt caactacatt tgttttttct  122280
aataacatct ttctagtggt aaacgcatcc tgtaggtgtt catctaaatc caatagacta  122340
cttattgttt tatcaccgcc attgtacatc cacattgcgt acatctcact taggtcttcg  122400
tagtctgctt ctcttatcaa tggaaatgtt aaaaaatcta ataacatttg gtcatgattt  122460
cctaacaaag cagttcctcc attaataata tgcttataaa cgaaacccag tacttctgcg  122520
gatttgctac ccctatctac gtagtcacct aaaagtatta agtcctcttc atcactattc  122580
caatgtttat taagaagcat tattagctca tcatagcaac catgtatatc tgatacaata  122640
```

```
aatactttat ctttcaatga ataatagccc ctttaactac ttctgctagc caataagtag  122700
ctagtactag tacagtattg acaataaatg ttattactat aaccagtgct aacttataat  122760
ttttactcct agcattatag tttatataat tttttatgtt aactctaata tttttaaaca  122820
aagcactccc atatacgttc agtgctatat atagtaaaag caatacgata aagtagcctt  122880
gagctagaaa cacgtcagac tccctgaacg agttattaaa ccatatgcta aatatcgcaa  122940
tcacttggtg aattataagc attgcgccat taccaaaaag aagtatacta aacgctatac  123000
cgactacgtc tctgtactct gaaagtagtc tatcatatac tattatccct ttagtaaaaa  123060
taaaagcaac aactgccatc tgtataagta aaaatattgt tacggctaat aagttttctg  123120
tatgcatagt cataatttag ccactccttt caaaatgggt aaagaaagaa taataggtat  123180
atcgttcttt ttctacccta ccttcatgta taaaggtaaa ctcaacaaac ttaactctta  123240
gcggtatatc tggtgctttc tcccaaggaa gtactcttgg gaaatcatag aatactcttg  123300
tggggtaaac ttctttcata agtatcctag ggtatctttt ctttggtata aatcttttac  123360
ctattatact tgagtagtca ggtttcattg taagtcacca tgaatagagt atgctctatt  123420
tgctttgtta aagtttactt gtttttttgtt tactaatctt attgcatctt ctaataaaag  123480
aggttttcct aatttatggt tatctaattc tggtgagtct acccctacat tcagtaagtt  123540
tggttcgggt ctggctaact catgaatgtg cccatgtaga ttaattaggt tatctctatc  123600
tcctaaaatt agtgggtaat gtgtcatatg cacaacctta tgcattcgtt ttaaaataat  123660
accaacgtct tcccaatgaa ccctatcatt cagggaagta ttgcgtttaa tctcttttcg  123720
tagaggacta ttatcgtggt taccctttat tagccatata gtgccattta agcgctctaa  123780
gacgttagct atactattta ccttggcacc cattgcaaag tctcctaggt gatatacaat  123840
gtcctctggg cgtactgtag cattccactc tctaattaag tattcgttca tctcttccac  123900
atctttaaat tgtttccgtg tgtccataaa agaggcttcc ccacaaatgt ttctatggaa  123960
gaagtgcata tcagatatta catattctct ccccatactt gctcctcctt agtgtgttgc  124020
aaaccatacg aatacagcta gttgtagata gtgtactgtt tggtcgataa ttagttgtgt  124080
ctttttatta ggtactgttt ttaagaacca tgcactttgt gcttttaaat agtccatgat  124140
aaaatgtgga acccataagc atactacaat tagcccaagt tttactggtg ttcctaagaa  124200
caatgtagtt gcgacaataa tatacgtcca gatgtttaca tggatgatta gtagatataa  124260
atcagtctgc tttcctttttg cgatatagtc actttgtaag gcatagtccc ctactgcatg  124320
agccattgta aggataatta catagtataa gtaattcaaa ttaagtcctc ctctttgtat  124380
gggtaaggac aagtgtcaca ttcaaatcca tattcgttag gtgctccctc taaaatattt  124440
ccgccacatt ctgggcaagt tgctagtttc attgttctgc ctcctttaca tgatttcaag  124500
atatagccct gcacttggtg ttgtagaaat cagcataact tctaggtcta agtgttctcc  124560
gataccttcg tattgttcaa taagtggttt tgtttctgat aaagtgaatg ttacaatttc  124620
ttcatccgtc atgtgctcta ctaatgtgac tgtgcgacca aattcaatat gttgtaataa  124680
atgtcctagt ttaatcatta taatttcccc catcaattaa taatagtaag ataccaccta  124740
tcacaagtaa ccagaatact gctaagatta gtaccattta gttgtcctcc ttgaacagct  124800
catcgtataa ttcttgaatt gcctcacgct ttacttttaa cattgcaatc tgtgctgata  124860
tgatattgct tggttttccc accaaacgtc cctctaagtg cccaatatcc atattgtatt  124920
gaataagggt ttgttgaaat ttttttctaa tctctgtgcg ttcattaatt ggttgctctg  124980
gttcaatctc aaacagttca aacattgaac gccagcgccc atttacgtta ttcaataatt  125040
cactaggtgt gcccccaata tctactgtgt catacccatt gtctttaaag aagtagccca  125100
ccgtttcgtt gtgataaaca ggatattctc tcccttctat gaactgtggt tctagtgcat  125160
ctgcttttgt acatttaatt ccgtatgtca ttttattaaa cctcccattc cttaatgatg  125220
tattggcttt tatagtttgc atagaaatct gagtcacttg agaagtatat atctagttct  125280
tttacttttt ctagtactcc ttgaagggat gtaccaactg ccatgttagt acctgtcccc  125340
ttatcaattc cgagatagag tgtaagtttc tttggttctg caccgagcaa ttcaaactta  125400
gaatgccaat agttatttaa ttcagctaat agtagctcag gagtggctcc tgattctata  125460
atgtctccct catcatctct aaggaagtaa cctctagcat catcatagaa tacatcgtac  125520
tctttacctt ctgtgaagat atgctctgtt ttaagtgtac atctaatttt tactgtcatt  125580
ctaattttcc tccaattcaa tttcttttat tgatacaaag ccaagtatat tgcggaaagt  125640
acggtcttca ttccagtata taaattgtgt tagaagtggt ttgtggtcat ctgtgtatgt  125700
tgttttttgt ctcgtagtag ctttcttcaa tttgttcatc aatattttgt accatttcat  125760
tataatatgt gactgcttta tcatatgagg tgaaagccct catttttacc gctctatact  125820
caaatttcac taaccatgct gagcttaatt tcgtcattta tttcttcctc cacttctttg  125880
attgacttga ttatatatct atggttctct ctaaatgcgt ggtaagcatc atcaagtgaa  125940
tatgcgtata atcttgttgt ttgcattaca gttctatatc cgttacgtcc aaccattggt  126000
tcgtcaactt ctacttctaa ctcaaataat agttgttttc taatcattgt ttttactccc  126060
cttttctatg atataatatt accctactat tatgattctg tcaacaggca aaaaaaagaa  126120
gtagaaaaat ctactcctat tcatcgtttg acaacttttc cataccatat agtaactgta  126180
gtagtacata tagtacaata tcaaatccgt caagtggctt tccaagtact ataactttaa  126240
caattgtcaa taccgctaaa aaaataaata gccacccgat tattttattt gcatgttttc  126300
taattctcat aactttctag tacctcttca atattctttc tggtttcgtt agctaactta  126360
ccagtccgtt caagccaacc tctaaccatt tctttttcta ctttgctatg tttattcgca  126420
tcctccttga taccttctac attttccatc aagttatcta agtcctccat aacatctaat  126480
aaagtgtttc ttagttttaa cacatcgata gacaactcat agttccgttt agacaatttt  126540
tcgttacgga taaagttctt ttttagttct tgttgtgttt ctagtagctg agtagtttta  126600
ataaatatcag cttctaattt actaattccg tctagttcat tcatcacatg tcctcctcat  126660
attctactac ttcctcaata agtttcagta cttcttctgc tgtgcccact gtgctatagt  126720
ccgcaaagtt ttctgcaggt ttcataatag ccactgaata gggtttgttc tctacataaa  126780
tatgcccgaa tccttttaaa gaatgaatta cctctactgc ccatccatta gcgtactctt  126840
ctcggtatac tacttgctca ctggttgctc ttactggttt attcattgtt aaaaccatag  126900
aagtttctta caatgttttc tacacgttcc atgccctcta agtagctacg tttctcaggg  126960
gagatatagt tcttgtaatg agggacttcc ttctcttcct ctacctcttt tgtagtacgt  127020
tcaatcagtt taataagttt tacttcgttc tctagttgag actggataat gtctaacagt  127080
tcatttttcg agcagttgtt tagtggttta cttccatagt caataattgt catagtagtc  127140
ctcctatttt aatgtgtact ctttatatcc tttatgtgta tcgtgcccgc actttgtaca  127200
aaagcctgct tgttcaatat ctattgaaga gtaccctgtt tgtactgcat acgtctcata  127260
agtatggtca cacgtatctt cttctgattc atctatttc tctaaacgaa tagcctctcc  127320
ttctgccact tcgtggttaa agagcaatac tgcagtttta ataggctcat atacctctgg  127380
```

gtggacggct tcattcatct taaagctatt tccactaaat tcattgaaag catctagcca 127440
ttcctgactg ttctcataag atacaattct gtaattcata cgaaagctcc tctcgtgttt 127500
tcttaaataa ccagtaccgt tcatcaattt cttttatctc tgcctctgtt aaatagaagt 127560
cttttaattt ggatagggta tcttgactca atggctcgtt tctaggtagt atacttactg 127620
ctaactgccc gtccttgcgt aatagtaacc cgtagtctct ctcctgtttc tgaggcatta 127680
ctacatagta cttaggtaaa ctagcagtgt ttgctactgc ttgaataaaa gtatctgtat 127740
tagcaaagaa ccatttacta aactctgact tggggtactc acatgcgtgt ctctgccctt 127800
ccaagataat ttgtaactta tccataagtt gttctcgttg tttatcaata aactctttta 127860
cctgttttgg tacttctacc tcattattca tagtttgtct cctttgttat actttgtcaa 127920
tagtgatata cacatacttg ccctctaact gcttaacaat atctagtatg tcatgaccac 127980
ctagcttaaa tgtgtttgtc tcaaaccctt cgatagtaaa ggaagaccaa ccgtaccaac 128040
cttcttcaaa gtccaagacc cccatagatt taagtactat atttttagtg atgtcttcta 128100
atgaagtacg ttctacagca gagaaaatct gaatctctgc gttatcaaga tgatacttag 128160
aagaaatgcc tccatcgtac tcctcttctg ttgtagtgtc ctcagctcct aacgcataca 128220
gtgcattaca aataagcatg tttaaggctc tgtgctcatg gtgatactca atttctttta 128280
ctttttcttt tattaagtaa ggttcgtttg tttctgcacc ggggctgtta tcaatagtta 128340
cccaaccttt taatatctgt ttacccatga ttgctcatcc ttcctttagt acagcctatc 128400
gctgtcacca gtaaatctaa attttccttt gtcagagtta ctgtttgttc atgtacacag 128460
tccggtctaa atacctctac tgtacgattt actacagcaa tatctacagt atcttccgtt 128520
gtctggctta ccttgataaa ctgtttggaa aactccccac ggctaacacc ttctatcata 128580
agctccattt ttttatagcc tcctctctgg aaagtccatg aaagttgtgg aaagtacgct 128640
cttgtagttc atctactgta tttggtaatg tacgaaattc gtctacccct agtgaaatac 128700
ttgaggctac ctcttcataa taacatttaa cgtctactcc cattttacca taaggtaaca 128760
ccattacttc tatatgaaac tcatatggag cattctgtgt taatggttcg tataataacc 128820
atgtctcatg atagtttaca ggaatatcta atagtaaact gtttaaatca tctagctgtt 128880
cagataagta tgcaattctt gtcattttac ggtcttctgc tataggcatt gaacaaccta 128940
acgtgtcttt tatttcttta atttctttgg taagctcagc cattaattca attattttat 129000
aaaacatttc tattccctct cttctatata ttccccttct tctaagaaaa agcaagcagg 129060
ttctccctct ccattttcag tatcacctag gtattcatca tctaagaatg cacagtatcc 129120
agttgagtag agggttacac agtccttatg gtacatcgaa tcgtccgtta accgcacaac 129180
ctcgtccatc tcactgaaca cttcattaca cgccccgcat gatactaact ccttactcat 129240
aggctgcctc ctttatctat tacgtagtct accagttctc taataacctc tgcctcctct 129300
acactagaga ggtctgccca aacttgaagt gtcgcatcgt tagccttacc agatattaaa 129360
ttgtgtaagc tatctgcaat agttagcttt gtacgttcaa gatagtgaat tagccagact 129420
aatacaatta gctgtttctc agttagctca gtattagtct ttgtgtaaac ctcatagtta 129480
tctaaggtta atgggaatgt ttcttcatta ttaattactt gaaacccgtt atttggttcg 129540
ttttcatatt ctccataagt tactctctta cctattttta gttttacata gatgtcttta 129600
ccttctttgt gtagtttatc taggtcacta ttataccact ctcttgtttc aattttagta 129660
agttccataa agctaaccct ccttactgag ttccttgata cgttgtttga tttctgcttc 129720
tgtttttctct agttgtcgca ttttgttttt atgtcgagat aattcatgtt cctttgcagt 129780
ttctgccatt gctaataagt tttctaagct tgctgtattt gccattagat tgccacctca 129840
tagttaaatt ttccattatg tttatagttt actactttaa tttctgatag tggggaatca 129900
aagaagttcc tccccttctc ccatggtaag ataagttctg gcacttcttc tgatattggt 129960
gcattcacct gttgttcaat aagttctaaa tgtcgttcgt aaatgtgtgc gttatcactc 130020
gtccaatata agttacctaa ctctaaccct acagtatttg ccataaccaa ttgtaatgca 130080
tgatactgaa taatattaaa tggaagtcct aagcaaacat ccgaagaccg agccttcaca 130140
tgtaagttta atttaccctc tacaactgtc cagtgagttg tccatacaca tggctctaat 130200
gacatatcgt ataaatcttc cacgttccat aaagtagtca taattctacg agagtttggt 130260
gtgctcttaa gttgttcaat aactgcctct acctgattta gctttaggta tggttgatgt 130320
gttcctgcta tcccaccacc ttttttaggt acgactttgg gaataagtga acctgctttg 130380
cgatttttag ctaactcaac atctccacta taaacaggaa taaaacgttc tttgttaaat 130440
aatgcgtaac catacgcttt tccaatagtg ccatcttctt gctcccattc gttccaaata 130500
gttacacctc gttcttttaa ccacgaaacc tcgttagaca tttcttgcca aatccactgc 130560
aattctgtta gcgcccattt aatacctaca tgcttactac gtaataaagg agcccccata 130620
tctggtgtaa ttgtaaagtt tacaccttca ataaacttag ttgttgcagg agttccatca 130680
gcatatactg cacgagtacc ttctggtagc tctgttactc cgttcttaat aatatccatt 130740
actaaatctt tataaatttt atcaaaatcc atgttgtgcc ctcctacatt tcttttccct 130800
ataatagaaa tatatcatat ctaaatttaa aagtcaacaa aatattataa aaaaaatatg 130860
agacatattg gtatgtctca tatctactaa attctatact aaactggcta gcttgtctaa 130920
agcgttatag tccgcatcgg ttactggttc tactttacct aataagtacc cattacctac 130980
ctgagagaag aagtcatggt tactagttgt tgtagagata ccattcatta caatagggtt 131040
tacgtctgca cttgttgttg ggaataaagg gttcatccct aagttagcta gagctttatt 131100
taaattgtac tccaaaaatg tattaacatc ttttgtccaa ccaatctcac tatatagttc 131160
agcagtatac tgtgtttcgt tctcccataa tttaaatgct aaatcaatta cccattgttc 131220
catttctttt tgttcagttt ctggtaactg gttaaaccct aactggtatt tatagccgat 131280
ataggttcca tgtacagact cgtcacgaat aattaattta ataatttcgg ctgtattaac 131340
catttttgcc tcacctaaat agcgtagtgg tgtgtaaaaa cctgagtaaa ataggaagct 131400
ctccaatagt acggatgcac tctttttctg tagtggtgta ccgtttcgat aaatatcgtt 131460
aataatgtta gctttatatt gtaaacgttt atttgtagct acccattcaa agatattgtc 131520
aatctctgta ggtgtattaa atgtgctaaa aattgttgaa taacttttag cgtgtactgc 131580
ttccataaag gctatgttat ttaaaacagc ttcttcatgc tgtgttctta catcatcaag 131640
tagtgagtgt acccccgatt ctgattgaac tgtgtctagt aatgttaacc caccaaacac 131700
tttatttatt aaatcttgct ccatatcaga gagctttgcc caatcattaa catcgttacc 131760
tacagggaca cgtgtgtcca accaaaattg ctcagtaagc tttttccatg tggcttggtc 131820
aattacatca tcaatcttat tccagttaat tccttcatac ttttcttgca aattcatgtg 131880
ctcatctcct taaattgtac aactttcaca ctctgaaacc cctacttcgc ttccgtcttc 131940
ttcggtgaat gttctaacat aataaattgt ttttatacct tttttccatg cataatgtct 132000
taataaagtt aagtcccgag tggatgtagc gccaccctcc accttccaag gataaagatt 132060
ttctggtaac tctgagcgca taaacaatgt taaactcata ccttggtcaa tatgtttttg 132120

```
tgctgttgcg tacacgttga ttacgtcaat catacttgta ttgtacgctg acttgtaata  132180
tggaattgtc ttctcagata accggggtgc agggtaataa gttttacctg ttttcccatc  132240
ttgacgttct tcaatcatag agataattgg gtgcaatgaa gaagtagtct cattaacata  132300
agcaatacta ccattcgttt ataccgttac tttcgtaata ctttaacact gctcttagca  132360
gtcggactag actatacctt atactatccc aaaatagtac caactattat agtcgttgga  132420
cgtccctcat tttacagagg tttcgatgct gatttcccat tgtattaccc ttagcacctg  132480
taacaaggct tttatttcag cataggctat ctaactaatt ttttctgctt tcgcaacatt  132540
cacgctcacc gtttccagtc acgttgtagt ttagttagct ttagggggtt ccagcaattt  132600
aagttgtttt tgactcatat tcacatatga gaaagcccaa tattatttag gcgccacagc  132660
taaacggttt tgatggtata gaccaccttc aataatactg tttcttaatg tttcccaatc  132720
ttttacatta ggtagtacca ctccatcaaa tacttccgcc accttactag agatttcctg  132780
atttagtgtt ggtacatatt catcaaagta agaaccgtct gcgtatttag agttctcaaa  132840
gttatggaat gttgtgccac gctctttagc aatcttatta cttgccacca aagtagcata  132900
gttaattaat tcaaacagag catccgtcat ttcaatagat tcaggtgagc catattctac  132960
ttggttactt gcgaaccacg catgtagccc cattgcccct aaaccaattg tatgggcttt  133020
atcattacca ttcttgatag taggtactgc ttttatattt gacacatctg taatatatgt  133080
tagagctctt accatcgtct caattgatgc cactacatca ttagatgttt ctaacaagtt  133140
aaggatgtta attgaaccta aattacagct aatgtctgta cctaactctt cgtatacttg  133200
ttcatcattt agcttagatg gtgtctgtac ctgtaatatt tcactgcata aattactcat  133260
aatgattttg ccatcaatag gattggcttt atttacagta ctaacattca taatatatgg  133320
gtaacctgac tcttgttgta aacggctaat ttcttcttct aaatctcgtg cattcattac  133380
cttacttctg atatttgggt tctgaatcat gttattgtat tctgaatcaa tgtctacaaa  133440
tgagaatggt acaccgtatt ctttagcaac atcatatgga gaaaataagt gaattacatc  133500
cccagactca gctagctcat aaaatttatc gggaacaact actcccaaag aaagtgtttt  133560
gatttgcttt gcggattctg cattttcttt tctagttgat aaaaagtcca taatatccgc  133620
atggaaaaca tttagataga ctgcgcctgc accttgtctt tgtcctaact gatttgcgta  133680
ccggaaacca tcttctagca ttttcataac agggacaacc ccgctacctg ctccctcaat  133740
tcccttaata gggtctccaa gagctcttag gtttgaaaga tttaacaagt agtccatgct  133800
ttaacatggc tcagactata tcttaactaa atttgttacg tttagttcta cgcgcttcca  133860
aaacaagaat ttcacttgta atgtactcta ctaggttact cgctaatatc ctcccgacaa  133920
tagctacccg ttcgatagtc gttacacttt tacaattttt ctcctcgaaa ttttctacac  133980
aacttagctt tatctccaag tttatctttt cttttaaagt agccggatac gttagctaat  134040
gaagtagata ggtacctact agcctctgac atatctttaa actcaaaaga ttcgtttgtt  134100
tcgatattgg ttatttttac aggaatagac gtagtatggc aaggttttct ccctagtacc  134160
ctaaaaccat gtttagtgtt ctctgatata gtacaccatt caaggttctc caaacggttg  134220
tcttgtttgt ccccattttt atgattcact actggatagt tgttagtgtt aggtaagaaa  134280
gtcatagcaa ccactctgtg gacaagtagg tacttcctaa taccttcctt gttatacata  134340
gctgttttgt agtaaccgtc tttatcagta gacaacttga agtatctgtc ctttttttcta  134400
attctgccga gggttgaaac ctcgtaggca gggaaatcag ggactgcctt ccagtattct  134460
ttttccatat aaccacctcc ttaaataagg agaaaaattg tacttagcac ggtattgcca  134520
tatctttcga cttaggttcc accgttagcc tacataaagt agacacccta ggtttctagg  134580
ttcacgtagt ttatagtgag ctatattctc taacccactc caccaccaag tttagatagt  134640
tgaagtgcac tgttcaacgt tctaccaatt gaagacattg aatcttctac ttgaattaga  134700
aaacagctga catactcccc tcttctaagc ctacctgcat ttaaaaaagt aggggttgca  134760
ggttggtatc tacggttaat tagctcatct gcaatcttca tagcaagctc ttcgtcacca  134820
tcacccattg tgagtgcatt aaacgctact ctatcttcat aacgctctag gtatcgttcc  134880
ccatcatctg ttttcattgc gtattgtttg tagaaacggt aagcccccat aaatgtgtcg  134940
aatctgaact ttttactata gatgaactta aataattttt ttataaattc cattgagtac  135000
ttgtcagtaa tcactgtttt atcgatgtac ccttctctaa taaggtaact aattttctcc  135060
tctaaagagt agaaaaatac tgtgttcttg tttacatgtt ctaaaaagaa tgctctaaca  135120
gcttctttat ctttgtctaa ctgaatcttt ccgttattag ggatattcaa ttggttatta  135180
agctcaatat atgtgttcat atctacaccc caagttcttt ttctagtttt ttaaccaaat  135240
caggtctaac accattaaat gagaaaccat catcagcttc tacatatggt aatgaagaca  135300
ctccttttttc ttttagataa gctaaagctt gctcatcatg agagatattt ttctcatcaa  135360
atgggatatt ctttccattt aacatatttt ttaaaaataa acattgacca cacatatctt  135420
ttgaatatac tgttactttt gtcatttact acattctcct aacttttttta tcgtatttat  135480
taattataca ctattttgca ttaattgtca aaaataaaga accaaaaaaa ctagagacta  135540
caaaagttaa ttgtagcccc ttttaataag ttacaccttg tcacctaaga aatcttctga  135600
ttcctgcgat ttattcgtaa ccttatcaag tagtaaaaca gaatagtttt taccagtttc  135660
aacctgcaac ctattaaaca ctttctgata ttcttctggt gtgtctgtaa cttctaataa  135720
gtattttgca tttaaaaatg atagtaattc aagtagttct gccttactac ctgccattg  135780
aactacaacg ttaccttcat cgttcgtgta tgttccaatt ttatttctag tagccaaaca  135840
aatcagtcct tcgtaaattt aatgtatttg ttaactgtat acacattttt aactttttcc  135900
caaacgttag ggtatacgtt catcaataac ttagtatctg cgctagcacg tttgtactct  135960
ggcattaatt taaatgtgcc cccatcaata ctaattttag attcccctaa ctcttccata  136020
tcagaaatga tactactttt tagctcatca atctcttctt taatactttt ttgcaattca  136080
tataatttct tgtaagagcg taagtccttc tctagtagct cctttttttg taaatctgtt  136140
gttttcatac atatctctcc ctctcttatt tctataataa gattatagca tgtcagatat  136200
gtaaagtcaa cactttttta tacaaaaaga attgcccatt ataaaggcaa ttcttgtccg  136260
ttgtcttctt caaaaagaat ctctacaggt atattatata atttagcaag ttttactctg  136320
tttttaacac gaggttcttt tataccgttt tcccaataag agattgatga ccagtgaact  136380
cctatcatat tggctaactc tcgtagagat tcacccctag cctctctcac tcttttaagg  136440
actttaggtt ttggtacctt ttcttccatg actatccctc cttattctta aaaaataaga  136500
gcctatcagg tagacaggct cagcatcagg aactatgcga aagccccgat ataagttact  136560
ttaccattac atttacgtgc aaaagcctct aactctttac gagcacctaa acggtcaggt  136620
tgcgaagatt gaacagtaat ttctttaggt accgttactt cacgtgtacg aatttcagtt  136680
ttaccatttt ttaatttctt ctcatactcc tctgtacgag ttgttgtcgt agaaatgatt  136740
ccataaaatt ttttcatatt aatagctcct tactgttttt tttaataaat tataatagtg  136800
gtaatagggt tttatgagac tcctactcat tgtaagcctt ccttaataga tacttacaac  136860
```

-continued

```
tatacgttta tagacctctc tcaaaaagtc tccgtaacgt cttaccttca tcatttaaaa  136920
cgtacacaga atttacaaaa gttttatacc cttctttttc agttctgtac tcgtaaggtg  136980
aatttggcac acgagtgatt tcttcatgtt tagagttaag taatgaaaaa gcattctctt  137040
gctctaaaag aaactgtacc ccatcaatta attcaataaa aggcttaaca ataggttcct  137100
ctgtactgtc tttacaatcg tattttcgtt ctcctaaaat ttgtagtatc atgtctatct  137160
atctcctctg tttaagtatt aatttgtgag tttccactca caatgctgat tgagagagtc  137220
gaactcccat tcccgggtta caaaaccgga gtaatagcca ttatactaaa tcagcgtaac  137280
ccctcaatag agggagtttc ttatactaaa ttaccatatc cgtaggtatt tgttttagct  137340
tgtttaaaca tgatactctt gatagctaag tcattgtact tttcatcgtc ttcgtcatca  137400
aggtacacat caacattaac gttcttacct aaaatatcga ttgtttcatc tttacctact  137460
tgtaagtctt tactgttaaa tgatacatca aaatagatgt cgtcttcttt tgtacgacta  137520
ccgaatgata ctctatcttc aaataaattt aaacttcgag agttaattac aacaggttgt  137580
agcccacctt caaattgaat agtaactgta taatactgat tttcaatatt aagaatgttc  137640
aaatcagcaa tagcttcacc aaatgagatg ccaaagctta attccaacgc aattgctcgt  137700
aagcaatcat agtttaactt aattctacgg ctaaacttaa caacactgtc aatttcccca  137760
tagtaagctt tgtctaactt atcttgcaag taagtacgaa tttcgtctgc atcagggtag  137820
tcgaaacgta aatggtaatg gaaacgtccc ggacgattaa gcataaagtc gtttacacga  137880
tttaagttat taacagtaag tgcataaata cgcttgcgtt gtgataaccc atcgaataag  137940
ctcaatagtt tttcttgtga ttcacgaccg tcacggtcat tgaatacttt ttcaaattca  138000
tcgaacaaga taagagactc ttggtcaata ctgtcaataa attctgcgat acccggataa  138060
gcttctgtaa ttaagataac aggcataccc tcttcaatag ctcgttgaga taagatttga  138120
gtaaatagtg atttaccaat ccctttatcc ccacttaaaa taacccctaa actacgattg  138180
attgttttaa atgtgtgtag tactttctca attttaacta aacggtcacc ataaacttta  138240
gattctttca atttaaaatc gtctgtaacc gccaatgaga acccagacat tgggttgaat  138300
ctaactttat aagtttgcgc aggcaactta tcataagttt tcaggtcgtt tgcataaatc  138360
tcataattac taccataatt gattactttc atatattctc tccttaatac tttttaataa  138420
attataaatg gagagtgatg gagtcgcacc acccgagcct aagcaacaga tttacagtct  138480
gctccgctac tacttacgga ataactctcc ttgaataacc aaccagatag gtacctgaca  138540
cacggacagc acctgtgtct ctctgttact ggatgattaa ttgtgtattt cgcatcacct  138600
aatatagtta tcaaggtagg acttgactat actagattta gctaggttct aactataatt  138660
tcctatgata gctcctacta ctaatcatat ttatatacag ttaaactaca cataactaaa  138720
ccgattacct tggttcgcat gttaagaggc gcaggcaacc aatggacatt gcaggtctcg  138780
aacctgcgac cgttcggtta tgagccgaat gctctgacca actgagctaa acgtccgtag  138840
ggtagtagca acaattacaa atgctactct cctgatgatt ataaacttat caaatcggaa  138900
agacaggact tgaacctgcg acatcagact cccaaagcct gcactctacc aagctgagct  138960
actttccgtg ttacctgttt aatttggtct tttaaactac tacacacagg taaagataaa  139020
ccctctgcca aggggagact atcatcgaac cgtatgtaag ttgcgatggg tagtagccat  139080
attatattag gttattagga agttcaccta tgcagaaggt gggagtcgaa cccacatgtc  139140
cattacagac cgatgtttct aagacaccgt tgtctaccag ttccatcact tctgcggttg  139200
tactaccaag gttacctcta aaaggctaaa ctcgtgtctg gtagggagcc ataccttaca  139260
tggattgcaa ggaacctaac ctcagtagca ccttttacta ttaagggttt ctgatttaac  139320
gttttcccta gaccgtacct taacagtaat actggtgaga ggatttgaac ccctcttacc  139380
tacaagcctc cgacaagcgc tatgggaaac aagcggtgca ttaaccataa ctatgctaac  139440
cagtacacta ctgttttacg cagtcctcat actaataatt catgtggact caacccccatt  139500
cagggaagtg ttagtctatt ttttggtgag aactggttaa ctccatgtac gtcaaacatt  139560
ccctagacta ctcacttaca ttgttattta atgtcacatg acttatgaca gccgtactca  139620
aaagtttcaa ggacttttac ctcactatcc accgacagta tgctcggcaa cgtctttcta  139680
ataataaatt acccatcact gttacagtaa cagaaccatt gaattaacga gcaatatcag  139740
tattactaaa agtagtctgt ctgtgtggta caagcactag cagtattaca acctatagta  139800
tgtctgtttg tcaatcgtta aattctttta caggagtact tgttaaactt agggaggtat  139860
aacaagtatg tgcacataac ccgagtgcta ctccctaaag tagcctatac gggttaacgt  139920
agatggaggg aatcgaaccc ccaaccgtcc gcttagaagg cggatgctct atccgattga  139980
gctacaccta caaattatgg gggtaatgag cccccataat aactcatagt agtttcatct  140040
atcgaggatt aaaatgaata tctaacttga ataaagtata acactattta catagcatgt  140100
caacactttt attaaaataa atttctatac ctcactaatg ccaatgacta tacgtaagga  140160
gagaacgttg atggcactgg ctacttagtt ggcgctaagt tagtgaggta tagaaagaga  140220
actacattga ccgaatcgta ttatacagcc ttagtagttg ttaacaatgt ttggaactta  140280
gtagcttact gcaataagct accccgaagc atcggggtgg gactgtggta agccccaaac  140340
ccttgggtat gctccatcct gcctccggag aagtcaggct caattctcat tagttaaagg  140400
tttactagtt aacggttagc tgattagtca tactacgtaa actactagta aaatatagtt  140460
ttccaattaa ggctaacaat cggtagagga tttgaacccc tattattggt tttggagacc  140520
aacgtgttac cagttacact aaccgactat gtaaagaagg aaagcgaaga ccttctttac  140580
agtaattaaa aaaaacaaac aaaaaaaata caatcatgga atcaaggtgg gatgtaagga  140640
gatgccatgt gtccacttac agtggaatag gtaactacag atttgcactg ttttacatct  140700
tgtttaatgg ttacctgtta atagctaact tccagtgata agtcctctta tatggtagtt  140760
catgtagtat ttgtttgaca atatggtagc tagctaaaat gacgacagta acggactcg  140820
aacccgtgtg ttccacgctg acaacgtgtt gggacagcct ctgccctata ctgccattat  140880
ttatgccgta gttttttttag aaaggaaagt ttttttataa tatacaacaa cagttgaagc  140940
gctgatgtta ctacggcata aatatatttt ttatgagctt ttaataactc aaaacttaat  141000
ataatagggc ttttactcct gcttcatgca cactcactgc attcggtcac acacccagag  141060
aggctgaact atcgggagct acccaatagc ttctctctgc ttttaatgta tggtctagca  141120
cggtggctaa caacgttcac ctaaacattc agcattaaat agtattgtta taagttcttc  141180
ttatatcata tattttgtaa gctgacttag gctacttgta ccaaggtctc ttgttaaacc  141240
catatttcta tggttctcgt caaagggagt cttttgaggt ttctaaggtc tgccaagttt  141300
ctcacgcttc cacctaactt agattctttt ccacaggaac gtctattata tcccccaaga  141360
gtcttgtacc ttacaatcca tgtacactcc acataacgct taactgatac tagcttttac  141420
tagtagttac tcttatgtca ccataagaca tacctgctac ctaaaacact atcgcactct  141480
aggctacatt cagaatcacg ccacgttatc ctagcaagct gttcaaactt tctgcactag  141540
gttctattat attaagtttt caattatcaa aagcagtttt tctttactat ttaataatag  141600
```

```
cacaacctct attattttgt caactacttt tttttagaga gggtgcccct aattttatat  141660
aggggcaaga gatattaaac atagctgagc tatgtaaaag ctaatgtagg aattgaacct  141720
acttaatgta agcaacacca gtttagctta taagcattgt ttgcaaagtc catgctatgc  141780
actcagtagg aatcgaacct attgccgaag gtaccaaact accctgagtg ctcctataga  141840
tatattatac cacataacga gatattaatt ttttttggtg atatagtata tctatatttt  141900
ttaaaatttt agaaatacct ttgatacatt ccggttatcc aacgtatgaa tatataaatat  141960
catgttattc tgattgtgtc aataactttt ttacattttt tttataattg tgtaatgtcc  142020
tatttctttt tttctgattc cttatattta taatatatac tatatagtac tatatatata  142080
tattaattac tattagatat tatatataga taataagaat ctaggaaatt taaaatagga  142140
cattctaatg ctgactcagt tacaataaac ttatggtggc taccttttta caaaaatgtc  142200
ctatttcatt ttttctatct ccttatatta ttatttataa tatatagtat taagtattat  142260
atattattat atatatagta tataatataa gaaagacaaa aatttaaaat aggacatttt  142320
acttaaacaa aaaaaagaga gcagttaagc cctcttatct taatgagaaa tagttattaa  142380
ttgttcccaa tctgacttcc tcatcttctg gtgtttcatc ctctggtttc gtatacaagc  142440
tagtgattct ttctggaaca tctactacgt tctcagtagc tgtctgtatc tggaatgcat  142500
ttacataagt taactcagaa tctctatcag ctagtttatg aactggaatc attggcaact  142560
ctgcaccttt cattgcacca tttacaattg acattgcatc attagttgtt acaccgagtc  142620
ttctagggaa cacagaatat gtcccagatg ctaatgaaac ctctacaact ttctctcttt  142680
tagggtaatt catgatactt ctcctttcaa aatatgttat aataatacta tatactataa  142740
taacacattt tacaaattac ttaaacatgc tgaacacgta agtgacaact gctcctaaga  142800
caatcataaa aacgttctct acaatatccc tcttgtggtc gaactcttta tcgtttactc  142860
cttccagtgc atctatagtt tcttccaact tagtaatctg gtaggttagg tgtgcatatt  142920
tttcttcgtg aacagcaagt cgcttatcaa gactattgac aatatctctc aactcactaa  142980
ccgcactatt cagttctaca ttgtcctgtt taatgccctt ctcggttagc tctccatgtt  143040
ggagtttatc ttccagtcgt tgtagtctta aaacaaggtc atttacttgg taatcgttca  143100
tatatgctcc tccctgtaag ttatgttgct ctatattagt cagatgtaaa ccacagacag  143160
actagtatac ctataatagc gcctaccgtg tagactatag gtatatagta cccattaaaa  143220
aacaagtata gactacctat actaattcca tagagcacga aagtgaactt gtatgatgcc  143280
aaagggctca gttctgcttg tagtttctta tactgtagtg cacgagtgac atagtaggac  143340
atcaagtaaa caaacatttg tagtaacagt acacagacca gtgctgtttc atacattat   143399

SEQ ID NO: 2           moltype = DNA  length = 143400
FEATURE                Location/Qualifiers
misc_feature           1..143400
                       note = Bacteriophage Myoviridae Spounavirinae strain
                        phiEF19G
source                 1..143400
                       mol_type = other DNA
                       organism = synthetic construct
SEQUENCE: 2
gttgttccct cctctccctt agagctacta ttaatatagt acactgagct gttagcaaac  60
aggtgtgcta aattaatata gagactaaaa atgtagacgg gagagtggta aaaatggata  120
atagcaaacg aattattaaa aaaattattt ttattaccat ctctgcatta gtcatggtta  180
ctttaagtaa gctgttctct aaatatgtta ttgtagaaca aaatgcccca tttcaggcat  240
tagttggcgg tgcctcatgt gcactgttat ctagtattct gtttgactgg tatactaata  300
aaaagaaaaa agagaacgta gagaatcaac ttaaagaagc aatcagtgac ttgcagaaga  360
ttaaagctat cataaaaaga tagcctatta ggaggtggga tgggtgtcta ttaccaataa  420
agacattaag gataaacgta gatatatttt tagtcaatct agtaaaacaa caactataaa  480
aagaggggac aaacgcataa gtagtgcaac aagaatatgt gcagtttgtg gaagaccgct  540
atctaagctc gtattaagaa caggcgtacc aacagtagta gtagaccata ttagctgtaa  600
gatttcagac attgttagac taaatgtctg tgaggatata aggtcttgtt atgcgtattc  660
tagtaagaaa ggggaaagct agctaatggg tatggcagat agacttaaag ataatgcaaa  720
acaaaaaaag ttagaaagaa caccagagca acaactaaga gacacattta atcaagcttc  780
aataaagctt atcaatcaat ttatggctaa cgttacatca ggtgctatag aagttgatga  840
tattgcagat ttaacaaggc tatttcagat ttatttacag gttaataata taaatgatgg  900
aatgcaagaa ggtacaggaa ctctacctgc acttacatct gagcataaag acatcatatc  960
tgaaaaggtt agcacagaaa agattattaa ggacggtgaa gaagaggagc taatttctct  1020
tgatgagtta gccagtcttc cagatgacca acttgaggaa gtcttagtta acagagagct  1080
acagatgaac agagagaacg aggcgacctt ctaatgacga caaaagcaca acatatagct  1140
aaaatggcta aagagatgta tggtacagat aaaattacaa cggagcagtt agcttatata  1200
acagatatgc tgaccccatc aacgtaccta ttgagaaatc actctgtgcg taatcaccca  1260
ataactttta ttatatcagg aagggatgca acaaaagcac aggcacatag accataaacc  1320
aacaaagctg tggtctttaa actctactaa acgggcatag taaaataata tacacgtaaa  1380
caatatactg gtaagagaga ctaaatccta gtgtataagg acagggttga cctaccgtgc  1440
taaatcagtt atactataac tgtaaaagcc taacgactaa atttctaggt agctaactaa  1500
aaggagttag tgagaactag ataaaaggca aataaactat gcaagctcaa taaaaataat  1560
aatatacagg aggtgattaa gatagctaag gacagaaaag aaattttcat agaaaagctc  1620
aaaagtgtaa aaggaactga ctttgaactt ataggtgagt ttacaaagca acgagaaaag  1680
actctatttc gtcataacgt gtgtgggcat gtttgggaaa ccactccggt tgtcctactt  1740
aactcaaaaa aaggcggagg gtgccctcat tgtcaataca gaaacaaagc aacttcacca  1800
aaagaatacg aaaaaagagt aacagacaca tttaaaggag aatacgttgt actcaatatt  1860
aatgagtata aaaacaatag tactaaactt aaattcttgc attctaaatg tggtacagaa  1920
ttttatctgc gaccagcaag tttattcatt aatgcaacta gttgtcctaa ctgctctaaa  1980
aataaccgtt gctcaactaa gagaactact aatgagttta gagagttgct tcttaaaaca  2040
aaaggatact cctatgagct aacggaagat gcagagtaca ccggagctaa caaaaaaatt  2100
aaggttaggc atacaacttg tggttatgtt tgggaggcta gagctaacca cctgctacag  2160
ggttcgggtt gtcctagatg taacgaatca aaaggagagc tattagtagc tactattctt  2220
aagctaagca acacctcttt tttgagagag cacacctttg acgattgtag aagtactaga  2280
cccttacctt ttgactttgc attaattagt aataacaaag tgcgtggttt aattgaatat  2340
```

-continued

```
gatggagaac agcacacgaa accagtaagt tgtttcggag gggaacagaa gtttaaaagt  2400
acagtaagaa atgataacac taagaatgat tattgtactc ataaaaaaat acccttactc  2460
agagtatcat acactaatag tcctgaacag attgagcacc tagttcagca gtttttaaaa  2520
agcatagatt tgttgtaacg tagagcaacc taaaccaaaa agtaggttga tgatatagtc  2580
tagtccccta ataaatatcg ggaaaccgag ggtaaccaaa tgggcaacca aagataataa  2640
atgaccaaca tagagacaag gcaataatta aatcaagaca attagggtta agattagccc  2700
ctttataaag caatttgtaa agaaaactct gttaaacggg catagctgaa taaccaataa  2760
gctgataaga gaacctaagt cctgaaaagg atagaggtaa tcccgtgcta aatcagtgca  2820
aagcactgta aatgcctaac gactaaattt ctaggtagct aaccaaatgg ggttagtgag  2880
aactagataa gaaaacctct taagaggaag taaagcagag caacctaaac caaaaattag  2940
gttgatgata tagtctagtc ccctaataaa tatcgggaaa ccgagggtat aacgtaagtg  3000
agatgggtgt tggttctatg ctacagtttg cagacacgca tagttatgat gctgttaaat  3060
gtctttatac attcccaacg aatgagcaaa tgactaaatt tgtacagaca aggttagacc  3120
ctgttttaca gaatgggtac tacagcacaa ttgtagacca agaagttaac tcattaaaag  3180
ctaaaaaaat aagaaatagt tttttgtatt ttcgttcaag ttcaaaaccg ggcgctgtgg  3240
aaggtgtcga tattgactat ctatctatgg acgagtatga ccgtgtacct gcattagcag  3300
aggcttctgc gttggaatcc atgtcttcct caccttataa gatagttaac agatggagca  3360
ctccatcagc acccgatatg ggaatacatg ggctctttaa agggtcagac caacattggt  3420
atttacataa atgtgagaaa tgtaattatt acaacgaaat gagttatgat gcatataccc  3480
cagaggctcc tgtagagagt agaggtaaca ttctttgtgt taacccaaaa ggggtcgatg  3540
ttgttgctaa aacagtagtt gacggctcat tccagtttgt ttgtcaaaag tgcggagaac  3600
cgttagacag atggtacaac ggtgtatggg tacctaaata tcctgataga acaaaaaatg  3660
gtctaggtac tagaggatat atgatttccc aaatgaacgc agtatgggta actgccgacc  3720
agttaaagac caaagaactt caatcattgt ctaaacaagc cttttataac tatactctgg  3780
gtgaataacg ccccttcaac tggaaacagt tgtcgaaaac tctgttaaac gggcaaagct  3840
gaataaccaa taagctgata agagacccta aaccctaaaa tagggcagtg ggaatcccgt  3900
gctaaatcaa gcgtaagctt gtaaatgcct aacgactaaa tttctaggta gctaaccaaa  3960
tggggttagt gagaactaga taagaaaacc tcttaggggg aagtaaagca gagcaaccta  4020
aaccaaaaat taggttgatg atatagtcta gtccgactgc caagagcagt aacaaaatac  4080
tacgaaagta gcggtagctc gtatccttac gcagacttga aattaactgt taacgactct  4140
gacgttgata gccataagag aaactattta atagaacctg ctaaagacag aggtgattat  4200
aaatttatat ctgttggtat tgactggggt aacagacatt gggtatctat acatggtgtt  4260
aaaacaaatg gtacggtaga tttgataaaa ctttttctg taggtaagtc caacccgcta  4320
gaccctaatg caatagatgt agacatacag tctataaaat tacagctagc tccttacaat  4380
ccagatataa tcgtagctga cgtaggagac tcaggggata aagttgctaa acttatgcaa  4440
atttatggaa aagaacgagt ttttgggtgc gtttacccat caacccctaa atctacaggt  4500
aacttagtac ctacttggag cccacaagca aataaagtat ccgctgacaa gttaatgcag  4560
aataaacgtt acattaacaa gatgaaagaa ggagaaatag gttactactc aaaaccagat  4620
acagagctta atttatataa agagcactgg aagaatgttg ttatacgtga tattgaggac  4680
gaaaagacat cgacaggttt tagacaaatt atcggcagaa aaggtgatga ccactactca  4740
caagcaagcg tttattccat gttagggtat gagtacctaa tgaatgtatt tacaggagta  4800
aaagagtatg gatttgactc tgattgggtg tcaactcaat tagcacctac gaaacctgat  4860
atatttacag aatttgtata ggtagattgc cttatttagt tttagtcaag ctgaataagg  4920
cattttgtat tgtttgatat atatttttgt ggtataataa atatagttag gggatagtt  4980
atggtagaca acaatgtaaa aataagtaaa agtacaattg aaggactaat aaataagtct  5040
ttaagttatg agtacgttat aaaaaataac gaattgctga caaacgaata tcaacatatt  5100
gtaaaagcgt atgggtttga caatttttat gacatgtatc tatatgcaga tagctgtgat  5160
tctaaagata tgtatttagt aaaaggtggt caaaaagact tgtctaagct gaaacccgtt  5220
aaaagaaaag ttgttagaaa tggtaaaact atgactacaa ctatttatga agatacaggc  5280
agttcagaca gtaataacag taacccttta gacaaagaga gtaaaaagaa aaaagagtta  5340
gaaccagtta atgctaagga actacgtaag gtcagcttag gtagtgatga agaagagaag  5400
ttagacccta aaaagatagc aaaattgcta gcagacacta aaaaatttgg aaataatttt  5460
gatacgcagt gtactgatta tcttattctt gaacaagact ctgttacacg aggagtggta  5520
gggtttacta gagaaggttc ttatttaaaa atgtctttct caatgtcaga tgaggctgtt  5580
gaaggtatga agatgttagc tttttcacag ctcacattaa aggcttggaa attgggtcta  5640
ggggctaaga taagcacaga taatgcacct gatgtagagg aactaattag cttatatgga  5700
tacaaaagaa ataatacaga gtatattgtg tcaatgagct cactgcgtag tcttctaggg  5760
gagccttagt cataagtgct acgttagtca ttatactagt attttcaact attatttttt  5820
taatttttaa tttactagta agtaaggtag ttaaagaatt ttataactta aagatgctag  5880
caaaagaggg actaacagat aaagtaacag atataacaaa tgatataatg catatattga  5940
aaggagaaat aaataatatg gaattaatta tgaataataa gaaactagat gaattaacta  6000
ataaggtagc cactgatgag gactacgata tttttgtaga gaagatgggt aagctagtta  6060
aagatttgta tgagaactac cagtttttac aacaaaaccc accagaagga gactacacat  6120
caggttattt tttagggttc caagtaatca gagcagaata cccagttgag tatgagaatt  6180
tatttagatt agctgtagat aaaaatttaa atgaactaga gataaacaag agatttgtcg  6240
aagctgttaa ggatggtaaa gttttaccac taggtgaggc tatcattgat gaattacaaa  6300
cagggtgtag ctctatacta caggcacaag aagtacgtgt aaatattgta tttggtacaa  6360
aagaatatat ggctaagcaa gaagaagagc gtaaagaacg tcaagctaag ttagaagaag  6420
aacgagaaag agctatggaa gtactaaaaa caaaagatga cgtgcttaac acattaagag  6480
taactgaggc tttggctaat gaattaacag atgaagtcgc agaaaaatat gatttaatgg  6540
agctagttaa cagtatgaga gaggggctga aagctcataa tggaaattaa aaattctttg  6600
gggaaagctc ttataaaaaa tttaagattg cttaaagaaa aaagagatgc aatgcccgat  6660
aacttagaat atacaagtca agttatgatt cctgtgccct actatctaat aaaaaaaggg  6720
gataatgcag tagaatcatt ccttatgtgt gcggggatga taaataggga taaagattta  6780
ggtctgccta tttctttaga gaaaggtaag caacaagtta agcttaacaa tggagaactg  6840
acaactattg tagaatgtgt tgctacttac tcagataaaa ctgatattga cggtgtagag  6900
agattcttag ttgaacatct ataaaaatta aattaacgag ttctattttg tgctatatta  6960
gatatgcatg aaatagaact cgtttctttt tttatgacta actaaggagg tttaatagat  7020
ggcaggagaa gtatttagta gcttgattac aagcgtaaat cctaacccaa tgaacgcagg  7080
```

-continued

```
tagccgtaat ggtatctcta ttgaccgtat tattctacat cataatgcaa caacaaataa  7140
agatgttgct atgaacacgt ggctattagg tggtggtgca ggtacgtctg cgcactatga  7200
agtcacacca acagaaatta tagggtgtgt tggtgagcag tattcagcat tccatgccgg  7260
aggcacaggt ggtatagatg tccctaagat tgctaaccct aatcaacgct caatcggtat  7320
cgaaaatgta aactcgtcag gagcacctaa ctgggatgta gaccctagaa caattacaaa  7380
ttgtgcccgt ttagtggcag atatttgtaa acgttatggt attccatgtg accgacaaca  7440
cgtgttagga cataacgaag taactgcaac agcatgtccc ggaggtatgg atgtagacga  7500
agttgtacgt caagctcaac aatttatggt agggggctct aacaacgcag ttaaaccaga  7560
gccaagtaaa cctacaccaa gcaaaccaag taacaataaa aataaagaag gagtggcaac  7620
tatgtattgt ttatacgaaa gacctattaa ctcaaaaaca ggagtgttag agtggaatgg  7680
tgatgcatgg acagttatgt tttgtaatgg agtaaattgt cgtagagtat cccacccaga  7740
tgaaatgaaa gtaattgagg atatttacag aaaaaacaac ggaaaagaca tcccgttcta  7800
cagccaaaaa gagtggaata aaaatgcacc atggtataac agattagaga cagtatgtcc  7860
agtaataggt attactaaaa aatcttaata ctagatttaa gaccatctta gggtggtctt  7920
ttttctttct ttgtaatatt cgtaataata tgtaatggct atgtaaccgc ttgttatttt  7980
ggctgtaaca attacatgtt atattagttc ttgtaagcaa cacaaataaa gaaaacattg  8040
aggagaattt tattttgaag aaaactagta ttttaggttt aagtttatta agtttaggtt  8100
tagtagtagg tttaggaacc gaagctaagg cagaagaagt aacagagaat ggtaagacat  8160
attggaaggt agagtcagga gacacactat cagaaattgg agctaagtac aacttagatt  8220
tcactaatat ccacaaagtt aataaaggtg ttgtagctga ccctaatgtt attttcgtag  8280
gtgacaaatt gttattacct ttagatgaaa atggcaagct agtggaacaa gtgaatacca  8340
ctgaaccaga tattgaagta caatataacg aaccagtaac acctgaacaa cctgtagttg  8400
tagaacaaga agttgtagag caacctgtag ttgtagcaga agcccctgcc cctgtagtag  8460
aggtacctgc tgacagtagc tcagcaaaag agtggattgc acaacgtgaa tctagtggtt  8520
cttatgatgc aacaaatggt cagtatattg gtcgttacca actatctgcc tcttatttaa  8580
atggtgacta ttcacctgcc aaccaagaac gagtagctga tgagtatgta gcaggtcgct  8640
atggctcatg ggagaacgca aaatctttct ggttagcaaa tggttggtac taaaattaaa  8700
tagcaataaa gacctcttta ttaaggggtc tttttttat gctatattaa tatatagtaa  8760
atagtaatat aaaatggtta tgattagtta tgtggtataa tagacttatg ttaaaaccat  8820
ttaaggaggg gaaacatggg ttatattcaa gatgagacat ggcagatggt taaaaaagtt  8880
gctaaaaaga atgggtttgt tggtgactgg attttaatta tccactcata ctatgagtat  8940
ggtggaaatc acgtccagat acatacaaca ataaacggag aaagctatag aattttaaga  9000
ttgttagata gcagagagat acttttatta gatagaaaag gtaaccctgt aatttatgac  9060
tatgaaacag ttaacgatgg tcaaaaaagc ttcttttata atgatatgga agagaaagaa  9120
atcgaaatac ctaatggaag atgcttaaac gataagacaa ggataaaaat ttatgtataa  9180
ggtaggtgta acagttgcca aaatggttag ataaagcact gggtatagaa aaatcgtcca  9240
tagaagaaac taggaatatg gaaaattata agatgcattt aagggaaata gacaccaatg  9300
tggtcaataa cgagccgtac agtatggaaa gtattgaaaa aggtatgaat ggtaagacca  9360
ctgcatatat gcaaccaatt attggagaga tgtcagtaaa ccccgggtat aaaactaaac  9420
cgtctatacg taactctcag gacttacata agacacttaa aaagtttggt aataacataa  9480
tattaaatgc tattattaat acacggtcaa accaagtatc gatgtattgt aagcccgcaa  9540
gaaattctga gacaggtgtt ggttacgaga tacgtttaaa agatattgaa gcagaaccta  9600
cttcacatga cattgctaat attaagcgta ttgaaagttt tttagaaaac acagcacaat  9660
ttagagaccc taatagagat aattttacaa ctttttgtaa aaaacttgtt cgggcaacat  9720
acatgtatga ccaagtaaac tttgaaaagg tatttgataa agatggtaac tttatcaaat  9780
ttgatactgt agacccaact acaattttct tagcaacaaa tggtgaaggg aaactaatta  9840
aaaacggtga aagatttgtt caggttgttg ataacagaat tgttgctaaa tttaatgaga  9900
gagaactagc attcgcagta cgtaacccaa gagcagacat cgaagtaggt cagtatggtt  9960
acccagagtt agaaattgcg ttgaagcagt ttattgccca tgaaaataca gaggtattta  10020
acgatagatt cttctcacat ggaggaacta ccagaggtat cttacatgta aaaacagggc  10080
aacagcagtc tcaacaagca ctagacattt tccgtagaga gtggagaagc tcactagcag  10140
ggataaatgg ctcatggcaa atacctgtag tttcagcaga agatgtcaaa ttcgtcaata  10200
tgacaccctc tgccaatgat atgcaatttg aaaaatggct taactactta attaatgtta  10260
tatctgcttt gtatggaatt gaccccgcag agataaactt ccctaacaat ggtggtgcaa  10320
caggctctaa aggaggctcc ctaaatgagg gaaactcaaa agagaaaatg caagcttctc  10380
agaataaagg gctacaaccc cttttaagat ttatagagga caccgttaac acatatattg  10440
ttgcggaatt tggagaaaaa taccaattcc aatttagagg gggagaccta agtgctcaac  10500
tagataagct taaaataatt gagcaagaag gtaaagtatt cagaacagtt aacgagataa  10560
gacatgataa aggtttagaa ccgattaaag gcggagacgt tatactaaat ggtgttcaca  10620
tacaagctat tgggcaagcg ttacaagaag aacagctaga ataccaaaga agccaagacc  10680
gcttaaacag actattagag ctatctggtg gagatgtaga acaaccagaa ccagaagagc  10740
ctaaagacag tcaaaatgat acagatgttt catttcagga tgaacaacaa ggtttaaacg  10800
gtaagtctaa gaaagttaat ggtaaggtag acgacaatgt tggcaaggac ggtcagttaa  10860
aatcggaaga aaacaccaac tcaactaagc atggtactga tggtataaaa aaagaataaa  10920
agataatgga gggggctagc tccccctcaa ctttgtttgt gttactagat agtacatgtt  10980
ctgctatatt aaatacagta aaacgtttag gtggtgaaaa gcaaattgtc agaagttaga  11040
gaaaaatata gtattttcgt accactggat attgaaaatt ctatacagaa gtctgaatct  11100
gtgaatgatg gtgaatggta tgttcaagga tatgcaacta ccccagattt agatttacaa  11160
ggagatatta ttttaccaca gggcattgat atttcttatt ttattgaaaa tggttggata  11220
aactatgagc ataaaaatga tgctgagttt attataggtg ccccaactag caattgttat  11280
gttgatgtgg acaaagggtt attcgtagag gctaagctat taaaggataa caagtacgca  11340
cagtctatgt ggaagctagc taatacaatc cagaaatcag gaatatctcg tcagttaggt  11400
ttttctattg agggtgcagt agttagtaga aatgcacaag ataacagaat catagaaggt  11460
gttaaaatac ataatgttgc attaacgaca catccggcta acccaagagc tacatgggag  11520
acactagtta aatcttggac tacaggatat ggcacagcac cagatgcaca agtagatgca  11580
ggcgcactta gaagagagat gtttaaagag gacatttcta atttgacgta tgcagtaaga  11640
actattgcag gactatataa taaaaaacct gcagagaaag agtttatttt acgtgaagtg  11700
gctaaggata tagaagtaga cacttccgaa aatgaattat ctaaatttat gttacaatta  11760
agtagaggga tttccttgaa agaagcaaca aactttattg aaaaaagaaa ggggtaagaa  11820
```

```
atagtggcta aaacattaaa cgatattata gaagattttg atgcacagtt aaatgaaaaa  11880
gtaaaaccta ctacagatga ggaaattaca aagtctgtag aagaacctac tgaaccagaa  11940
aaagttgaag aaggtgctga ggttgagccg gaagaaaagc ctaatgaatc tgaggagact  12000
acaggcaatg acggagaaga atccggagtt actgaaacag ttgaagcaga acaggaagaa  12060
ccagaaactg ttgaagaagt agcagttgag gaacctgttg aggaacctgt tgaagaatca  12120
gcggaaactg ttgaaaaatc tgataaaact aaagaaaaata aagatgaaga agaggaggaa  12180
gacgaagaca aaaagaaaga aaaagacaaa aaagacaaag ataaagaaga caaagaagac  12240
atcgagaagt ctaccgaagt cgaacaagtt atcaaatctt ctgaaatctt aggagctatg  12300
gaagctatct ttaaaaatat gttaggtcta agtgaaaagt tagacgaaat tcatagagag  12360
tttaaagaag ctaaagaagc taaagaaaaa gacgaagcgg agtctgttga gaaatcttta  12420
cttgataacc ctgaaattaa aacaggaaaa gaggactcag aaggcaaggc tgttgggttt  12480
gttaataagt ctgtagcagt tgaggaagag gtggctaccg aagaaccaac tgtagaagta  12540
gttgttgatg gtgaacaaga cacagcagaa cctgaaaaag aagtaccgtt ccgtgataga  12600
gtacaggcta ttagaccaga ctttatggaa acatataaac gtgtgtctgt tagcggagta  12660
gctcaacgtg gtgaattaga atcagttaga cacacttggg gaactgctag aacaaatgat  12720
gacctagcta aaattgaagg gtttattaat aaatataaat aaatttacta tatagtgaac  12780
gatttttaat tgtactgcta tattaatagc agaaacaata aaagacctga cattccctcc  12840
tgaacctcca cagggtcagg tcttatattg agaggaatat aaagaaaggt gatttataca  12900
taatgacaga gaaaaagaat acagaacgac aattaacttc cgtacaggaa gaagtaatta  12960
aaggcttcac tacaggatat ggtattacac cagaatctca aactgatgcc gccgctttaa  13020
gacgagagtt tttagacgac caaatcacaa tgctaacttg ggcagacgga gacttatcat  13080
tttaccgtga catcactaaa cgtccggcaa cttcaactgt agctaaatat gacgtatatc  13140
tagcacatgg acgtgtaggt catactcgtt ttactcgtga aatcggtgta gcaccaattt  13200
cagaccctaa cttacgtcaa aaaacagtta acatgaaata cgtttctgat actaaaaata  13260
tgagtatcgc aacaggttta gttaacaaca ttgaagaccc aatgcgtatc ttgacagacg  13320
atgctatctc agttgttgct aaaacaattg aatgggcttc tttctacggt gactctgact  13380
tatcagaaaa cccagatgca ggttcaggtt tagagttcga tggtttagct aaactaattg  13440
acaaacacaa tgtactagat gctaaaggtg ctagcttaac agaggcttta cttaaccaag  13500
catcagtatt agttggtaaa ggttatggta caccaacaga tgcttatatg cctatcggtg  13560
ttcaagcaga cttcgttaac caacaattag accgccaagt tcaagtaatt agcgacaacg  13620
gtcaaaacgc tacaatggga ttcaacgtta aaggttttaa ctctgcacgt ggtttcattc  13680
gtttacatgg ttcaactgta atggaattag aacaaatttt agatgaaaat agaatgcaac  13740
ttcctaatgc tcctcaaaaa gcaactgtta aagctacttt agaagcagga acaaaaggta  13800
aattccgtga tgaagattta acaatcgaca cagaatacaa agttgtagta gtatctgacg  13860
atgcagaatc tgcaccatct gatgttgcat ctgtagtaat tgacgacaag aaaaaacaag  13920
ttaaattaga aatcactatt aataacatgt atcaagctcg tccacaatat gttgcaattt  13980
accgtaaagg tttggaaaca ggattgttct accaaatcgc tagagtacct gcaagtaaag  14040
cagttgaagg agttatcaca tttatcgatg tgaacgatga aattcctgaa acagcggacg  14100
tattcgttgg agaattaact ccatcagtag ttcacttgtt cgagttacta ccaatgatgc  14160
gcttaccatt agcacaagtt aatgcttctg tgacattcgc agtattatgg tatggagctt  14220
tagcattacg tgcacctaag aaatgggctc gcattaagaa cgttaaatat atcgcaacag  14280
gtaacgtgtt taactaacgc taatctttaa aagactaagc aaaattgaat aaaaatggaa  14340
taggggacgg ttaatactgt tccctatttt tattataaaa tacatgtatg gaggaaataa  14400
tatgttaaaa tcagaaatct taataaataa aacagtaaca acagcttttg gtgaggcaac  14460
atttgaccat aatggggaaa ccacagacct aacagtagaa cagcaagaac atttagggac  14520
taaagttcca tatatacaat atataccaga tgcacctaaa gctaaagaaa aagaagctac  14580
tgcagaaaaa gcagacgagg cacctaaaaa ggctaagaaa gcgcctgcta agaaaactac  14640
aaaatctaaa aaagaggaag actaaggagg tatttatatg tacccagact acggatacga  14700
ggaacaaggg gacaatacat accaatacca accatatgca catgggaacc ctaagcatat  14760
agatttagac aaaattgatg atatacagcc tgctgattat ggttggacac ctgctacgct  14820
gaaacaatac atgtttggtg tagaagttgt taaccctgaa acaggggagc ctttaggaga  14880
tactttctat gaacatatca tagattcagc aatagctaaa gcagagaaac gactagatat  14940
tgctattatg cctagactta taagaggaga acaccatgat taccaccaat cagatttcaa  15000
ctcttacatg tatactcatg tgtttaaaag acctattatt caagcagaaa agcttcaatt  15060
agaagttaat ggtagagggc tatacagata cccgtctaat tggtggaaag tgtatgcact  15120
agcaggtcat atacaaatgt acccaacatc cctcatgcag actggaacac agtttggtta  15180
tgaaatgacg ttctcagggt acccacaatt agcaggaatg cctccatcag gaggacaagt  15240
tgatgctcct caaatgattc atattgacta tgtggcagga atgctaccta ggaaaaatag  15300
aggatacaat gaagactggg agtgccctgc ggacttagaa cagcttgtaa taaaatatgc  15360
gttaaaagag atattccaac aatggggtag acttataatt ggtgcaggta ttgctagtaa  15420
gtcactaaca gtagatggta ttagtgaaag tatacaaaca acacagtctg ctatgtatgg  15480
tggagcttct gcagatattc gacaaattga cgaagacata caagaattag aaaaatcatt  15540
ggtatcttac tttggaatga acttaggtat tatttaaaaa agggggttaa caaatgggtg  15600
aaaaaccaat tagatttggt ggagcaggtg aaacaggtaa ccctaacaag caattaaata  15660
ctagtagggt tgaatttgaa acaaaaggta tggctagctt cattgaaaat agaggtattg  15720
acgttttgtg ggaaagagca tggctatgta catgccgtaa cccaatgacc ctctcaccta  15780
agtcggattg ccccatctgt aggggaagag ggattgctta ccaacctgca gtaaaattaa  15840
gaatggctat acagagtcaa gagaaaggta tctctaatca agatttagga ctactagaca  15900
caggaaccgc tattggaacg actgagctag attctaagat aacctttagg gacagaataa  15960
cagtccccga agttaaaata tatcaaagct ttatttttaa tgtaaataaa agaagagtag  16020
ctaatggact atttttaagc tatgatgtga acagtataga agatatttat ggtaaagacg  16080
gacgtatctt agttgatgga gtcgatttta gaatggacta tgacacaaat actatttatc  16140
caaatgaatc tttaatagat actaatatat ccataaatat gtctgttaca cttagatata  16200
ttgttataga cctgttaaaa gaaagtagat accagtatac cacattcggt gttaaacaaa  16260
cacaatttga atcactacct aaaaagctct tattgaagcg tgaggacgtg tttattgata  16320
gtgaaccatt ttcattagac atagatacag caagccgtat ggaagagcta gagggcaaaa  16380
aagatacaag tgaagctatg gtagacccta agcgtaaagc tacaaaatca ggaggcttct  16440
ttggaggtaa gttaaatggc tagaaaagga cagagacccg tattatttac tgattcaaaa  16500
gcaatacttg gcaatctgac tcgtgcagtg gttgatgaag tactaagtga tgcgcaagat  16560
```

-continued

```
gttgctctac gtaatgggtc ttctgtacag agaatgccta gctatttgat agtaacagag  16620
tctaggatgg caaaaaatgg ggttatagat ttgaaacctt tctttgcacg ttctaataaa  16680
aagaaatata ataaaaaagg ggaatggtac ctatacatcc ctattagtat gaaaacacgc  16740
aacatgtcaa gacgattata cgatgagctg agagcagttc cagtaggcac aaaacctgta  16800
actgttaaaa tggactatct gtatgataga cggaagcaga gcccatcagt gtctagtatt  16860
aactataaac ctaaatctac taatgtaact gttataccac agagttgggg taaaggtaca  16920
cgtaacacct atgtagcttt ccgtacagtt aacgctaatt ctcctgcgaa tagttggata  16980
ataaatcgta gaaacgttaa tgatgatgat atgagtaaga caatgctaag aaacatagac  17040
aggctcatga agtggaaact aaagaattta ggaggatagt gtatgatacc aagtttagac  17100
acttacttgt ataaagaatt tgaagaaagg ctaaggataa ttctatcaga gtgctatatt  17160
atagacgaag ctttaaaggg aatggacaaa gaagctttag aatcttttaa aaacacttat  17220
tgctctatag atggtaagcc acctaagaga gaagtagaga tgtcctattc attcccacaa  17280
gaacatctgg attcatttgc tcgatttgta gtaactctcg gtagtagcga agaagatagc  17340
aagtctattg gaggaatcca aggaggctac gagtatcgag aaggtaatgt aattagtgag  17400
gaagccacta ttattagaga aggtgacaag ctgattataa atacatcaaa accagtagcg  17460
gactatctaa acagctcaga cataagtttt gcagaaagcg accattttag gattgaagat  17520
aataaacctg tatttgattt ttcatacaat gaggagttag aaggtatatc cattaatgtg  17580
tcgtatataa gcaaaatatc agatgatgat gttgcaggtg tatacaaagg ataccaatct  17640
aacgataatg ttagtataat tggaataagt tctaatatag atactgctag gtgtttagat  17700
gcaattgcta gaattatact aatcaccatg agagacagtt tagatgaaaa aacagggtat  17760
atgttgcaaa cactacattt tggtgatatg caagttgtca tagaatcagg tgaaacactt  17820
gtgtttggta gaccttgtac tgtaaactac agagttacta attctattgg atttgattta  17880
caacaaagaa tcacagagat tattacaaaa aggaggatga aatcctagtg gctaaagaaa  17940
cagagaaagt agtaaaaaaa gaagttaaaa aggagcaacc taaaaaacct aaaggttatg  18000
tccatgtcga tacattttta gattatgcaa aagtattata tggactaaat aaatatcagg  18060
tagcgggttt cagagcacta atggcaggta gagaatacca acacgaggat gctgattttg  18120
ttccattttt agaaaagtat ataggaaagg aagttaaata ataaatggct gtagaacaat  18180
tcccaagaaa aaaagtatca cgtccacata ctgagattac cgtagacaca agcggtattg  18240
gtgggtcatc aagtagctct gacaaaacat taatgttagt tggctctgct aaaggcggta  18300
aaccagatac tgtttatcgt ttccgtaatt atcaacaagc taaacaagta ctacgtagtg  18360
gagatttgct agatgctatc gagttagcat ggaatgcatc tgacgttaat accgcatcag  18420
caggagacat tttagcagtt cgtgttgaag atgctaaaaa cgcaactctt acaaaaggtg  18480
gtttaacatt tgcttcaaca atttatgggg tagatgcaaa tgaaattcaa gtagcattag  18540
aagacaacaa tttaacacac acaaaaagat taactgttgc attttctaaa gatggttata  18600
agaaagtttt cgataactta ggtaaaattt tctctatcca atataaaggt agtgaagctc  18660
aagccaactt tacaattgca caagatagca ttagtaagaa agcaacaaca ttaactttaa  18720
atgtaggttc tgaaccagaa agtacgacag aagtaatgaa atatgagtta ggtcaagggg  18780
tttactctga gacaaatgtt ttagttagtg caatcaatag tttaccagat tgggaggcta  18840
aattcttccc tataggtgac aaaaacttac ctactgatgc tttagaggca gtaaccaaag  18900
tagatgttaa gacagaggct gtattcgtag gagctttagc aggagatatt gctaaacagc  18960
tagaatacaa tgactatgta actgtagctg tagatgctac aaaacctgta gaagactttg  19020
aattaacaaa cctaacaggt ggttctgacg gaactgctcc tgagtcttgg gctaataaat  19080
tcccattact agctaatgaa ggtggttact acttagtacc attaacagat aaacaagcag  19140
ttcactctga ggctttagct tttgttaaag accgtacaga caatggtgac ccaatgcgta  19200
ttatcgttgg tggaggcact aatgaaacag tagaggaaag cattactcgt gcaacaaact  19260
tacgtgaccc tagagcttct ttagtaggct tctctggaac tcgtaaaatg gatgacggac  19320
gtttgcttaa attaccgggt tacatgatgg cttcacaaat tgcaggtatt gcaagtggtt  19380
tagaagttgg tgaagcaatc actttcaaac acttcaacgt aacatctgta gaccgtgtat  19440
ttgaaagtag ccagttagac atgttaaacg aaagtggagt aatctctatc gagtttgtac  19500
gtaaccgtac tttaactgca ttccgtgtag tacaagacgt aactacttac aatgacaaat  19560
ctgacccagt taaaaatgaa atgtctgttg gtgaagcaaa cgacttctta gtttcagaat  19620
tgaaaattga actagataac aacttcatcg gaactaaagt gattgacaca agcgcaagct  19680
taatcaaaaa ctttatccaa tcattcttag ataacaaaaa acgtgctcgt gaaatccaag  19740
attacacacc ggaagaagta caagttgtct tagaaggtga cgtggcatca atcagtatga  19800
ctgtaatgcc tatccgtagc ttgaataaga ttaccgttca gttagtatac aaacaacaaa  19860
tcttaacagc atagagtgta ggggcagttg cccctcctct tacataatga ataaaatata  19920
ggagtgatat atacatggct agtgttggaa atcaaacagt ccacacaggt aacacagttt  19980
acctaatgat tggtaataaa attatcggtc gtgcgcaatc tgcatcaggt gagcgccaat  20040
acggtacaca aggtatctat gaaatcggta gtattatgcc acaagaacac gtatacttga  20100
aatatgaagg tacaattact ttagaacgta tgcgtatgaa aaaagaagac ttagcaagtt  20160
taggaattac agcgttaggt gaagacatct tacaacgtga cattattgac atcgtaatga  20220
tggataattt aactaaagaa atcgtagtag cttatcgtgg ttgctctgca atttcttact  20280
cagagtcatt cacagctaac gaagttacat cagaaagtac gcagtgagat tataaataca  20340
aaatttatat agctgtgcta gttcgtaaag agctagtatc gagagttaat tgctttgaat  20400
ccctaaagct caacgaccca aacagtaact ggaaacggta agctgagagg tgcgaaagca  20460
gaaaaaatag ttgagatggt ataaggttaa atcctaagta ctgatacaat gggtctttag  20520
cagggacagc cctaagtcaa ttgatacggg acaccttcaa cgactatcct ctgacggagg  20580
agtaaagcca caagccaatg gtggaagaaa aattctctac cctaacaagg gtacccatat  20640
agtctgagct aacatgaaag tgttagaggc aaacgcctac ttggaagttg cgttccaagg  20700
taacaaaact gttcacatac ctaacttctg caaaggttaa atagcagacg aactccaccc  20760
agcttgactg ggtggttctt ttacggtaca atacttttat tattgttaga tatttaggag  20820
atacaacatg agaaaaaaat ggacattaca agaaagaaat attcttataa aaaaatgggc  20880
ggagactaac aacgtaaatc tcttaccaga aacagcaacc tttacaggaa ataagagcac  20940
tatatactac gtatggtcag atggggagct tcaaggctta ataggtaaaa cgaactttga  21000
cagtataata tctggaagta aacctacagt taacggtctg acagaagaga gcaaaaatat  21060
tagggctaaa aaacgctttt tggaatatgg gctcgaatta ctagaggagt atcaaggatt  21120
caatacacca cataaggtga gagtgttgga tggagtatac gcagggtatt atggaaaaac  21180
ctcattagcc acagtcaatc aaaaaagtac cagaggtaaa atagcgcagt taaacataac  21240
tattcttaca gaaagtgaga aaagacgata tttcagagaa tatgcagagt ctcggggata  21300
```

-continued

```
cacaattatt aactaccctg aaaaattagc tgttcgaggt aagtgtactt tgttatctcc  21360
ccaaggtaat gagtgggaga cagtctggta ccattttgct tatcaggaga actgcaattg  21420
tccgttagat gttaaacgta gtattgggga gcgcatggtt agaagtttgc ttaaagagaa  21480
tggtattaac tttgaagaac agaaaaagat agttattgat ggtagaacat tattttttga  21540
tttttactta cctgatgaca atacctatat tgaatataat gggaaacagc actatgaaga  21600
caccggaggt tactataagg gtaaacttca agatttacag gaacgtgaca aactaaagga  21660
gcagtggtgt aatcaagcag gtgttaatct tgttgttatc ccatacactg caaatagcat  21720
aaacgaagta gctaatgttt tatccgagat agtaccaatt aaaaagagac tagtttcagt  21780
tgtttattct gatagtatac ctaatgagga tattattgat tactataaaa cacatacagg  21840
taaggaaact tgtaggaaat atgatttaac acaacgtaga ctgagcttac tttgtaacag  21900
agtcggcttt aataaaagga ggtacctaaa gtgaaatatc catatttagt agaattgtat  21960
gcaaaacatg taattagaga tgcagggtac atagaaaatg taccaccagt tatttatgaa  22020
gacgttgtga aacgtgttga agaaataaaa agagaagaaa acttaacaat agattaacta  22080
gtataagttt aaatagacct aattcagata taggtctatt ttttttgcca ctataaatac  22140
aaataactag atagtgtggt ataataaaga tagtgctata ttaatttatg agtaaactag  22200
gaggaaataa taatgacaga aaataatgaa aaggtattta cacctacacc aaatttatca  22260
cgtgagcaat taatagaaaa gttgcaacgt ggagaaaact tgacggatga agaagtaaat  22320
attttgaaat attacaatga tgcagaagaa cgtaaacagt tagatagaat tatcccgggt  22380
gttaatgatg tattttctaa gcattacaac ttaaaagaat atggtttaga atttgatatt  22440
aaaataaaag cacctaatat tatcgaaaat ggtaaaattc aggcaagaag agaagcctat  22500
ttagaaggca tgggaatggc agttagcaac tttattttcc aaagttacca aatgttagca  22560
actattcgag tatgtggagt agaggtacca aaagtattag ctgatgatga aaaaatttat  22620
aatttatatg tattaggagt aattgcaaag gactatggtg aatggctaaa ctcctttcga  22680
tactagagtt aaagaactag gcggaataaa agcccttgtt agaaatagct atagtagaaa  22740
tctatgggca ataatgaaaa aatttaaggt actaccgagt gaccctgcgt ggcaaaatct  22800
cacaagtgac caagtagagt ggattttata taacatggaa agagacatag aagaacaaga  22860
acgactagct aagggaatgc agttagaaag tgagttccaa gactatgacg attcatggta  22920
tgataaacca catgatgagt tctctccaat tcgtgaaggt gacgatgagg aagaaattgc  22980
tcgtaaactt agtgaaatca caagtgagga agacatggct aaacttaaag ctcgttggga  23040
ggcaagccaa gaagttgatg ctatccgtgc agaaggtgga acaacaattg aagaagatac  23100
gattaacgaa cttattgcta acaatgttaa aaaagcaatg gaagaggcta gacgtattga  23160
gaaacatggt ggaaacaaat ggcaagagaa atcatcaatt gagttagaag aggaacgtaa  23220
gaacctagag tttaactcac agttgaaaca aggagatatt caggaggcta tcgatttgtt  23280
taacaaagat gtcgagccaa catcattaga tgacgaattt caaatttaag ggtagggtat  23340
tccctgccct ttacttgtaa aggaagtgtg gaaatgagca acaattatcg tttttatgtt  23400
gaggcaatga ctggggatgc tgttgcaaaa cttaatgaaa tagacaagtt aatggataaa  23460
attgattcaa agagtgcaaa gggcacccag aattttttcc atacaagtca gaaagacatt  23520
gataaagctg ttgaggaaat gcaaaagctt atcaaggcaa aaaaagaact agatagagct  23580
tttgataatc agaagataaa tgcagaaagc atgggagaca tgacagcata taaacgtgct  23640
gtatcggatg cagaagaact aactagaaga tttaacaagg cacaaaaaga atttcaaaat  23700
catgctagaa tgcaagctaa ccctaattac ataaatgcta gtacactaag gcaacaaaag  23760
gcatttcgtg atgagttaac agaacaagag agagcaataa gaaatatctc tagggcacaa  23820
caggaactaa acagagtgaa ctctagggtt aaccatcgtg caaaccaagc aagcgcaaca  23880
ggaagaatga cttacaatca gtcagagagt atgaagcgtg accttagacg tactggtgta  23940
tttgaaagcc taggttcaga aaataaaagc agacagcaag agctacgaga acgatataaa  24000
cagagacaag aagagctagc agagactaga agtaatacaa atttagatag acaagttcgt  24060
aagaataggg aaactagtat tcaggctgag ataaaagaaa ttgagaaaga aattgaagct  24120
agaaaacgcc tagcagactc tattaaagag actgtagaga acttaaaatc taaggaagct  24180
tcactaaatg catctgacat aaaagtagat gctgatagaa agagtgctcg tggtgttcta  24240
gctgagcgtg caccttctat atcaatggct atgctaggag gtaccgccgc cgccataggt  24300
ggtttatacg caaaaggagc aactgctaac gcaggtatgc gtgatgcatc tatatcttta  24360
ggacaacgta caggtactag tgacttccgt gcattaagaa aaagtatgca agaaatgggt  24420
attgagaaac agttaggcta taaaggtgct gacatgttac aattccaaga agatgcattg  24480
agtaatattg gttttacaag taaagaggac ttagcaggga gtacaagagc cttagcagag  24540
ggctcaagag cagttccagt agacaatgag actttaagtg acttcatgaa tagtcaaatg  24600
aagagcgggg ctattagtgg tagagaccaa attaagaata ttcaagaagg tttcttaggt  24660
gctatccaac gctcagggat ggcaggtcgt gagaaagaac agctagaagc tcttaaaaca  24720
ttaagtgagc aaagctttac tggtcgtaac ggaagtaatc aagagcttaa agaacaaatg  24780
gcaatgttaa caatgctaaa ccaaacaggt aagcgtgctg ttcaaggtga gcaaggggca  24840
cagttaatgt caagtttatc tgcaggtatt caaggtagtg tatggaacaa taaggcatct  24900
ttacttttag gtaaagggac acaattccaa gggctagcag gaatgtacga cttaaaagct  24960
atgcaagaac aaggagcaac accagagaac ttacagaaaa ttattggcag tgtccaacaa  25020
tcagttcccg gtgacgaaaa gtctcagaag tatgctttcg gtagtgcttt acacgaacta  25080
ttcggtacag atgctaagaa tgaccaaata gatgcaattt gggaggctta tgccaacggt  25140
ggtttaagtc aggataacgt agacagaata atgaatgaaa gccaatctac aggaaaaggc  25200
aaatacgata agaacataga agactatgca aactctaaag aaggaaccgc taaccgttca  25260
gaagctgtta cagagaaaca agcttcacag attaatgata tgggggacat cttaagagaa  25320
actaactcta aattaggagc acttcctcct gcgttatatg cgttaggagc aggcttagga  25380
gctatggctg tttcactagc cacatcaggc tctattggtg gtttatctag tttaatcaaa  25440
aaaggaactc gttctacttt tagtacaggt ggaggggtaa ctgcaggggg cggattttta  25500
aaatcagcta aagaagcatt ctctgcaggt aaaggctctg gcggatggtt ccaaggtatt  25560
aaaaatgtag gtagtgtagc taaggactcc gcaatgggtg tcggagctaa ggctgttgaa  25620
ggagcaaaag gactaaaagg tgccggaatg ggcagtaagg ttcttggtgg cttaggaaaa  25680
gcaggtaaat tcctaggcaa agttgcaacc cctctagcga taggttcctc tctactagat  25740
attgcaaccg cagatgataa aacaaaggcg gtaggggaga gtgttggagc tattggtgga  25800
ggtatcggag gagctaagtt aggggcaatg attggtacat ttattgcacc cggtcttggt  25860
acaggtatcg gaggagctat tggtggaggt atcggcgcca taggaggtac tctagcaggt  25920
tctaaactag gcggtaaatt tgttgatggt gttcgtaaat tcttcggagg agaagaagct  25980
catgcggaag aagcagactt aactgcaggg caagatgttg cttctgggca agagagtaaa  26040
```

```
tcaggagtac aagaagccag agacacggct aacaaacgag tcctatctga gaaaacacgt  26100
gcagagaata acgcagaaga gtccgccaat ctctctatct attctaagtt attagataga  26160
gcccaacgta tactaaacca agcaaaaaat caaaacggta tattcggtaa ctcaggtagc  26220
tctaaagatt cttctgacgg aatgggttca gatgcttcta gtaaagactt tggaggagac  26280
tgggagaaag ccattagaca agcatctaag aaaatgggag tagatgtttc tgacgatgaa  26340
atagatacaa tacttagatt gattcaggcg gagtctagtg gtgacgagag cgccgttcaa  26400
cagataattg atgagaacaa cttcaatggc aatggtggag ctaaaggttt gctacagtat  26460
gtccaaagta cttttgatgc atacaaagta gacggtcatg acaacataat gagcgggtat  26520
gaccaattgc tagctttctt taataatagt aattggaaaa atgacctaaa ttcttgggat  26580
agccgttatc aaaacggtag tacaggatgg ggtcctactg gtaataaaac tagagcgatg  26640
ggtgggcaca taactagccc agagtatgcg ctactgggag aggtagcagg tcaagatgag  26700
tatgttataa atcctagtca gccaacagct ccacgtttat tagcagaagc tactagaaaa  26760
acagcccaaa acttccgatt aacaggtaat ggttctggtc atgattgggg agcttcaatt  26820
tctaaaataa atgcaacagg aggagctcaa tcaggttcag ctcctacgat gacaaataca  26880
aatgaggtat cagttaatgt caccatacaa ggtggaggaa caagtgatag tatagctaga  26940
gaaattggtg ataagtcagc aggaattatc agcaaaacac tcgatgctac cttcacagat  27000
ttcttcgcaa aagaatacag gagagtgtag aggcttaatg tctctacttt tctctaagga  27060
ggtttataat gtcagtagag ttaagatacc cgagatttga tttaactttt tttacagaga  27120
cagacaacta ccatatagtt tatgatgcaa aagatgggct tactggacgt aataacaata  27180
acggtgaagc agagaaggta agcaataatt ttatggcaga gtctgtaatt agtttaacta  27240
caaaaaatgc tttagaggat gatagtgcag tcttctcatt cgtattagca ggggacgtgt  27300
attgggatag agtactaaat gctaatgatg cagttattct taaaatagac ccagatactt  27360
cctccactaa aaaatcagat aaccctgtac tactagttgg tttaatatct gaggttagac  27420
tagagggtga ctatggggaa aactctaaga tgtacaggat aacaggacag tctttcgcaa  27480
aggcgctaat gcagtttgac ttaggtgtta ttcaggaagt aagtgtagtt ttgacagatt  27540
taggttggtt gcctgacgat gcacaagaag gtataaaaat gtctggtagt agtgcaagtc  27600
aaatagcaga aagcttaatg aaaagatttt tacaatatat gaaatttaat tttaatggtc  27660
aaggtataga taagttctta gagtgggagc tagatagttg gacagaggcg gagagactaa  27720
tagatagtac cccttacata aactatgaag gttctttaaa gcaacttata gatgatgtaa  27780
ccgctaaacc gtttaacgaa ttatatttcg atgcaacacc agagggtaaa tgcagaatga  27840
ttatgcgtag aaccccattt gataaatctg attgggaaaa attacaaacc tacacagtaa  27900
catctgcaga agtaatatct gaatctgtag cagttaacga tacagaagct tactctatat  27960
ttaacatatc tattaataac ttgtatggga ctgactctat gatgttaggt tctaaaccac  28020
aagtattccc tgatttagtt tctaaatatg gttataagaa actagaagta cctaataggt  28080
atttagaagg agcaattata gataagagta acagtggaga taaagctaac acaaaacccg  28140
aaagtgataa tgatagtaaa gagagcgatg gctcaacagc taaacagatg tttgacagag  28200
agtacgctct tgtcttaaac tatctaaaag ggtatcctgt tgatgtgcta agagttaaaa  28260
aaagtaatgt aagaacatca ataacacagg tagacagacg tataacagat aacgaagcag  28320
ataaaattat agaccactat attacaaatc aagcattaag taaagaagac ttttctaaat  28380
ttacaggaat aaccgaagaa aatatagaag agggtaacgg taaagtagaa cctacatata  28440
ccgcagttag ggacttcctt aatgggttag ataaaaacct aggagtatct agcataaaag  28500
agaaattaat gaactacttc aatttgatac ctaaccaagc cacatctatt gctagtgaat  28560
acaaagcaca aggtaactta ggtaaactaa aatatgaaga aataatggag aataacccaa  28620
gtgatagctc aaccgtcact ggttcagata aacgatttgt ttctgagttc actaaaagac  28680
tagcaaattg gtactgtgaa aacgctaatt tctacagtgg ggatattgta gttaaaggtg  28740
accctaaata tagattaggt aaccgtttgt ttgttcaaga tgagcaaaat ggtgagttgt  28800
gggaatacta catagaatca gtagaacact cgttctccta tacacaaggg tatatcacta  28860
ctcttggggt cactagaggt ttacaaaatg gaggaaacga tagattcact catttatggg  28920
gtaaatctga ggacttctcc ggaggtatgc taggtgagaa aaccttgcaa gcactactag  28980
acgaacaagc agaagcaaac agtaaaaatg atggaggctc tgatagtgga ggtagctcag  29040
gtaaagagta tacagcaggt gcaggaactc agctagcggt attcccatta gacgtaatta  29100
atgtaactca gggagaaaat ggtggataca gccacatggg agcacttgca atagactttt  29160
cagatggtac tcctcataaa ccttactatg caccatttga ctgtgaatgt gtgtacactg  29220
actcttactc aggggttgca tggcaatctc aaaagcctgt taaatgtgta gatggtagcg  29280
ttacttacgt aacactatta tgtgtacacg acaacaactg ggcaagcaac aaagtagggg  29340
ataagaaagc taaaggggaa gtgatagggc actcaggaac tgcaggacaa gcatcaggag  29400
accatgccca cttcgaggtg tctaaaggta aatggcaagg ttggagcaca agcagtgcgg  29460
gagtttactt tataaaaaac ccttctcatt tatacgatgt attttctata aaaaataatg  29520
taactggaaa aacaactaaa attatgaatg gtggagggta caattggcgt agtatagact  29580
gggacgataa atctggctca ggttctggaa agaaaaagac agttggtgct agagccatgg  29640
ctactccatt cggattacgt atgatgcgta gcgctcctgt agaaccagaa gaaccaaaag  29700
ttgttaaaca agtagaaact aaaacagttg ttgaaaagaa accaaaagta gaagttaaaa  29760
agctcccaat actttatggg aataacattg ccacagaagc aactaaatgg ggaagagctc  29820
actcgaaaac agagtccaca ttccaatctg ccttcaattt tggagctaat acagataaag  29880
acccatttga ggaagacatt atagcaacag acagtgcagg atttgtttgg tggtgtttct  29940
accatgcggg catatcacta tctggtggag ctagaatggt taccactcgt tcactactct  30000
atgataacca attacaaact atctctacta gaggtcagaa gtctttagag ctatttgata  30060
agatgaaggt aggagattta gtttggttta acagagctag tcatgtaggg atatattgtg  30120
gtgagggcaa gatggtctct tgtaatggaa aaggtaacat ggatgagtcc ccaaaaacag  30180
gtattgttat tgtcgacatg tctaaaggtt attggtggaa cgcttttgac ggaaatgtac  30240
gtagatataa ataaccctat tttttagggt tatttttttt gtataggtag tttttagtta  30300
ttgtgctata atagataatg aggacacatg atgagaggat gaataaattg gtaaaacgca  30360
gatttcaagc aggtctaggc tcagaaatta aaagagtata taaagaagga caacaaatta  30420
acacgctact attagcacaa gtaattcaag taaactataa atataataca gtagacctac  30480
tagctttaca gcataaagaa gtatttcaaa attcctatgc aaatgaggga cgtttctctg  30540
caagacttcc tatggaattt ggcggtagaa atatcgttgg acagccttat gggcaggtta  30600
acccgatagc agtaggaaca gtagtattag ttggttttat taattccgat aaagacatgc  30660
ctattgtaat tagtgtttat aataataacg atgtaagcaa gcaactttca agaacacaat  30720
tttcaaattc agaccctaaa gatttagagt taattgggga tatgcaccaa aaatttagtt  30780
```

```
tatacccttc attgacatat gatagcgttg atggagaagg aggacgtgtc gttacttttt 30840
ctggtaaatc atttattgct tttgatacaa aagaagtagc taactcctct acaactgatg 30900
caggttatgg tactaaatat gaggacttag agacatcata ctataataat ggtgacctaa 30960
tagagcctat gaaaggtaga gcaccaaatg tactgtttaa gcatcaaggg gtacttgacg 31020
atgatggcaa accagatttg cacgatttgc taattcatat taacccagat ggtacttata 31080
gaacttctat gatgaacaaa gaagaggatt ggcgcacact atttgaaatg acaccagatg 31140
gcagagttaa attaagaaaa caagactcta ttaatattga tggtggcata gaaataagtg 31200
agctaggaat caacaatgag gggttcgttt atttacgtaa tggggatatg gatttagaag 31260
tacgaaaaga cggtatctat tcacaaggga aactgtttac agccgatgta gacctatccg 31320
atgtatatga caaactaaat gggttgtcta tacagattaa ggaaacaaat ggtcaattag 31380
agattatagc taatggtgta gaagaacaaa atggaaaaat atcagaactt tctacagaaa 31440
taacaattgt agcaggtaaa gttgaatcaa aagtaacaaa gacagaagtt caggatatga 31500
ttgacagttc ttttgtagat atgtctgatg cgattaaaaa agcacaagaa gatgctgaca 31560
aagcaaataa agtgattgca gatatgtcta gtgataatag actgactccg agtgaaaaaa 31620
tagatttatt aaaagaatgg gatattataa aaaatgaata tccaagctat ctcgaacaag 31680
cagaaaccta cgaggttgac agtaaagact acactgctaa gtacaattca ttagagctat 31740
ttgttacccc tatattggct gacatggagt caactagctc ggtagacgga gcaacacttc 31800
gcaaaacgtt taattcttac tatacagcaa gaatagcttt actaaactct attagtaaaa 31860
aactaaaaga cggtatcaca gaggctatga aaaaagcatc ccaagcatca ctagatgcaa 31920
cacaagcaat ggcagatgcc tcacaagcta agattgatgc agataatgct aacaaactta 31980
tatctgatat agcaagtgat aacaagctaa caccttctga aaaataccaa cttaaaaagg 32040
aatgggatgt aattgttaag gaataccta caacaattgc acaagcagag aagtacgcag 32100
tagacacagc agagtataca gctaaatata aagccctaga gctgtttgta gagcctttgt 32160
ttaaagacat ggatgaaact agtatagtag acggagaacg ccttagagcg acattctcgg 32220
actattacgc aagtaagatt gctttactaa aagaagtaac ggactcagct aaaacagagc 32280
tagatgccta tggtaataaa atatctgtaa tggaaacaaa cattactcaa acgtcagaag 32340
ctattacttt actagctact agagtacaaa ctgtagaaga cggtgtacaa tcaaataagg 32400
cacaaatcga aatacaagct gaacaaatta gtcaaaaagt aactgctagt gaggttaaag 32460
gaattgtaga cgattctatt aacaatctaa cattaggtgg aactaactta tttgttataa 32520
agacacagac agcaggtttg ctaaacgaga atgatggaac tgtaggtact gcagtagaca 32580
actcagtagt gtcagactac attaaagtta atcaaaaaac accatatatt gctacacttt 32640
acggtaacac tggcacaaac atgattataa cagactggta cgataaaaat agaacattta 32700
tttctgggga agctgtggca gactctgggg attttagtaa aaagtatgtg tcacctgaga 32760
atgcagtcta tgctagggta agttataaga aagcaaactc tgtgaatatc aaattcgagg 32820
caggtacaaa ggctactgat tacagccctt catgggaaga cataaaaggt gaccaaactg 32880
ctttagagga atacattaaa aaagtagaag aacaagccaa gaaagctcaa caagatgctg 32940
aaaatgctaa aaatgatgct gaaaatgcaa ataacgcaat agctgatatg tcaaatgaca 33000
atatgttagc accgaatgag aaaaaacaaa tactcttaca atgggaacag attaaaacag 33060
agtatccaat aaacttagac caagcaacta aatttggggt gtcttctcaa cagtatacaa 33120
cagcgtataa cgcactagac gagtacttaa aaccaatact agctgacatg acaacaactt 33180
ctgtagtagt tggttctact ttaagaaata cgtttaacaa ttactatgac aaaagaacta 33240
ctttactaaa cagaatatct gacgtagcaa aaaatgtagc agacaaggca caagaaactg 33300
cagatactat caatgataat ttacaaaata ttggtgggta caactatgta gggttctctt 33360
ccggagacaa tatgttgcct agactgatga ttaaaaacgt tggttactac acattaggtt 33420
cgtcaaccac agagttcatt gacagcatgg tagctgtaaa aggtgatgca acgacccaac 33480
ctttcgatta tactgtaggt acttctgata aagaaattgc tggtggcggt ttagctgatt 33540
atcgtatgaa agaaataaaa gaaggtcagt ggctaacagc ttctgcgaat gtgcaggtaa 33600
taggtggtgg ctccgctagg ttagctatct acactttaga aggggataac tgggtaggtt 33660
ctaacagtac acctatacaa gtaagtgatg gtttgaaacg tgttgtggct caaagaaaag 33720
taacaggctt aacaaaaggt gtgttaatac gtattgagtc agccgacact aatgttaaag 33780
agtttcgatt tggtaatgtt caactagaag tgggtatcat cccaactcct tggaaaaagt 33840
ctgatataga tattcaagag gacataaaca atgttgttca gaatatcaaa acatacactg 33900
cttgggctaa cgatttacag ggtcttgatt ttacaagaga aaaggttgaa ggaaaaactt 33960
acatgtatgt aggtacctct atgaaagata gtgataacta ttcagattat acatggaggc 34020
taactgatga acatatagaa ggtcagatta atggtaagga aggcgcatgg atttactctc 34080
caacagcccc tgctaaccca tcgcaaggac ttatatgggt agacttgtca aaagtcccca 34140
accaacctaa gcgttgggta gattcagaaa ctgggtgggt tgcattaaca ccagaagagg 34200
ttaaagattt gccttggggt gaagatggca caagcttagc cgactgggtg tcacaggcag 34260
agcaaagaat atcttctgat agcattataa atactgtact aggttctgag gatttcacta 34320
gtgtgttcga tacaaaagct aacacttctg acctaggtaa cttggctacc tatgaagact 34380
tagactcaat aaaagaggac tataaccggc taatcaaaga aggcataaat ggtattgatt 34440
ttactcctta tgtgactaac tccgaactac aacagcttaa agacagcttt aacttctctg 34500
ttcaacaagc cggagggggtt aacatgctta aaaactcttt aggattctct gggttagact 34560
tctggaatgg tacagtaggg aagaacttac tacctaactc tacttggaat ttaggttttg 34620
gtagatgggg tggtacttca atcactagtt ttgaaatatt accaccagaa gatgacaagc 34680
ctacgagtaa catattagcc tcaatgccac ttcgctcttc tactaaagaa ataggtaaca 34740
gacctcaccc attaaaagtt aactcgggtg aaacgtacac agtaagcttc gactataaag 34800
aagaagcatt atcttacaac aaggacagac ctatccttgt tgtaagaaac taccctgata 34860
agaacacaga ccaatggatg gagtactcaa tagaaggttg ggcagtaatg gctaacggaa 34920
gcactactga cttaactgtt tggagacgtt ttacaaaaac atttacaata ggtactagtg 34980
gctacttaga tattttaccg aaaaccataa tagaatcgtg ggaacacagg tctttttgga 35040
gagagctaaa aatagagaaa gggacacaag ccactacttg ggtacctaac aaggaagacg 35100
gggcgtttac tggtgatatt gttgagacta ttcaaacaga agaattagcc aacctcgggt 35160
ttggttccgg atttattagt tctaaaagac ctagctcttc attaacacaa tctgtagaac 35220
tacctgaaat aggtgctaac cttgagtatt cactatcttt ttatatgaag gtaactacag 35280
ataaccctgt agctgacttt aaatgcggta ttcgggttta tgatggaggt actctaactt 35340
atacattagg catagaagat gcaacacagc caataccact agggttccaa caatacaagc 35400
ttgtgttcac tcccacaagt acctctacta aaatagaaat gtttgtagaa aatgggcaag 35460
aggcatctgt tattatatca ggtattatgt ataatatcgg gagtatacct cttaaatggc 35520
```

```
aaccatatcc aagtgagata tacaatacga atgttaagat tgatattaat ggggtaaccg  35580
ttaaaaacaa tcaaacagat gggtatacaa tgattactcc ccaagagttt tcaggatact  35640
ctcgtattga tggtaacata gaacgtattt tcactttaaa tggacaggta acagaagtta  35700
aaatgctaaa ggctgaaaaa cgtataacta tggaaccagt atctgtattc gctatgaaca  35760
cagtaacgga tacaaaaaga attagaggtt gggcatttgt gccatcattt gaataaataa  35820
ttcaactttt taaccgaaaa cctcacttac aagttgtttt cggttaattt gtgttatact  35880
atatagagaa ggacacgaaa ggacgatgag actatatggc tttaaacgga acaaagtata  35940
cagcctttgc ccgacataga ttagttttag agtggcgcgc aaatcaaaac attgcaggga  36000
actactcaac aatcagcgta tggctatatc tacaatctat ggataaatgg gggagacttg  36060
atgctcccgc tattggtgat gccaaagtta ccgtagaagg aactacacag acagaaaaag  36120
cttcctctat gttaaatgct ttccaaaaga aactattact agctaaagag tggagagtta  36180
accataataa tgacggttct aaaagaataa ctattggggg tagctacttt gtaaacgtta  36240
cttttactga taatggtgta ccaacatatt acggtacgat aactatacct aacttttcag  36300
tagacctgaa tagaatacct agaagaagtt cattaaaccc tgtccctaca ttaaatttac  36360
cggggaactt accaataaca ataaataggc agagctccac attcaaacat aatctaactg  36420
cttgggtggc taacagagat aaccccacat taagtaatga tgcccattgg acgtacttga  36480
caaatcttaa taatgtagac actagtgggt catttagttt tacagtagca aataacaaaa  36540
ctatttttac tgcattaaac aataggacta gttggcaagg caaggttaaa ctatggacta  36600
tagggttaga tgatgtagtt agtcaggaga gaacatacaa gattgtcccc ccaatgaatg  36660
cacaagcatc gggaggtaag ataaccttaa atgtgggaga gaaaatcaat gtatcactaa  36720
gtaactatcg gtctgatgca aactttactt atgatggggt atttaacatt agtgggctca  36780
acatacccat tgctacaaat tcagcaggga acacaatgtc gtatacacta actcaaacag  36840
atgtagacaa tatattgaag aaaataccaa atgcggattc ctcgtggggt caagtaactg  36900
taacaagtaa gtatagtgga gtacaataca ggactccatg gacaggacag agaatagata  36960
taactatacc taaaaacaag tatgtaccaa gcattaatgg taccccctact tatgaagata  37020
caagtagtgt ctctgtcggg cttacaggtg acaatcaggt agctcttcaa ggtaagtcta  37080
atatcaaagt gactatccct gctaactttg caacggctaa tggttactct actttgaaaa  37140
caattgatgt gtctttaggc ggtacatcaa aaacagtcaa ctattcaaat gcagaaacag  37200
ttgtagagtt aggggctccc gctaaccata catcagacac cttaatagtc acagtaactg  37260
acagtcgtgg gtttaagtct aactggacaa agcatgtaga catttacccc tacgaaaacc  37320
caaatatgta ctttacagtc acacgtagaa ataactttga gacaactaca gatattaatg  37380
ttaatagtac atggtctcct atcactatag gtggtgtaaa caaaaatgct gtccaatcag  37440
taacctacgc aacaaaagta gcaggtgttg gtacttatgg agcagaaact gctttaaatt  37500
ttacagctaa tggtagtatg gtaacagtaa aaaatacacc aatagaatta gataatacca  37560
atacatacga agttaggttg agtgtaactg ataagtttag tacgtttact agaacagcta  37620
ctgttaaacc gggtaaccct atcatgttta ttgatgccga taatcgaagt ctgtttttag  37680
gtaatgcctt tgttgacaat aacaataatg agctaagagg cttattagag atagaaagag  37740
ataagtggca ggagaatggt ttagtaggaa tatccttaaa caacagtgat atatcagcag  37800
tcaatggcat atggttctcg acagatacat caaataacgg aggtgaaggg ctccacttta  37860
ttaaatcagg taaatcaaga aattcattga cttgggatga ctatgattac ttttatatga  37920
gggacaatgg attctatgtt aacaatgact ctaaccctat atttactgtg actgatggtg  37980
gggatttaag gttccctaaa ctggataact tatgggatgg ggcggcttac atgcacaaag  38040
accagataat agtaccacgt aaaaaactca gtgaatgtag aaatggttgg gctttaacgt  38100
tcagttctta cgataaaagt acaggtaagc tgtccttatg ggatataatt acattcttta  38160
ttcacaagac cgcaccggat tctcctttaa gtggtacagg tcacaggttc ttcttaccag  38220
atggtaggga tgctacatct caaaagacaa aatatatata cgtcaatgac tatcagttaa  38280
ggggtcacga agaaaatgat gacaaaggcg gaacagctag cacaaataac agaaataagg  38340
ttcttatgag ggtggatgaa tggtaaatat gagaacaata tacgtagaag taaatgatga  38400
aggttatgta gaaggttggg gcagtaacct gtcaggtaat aataacattc atagtgtaac  38460
aatagaggat aacgaccagt ttttttataa aaactcctta aattttaagt attcaaatgg  38520
ctctctagta ttcgatgaag ataaggcact gcacagtgct aaactagcca aaaaagatga  38580
aatgttaact gcatgtaact atgaaaaaaa tctacctttg acttttaaac tagacaacga  38640
aaattacttt gctcaaccgt taactgcgga agaacttaat gaaacaatat tgcctctgtt  38700
gtcaggttta acagagactg ttcctcttga attagttaaa gtaagtgacg atgtacaagt  38760
aacattacaa gttggataca gtgtaattaa aaatttatat gattatacaa atctaataaa  38820
tgaatactta aataaaaagt tagaagtaga tgtgtttaag atgatagatg aggctactac  38880
ttttgaagaa gttgaggaag tatcatggaa aactacaact agtgatgagt tacctaatca  38940
acctaaaata gaagacctcc ctataaataa caaccaagaa atcgtagata agttaaaaca  39000
agagaataaa gagctaaaac aaagagtaga atttaacgaa ctagctttaa tggatgcaat  39060
aaacatgttt tctgaaatga acaagtaagt tattattaac taaaggaggt gatatttcta  39120
tgtacccata cttatcaatg ttatatgcat cttatgtaat caaagaccct gagaactatc  39180
ctttagagaa ggttccggca ctaattagag aagatgtgga gaaaatcgtg gaagagatgg  39240
caaaaaagaa cgaaaaacaa ggatagttaa tttagtaatt ggagtaacaa taggtttaat  39300
catagggcta ctaatttaaa ctaatataaa tgagggtagt ttgtgctacc ctcttttta  39360
tactatattg tactatatta aggaacgaaa ggagcggtta ctatgggaca atcagatggt  39420
atgggcggta cattaaaacg tattgcgatt caagtaggta acgacccgaa taaaggttgg  39480
tatcgatttc aagtaaaccc aactcaatat aaatataata agccacatcg tgttactata  39540
tttaaaacta aatcaaacat tataacagaa gactttggta aagatataga aactatccaa  39600
ttttctggta caacaggatt cagggtagat agcagaggta aaaatggggc ggacagacta  39660
aaagaattag aagaaataat agataattac gcaaaacagg gcggtaatgg taataggtct  39720
agtgtagaga tgaaatttta taatttcaca gacgataaat attttgttgt tcatttagca  39780
ccagaagggc tatccattga acgttctgca gaacagccat tattatttaa ttacacctta  39840
agtttagtcg tgttaagaga ggcaggacag ccctctgaga gagctcaagt aagccctcag  39900
ataggtaatg taagtcctag cattggacgg acatacaatg cacaacagga cactagaaca  39960
cctgctcaaa tacttcatga tgaatatagg agaagtgtta tgctaaatac agcagtaaat  40020
cctgcagtaa catcgggagc ctataactat ggtgtaaatg agttaaaaaa aataatcgga  40080
tatggagggt agctcatgga aaaagtagaa caatcagcag atttgctaag atttttaga  40140
tatttaaatg tcgatattaa cggtgaagtt gtagccaatg ttattgacga ccaaccaaac  40200
tttatatcaa ggttctacac ccctcataca cgagttaata aaatatctag tacactatta  40260
```

```
gatattgttc gagataatga tataggggaa acaaataagg ctttgtctaa agactcctta  40320
acttataaat ttttaaaaag tggacttaag ctttcatctc cacgtattta cgagctagca  40380
caaattgtag tactagaatc ttttgctctt atatatgcta tcgaagaaga accagagatg  40440
tttaaaatga ttaacgaatc agatgtaaag cagactagag agaatgttaa atacttaatt  40500
gattgtttag gaggagcaaa agattataca gacatagtga tggacttaca atctatggat  40560
gtcgctctag gatatattca ggagcaagtt cctctaatac aaggaggttt accagtaaat  40620
ggcacgatat aaaaaacatt taattgtata tggggataca atgcaatcca tagcacaaaa  40680
agaaacaggc tctgtagata attgggtaaa aattgcggag tacaatgact tagtttaccc  40740
ttacatagta gatactatgc aagaaaaaat gagcaactta gaacatctag ctacacttgg  40800
ggacaccctt tttatacctg atgaaggtaa cttattggac attaatacaa gctcattaaa  40860
ccaaagagat atggatttct tattaggctt agctttaggt aaagacttgg atatgacaag  40920
tgatacagat tactacgaga atcatggaac aagtgatgaa gtgtttgcaa taacacataa  40980
tgggcatggg gacttgaaga tagctagtgg ggcagacaat attaagcaag ccactatatc  41040
aagattgatg acagctaagg ggtctcttat gttgcaccca gagtatggta gtgacttgca  41100
cttaatgttc ggtaaaacaa caattgaaca aatgaagata attagtatag aagtatgcga  41160
tacagtactt aaagatacac gagtagcaga atgcgttcta gtgaaccatt atattgaaga  41220
agaccgatat gttggtaact atagagcaac cttaaagtct actagagagc aatttgagtt  41280
tgttgttcaa aacgataact caggggctct aattattgta tagaaaggat aaggtttaat  41340
gagactaaag aaaatttcag agatactagg tagactaatt gatgtaacta tgataaacac  41400
acatgagata aacgattttt cagttggttc tactattcgt tctatttatg aagctgtttc  41460
tatggagtta gaacagtact atattttagg tagagagaat attttatggg gaattgaaca  41520
aggagtccta aatgcttttg actttaggaa aagagaagca aaaagagcgt atggtatggt  41580
aacactagag ttccatacgg ttactcagac ccctgtgtat gtgccaacag gaacaacatt  41640
cgactctagc ttgtctggtg cccctagcac gttaacattc caaacgatgc aagactacat  41700
aattccagaa ggtgttataa cagcaaaggt agaagtttat tgtacaactg taggtacaaa  41760
agggaacata cctaaaggaa gaatcaatcg ggtaattaac aatatatcaa acttaaaaac  41820
cgtgtataat gagtttgatt ttttaacagg tactgatgag gaaagtatag aatccgttaa  41880
aaaaagattt catgcatttg tggaatcacg tggtagagca acgataaaag ccttagatta  41940
cggtacacgt caagtagagg aagttgcagg agtttatatc aaagaagaag taggctacgt  42000
tagaatatat gcacatgact taaacggtga tttaaaacaa gaaacactag ataaaataaa  42060
agtagctatt gaggactaca gacctgcagg cattaaactg gatgtattcc ctgtaataaa  42120
atccaatgta caagtgagtg caactgttac tataagtgac aaatcgagaa taaatagtaa  42180
attagaagaa agagtggagc ttacaataag aaactactta aatagtcaag ttgtttcaca  42240
accattaatc ttagctgacc taattcaggt tataatgaat attgacgatg ttttaatcta  42300
tgactgtaaa attaacaaca tggaagggaa catggctgtt agggacgaag agataattcg  42360
tgcaggagag gttattgtag aactgatata aattaggagg aatataatgt gagtaacttt  42420
tataaaaata tccaccctct gttgagacgt ggtaagaaac ctaacaagta tgatgatact  42480
aactttgcag tgcttaatgc gttgaactat gaattaactc aggcagagca ggagaccatt  42540
gctagtaaga ttcattcttc attagaaaca gctacaggtg agtacctaga tacttggggg  42600
gactggtttg gtgtatatcg taaagatgat tggaatgacg aatattatag aaaaagaatt  42660
ataagagaac ttttactaaa aagagccaca attcctgcta tcattgatgc gttattggat  42720
ttccttaacg acaatgatgc agtcatccaa atatatgaac cttggagaaa cattttctat  42780
acaaataagt caaaattaaa cggtgacgac catttaatgg gttactacta ccgttttgca  42840
attatcgata tttcaattga tagaccgttt cctcctgaaa ttgtagagat tattaaggct  42900
ttcaaacctg cgggagttct attttatcta aggctagaca caagcttaaa taagaataaa  42960
acaactgtag aaagcccata tgtataccta gacgtgacga ataagacaga attagagttc  43020
cttaacggtt tatactatga cctacgaggt aacattaacc tgtctgacca acgtacacaa  43080
gtagtagaga gtaatatctt ccatacgaat aactctatgc taaacgggga agatgtgctt  43140
gcaggagcat ttgaccacgg aagaggctac attcacttag caagtacaac attgcttgat  43200
tacacaccaa aacctactga ctctatgagt gacttaaaaa cagctctagg agaatcaggt  43260
gctgatatgt ataatcaaac aaaagaaaag gacggaagaa cagcttctat tcaagtacct  43320
gcaacaaaga atgttcacac cttgtactca aacagcattg actttggtgg ctatgattat  43380
tcggggaatc cgaatgttat gactaagcct tatattgctg acaatataac cggcggtaca  43440
acaggagtag ttgtaacacc aattgatgat ggcgcaagac tagaaaaaac acgagttgat  43500
atatctggaa cgtttaactt agcattgggt aatcttttga ataatacaga ttatataatt  43560
tcatatgatg tacttgtgga aaatggatat gtaggagatt taaaaacttg taatgttgca  43620
ttagaaggac agtttgaagg aaagcctaac tattttggta ttttttatat gaatagtgta  43680
acatcaacag atgtatggca aaaggtttct gtaaaattca atagtggtgc caacatggaa  43740
aaattaagtg gttttaagtt tagagtatat ttatctcaac gtgttcaagc agcattaaaa  43800
ataaaaaatg tgaaaattga acgtggttca acagccaccc cataccagcc aaatttactc  43860
gatgcaccat attatctggg taaggtggct ttgggtgaga atattgctaa taagtccgtt  43920
gagtttccaa taaaatctag caattatctc ttatataacg ctagaatggt agagcctttt  43980
gttgtaggag aaccttatac aattaccata aaagcaataa aaccagccag tcaaacgttt  44040
atggtatata acattgggga aggaactact tattacggaa aactaaatcc agttgaggga  44100
ttgacagacg tatggtcact aacattcaca ccaagaaatg tttcgtcaac taatcctagc  44160
gatttacgta tttttcagta cccatcatca acattaggca catgtcaaat tgattggtta  44220
aaaattgaaa aaggtgacac cagaactcct aacattgatt cctacgacta cgtaggttct  44280
ctgatagaag atacagaaac acctacgtta gacccgacta agtatacatg gacagtaaat  44340
ggggatataa caaataaaaa ggcatatatg gtgtttgata ttaagacatt tatcgaagaa  44400
aattatgcta tagaatttga aaaacttatt actgacctag gagaagacca agcattaaat  44460
accgtgtttg aaaactttaa catctctaca acacttaagg ctctagtaag tccaagttca  44520
ccaatcagtt tctcggttga actatacgat ttttctacga gtgcatggca caagttaaac  44580
acggatagct tagacttacg tatgcgtaca ttcaacttag tagcaaaccg tatcacagac  44640
tatctaaatg attacaagct attatttgtt cgttacgtgt ttgataacga aacagataaa  44700
gatgtaacag ttgaactaga catgctaaat gtactattca agtatcgttt aggtgagggg  44760
tacagtatag gactacaatc atctgtggaa tcactaacgg aactcgttcc tatagaaggg  44820
taatagcaaa taatatgtta taatataaat agggcaccta gttgtgtcct atttttttaat  44880
aaacatgcta tattaacaat tgaatgataa agaaaagagg taaataatgt ggctattgca  44940
actaacaatt cacgagtgta tgcctcactc caattaaaaa ataaacaaga cagtatgtac  45000
```

```
ctagcaattg gtaaaaccac tccttggact aatgaagatg ccccccctgc accagaccct  45060
actacggcta ctctaacaga ggttatcggt tataaaaagg tagcaagagt atctttatgt  45120
agagaatatc taccaagtga cgattctaaa taccctgtgg tgtcctatgg ttcaagaaaa  45180
tttacgctaa ttccagatga ggacggctat aaagagcaag cgtggatggt gtatgtagaa  45240
gcagaaatta caggagatga actaccaata ggaacattta ggcaagtagg tattcatact  45300
gacttagtgt ctaaggcaag ttcagaaaag aaagctttgt tacctacaga tgtaacagat  45360
gcaggtattt tgcaattttt tgaaaataga cagcaacaaa atagaacaag tgatgtaatt  45420
ttaaaagaga agtttattat tacaatggaa aataagaagt cagttaaaca ataggaaggg  45480
tgacatagat ggctaaaaat attacaaatg atgatttagg taaagagcct tataacaata  45540
gatattacca aggcaaacga ttttcaggtt tactatttaa accagataag ccgttacaac  45600
aagccgagtt aaacgagtta cagtcaatta ttcaaggaga tttaggcaat gtggctgaat  45660
ccatatttag tgacggtgac atccagactg gtatggaata tgtactacaa gataagaagc  45720
ttactattaa aaaaggtaaa gtattcttag gcggtaaaat gcgtaacttt gacgaacaga  45780
gtatcgatat taccggagag ggtacggagt atgtaggtgt taaacttgta caaaaagtta  45840
ttacagcaga agacgaccca tcactgttag accaaacaag tggtgttcct agccatttct  45900
cagaaggggc tgaccgatta gacgaagatg tagtactagc agttaatgat gattctgcat  45960
caaacattta ccactttgtt aacggtgagt tatacattaa cccagatact cctgagatgg  46020
ataagattaa taaaatacta gcagaaagaa cttatgatga atctggttca tatcgtgttc  46080
gtggttttga tatgtacaca gaagttcacc caacagaccc taacaataaa attcagttag  46140
ttgtcgattc aggtcgggca tatgttttag gttttaaagt agataaacct acaactactc  46200
gtattgatat tgaaaaatca agagagttag aaacaatcaa taacgaaggt ttctactata  46260
gcaatgcaac tcgtaaaaat aaattaggta attccccagt atcttctgta gaccgtgtaa  46320
ctgcacaagt tgaagttgct aaagaacagg tttctcgtgg ggtcgtaggt ggaggtaccg  46380
attaccttaa aaacacctct gtaacaaaag ttattcgtgt atggactgag ggttcaggag  46440
cacaggagta caaacaaggt gaagacttcc aattagtaaa cggtcaagca atatcttggg  46500
cacctacagg gcaagaacct cctgcagggg gaacctactt cgttcaatat gtttataata  46560
aaacaatgat tgaaaataca gattacaaag ttgtaattac tggtgaaggt gatgctaggg  46620
aatggtatat cgactttaac gagatgacag gttctaaacc agtcgatgaa tcacttgtta  46680
acgtagacta taaatacttc ttagctcgta aagacctaat tgtattagac cataacggga  46740
atttcactgt ccataaagga caacctaacg ctttaagact agtagaggca cctaaccatg  46800
tagacccatt agttttagct attggtacag tagtagttta cccagactca aatactgctg  46860
atgctaaaca atggacaatc acacgtctaa caatggaaga gctacagaag ttatctgttc  46920
gtgtggaaaa catggagtat aaccaagcag tgttctactt agaccaaccg gcaatggcag  46980
gagaaaaccc tatctatcta cgtggagtat tctcggatgc gtttatctca ctagataaat  47040
atgacgttag tcacccagat gccacaattg cttttgactt tgacacagca gaaataacat  47100
taccttatgc agaaattaat aaaacagttc caacaattat cgaaggttct agtgaagcac  47160
atgtgtgggg cagactagta acagcaccgt ttaccgaaga agtgggtatt agacaaccat  47220
ttgctacgga agcaatgaac gttaacccat acaacacctt taacaaacag ggtgccttaa  47280
agctaaaccc ttctgcagat aactggattg aagatgagcg tatcacagtt accaaagaag  47340
aaacatctac tatgactgtt cgtcaatggt ggagacatgg tggagcatct tggacaaacg  47400
atgagatgaa catggtatct aacatcacgc ttgaccccgg acaatcgtgg ggaggtgcct  47460
ctggtacaga agaccaacgt aaacaagggc tatccggttc tactttaacc agtggtggtc  47520
agcaaaccaa agaatcaatg attgagttta tgagacaaat tgatgttgag gtttacgcag  47580
agaacttgca acctaatgct aacaacttat acgtaacatt cgatggcttg agagtacctg  47640
ttaccccatc ttctggttac cgtaaaggtg ccacagaagg cactggtatg gcaaatgcag  47700
acggaacatt taaaggggta tttaaaatac ctgcaggagt tcgttgtggt actcgtgaag  47760
tatctgttag aaacgataca aacttagcaa gtactacgtt cactgcgcaa ggtacgctaa  47820
aaacaactga ggatattatc ataaaaaccc atgttactat taacttggtt gaccctctgg  47880
cacaatcatt cagttttaac actaacagag ttgcaacaag ttttgacgta ttctttgcat  47940
ctaaggataa cagtacaaat attatttgtc aagtacgtgg aatatcagaa ggtgggcaac  48000
ctaataaaac tgtgtatgct gaaagagtgt taaaaccttc tgaaatcaaa gtatcagatg  48060
atgcaagtgt tcctacgaaa atcagctttg atgacccact aatgtgtaaa gcaggtcaag  48120
aatactgttt agtattcatt actgactctg ataaatacac aatgtggatt gcaactatgg  48180
gtcaaaatag agtagacgaa ccaacacaaa cagtaacatc aaatccttac ttggaaggtg  48240
tcctatatag ttcatctaac gcaagtgcat ggtctattca ccaactgtct gatttgaagt  48300
tcactgtata cacggctaaa tttaacgaag aagctgtact tgagttcgat gttatgaaga  48360
acgttaatgt agaccgcata gtgttaatgt ctacctacct aacacctgca aacactggtt  48420
gtagatggga tatgaaacta gtccttgata atgagcctgc aggtacaaca gtagatgaca  48480
aaccttggtt acctattgct aactacgtag acttagatgt taaccagtta gctcgtgagg  48540
ctaagcttag agcaacattt aaagctaacc aatacatctc accaatgcta tccttggacg  48600
acattatgtt cgcaggattt ttaacagcat tgaaaggtag ctatgtatct cgtacaatag  48660
atttaacaga ggctccatac aacacggtta aaatgtcata tgaacaattt acacctgccg  48720
gaactgttgt gactgctaaa tatagtacag atgaaggtaa aacatggaag acatttacag  48780
tacagcctac aacaacacaa cgtacacaag actttgttcg tgtagactat gttgaaaaga  48840
ttaatacggg tgggacattt aagtccatta aattccgtct tgatatgacg acccagaatt  48900
catttttgcg cccgcgcgta agacgcttac tcactaatat gaccgacaaa tagaagatgt  48960
aactgtaatg taacatttct atgcctccta ctgtggtata cttactgtat acaaaatagt  49020
aggaggtttt ttaatgggta aagcattaca attagcaggt actacatttg gtaaatggta  49080
cgtaaaagag cgagatactt ctaagaaagg tagagcatac tggatttgtg agtgctcttg  49140
tggaagaaca gttcaatcta ttccgagcgg tactcttact acaggctcat ctgtgatgtg  49200
taaacaatgt gcaaatgaga aatctttagt gggtaagact tttggtaggt tgaccgtcat  49260
taaggattca ggtgaacgag caactaatgg tagtatcctt tgggagtgta aatgttcctg  49320
tgggaaaaca agccttgtca ggggttcaga gttgacaggg ggtcgcacaa agagttgtgg  49380
ttgttactcc acggatgtac tcaaaaaagt agccactaag catggattgt ctaaagtgaa  49440
cggaaaaccc acaaaattat tccgggcatg ggcttcgatg aaacaacggt gttacaacaa  49500
gaaccatgcg agttataaag attacggtgg aagaggtata accatatgtt ctgaatggcg  49560
tgaagacttt gaaactttcc atgattggtc tatagctaac ggattttccg atgacttgtc  49620
tattgataga attgacaatg acaaaggcta ttcaccagac aattgtcgat gggtagatgc  49680
taaaacccag attcgaaata gacgaaatac cattacttac aactggaagg gttcagagta  49740
```

```
caccttagct gaactgggag aactaacagg tataaacaag atgactataa aatctaggct  49800
gaactccgga gccactcttg aagaagcact agacccaaaa gtgaatacgt cagttttgac  49860
tatgagttac aagggagaaa ctaagcctgt caaacaatgg tgtaaagaac tgggattgaa  49920
ttacgcaact gtacgtagca gacactataa aggttggact gatgaagaag ccttaactgg  49980
tatacgtaac aaatagcaac agaataagta taatagactc tatatgttat aatagacata  50040
tagagtctat ttttttgtt aggaggaata aaattgccag aaacacacag acaaacaagc  50100
tcaggtgcgc ttatatttaa accaactata gctgaacaag agcataaaaa tgctatggaa  50160
tctataaaac aagagagaac agagctagag aaagaactag ctaatgttaa agctatcaaa  50220
gatgagttgt caaaagagct agcagatatt aaacaactga aagatgaatt atcaaaatag  50280
tttctaaatt gtcttattta ggatttctgg ttcccttata ctattaacta atatatttaa  50340
ataactatat ataaaatata taatatataa ataatatata ataagactac gaaaaatata  50400
aaataggaca aatcaactct gtatacacct tgacaattac ctactatgtg atataatgaa  50460
tatattgatt atactaaggt gggtatgtca aggagcatgt atactaatct aacttaaagg  50520
agatttatta ataaatgaga ctagtagtag atattatgca tactcagata aggtatgaag  50580
attcggaaaa ttatcttaga ccagaaattc ataaggtaat gcattcagaa ttaggagtta  50640
aagcagatgg ttatcaattt agtcctgcat ataaagcagg ttactgggat ggtattattg  50700
attttttcga taaagaaaat gacacgttcc ccacagggtt actacctcat gtagaaacaa  50760
tactagggaa ccttcaatca actttatcaa agtcaggtta catttttcag tttgagataa  50820
ttgatgatag acctgatgag ttcatgtcag tagatgacat ggataaggag atagtgctta  50880
atggggataa caatgacaag ataacattaa gagactatca atatgaatct gtggagcaag  50940
ttattaagaa cagaataggt attgtaaacg ttagtactgg tgggggtaaa tgcgtagtag  51000
catctacgaa cctactgact tacgataaag ggtacaaaac atttgaacaa ctgttcaagg  51060
aacacaacat tgatttaaca caatcagagg caactatccc taacacattt ggggttacat  51120
tagtgaatga aaagggagaa ccagaaacgc ctagtcattt aactattaat ggagttagac  51180
atgtaaacaa ggtaacaact gagcatggat ggactgaaac aattactgac aaccatccat  51240
tactaactgt atcagaatct ggtagcttta aatgggtaga agctaaagac ttgaatgtag  51300
gtgattggat tgttggacgt aaaggtgata atttatttgg aacgaatact acatgtaccg  51360
tggagagcgc atatagctta ggtttattaa cagcagacgg ctattgtggg caaccaaccc  51420
agattacatt aaccaataac caaccggaga tactagcgga cattcaagat ttctttacta  51480
aagaagggct gtccactaag gtagacccta acaaagactc taaagatagt aagatagtta  51540
ggggtaccgc aggagctaga gaactttata ataaatatgg cttatcacaa ggattagcca  51600
aggataagtc aatcccagag tgtatcatgg aagcaccgaa ggaagtacag ttagcttata  51660
taagtgggta tttagagtgt gaactgagta tggaggtacc taaatgttca atagaggtaa  51720
tttctgcctc cgagaagtta cttcaccaat tacaactctt attaggaaac atgggagttt  51780
cctcaagatt agctaagaag gtagttaaag ggtacgaggc taattggtat ggtagattaa  51840
ctatcggagt gactgactca gtttacctac taaaacaatt aacatttaaa acagcacaac  51900
ggaacgaaag aagagcctta tttattgaaa cagcagagtc ccgtaatagt aaccaccaag  51960
gacaacctgt accttttggt aaggagttag ttaaacgata ctgcgataac tacctagggg  52020
acactaaagg acttagtaag gcattcaaag taccaagaac aattagctta catcggctta  52080
aaaatttaat tcatgagttc cctaatggaa acccgacaga ttttgctaac ctgacaagat  52140
taactgatgg tagatatgtc tattcacaag taacaagtat tgaagatatg ggatatgaac  52200
caacttatga tttacacatg cccgaaacac atagttttat tgcaaatggt atgataaacc  52260
ataacactga aatagcatca ggacttatac agcaaataac cccttactta gagtcaggag  52320
aacgtattgc attttttacg aatagttctt ctattttttc acagtcaatt gaccgtattg  52380
agaaaagact tggaataaaa gtaggtgctt ttggtgcagg taagaaggac attcagcaag  52440
ttacttttgt aatgatacct acgattgtat ctgcaatatc tgcagaccca gaggctaagc  52500
ttaagctgac tgctaaagaa agaatgtaca agaaaattgc taaggatata gctccaaaat  52560
ttgaaagagg gtttaaccaa aggagtttgc ttgaaggata cctaaataac tttcaagtta  52620
agacaaaagc agacctgcag ttgaaacatg aactagaaga aattttttat tcatgtggta  52680
cgaacaaaca ggttattatg aaaatgaaag ggtatcaagc agaataccaa aagattgttg  52740
aaaagaaaaa tggtaaagtt cttaagaagt acaacgaggc tatggagttt ttagattcca  52800
tatctgtaat gattgtggat gaggctcacc atacaagttc agatacttgg tataaagtgc  52860
taacatcttg taataacgct cagtatagaa tggcacttac tggttcgatt gaccgtacaa  52920
atcatgtgct ttggcaaaga cttcaagcta tattcgggga gattacgact aaggtgtcta  52980
acaacacact tattgagtta ggtcactcag ccaaacctaa aataacaata ttccctatta  53040
tagctcctgt agatattcaa accactacgt atatggatgc ctatcaaaaa ggtatagtag  53100
acaatgaata tagaaattct cttattgcaa agttgactaa gaagatgtat gataaaggta  53160
atgggatttt aattataatt aatcgtatag agcacggaga ggctattagt aacttactaa  53220
aagaagaggg agtagctcac tactttatca atggacaact tgaaaatgat ttaagggatg  53280
aaaaaattca ggacatgcgt gatggagcac ttaaagtaat gatttcttct acgattatag  53340
atgaaggtgt cgacatttca gggattgaca cattaattct tggtgcagga ggtaagtcct  53400
taaggcagac actacaacgt gttggtcggg gcttacgtaa gaaaaaaaca ggagaaaaca  53460
aagtagaagt attcgatttt tatgatttaa caaacaaaca tttgaaaaaa cattcagagc  53520
agagaagaaa aatatatgaa gatgagcaat ttgaaattgt tgatattcct attcctaaat  53580
aactataata aagaaagggt ggcatacaat tgcaaagtcc atgcctaaat attgaattaa  53640
aagaaaaatt taaattaaac aaaggtataa cagacttttt agagagagtt gcagataaat  53700
ctcagagatg ggtgaaaca gtagcctccc ctatccgtaa aacggatatg gcaaaagaga  53760
ctggaaaaaa ccctagaaca attacaagat atattaatca attagaggaa ctaggtttaa  53820
taaaaaccga aacaaaaaga ggaatgaatg gagggacttt agtcgtgttt aacacagata  53880
tgcttaattt tgagccaaag gaaaacccta tcacgtctga tactaaacaa gcaaaggaga  53940
ttagagaaca agttttccct aaagccccaa ccaaagtacc aaaacgcaga tacagaacaa  54000
aagcggagat agctgaggca cgtatactta gtgaaaaact taaaaaacgt gaagacattt  54060
taaatgataa aattgagttt aacgttgtta ctagaagttt tttcgatagt tttgacgaac  54120
cagaagcgta ctttaaaggc tatttaattt caagaatgta taatgcttat gtgacaatca  54180
ttccttatga aaaatataat agactgaaaa atttagatga gaaaaaggct aaacaacaac  54240
tacgagcata cgaaagctct tacaattacg atgtgttgcc tagaagattt gttgggacac  54300
ctcagtacaa aaaatttgta gagctagcta aatattgtga agagaacaat atcaatcctt  54360
tagtttattt aacagtgcaa tttgatagaa cagagttttt gatttctgta ggtaaagcac  54420
gagtaggggc tacaccctat gtaaatactt tgttatgtgc agaggctaaa gaggcttaca  54480
```

```
caaatagaaa actgttctac agaatgttac agaaccaata tggattgtat acgtctatca 54540
attcagaagc tacttattat ggtgcaactt atccaattat ttcaggacta ttgaatgctt 54600
acaatatgcc acagaaagac ttgtcacagt tagatactgt gatttgtgac ttagaatata 54660
aaaaagatat tgacaaaaaa gcaggtacgt tgtactctta ttatacagca acacttaaat 54720
cgttaggtga atctgacgta tctagtgaag ctaaagaaag tattgctaac ttcttgaaag 54780
aacaagttgc aaacttttct agtaaacgtg ggctaacttc aacacagtat gccttagcgt 54840
tccctattca gataaactct gcacgcagtt tattaatgaa tgaggaagac gaagaactac 54900
tttatttatt gttaggtaac cagtcacgat tatctaatgt aacaaatgat gaagctgaaa 54960
tgtttattaa acaaggtaga aaattaagta tgtcttggtg gggctcacag aacttctcaa 55020
gaacaatgtt catgttagcg gactactatg ggtttaaaac aaatatatct aagttaggta 55080
tgtacattaa agaatttggt gaggagaaaa ttcctttaga ttctgtaggt atgttagatg 55140
taaatagaat ctatgatgtc ttaatgactg aacaagagat tttagagatt gacaaaagta 55200
actgggagaa ccaaaaagat atgcgtgacg acaaataaga aatataaatg ggagagggac 55260
ggatagtaag atgagtcaaa ttcaaaaaca agttatttat agagcattaa gtgagccatt 55320
ctttgcaaag gaaatcctaa gtaaaattcc aatggatgag tttaaagatt ctggatatga 55380
gatgattgtt tctacaatca acttatatta cagaacacat gatgagagct tagaggaaca 55440
gagtttatta acactagtag aagataagat gttaaaacaa aacaaaagtt tggaagctca 55500
aaacaaagtc tttgaggtag ttagcgactt atacgaacta gagaacgaag atgtagactc 55560
agaagttatc agtgagaaca ttcagaacta cgttcgtaag gtactaacac gagaagcaat 55620
catgaaatct gtaacaaatg aaggcacact aggctctgat agtaatattc aacagctaat 55680
ggatgacttg agagacattc ttactatcga gacagcaggc aataattcag aattgctaga 55740
cttcttcgat gacgtagata aaaagatgga gttacttgca aacttgcaac aaaacaaata 55800
cccaactggt ttcacagcta tcgatgctat ttccgatggt gggctagctc gtggagaagt 55860
cgggatggtt gttgcaccta ctggtggtgg taaaactact tgggcagtta accaagctag 55920
aaactatgtt gtacgtggtt taaatgttct ttatgttcct ttagaggaaa aagtagaccg 55980
tatgattgtt cgttttgaac aattattatc acaacaaagt aagaagaaca tcttagttga 56040
tggtgaattg aataaagact tgtataccca aatccaacaa gcgtatggag cgggtaaaga 56100
acagatgaat tggggtaacc tttggattcg taaatataaa ccacaagagc taacacctag 56160
cggtttatct cagttaatct ccgatgtaat gattcgtaaa ggacagcaaa ttgatgttgt 56220
cattattgac tacccagatt taatgaaaaa tcctcatgca agtggaagta atggtgaatc 56280
agatgcagga ggtaaactgt atgaagatat tcgtgcgatt gcacaagaat atgattttgt 56340
ttgttggacg ttatctcagt tgaaccgagc aagctatggt caagatatta aaaatgcagg 56400
agctatcgaa ggctctaaac gtaaaatgaa cgcagtagag cttattttta cattaaacca 56460
aacatcagag gagtttagta acggatattt gagagcttac gtagataagt tacgtaataa 56520
tagtgggatt gcctatgata aaatgttgta ttttaaagta ctcccagaaa ctatgactat 56580
tagagatgaa acaccagaag aacgagcaga acatgaagca ctgttagcag ataatgcgat 56640
gaatagagca agtagccact ctgatgagaa taactacaca gcaaacgatg ttaataaaaa 56700
gataagtaat ttgaataata ccctttcagg aggttggaat taatgaaaca tattattaat 56760
ttttcagatt ttcatatgca cttttttaaa gatttttcaa aaccagaccc agagtatgga 56820
actgataggg caaaagagca aattactata ttagacaact tgatgaacta tgcacgaaac 56880
aaaaatgggg atgttttatt taatggagac atgttccata aacgagtatc tattgatgtt 56940
agaatattca atatgttatt tcaagtaatt agtagctacc ctgatgttga tgttatcatg 57000
gtcagtggta atcatgataa ggtaactaac tctctatatt cagatagtgc tttagcacca 57060
tttagtgctt taccaaatgt tacagtttgt tctacgttaa acaagattgt taaagatgat 57120
tatacgttgt atgctgttag ttatggggaa gaggtcgaag agatgaaagc ttggataaaa 57180
gaacaagctg acaatttaga ccatgaaaca gttaatattc taagtgcaca cattggtgta 57240
gatggttcat ctactgggaa gtactcccat acacttggtg gtgcttttaa agtagctgat 57300
ttataccctg acaagtttga catagttaca ttgggtcact atcataaacg acaattttta 57360
ggaaacctat ctaatgtgtt ttatgtgggc aataccttac agacttcttt tgcggatgaa 57420
ggtcaagaaa aaggttttta tgatattact atagagggta agaagtggga acaaaaattt 57480
attaaaactg actatactcc gtttgaaaca gtaacagctg ataacccatc aacaacaggt 57540
tctatggaga aatcttatat ccagtttatc ggtaatgtgg atgaggttga ggctgtaaag 57600
agaataaaag aagagaataa cttaagcaat attagaataa aagttcagaa ggactaccat 57660
gttgagccac gtataaacat aacagcaggt tcgacaccta atgaagttgt caatgcattt 57720
attagtaaaa agtaccctaa cgcaaaaata attaaagaaa aagctctcga ctgtttgaga 57780
gaagcaatgg aagtataata attgtttagc ctagatatat ctaggctttt ttgcgttgta 57840
ctattgactt tattagtatt ttgaagtata atatgtttat tgaaataatt aatattttgg 57900
gaggaaaaga tgttaaagtt taaacgagtt agcgcagaga actatatgtc cattggctct 57960
gtatctattg atttagacaa ccaaggactc gtacttatcg aaggtataaa tgatacaaac 58020
gaaacatttc agagtaatgg ctcaggtaaa agtactttac tgtctaccgt tacttatgca 58080
ttgtatggag ctacccctag tggtttgaaa gctgatgctg taattaataa acaagcaaag 58140
aaaaatatgt cagtgatttt agaatttgaa aaagatgggg taccatatcg tatcgaacgt 58200
tatcgtaaac actctaaaca taaaaatact actagatttt tccaaggaac aaatgatata 58260
actcagaaat ctgtagcaga cactgataaa aagattcaag atgtgttcgg tattgattac 58320
ctgacttatg ctaatagtat catgtatggt caaggtaacg tagaaatatt tgctacagca 58380
actgataagg gtaagaaaca aatcttagag aatttagccg atattggtgt ttaccgatat 58440
gcacaggatg ttgctaaaga aagagcacaa aaagcactag ctcttgcaga agagctgaac 58500
agacagtaca ttgctaagac atatgaaaaa gatgggttaa ctcaatctta caatagtgct 58560
ttacaacaat atgagaatac agaaaagctg attcaacaaa aagagagtga gttagctaat 58620
gcagaattag ctattaaaca aagtgagaag aatctgtcag agggaagagc gctacgtgaa 58680
cccgaattag aaaagctaag agagcagatg gcacaactaa cttcccctgc agacgttcgt 58740
gaaattgatg tagaagttga aacacagtat tctaacgtta gtagattatc tagtgcaaaa 58800
acacagaatg atactgctat tgagaaatta aaaaaagaac tagaagatgt taaaacaaat 58860
acaaattgct acctatgtgg tgctttattg agcccacagc atagagaaca agaaattcaa 58920
cgcattcaaa gagaaatagc ggataaagaa gcgtttatcg aaaagcttaa tagtgcatta 58980
gcagtgtatt ctcctctgtt agagcaagca agagctaaac aagaggaagc aagaaaagct 59040
attcaagaac atactaatat ttatcataaa cttaatggtg aaatgaatgc gttgtatcat 59100
gagatagata cattagagaa cacattgaac acatctatta ataataggga cagcattaag 59160
gatatgttag caagactaca agaaatacct aaacctcaat atgactatga caaagaccgg 59220
```

```
gaaatagaag atgagctaaa taaaattaac caattaaaat tagatgccga agaagaagct  59280
agtcaatata aaactattgc acaagaaatt ttctctaata aaggcatacg ctctgaggta  59340
cttgacctag ttacaccttt cttaaatgaa agagcaaacc attacttatc taccctttca  59400
ggttcagata ttgaaataaa ctttagtacc caaacagaga aagcagatgg tagtttagct  59460
gataagtttg acttagaggt agtgaatggc tccggtggaa acacatatca agcaaactcc  59520
gagggagaga agaagagaat tgatttagca atatcttttg ctattcaaga tttagttcag  59580
tcaaaagcaa acattgctgt taatttaggt ttgtatgatg agtgttttga tggtttagat  59640
gcaattggtt gtgagaacgt tattaaaata ttgaaagaac gccaaaagaa cattagtagt  59700
attttcgtaa taactcactc ggagaacttg aagccattgt ttgagaacgt aatcactatg  59760
aaaaaagttc aaggtcgttc ttaccttgaa gaaagtaaat aggtgattac atgaagattt  59820
atacattaag tagagagtta aacgaaggta ctatatttgt acctacaagt agtagtaatg  59880
aagggagact atttagcttc ccgctagaga cactattcga ttggtaccct tgttgcccaa  59940
gatatgagta tcagtacagc acttctcgaa aaaaactata tttgagattg ttagactcag  60000
acaaaacatt agtagctaga tacggtgttg ggataataa aaagagagtt atttcaaaaa  60060
tagcttgctt taatgagaat gaatggtata atgaagaagt ggcaaatgag aatgcagagt  60120
tgtttaactt tgctaaacaa tatgacattg ttacaccttt aaaagaagat tacaccttaa  60180
aagaagtaga taatagtatc tctaaagtac tggacattct tgatttactt tacacaaatc  60240
aaaaagttaa agtagaagaa gagcttataa ataaagtgga tactctacaa ttgagtaaac  60300
cagactcgga tgaacttaaa caagcgtata aggatatatc tgagtatatg aggttagaca  60360
gagaggaaaa agctacttat gtattaagca ggtcactaga ctctttaaat agtgtttatg  60420
aaaaatttgg taatgtgtat acaatgttaa atattatgag gaaagtagtg gcttaaatgt  60480
ttacagactt gttatctaac gaattaggtt cacctaaata tgcagtaagg gactacaggt  60540
ataattgccc tttttgcgac tacgatacta agtataagtt ttatgttagg gtagaagaag  60600
gacacccaaa gaataactta tggcattgtt ttaagtgtgg tagttcaggt aacccagtat  60660
cttttgtaat gaagtattac aacgtgtctt ttaaagaagc gctagagata ttagaagaat  60720
acggctatag gtttaataat aaaaattatg tgcctaaatc agataagtta actgatgagg  60780
aatacttatt acttcttcta ggttcgttag gtaagccaaa agaagaaact aaacaagcta  60840
aaaaagagtt agtagcaccc ccattgccag atggttttaa actactaagt cagaacctga  60900
gagagccaga agcgtaccct ttcttattat actgtaataa gagggggttt acattgaatg  60960
atatttatat gcacaatatt ggatatgtaa aagattcttg ggtaccctta gaaaatggta  61020
agtcagttag actcaaagac cacttagttt ttttaactca tggaaaagat ggtaagtatc  61080
aatattggaa tactagggct attggggaaa gctttattaa gtctttgaac gccccaagta  61140
aagagggtga gcattcaaaa aaggatacta tatttaatat taatagagct agtcaaaccc  61200
ctcagatagt tataacagaa ggtgttccag atgcattaac agttggtgag tctggtgtag  61260
gtacttttgg taaacaagtg actgacgagc aagttgaact tattttagat agtgtgaatg  61320
aagagcaaaa aatatttatc tatttagata aagatgctaa aaaagaaatt aagaagttag  61380
cagagaaact atataagaga cataacgaga cttatgtagt tataagccca acaactcaag  61440
atgcaaatag tctagggaga gaagaggctt ggaatattat aaataactac tctgtaaaag  61500
cagatggagt agggttaata aaattaatgt tatagatagg agagggaaaa aaatgaagta  61560
tacactagaa gatttacatg caggtatgaa attacgttgc acggacaata aaaactacag  61620
tttttggact acgaataaaa tctatgaagt aactaaaaaa gagtcaggtt cactatgtat  61680
ttttgatgat tatggaattg agagcctaga tgaggacatc ttagtacgtt taaatggtaa  61740
tacagggaac gcagaatttg aggttgtttc taaggtgatg aaggatgcag attacacaga  61800
agaagacctt gaagaaggga tgttacttca ctgcaaagat gatatgagct ttccatggtg  61860
ggctacagga caaacctatg aaatctataa gggtgaaaaa ggaattttat ttaccaagtc  61920
aggagacggt aaccaatact gtgctaaaga aatagtagct cgattaaatg gtagtgcaag  61980
cgggtctttt gaattactag aaagaccaca taaaacagag ttagaaaaga aagtagaagc  62040
aagaattaag gaactaaaag gaaagaaact ttgtttattc tacaagcaac aacaaattaa  62100
gatagaagaa aacgaaatat ctatagaaat cagtaagcta agtgaagcat taaaagcgat  62160
tgacgtatta agagaatttg aataagaata actataggag gacaacaaac aagatggaaa  62220
gagtatcagt atactttcta aatagcagaa atattatgga tgaggatgag acaaagcgta  62280
cttatcatgg aacatttaat tcaatgaaag aagcagagca gtcagttcgt gactggtgga  62340
aagcaaatga ctttaagtgt ggtaccctta gaattattga aggtactgag gatgggattg  62400
ttcgttggga ctacggaaac catactgggt tctatctatt tgtaccagaa ggtgctgtag  62460
taaaatacac aatccgtgaa ggcgctaaga aaccaaaacg aggaagagaa aatgatgtag  62520
cacatgactt gttcacagca gacgatggag tagttattcc cgggagatta ggttcaaatg  62580
ttatttctac tggaataaaa acatcgtttg accccaaaca atatggttta ttcattaacc  62640
ctcgaggtgg tatgatgaaa tacccaatca ctttaggaaa cacacaaggt gtagtggaag  62700
gggaatatcg tggagaggtt ggtttaccac ttaaaaatac gttctcttta caattagatg  62760
caagagctgt ttctaagaac gttttaacaa tcaatgaaga aggtaaactt attaacatcc  62820
cagtaacagt agctcggtca atgtatccaa gctttaatgc tctttatgaa aaacagctag  62880
agaagctaag tgaggagcta cagctagtct atggaggaga agttagaata tctaatgctg  62940
atgagtatgt ggttgcggga acactattta tcccaaaagg cactcgttta tgtcaagctt  63000
tcttactacc acgatacgac acacagtttg ttgaagtatc agcgttaggt acaactgaac  63060
gaggagaagg cgcatatggc tcatctgggg tggtatagct atgctcatcc cagaatttaa  63120
gccaccatta ttgtacgtta tgggtagctt ttctgttatg ttagaaaaac accagtgcag  63180
tgtaactttt gatttaagag agccttattt aggtacctct tacgataaaa tagtgaagct  63240
tattaaaatg acttacccaa actatagctt aacttatgta gggatgacag ataataaata  63300
taagttcaca ttaaagaata aggaggacta gcatgtacac caagaaagag gaagtagtga  63360
cagttaaaca cctagttgat aaagagcaaa ttagagtagg ggacatagta ggttacaaaa  63420
agactattag agggttcgat gcaaaaagag taaaagacac actctcagta acaaatcaaa  63480
taggtgtagt ttctcgtgta tgtgacgagt acattactgt tcatgacttt tttgataagt  63540
gctcacgaga aatatgggca aagacatttg aaaatttaga agttcgcaaa atagaggatg  63600
gtaacagcct actacggagg tatgaaaatg aatttcgttg attattttaa tcagatgcag  63660
aatttagtga ttgaagaaaa aacagatgag tatgttttac tagagaaaga acatggtcaa  63720
aagtatgtga catatcaaga gctagaagga gcgttaagta cagtagcacg caacactgca  63780
tttatggtag aaaattataa ccttatgcaa gatattaatt taaaaattgt attgaaaaaa  63840
ttaaaagaca gtggtacaat tacagaagag cttgaaaaag agattcttaa agagttcaaa  63900
aatattgaaa gtttaatgga ggacgaaaca tatgagtaaa gagagtaaac gcaacaaacg  63960
```

```
tatcggggag ttatcggaag cagacatgag agtgtgggct gagtggttag ccacagggca  64020
ggttcatgat aaaaaccacc aaaaacagtt agaacgctta agtaaacgtt cagtatcatt  64080
atctgatgta actactattg tcgaatttat gggcaaacgg aatgatggtt atatttcttc  64140
tttaattgaa cagcaggctg tatttgacaa tttattaaca aaactaggtg taacggaaga  64200
gaaccgctta gaggctaaag cagagtacga aaaagagtta agccttattc aagaaaaaat  64260
ccaaaaagag ttagagtcta ttaaagaaaa taaagaaaaa taatatgaaa gaggttagct  64320
gaatgacaga ctacagcgca gtaggcaaga aaagtcgtaa caaaggcgga cgttttgaac  64380
gtcaaatggc taaagaactc acagagtggt ggggatatga gtttaaccga gtacctgctt  64440
ctggggggct tcactgggct tctagtaata acgttgccgg ggacattgta gtccctagcg  64500
atgctaactt cccatttgtt atagaatgta aaaatcgtga agactggacg attgagaact  64560
tattcttaaa taacaaagaa attaagaact ggtgggcaca agttgtgggg gatgcaaaag  64620
aaacgaaaaa tatcccacta cttatattta ctagaaacag agcaaagaat tttgttacta  64680
tggcatataa tgaaaaactt gttaatgaga ttgaaaaaag aggttaccct ttgatggtct  64740
ctaacataac atatgtagac gactacaagg atactcattg ttacaagaca tttactacag  64800
ttttagatgc aataactagc tttaagcctt atggtagcaa agataaagac tactttttat  64860
tttattttcc tagtgactat gactgggaag atagcctagt ttatgaaaca accataatgg  64920
atgatgctaa acaaatggat gcagaggatt cactagatgc actagttaat tcttatttag  64980
gaggagaata gtatggctaa aacatatcag gaagctctag caacggtaca gtcgtatctc  65040
gaatcagata gtgtaatgaa agaaacctca agtatatctg ttagtttctc agctaactgg  65100
acaggtgagc gggaagacta cgttattgat acattgacat acgacattga tttacgagta  65160
ttcagcttag aaactgcaca tgttgtagct atagggaaga aactacctca agatagcaat  65220
gagcatgctg aactccttaa aaaacttaaa aaagaattta aacaagcttc taaaaaacta  65280
cgggaggact agagtagatg atagacaacg ttaatagtcc tagtcattat acgcaaggag  65340
aaatagaggt aatagaggtt atagaatata ttactgctaa gtaccctgcg gaaattagat  65400
accatttagg aaatgttatt aagtatattt gtcgagcacc tttcaaggga aagctacaag  65460
aagaccttaa caaaagttct tggtacttga aacgagcaca actggtttta acacagtcac  65520
caagtagcta tataggtaaa tgtaagaaat ttttagagaa tttcctattt aagaatagcc  65580
atatcagaga tgctcagcta atagaaattc cagaagaacc tattattgag aaatttttat  65640
ttcaaacagc acagagttac aataaagaac agcaaaacta tattatttca gccttaatgg  65700
aactaaacag tagttcaggt gatgtgaaaa ctgttcttga aaatacagaa aactatttaa  65760
aatttattac aacttagtac aatataatgc tctttctacg aaaagctatc ttttatattt  65820
atggtataat agagataggg aaattaaaaa gtagaaggag cattttataa tgacaaaagc  65880
acccagagtg aaaagactta atatttataa cactgaccgg tactttaata ttaatttaat  65940
gaaaaaagaa gatatagcaa aaaaaattaa agttaaccga ttgaatgaag aagagataga  66000
gagggaaatg gacgaactag caagcaaccc attgaagacc cctataggct acatggatag  66060
aacaaatgaa aaatcttata tactttatca agagaagtat acgaacgaca gacttattca  66120
gaaattattt aaacatgcag ggtctgtgtc ttattacaca gatacaattg taccatacta  66180
cataattgag caaatatcta agaatttaac aagtgaagta atctatccta caaaaaatag  66240
ctatgagaac agagagattg aaaatgttca actagctttc actgcttgcc ctgtaacgat  66300
tgactgccca gtagtactac ctgatgttag cccgtatgat gtgttatttg cactacatcc  66360
tctaaaaaca aatgtagaca agattcaaat atcgttccct tgtcttacag aagaagagtt  66420
cgatactaga catgaagaat actatcataa agtaggtagc cactatgagg ttaaatcaga  66480
gtacaaatat aaattcttta agtatgtaca aacttcctta tctatttggg ctatgaacat  66540
ttggctagtg tgtgatagtg atgaggacta caataaaata gacagatata ttcagaaaga  66600
aaaaattaaa cgtaatgcta acagagagcg tgcattaaag agaaagggta atcaggatga  66660
gtaaagataa aacgattaac cgaacagaca tagctcgaac aatctctcac catactggtt  66720
atcgaatgaa agatatattg aagattttag aagtagaaga tgaagtagta gctcaagcag  66780
tatcacaagg tatttctgta aagaatcaca aattatggaa actaaacatt aaaaaaaagc  66840
cagagaaggt agcatgggat ggtataaact ctaaaagttt tatacaacct gaaaaatatg  66900
tagttaaatt tgtaccatta tctaagttga aagagtcaat agacacttat aataaagaga  66960
gcaaataaag ctctcttttt tgctctttct atattgacaa ataacataat acaaagtata  67020
ctagtgtcat agagcaacag agaggagaaa agtgtaattg aaaattctat tcttacaaga  67080
gtacattaga gaaaatcatg tccataatgg aaagaacgga caaacagttg attttaaaag  67140
aacagaaatg ggtaaaaaac ttacaggtct gttaaataca ataggactga caggtaggga  67200
ctatgctgta gactatgtgt acgacatgat tccggaagta cagaaagtca accctagaac  67260
aggtaaacca attaagtata agacacctac gttaagacag cgtaaagaac cagaggaacg  67320
gttactcaga cgtttaatga aatacaaacc agatattatc atcccaatgg gggagatggg  67380
ttgtaaaaat ttattaggaa gtacttctat cacaaagaat agaggagtac caactaagaa  67440
aacaattacg aatgagaaca tactgagaac ggctgatgag caagggcttg aggtagacga  67500
agtagtagac tcttttgaaa cttgggtact acctatgttt agtatggaat actggacagc  67560
taacccaaac attgagaact ttatcatggc ggatattgat acattgggta agtttgttca  67620
agaaggggaa caagcattta tccctaaaaa agtagattac gaatttgttg ataacattga  67680
acgtgtaaga caaatttttg gtttttaga caaaacgaag ccagtaactg catgggactt  67740
ggagacaaat agtttacgtg gtgacttatt aggggctaag cctcttgtaa tgtctatgag  67800
ttggctagag ggacaaggtg tgactatacc gttagaacac catgaagcta aatggagccc  67860
agaagaactt aacgaaatat atgacttatt tgagaagttt ttagcggaca gacagcaacc  67920
aaaagtagga caaaatatcc agttcgatat tagattctta atgaacacaa aaggatttac  67980
agagtttgaa gacaacagag atacaaaaat tgcttactat ctaattgttt ctcagaaagt  68040
agacacttca aaacggctat ccgatattgc atatgaatta acagatatgg gaggctatga  68100
cgaaccgtta gagcagtata aaaaacaata taaagaggac tatattgctc gtaagaaagc  68160
agagattgat gctttcaaag aagctgaaaa agaacgagta gagtgtgagt tcaagatagc  68220
aatggataga tataagcaag aagttaaaga agctaagctt attggtaaac ctactaagtc  68280
cattattaaa ccagtaaaag aaaaagttgt agtacctaag aaatcagata ttaaacttat  68340
taatgagatt gacggtggta actttaacta cgactggatt ccattagaga ttatgcaccc  68400
atatgctagt ggagatgtcg attgctgtct acgtatctat aacgttctat ataaacgaat  68460
tgaggaacat cctaagatgt tggaattatg gttgggcttt tatcctagac taacagcaac  68520
attagcacac atcgaggctt ctggtgttct attagactct gaatacgcag aattagtaga  68580
gaacatctat acagaagaag aacatcggtt gcttaatgaa attagaaagc taccagaagt  68640
aaaagaagta gaggatgaac atatgatgtt ctacaaagag gggcttaaag aaatgacaaa  68700
```

```
gcctgtcaaa gatagagatg cctctgttgc cagactacga gataaatata aaattactga  68760
tagtgagaac aaagtacatt ttaaaccaag ttcgtctgaa cataaaggta gactgctatt  68820
taaagtaatg ggacttacac taccttatga taaagaatct attaaaaaag aaacttttga  68880
caatggggta ccagaacatc agctaacatg gagagattat aaaacagata aacatgcact  68940
agcttatatt gcagaaaatt atccagaggc taaacatgtt gctgaacttt tgctagagta  69000
ttctaaagta aacacactaa aaaataactt tgctcaaaag ttacctaaat tagcatctaa  69060
caaggatggc atgattcatg gttcatataa cagtacaggt acagaatcta cacgattgag  69120
tgcaaacaac ccgaatatgc aacaattaag tagtaaggtt ggagacccta gacgttttga  69180
ctataaatat ccaattaaac gtttatttag aacaagattt gagggaggtg gaatgctaca  69240
actagactac tccgccctag aaatgcgtat tttaggtttg attgcaaaag ataaagcaat  69300
gacacaagca tttattaatg gtgaagatat gcatgaggca actgcatctc ttgtatggaa  69360
gttacctaaa gataatgtac caaaagatat gcgacaacgt gcgaagagtg tcaacttcgg  69420
catcgcttac ggtaagcaca attgccgtct tgtagcgtaa gctactcgat taaacttacc  69480
taaacgggca tagctgaata accaataagc tgataagaga acctaagtcc tgaaaaggat  69540
agaggcaatc ccgtagtaaa gacgatttaa taaactccac taaaggagtg gtattatgga  69600
aattggaaca agaacagaca acaacccttt atatagaaaa ttaagaactg tgcataaaga  69660
catgcgcaga cgatgtctca ataaaaatgc taaatcatat gagttatacg gaggtagagg  69720
tgtaactatt agtaaggagt gggagacctt aaatgggttc ctagcaactg tagatttagt  69780
agatggttgg gacaaagata cattcctcac aacagggcta tccttagata aagacttaaa  69840
aggaggagcc gagtatagta tagctaactg tacatggatg ccacttaatg ataacaaaag  69900
cctactatca atgaactaca agaatgtctg tgctattgac ccaaatggtc aatattatgt  69960
tatagacaac attgacaagt tttgcagaga gcacaacctt aatcattcca atatagttca  70020
agtaattaat ggtagataca agcatcataa gctatgggta ttctggtatg aaggtgataa  70080
acctaagaaa gggatacaac cacacatagc gattagccca ttgggtgaca cctactattt  70140
ctataaagct cctgacatgg aaaagtatgg gctaaattct aaatgtgtag ctagatgctt  70200
aagaggagag agaacaaaac ataaagggtg gaagtttatt aaatctgaaa acctctaacg  70260
actatcgaaa agtgagtagc tgtcgagagg acacctacaa tataactgag tagagtacac  70320
caacaggtgg aaatggtaag gctcctagag taacgactag gagcgtgata tagtctaagc  70380
ccctaataaa tatcgggaaa ccgagggtat aactggaaag tcctttttca attgcaccta  70440
agttaggtgt aactgtagaa gaagcagagc gtatttttga agagtacttt gcaagtaagc  70500
caagtattaa acaatttatt gaagagacac atcaatttgc tcaacgttat ggctacgtag  70560
aaacactaca aggacatcgt agactattgc gtgactcatt ctctaaagat aagaaagtat  70620
ttaatggagc aatgcgtaag tcagtaaata caatcattca aggaactggt gcctacttaa  70680
ctaacctatc aatggtatac attgacgagt atatcagaaa acacaataag cgttcacgta  70740
ttgttatcac tgtacatgac tcacttgtta tcgattgccc acgtgatgaa gtggacgaga  70800
tggcaaaagt ggctaaatat attatggaga acttgccaat tgatttctta atgattgagt  70860
gggaaggtaa agagatgcgt taccctattg tggcagatgt agagattggg gagaattaca  70920
atgatatggt tgattatgat gcagaaatta tcaacgagtt tgcttcttac cgaggatacg  70980
taaaatactt caaagaccaa gctaagatta aagattacta tgataacaaa cttatctcag  71040
aagagcaaaa agaccaaggt atcaaagtta tccaagatgc aatagagtca tataaacaaa  71100
tgacaattta ataaaaaaat gttaaaaata gcttgactat tgacgtatag tatgttatta  71160
taatatggca gacaagtttt ctgtattaat acaagaaggg ggagttagag agtgtgctta  71220
atttacgagt agacgattta gagttcaaaa caattaaaat tattgatgat aacggagaag  71280
ttgtgacaca tgatttacaa acagagttac aagtcaatga atttaatgtg agaacagcat  71340
ttttagagca acctgctaag tatacttatt ggacttcgat actagagcgc ttgcgcatgt  71400
atcaagaaaa ctatgagtta aaagcagaga agaagaaagc agaactatat gagccttctc  71460
gggttgcctt aatcaatcaa ggagtagcta aacctacaaa agaccagatt gaggcacaga  71520
ttatgttaga tgaagactat tacaaactta gacagagtat agttaaccta tcatttaacg  71580
tgagacaact gcaatatata gttaaagctt ttgaacaaag aaaagatatg cttattcagt  71640
atggagcaga ccttcgtagg gaatatgagt atagccaaaa ggttagtatg ccagacccaa  71700
tgaaaaataa ggtaaataat ggtttctcag actttcaatg gaatttagaa cagtaaaatt  71760
agtgataaaa aaaataatat aatataaaaa aaatagaaat ggagaaattt aaatgaattt  71820
tcaagaacaa ttacaacaac aattaaaaca acaaaatatt ggagaacgtg aagcggtaga  71880
ctacccatca aatcatttaa aacataaaga attatacttc cctaaagcag aaaatggtca  71940
gccatcaact ctatatgtac gtgtgttacc tcctgcagta ccgggagaaa actataatgt  72000
tagcgctcgt gaggcattct taacaactcg taatcgtaat ggtaaagatt taaagagcaa  72060
ctttatcttt tcagaacacc ctaatgcaga agacatctta gaacaagcta tgattcgttg  72120
gaacgcagaa aatcgtgtac caaaccctta tagccgtaat acaaaacctc gtcaacgtta  72180
ctacgttaat gtagtgcagt taattattaa ccaacaaaca ggggaagtta gctatgaaac  72240
agattctaat ggtcagctaa tggttcgttt acttaagtta cccacaaacag cttgcatggc  72300
tattaatgag agcttaagta acccaatgtt acgcccacag ttttcacctg atgtaccaga  72360
agaagtagcg caatacagct ttatttcttc tgcagatgca ttccctattt caattacaaa  72420
accaccacgt agtaacaaac ctacttcgta caatgtacaa gtgattagta atcgtagttt  72480
aggtgcatta ccacaaggtt gggaaaactt attagaagac ttgaaatacc aagctacacc  72540
ttctgtagag tacaatcgtg agtttattga gtactttatt gatgtagtag acgggaaaga  72600
acctgtgcat caaggagcac aaagtcaagg aacccaagct ccacaattta atcagcaacc  72660
agtacagcct caatttaatc aacagcctgt acaaccacaa tttaaccaac aacctgtaca  72720
accaatgcaa caaaatactg gttggtcgcc acagcaaagc caaccacaac agcctgctac  72780
aggttttaat gcaacgaaca tgggaacacc tccaaacatt aatggagggt ttagccaaca  72840
acctgtacaa caacctgtac aacagcaaca accgatgggt tctttcaatg aacaaccagt  72900
gacagaccct tctaccattt ctgatgcgga tatgcctttc aatatgcagt ccatgcctga  72960
tgtatcacca caacaaaatg ccgtacctga gcaacctgtg actaatacac cagagccagt  73020
aagccaacca gttgttaacc aacagccaaa taacacacct agtgtagacg acctattagc  73080
aggtatggta ggcaacgttt aacaataatg aaacagttag gaggggcata ctgccccttt  73140
taattctgtg ttaactatcc aaaatattta gtaggagtga ataatattgg caagaaaaag  73200
aaaaagtgaa gaaatagatt ttggaactat tgatttgaca aaagaggtag gactaactac  73260
atttacggac acaaagttct ctaatgtatc agacagacta ccaacaatga ttccacagct  73320
tgattacatt ttaggtggag gattgccatt tggacgtatg gtcgaggtct ttggtaagaa  73380
ctctagtggt aagtccactt tagcagtcca tctgacaaag gtagcgcaaa tgctagatgt  73440
```

```
accaactgta tggattgacg ttgaaggtac cgcagaccca gaacgcttag cagaactagg  73500
ggtagacttt agtgcaggcg gagtattcat ggtagagcct aaacagaaca aagacggtag  73560
taaagataca atcacggtag aacgtgtagc agaagagtta caacgactct taccagtatt  73620
tagtaagctt ggaaaacctg tattaattat ttgggactct gtagcgcaaa cagcttctga  73680
gaaagagtta gaaaaaggtg taggtaacca acaaccgggt ttgtaataaa gctccgttag  73740
gtagtaatat ctaaaagaaa cctatcttta tcatgggaaa cctctaggag gcaatcatga  73800
gtgaagctgt agaaatacag aacatgcaac gactatcgaa aggggagttc ttgtcgagag  73860
gacatgaatg agaaccgagt agagtacacc caagtgggtg gaaatggtag ggctcctaga  73920
gtaacgacta ggagtaagat atagtctgta ctacatggtg acatgtagca gttcataaga  73980
gaacgctata agcttaacga acttatagga acataataga ttaaggcaaa agcaatggca  74040
cagtttgctc aaatcattgc acctttaatg acaaattcaa aagcattatt tattgctatt  74100
aaccaagcac gtgacgagct aggtagtatg tttggtggag tagactctcc cggaggacac  74160
gctttacacc actgggctag cttacgatta gaagtagtta aagcaagtca gattaagaat  74220
aaagagctaa atgcattcgg tgcagaggaa gagacctatg taggacatat cctgcgtgtt  74280
aaaacagcaa aatcaaaagt gtcccgtcct aaccaaaaag cggaaatgta cttaatgtcc  74340
gacacaggac tgaacttaga ggaaaacatt tatcgttcat gttttgcaac taataagcag  74400
tatgccttga ttagtggagg cacgtggaag tcttatacaa cggatgcagg gcaagagatt  74460
aaatttaatt cagataaagc ttgggtagct tatttacgtt cagaagaggg aagacctgtt  74520
cgagacgaac tatttgctaa aatgatggta cgctcattcc cacatcgtta tgctccattt  74580
aataatgagg acgtggatgt atgcaaaatt ccattatatg aatttactaa agaatatatg  74640
gaaaatcata aggaacaacc taaccaagct actaaagaag aagtccccga aacaggaaca  74700
gatgtttcag atttacttaa acaggtagac taatagataa gggggcattt agccccttta  74760
ttagctataa aggagaggaa cttattttgc gcaaaggact agcacctaac ccattttttg  74820
aaatattaga aaaacatcaa gactcctcta aacgtactat gactatgaac agcagtggta  74880
cacctagttc actacaacca ataagagaca tgttcttaaa ggcaatgaga gaaggtaaga  74940
aagtcctaat agagaactct gacttaagta gtgcgaactc tgttgttata gagatagaat  75000
atgtaggtaa tcgttggtgt ttaggttatc aacgagtctt attttatggt atggagttaa  75060
aaataccaca cactatccac ttctgtgatg tatatggagc ctatgggcac gatgctcaga  75120
aggttaagag acaagttaag gtagtgtttg agggggacaa ccctttttgag tagagatgtt  75180
caaaaagagg aaaaagaaat acgtaatggt aatcggttta ttacagagac tcatggcaaa  75240
ggagtgtttc ctagagatgt agaccgattg taccataagt atagtaatct tagatataaa  75300
gtctataaca ctcataaaga ctcgttcaat agtgaggctt cacgtaagga gctcaagagc  75360
tatattgatg agcaatttat aaagttaaca aaagagtatg atataaatgg agaggtagac  75420
tttccgggat atattaaaaa agctctgaat ttacgagtaa ggcacagcta tgtaaaagga  75480
cggttccgag ataccgctag agaacgtcta ggcacccaag ataacgaagt agagttattg  75540
ttagggattg acgatagctc tcaggcagat attgaggatg cagaacttat tgaatcgtta  75600
ttatcaaaag ccaatttttc agaaattgaa ttagcagtat ttcagcagtt aattcaagga  75660
acagtaaggg atgctcgtat tattactgaa ttgtcagaaa actacggggt gtccaagaaa  75720
gccgtaaaag atgctataaa aaatgttcgt gagtttgtct taataaattt aacagattag  75780
agtaatacct cctttatgtc tgctatatta gcagtagaaa cataaaggag gtattttttta  75840
gtggaacaaa acaacactgg caagtatgca ccatttattc gtttaattgt gatgggaatc  75900
tcatttgtgg caactggttt gactacaata tttggttggg aacctttacc attcacagac  75960
gaacaaatga accaaggttt aatgttagta ctatctgtag gtcttgccat ctacaactgg  76020
tacaaaaaca acgctgtaac ttcttatggt aaagcaaaag aagaagcagg aaaagaagta  76080
gtcggaacta gacaagactt caaaaacaga gactaagtac gaggggtgta acccctcctt  76140
agttaataca aaggagcttc gacatgaaga tagacgagat aagcaaatta gaattgccta  76200
atctatttgg aaaattcctt gtggtagaga ctatttcgga tgggtacact ggaaccgtat  76260
ctggtcacta taactacgag atagaccaaa aatctgagga aacttatatt taccctgtat  76320
tttggaatga taagcttaac aaatttatta ggtcagatga attagttgta tacactaata  76380
aaaataaagt atactatgtt tgtaaaacaa ctatagaccc atataatcat gcagtagtag  76440
atgagctcac ggtagaggaa ggcatggaca aagacaagcg taccccttcaa gcgtttaaac  76500
tttttgtaaa tgacctattc tcatttggta gctacaatat ctttctaaca ggtaacctat  76560
cattagaaaa caaccctgat attgttctag ttagcagtgt atcattagac aaacagaccg  76620
ctaaaatgta cacagaacgg acattagaac taactgctac ggttttacca gagggagcta  76680
caaacaaaaa agttagtttc tcagtagata aaccagagct tttagggtta acagtctctg  76740
acaataaagc aactgtcaca agtaaagata aggcaggtac tgcaattgtt accgtaacta  76800
ctgaggatgg agaacacact gataagtgta cagttcagat agaagagtac ataaaagtta  76860
caggaattaa tgttagtgga gaatctgctt tagaaaaagg taagacatac aaatttactg  76920
ctagtattgt acccgataat gcaacgaatc ctaaatttac ttggtcttct agtagtgata  76980
ccatagctag tgttaatgca agcggtgacg ttgtagcttt agcattaggt gaagcagaca  77040
ttatagcaac aactgaggaa ggtagccatg taggtaaagt acatgttacc gtatcagacc  77100
cagaaccagt agaaccaact gaataacata gaaaagagga aagaaaatgg ctaaagaaat  77160
attaaatatt gaagacctgt taaaaccaga gacactagaa gtagcaatag atggtaaata  77220
ccttattgta ccaacattgt cggatgggtt tacaggtaca gtagcaggcg gatatgcata  77280
tgctgttaca aaaaaaggaa cagactacac agttaatgaa ttaatctata atcaaaagga  77340
taacacattt aaaccttctg atgaaccaat tattataact gatgataatg aaatattctt  77400
cattactcgt acattagaag acccatataa ctaccctgta gttgctacag agaaacttaa  77460
aactaaagat gtaaaagaaa aacaagtttt acaagcgttc ttagcatttg ctgatgacag  77520
atttaagcta ggtgtttaca atgtgttcct agcagatgaa ccatttgtat atggggacaa  77580
aacagaatag tttcattata agagacccgt taaggtctct tttttttttgt atatagtgtt  77640
gacaatgttg tagtttagtt atatactata cttatactgt ataaggaggt aaccacatga  77700
acgacaataa ggaaaaatgt attaaacaag gaatacgaga tacttataaa gggtacgata  77760
ttttattaga tgaagagaat ggatttttct atgttagcgt acttgaccca gatggcaaag  77820
aaatcattag tgggtttgta gaggcggata aacctattga agaatactat aaagagctcc  77880
taggtaaatg cgaccaagat atatcgttta aagaccttttt agggttctta aatggacgta  77940
gagacactga acgtacagac atacgttttt taaagagaga cagtggggta taattaaatg  78000
acaaagataa aacttattac aaaaaagaac acccaaggct atgtcatgaa caccctgcta  78060
cgtagatttt ataaaaataa tgtagacgta gaatttctta ataaattcaa tctacctgat  78120
attcataacc acatagggga gcatgatgct gttatcatag tagggtttcc tttctttgaa  78180
```

```
agccaacgag gtgcgttaga cacggcactg tcatctatgg acaacccgtt tagcaaggtg  78240
taccatttag caacatttgg ggacacctat cgtaatgaag gtagctttcg ttcatttgta  78300
gacgaggtta taagccccgt tggtcatttt gtagaactaa taattgacct aactaagttc  78360
actaacacag gtacaaaaga ggatgaacaa aatgtagtgg ctcttgctaa agaggcatta  78420
gtgtttgcca aagatattat agaagagaca gacaactaca atcgttatga agttacagac  78480
agaactatct cttgggttct tcttgtagat ttgcttggag agaacctata taaggtgaca  78540
gagcctagta aagagctaga caccattttg aaagaacaag aagtacttgt agatgccttg  78600
aacataaata tgcaggacta tgtgctaaga acaataggga agatgtctgc aaacgtcatt  78660
aatggaacag tggtttgttt cggttatgca gaacagcatg tcaacgaagt agcccataaa  78720
ttaattaatt tttataagtc acataactat caaaaagtta ttgtctttat tggtaggcac  78780
acaaaaggtg acgacatgtt tagtgtaagg agctatggtg tgaatgccgg agaggttgtc  78840
tataaagttc ataatggtaa agggaaagac acaacggcaa ccgtcttctt aggtaaacct  78900
agtgaagctg taaataacac actgctaagt gtgctttctg aaattttata gtttaacttt  78960
gtggtataat aaagatagat aaattttgat aggagtgtaa atttttgaaa aacaacgaac  79020
ctttagagaa gttattagac aaattagatg aaccaagaat tttacaaaca attattatag  79080
gtagtttaca acggagcttt aatcgagtac acgttggtaa atttaataaa ctagcacagg  79140
agtttgactt agataaggag aacctgtata gcttaaaggc actagttaag gaaattgaag  79200
aagataaaga gttacacgaa ctttacgaag ctagtatggc aggcaaaatt acgctagagg  79260
ctgttcgtaa agtattgtta caagatgata agtcatcgtt tgatgtactg tcttcttacg  79320
tagtagaaaa tcaagcagtg ctagcccgta accgagagtt cggtaagtta caacgtgagg  79380
gagcttatct tgaccatcta attagtggtt tgaagacata cttattaact gaactaaaag  79440
acatgtctag tttaaaatat atcaataaaa atttaaaggc accgaaagta tcctcagacc  79500
gagagcttat tctgtgccta tctgattggc atattggtgc ttttgttaat aacattgaca  79560
caggtggata caactttgaa atctttaaag aacgacttga aaagttatta gaagaagtat  79620
tccaagtggc tatggagcag gatattaaga aaattcatgt ttaccatatt ggggatatta  79680
ttgaacacat taatatgcgt aatgttaacc aagcatttga agcagagttt cctgctacgg  79740
agcagattgc taaaggaatt agagttcttg ctgatacact caatttacta gctaaggcag  79800
aatttgaagt gtctttcggt atggttggtg gtaaccacga ccgtttccaa ggtaacaaga  79860
atgataaaat tcataatgat aatgtggctt atcttgtagt agaccaactt catttcttac  79920
aagaattagg ggcattaaac aaagatatta aacttgtaga caacagaagt gacgtttata  79980
gttttaaaga tacagttgca ggtaaacgta ttaaagtaac tcatggtgac actgagggca  80040
aaaaagtgga tgttaaaatc cctaaacata tcaaagatga agttattgac tatttaatca  80100
tggggcatat ccatacaaca cgtattattc aagaagactt ttcaagattc catgtgtatg  80160
tcggctctcc tatgggggca aacaactact cagcagagaa taacttgcca acaacaagtc  80220
ctgcacagct aattatggta ttagaccctg agcgtgatac accgcagttc atgccagtat  80280
tcttatagga ggtactcgta tggaaggtaa tttagtttat attttattgg ctattgcata  80340
tgtaggtgaa ggtataactg cctttactaa tactaagcgt aaagaaagat acatgattga  80400
agaaggagag gctcctttgc cacgtagttc ttatgtattt ttaggcatta actacctttt  80460
aagaatagct atagcaattt ctcttatctt catcatacca actagcttgc aacttaacgt  80520
aacaggtatt gctttgttca cactaatggt atttgtagtt ccttttatag caagaattat  80580
cgaagttgtt attagaactg caattgttcg ttatgttcaa aaacaatata ttaagcagtt  80640
agaagaacga aaaggtaaaa gagagactaa ctagtctctt ttttgctata ttgaataatg  80700
aggtgactaa gtatgaattt tacagaagta ataagcccta atggggagac atcattaata  80760
gatgtaaaca acccaccaac attaatcaga cgtggggtct tatctattaa aacaaaggtt  80820
aataatgaag tgaaggaaac tcctgtttat attgttgaac tagccgagga gctaacaggt  80880
actgatgtag tatctgtcta taaagtaaaa gagattggag attctatcca aaaagactac  80940
attgaagaaa aagtgacccc taggttcaaa agcacaacat atctgggtga gttagcacaa  81000
aagattaaag gacggtcgat aaaggaacaa cgaagagttg aaacaaaacc accattattc  81060
ctagccccag tagttaatgg aatcgataca ttcacaggaa tcgaaggtaa aggtttctac  81120
gaacgtgaag aggacagaca tattctatta cctgatggaa aaccgggcat agcctatgga  81180
gataatacag gggtttttat cggtttgagc tcgattaagt gggacaaggc atatgtagac  81240
gtggagtcta taacaaaggg ttatttgtca cagaaacaga tatggtttaa cctagatggt  81300
caaagaccac aatttagaag tgagacacta taatgacaga taaacaattt tatgaggcag  81360
atattcaaga gttaatttta aataagcaaa gaatattcgg ggatatagga aagagcgcta  81420
ttgtttttga gaaagcaatc atgcaaggta acacaatatg tgattgccta gtcttcacag  81480
aaaaacgagg gctcattggc atagaaataa aaactgaacg tgactcgaca aaaagattaa  81540
ataaacaatt atctgattat gaaaaggtgt gcgactacgt atatgtatta tgccacgata  81600
accatgtacc taaagtagag caaatacttg ctagacataa tcataaacac gtaggtatcc  81660
tagcttacac agagttcatg ggagaggcaa tgttaggtga gtataaacaa cctagccgtt  81720
cccctaaaaa atcagcttat catatgttaa atatcttgtg gaaagaagat ttaataagaa  81780
tgcttggtac attcagacgg tatggtgata gactagaagc taatggagct aaggttatga  81840
aaacaaacag ccgttctggt ggagtatctg gactttatgt taaatctaca actgctagaa  81900
gaatgactaa acctgaactc attaataatt taataaatag agtaggcggt accgaagagg  81960
ctacgagagt gttctgtgat gtgtttatcc ataataggaa tcacccagag aaagcaatta  82020
agttaagaca ttttaaagca aaagagaata ggggtgacct agatggggtt taaaggtgca  82080
aaatatggtt cttggaatac tgtagttggt aagaactatg tgggtactgg gggcagaaca  82140
agtggtagta acacaaaacg gctgtccaca aaaggctact accaagtagg atttgttaaa  82200
gaatatcaga acttgacaga aaaagatatt atgttaaaat tagagtatgg aaaagactta  82260
gtgtctagct acactggtgt acctgcagat atgattaagc tacgtaaaaa gaaagaggag  82320
caaactctag catctttaga cacagtttat tatgttagca ttggtaagga acctgtaggt  82380
aagctgtcta tacgagctca gagacgtttt agagaggtag ggttaacatt tatataccta  82440
gagaagaact acgtacagag gaagcttaga ggcggtaatg tacgtagtgt aggatatact  82500
aacgcaacca aatctcagaa acgtaaagca gatagacgga agggcaataa gtctaaaaca  82560
actagataga tggaggacta ctatgagtat ttatgatgag ctaattggta aaagtgttat  82620
agccctagaa tatgcggagg atgggtgtga ggcaagcctt gtactaaatg atgggtcatg  82680
cttaaaagta tcttgtaacc cagagccaga ctgttgtggg tataatgatt ttgaagttat  82740
tctcccagat ggttttgatt tcacagataa cattattaca aaagttgaag ataatagtga  82800
agaatgttat ggcggttcaa cagttaggat aggcattttt accaatgatg cacggatagt  82860
tattgaaggg gactacggaa gtggttctgg gtggaactat ggagagtatg tagacgtaga  82920
```

```
aattgtaaaa taatttacta ttagatggag gtaagctatg cttaaaaaag ggaaagaagt  82980
aacactaaga aaattttata atattatcac agataaggaa tcagtattgc taggggcacg  83040
ctacacaagc tcaataatga ctacagatat tcctattaca acaactttttg aagatgttga  83100
ggtagacctt aagaaagaaa cagttgcagg aactatttca ttcagaccag taggagaaag  83160
acagattaat gcattaagtt tactaaaaga agcaagcaca gcttatgggg gttacggaga  83220
gttcctagat gatactattg agaaaccttt aatcaatagt gattttgcag tagatgttag  83280
cctagcagac tctgctttct ctaacctaca agagattcca tttaacctat atatgtcctc  83340
cccaaaagtt ttttatacag aagtatcaat tagagggcgt aaacatatgc aatatgtatt  83400
agaggatgag tcttctagcg gtgtaacaag tacattagca ctggtattcc gtaaaaaatt  83460
gtatgatggg gaaacattgc taggtgtgca tacttacacc gaagcactag caagagtaga  83520
gggaattaaa gtgttacagt ttatcgcaaa tggctctgta ctagaacaag taatcggtgc  83580
agtgtctgtt ttagggggta gcacaggaac aaccctgttc cctatgtttg acgatatggt  83640
gatgcaattt gtgatgattg agtctgttcc ttgggtgcac atttcttgtg atacaggagc  83700
aattgctttt aaggaagaag acatccgcaa tgtaaccatt aagtcagcta gaccgggaga  83760
atataaggtg actatctact tgctagacga aaaagttaca ttgttaattg gataaaattt  83820
taaaggaagt tgacaatata tgttgacttc ctttttgta tgtgctaaga taactacagt  83880
tggataaaaa aaataaatgg tatagaggga gagatttaac atggactaca aaacaaaggt  83940
atatgtagga gcgcttagtt ggttaggtac tttaggagag aaacgatatt tagggcaaat  84000
gcgtgatgta ttagctgtgt acgagctagg tagtcgatac gcaggttact atacagaaga  84060
tagcgactat gactatatgg ttgtatacat gccggctcct tatgatttaa tgcatcctac  84120
aacaatttat aaacaggaaa cagagattga tggaaataag gtagaggtaa aatatatgtc  84180
tatcgtggaa tatgtttacc gtattgaaaa tggagattta gaggctttac aaatgttaaa  84240
tgccacaagc tcccaaagtt tcttcggaga gcctattgaa ggtattgaca ataagcgtac  84300
tcgtttagtt acgtatatga aagaactaga atacagaaga gaaacattta cttatttagc  84360
accagagaag ttgtttagag gaattaatgg tcgtattaaa gccacaaaaa cacgtatgga  84420
taaggctatt gagaatgacg atatggaagt agcggtaaaa tgtgctatcc ttattcgtta  84480
ttttatggac ttattagttg tgctagcgga cggggaatct attcgtgaag gtctcacgtt  84540
ctctcctatt attgcaaata tcattagaga gtttaggaaa gactgtgagt cagcacaggc  84600
taagacactt atcaatactg cacaagtgct attagaggcg gatagagaag agattttaaa  84660
tagtattaaa gaccatgggt tatcagatgg ttacgctcaa tcagttagac aatatagttt  84720
aacaggtcga ttgatagatg tactattagg aggatattat gactaagtta gaacaaaata  84780
aagaaatctt agatatattt aatagaaaag gaaaagtaac agataaagta gaagaatctg  84840
ccaagattat gctagaatta gaccacgatt atgactttgg tacaggggac attgcttata  84900
cagagcgtgg cacagataag aagggacgtt tctatttaga aagtcgtttg tttattcata  84960
aactcatgcc ctatgggttc attttaaacg ctgtagtaag taaagtacac tatggagacc  85020
aagaggagac cttagaacga gaggtatccc gtgtatatga gctagagtac aacctaagag  85080
ataaggtagc tgtgctaatt aagaacggta aaccactaaa cttctcagaa aataacatta  85140
gtaacatgtt ttctgggcac gtagcacaga atattcttga acaattagat acaatgtctg  85200
gttcagatat gtatgtatct gtgtatgaac gagttagtcg agttaaggat gaacaaattg  85260
gtaaagtatc tcggttcttt gatagattga tgaagtacaa caagattgaa ttaatttata  85320
agagtggcgt tcctgaaggc tttgctttgg cttatgctta tcgagtagtt gttgtaggag  85380
aaggcaaagt ccgtaatgaa tggtacgaac ctgtaaagag tgtggactat ttagataagg  85440
aacaaacaaa tccggctaaa cacctaggta ttccaaagtc tatctttaag attatttgtg  85500
aaggtgggtt agagtggaca ttctaccaaa aaatagctag tcgtttccat aaatcattag  85560
ttaacagaag tactaacaaa actcctaaat cccccactgc tatgaagaag atagagaaag  85620
agattgctaa gttacaacaa gcctatgctc gttttggcgg ggtactgtat aacctttatc  85680
agtttactaa agagctagat gaacaatatg gtatctccca tagtaaggat attatcgaaa  85740
cagagtggga atctatatac gaccatatta ttgcaggagt agttaacgat aactataata  85800
gtacaactgc ttatgatatt tctatggttg caaacctaga tttctacaga actgttcgtt  85860
atctatacta tcgagtatat gttgagcaag ggcttacttc acaagcagag gctagataca  85920
catacagaga ctacttgaga gcacaccatt atatgaatgc ggtacctgtt aagtacccta  85980
aagctcttaa gactgctcat gacattatta ttatgaatta ccgaacaatg aaggataagg  86040
tattgaatag taactttgaa agtagtgtag ctaaatataa atatttagaa gaagtatcag  86100
ttagaggtgg ctatattgtt aaggtaccta atagtgtgga agacttaact aaagaaggtt  86160
ctagtttaca ccactgtgtt gctacttatg ctcatcaagt agcagaaggt tctactcgta  86220
tcctgtttat gcgagataag acagagccag atactagctt agttactttt gaggtaaaaa  86280
ataataaact agtacaagca agagggctag ttaaccgtga cttgacaaat aaggagcagg  86340
agttcctaga caaatggtta gttaaagcag aaattggtaa gtattagttt gcctaaaaag  86400
gcggaatatg gagtgtgtat agaccaattc acaatgaaaa aagtacacta aacagttgtt  86460
atttcattat taggtaaaac aacttatttt agatagctga tattgaccaa caaatatttc  86520
ataatgattt agctattaaa gttacaaaaa ccctactaat acgtggggtt tttgcttgtt  86580
tcaattacat atgaaatttt acagatgttc tgctatatta gttacagaag ctaataaaac  86640
aaagggtttc gacccttaaa aatgatattt catataatta aaagttgaag gagtttataa  86700
ctaaaatggc taaaaaagaa gtaaacaaca gctcagtatt actgaatcta tacaataata  86760
aattgcttgt atctaaggta gacgaggcgt tagacgaggg taaaccatac gatttcatta  86820
ttgcttttttg taaagagaag ttcgattttg aaattaataa acctgcatta tctaggtaca  86880
aagagaaacg tagagagtct ttagaaacag gagtagactt ggaatcacta cttgacaaac  86940
gtagaaaatc aggtaaaatt attgatatta agtctaaaga ggtaacccca cttcctaatg  87000
aaacatacga taacacattt ggacaagtgg aacagatata caatgatgta gaggtgttag  87060
atacaatcat acaaaaaggt tttaactctc taaaagaggt agactatgtt gaagccccac  87120
ttgctatgaa agcaattgaa gtaaaagcta agataacagc taaccagttc caaggtctaa  87180
gtctaacagg tctaagagag ctaagattaa gacagtctgc taaagaacaa gcaatgactg  87240
agattattct acaatttatt ccagaagaac agcatgaaga agtattcaat gcaattgaat  87300
cagcagagaa agagttctat gaaaacttag atttaacaga ggaagaccaa agaatcacta  87360
aagcgttgca agcatcaggt atggatataa tttaggaggg ctataatggt tgaaaatttg  87420
agagaggtaa attataaaac attaacctta gaagaaagtt tacatgcatt acttgaaggg  87480
aagaccctta ttgtaaaagg gctagaacaa agacgtaagt tagatgtgct agtaaggatt  87540
ttctcagaag gtgttgtacc tgttacgcag ataagttatg atacaacccc tgcggatggt  87600
tattggagaa caggatattg gcagatatac gatttgccaa ttaatgccct tagcacatac  87660
```

-continued

```
ccatgtttta tctatgatga tttaaatacg gatgaactcc ctaaatttat gataggggac  87720
actgtttact acacaagtaa agaggactct atcaaagatt ccgccattgt aatcagtgtg  87780
tacaaagacg atgttaacaa taagtggtac tacaagttaa gtagagacaa cgaaatatat  87840
gcagagagtg agattagaag agacaggtta taagcctgcc tcttttttttt taaatttatt  87900
gttgacaaat atctataact ttgttatagt ataaatatca aggatattga taataaattt  87960
tggaggtgcc atgatggcaa atattttaga cacattaaag tggttagata aaggggacaa  88020
agttactatt gaatttgata aagagcggtc gaagtatgca aaactgactt tgcacgattc  88080
atcagctaag acaaatattg tccgtaacat tgttttttat gatttagaca aaggagtgta  88140
tgcttacact ggtgaataca cccctgtatg ggataactta ttagatgata tgcgtaagac  88200
acaaggcgca ggacctgaaa ttaagactac aaaagtaaat cagttagcta cctatgaaga  88260
tgccttaaag tttattgaaa caaatggtac gttttatgta attggtgagg aagtaattgt  88320
taaggttaaa gatgcaaaag agctagcatt gatgttaatg tactttagag atgctattga  88380
agaactaaga ggagaatacg accctaaaaa acatcatgta gatatgacaa ttgaattatc  88440
aaaagatgtt ttgaaaaaaa tggcagtacc tagacatgaa ttagacttat ctttaggtgg  88500
cttaatgaga gctgtatcac ataatgttgg agaagacctt tttgaaactc ttgggtttga  88560
ctacatgaag caagcttggg aagtcttagt taattgcttg tcactagaca ctatccatga  88620
ggtacctttc cgtgtgctag acgaattaga gaaagtaaca gatagcatgt ctactacaga  88680
ccatattgtt accttgtatg ccggtagaga acttaaaaaa ttctattcag aggaagagta  88740
ctttgatgta atcacacaca atttagctga tgtgattatg gattggtcaa ctatttttac  88800
tacagctgtt cttaataata cagaagatga tgaacacctt aaagagttac agcttaactt  88860
tgagagattc aagctagatg tagcagaggt tctattaggt aacgttgcaa gacatttact  88920
atatgcagga gttaccgata gctttaacga agttaaccat tatgttgtcg gagcaggtaa  88980
cctgattaga acagaaggtt tgattagaat agaagagtta actggaacat tagacaaccc  89040
taaagatgaa gatagttctg aaacagataa taaagagtta ctagatgaca tctttacaaa  89100
tacaggtgat gatggtgttg aagactttac aaaagaagta gacgagcttg ccatgtttga  89160
gaacgaacat gctgaggaac ttttggaagt caataacaaa ttaaaagaca atcaagagtt  89220
attacgtaaa actgtggagg cgatgggtat ggcttcttac tctactattg attcatcatt  89280
tgaacaagag gaagaaacag atagcaacca cacagagact tgtgaggata ccagagcttt  89340
ccaaatgtta agctatgcag tacgttcagg agacaaatta cttgaacgtg tagagaacca  89400
cccacaaact gaaaaagggt tgaaaatggc taaagattct ctaaaagagt ttgaccatac  89460
agtgaaacca gaattagaag cttatttaaa agcagaagag ctagcggaag acgttgatag  89520
acatgcaatt gtaactacaa ttatccgtat caaggacact atggaagcag atatggacgg  89580
ctgtaccgac ccaatagagc aaggtttatt ctacgcagga agcctaaata tgttagaaga  89640
aatggaatca ttgttacggg ctagcaatag aggttatggt tgggacgtaa cagctatcta  89700
tcttatcttg tccattgaac tagcttatgg gacttacggg ttgtctgatt tagactttac  89760
aattaaaaat aaagaggaaa ctcgtaaaga agaacaagat gcaattaatg gtattgtaaa  89820
cttcttagcc aatcttttaa atacagtact agaagaagaa tcagaatcag aagaaacacc  89880
tgtagtagtc gaagaggaag aagaggataa ggatgacttc tcactatcta cagaagacac  89940
tgctaagtta ttggcagact ggtcaaatgg tctacctacg tatgtcgtta ctcgtaaata  90000
cggaattagt atgggagctt tatactctat cttatatgca aatggggcag acgttaaatc  90060
ttctaaagta gcagaacgag tggctcatgt ggaaaatgac aaagatatgt taaacgcagt  90120
tattcgagac tacaagaatg gtactcgttt agtagatatt tatactaaat acaaattata  90180
taaaaatggt ttgttctatc ttttagataa atatcgagtg ccacgtagag gacgtacaaa  90240
gaaataacaa tgattaaggt agtggtgctc aactactacc taatctttta ttagggagga  90300
acttaattga ttctttttat atttagcatt attacaatgc tatccatgtt cttactatat  90360
ttgtttggga tggcttctgt ggctgtaatc aaagtagggt ttcttatagg tagtcaaaac  90420
gatatagcta aaggcataca ctctttactt ttcacaggta ttgcacttac tgtagtcacc  90480
ggaataacta gacagtgttt actattattt taaaaaaaat tggaggattt agcatgttgt  90540
tttttattgt tttagcagta tttataggcg ggcttgcttt atggggaatg tatgatagtt  90600
atgggtacct agactggact tcatggttat ttagtattgt ggtaggctct gctgtagcta  90660
cttttttcac actagcggcg gttggaatta ctttcgatgt tgtaccaagt catggggtaa  90720
cgaaaagtca tgaattacac cctatctatg agaacagtaa agtagttgta gaggctaaaa  90780
aagaccagtt tgagattaac gtagatggcg gtttggtagc tattgatgca gaaggtacta  90840
ctatcctatc tactaaagga gaggttaagc ctaaaattgt gtttacagag aactatataa  90900
acaacaactg gtggactcgt ttcctaggta tagcaggtaa ggtaaaagac acttcatcag  90960
ttctttattt agactcagat accttagtgt acaataagcc ggaaaagaac agtagcgcac  91020
cagatttaaa aattaaataa ataatttaga aaaagggggct tgcataaagt ctctttttat  91080
gttaatgtgt atttatagat aggagggcta ctatggaagg tgaagtagta tacttagatg  91140
agtttatgaa ttttttaact gatagtggaa taaatactga tgatattaac gtagtagatg  91200
atagacagga gggctagtat gtcttataca aaagaagcat tagaagctag aggctatcag  91260
tttgacaata tgtctatgat agataagatg gatgccttgt tagaactgct agaggaacca  91320
gaatttcgag aaaagatgaa agaagagtac gcagagttct ctaagaggca caataacgat  91380
gaagaatgaa aagttagagt cttaccttat gaaagagatt gcacctattt tagatgaaat  91440
agagatgagt gaagaattga taaagggaat ggagaacaac aacccatccg atacggttac  91500
agtctctttt tccaaagaag aagtagacat actcttagca atgttagacc ttgaggtacc  91560
tagattagac agtggttctg aattgtttag ccctaatctg gtaagggaag ctaaactaca  91620
attaattaag aacaagctaa cttcaaaatg atttctcact agaattaatt agtgagaaaa  91680
aaattaaata aagctattga caaataacaa aacatgatgt aaactaagtt tataagataa  91740
agaagaggag agatacacat gaatgaacaa aagaaagtat atgcaaaatt aacagaggac  91800
gaggcagtat ttgcttgtga actaggagat aaaattaaac aaattagaga gagccaagag  91860
ctatctcgat tagaacttgc aaaacgagca aaagtagacc actcaacatt aatcttaatt  91920
gaacaaggta aacgactacc aacattgcgt attatgatga agttgagcaa agcactacac  91980
cgagaattag ctattagctt tacagattaa ggaggaggta tcatgagagg gagcctagat  92040
tattacaact atttgtacca aacaatcgaa aatcgaccta cggaggagct agatgtcctt  92100
tatgacggtc tttataaaaa agccggtgac ctgtttgcaa tagataactt tcaaggagtt  92160
aaagaaggca gactaatttt aaaaatatta aaggctatta gagaagaaat taatagtaga  92220
attgatgaag aaattgacct ttacttgtat aatatctatg acagtatatc agatgaagac  92280
aaacgagtaa attggctata tgaggtgtag gtatgtttag tgttgttaag gctgacagct  92340
atgttaaatc agacatagaa atgtatgaat ttaagaatgt aaaaagtttg gcattgacta  92400
```

-continued

```
agaaagagaa agaactatgg acaggcaaaa ttgctaaata tgttaatgag tttattgtaa  92460
atgcttatgg agactaccat gggaataaaa tacctgaaat aaatgttgta atcaatggta  92520
agctaagaag aaccctaggt tcttttgtcc aattcactaa cacaaacaaa cactgtatag  92580
agataaatgg taggtttgtt aaagaagtta ttctattaca agaaacaccc ttagctcaaa  92640
gagcgcttga tattttaatg gatgtagcca gacatgaagc tatccactat acactttgtt  92700
atttaaatag tttaagtgga ggagacctac caacgttcaa ctaccatgac ggtggggagg  92760
actttgaaaa agatttatgt ttgacaggaa cttcacctag tggtgctacg aaagaagagt  92820
atatttatag ttcttttaca ctaggagcca tcagatgccg acaccatagt acttgccctg  92880
aatgtgggtt ggaaacatac atgtatacac gaggacggta ctattgctat aatgggtgtg  92940
taggggataa cggtagaaaa attatattta gaccacaagg tgatattgca atttatattg  93000
atgaaccaaa atctaaagct aaaccaaaag tagaggaagc tctaaaagac tataaaggag  93060
cgttaaagct accttataca ggtacggaag aaataaaata aaaaaaaata gttaaatgta  93120
ttgacaaata acaaaacatg atgtaaacta agtttataag ataaagaaga ggagagattt  93180
attatggcat acgtaacaaa tattgatgta gtagcagatg ggttagattt gtataatggg  93240
aactatgtgg tagaacgagg tcaagtagtt acttttaaac tacatgtagc gacatggaac  93300
aatgagccta cacccgaaaa tgcttatgcg attattcgta ataatggggt agattataag  93360
agtaaagttg atgaatttgg caatgcagag gttaccttcc cagttaatgg tcgtcctgac  93420
caagtaacaa ctagcatctt tgcattaact tctggatatg agggggatat gcctcgtgta  93480
atgtcagcta tctttagtga cgaaacagaa attaaacaaa ctgtaatgaa cgttacagca  93540
tctattaatg gggagccagt tagtcgtgaa ggtgtatttt tagaacgaga ccaagtagtc  93600
actgtagatg ttaaagcaac attatctaca ggtaagttct gggaaggtgc acaggtaggt  93660
gtgtacaata acaacacgga atacttaggt gacctagatg cagatggtta tggttcagta  93720
actttccaag taaaaggaaa acaagggatg gacacatcag ctatctacgt attcgttaaa  93780
gaccatgaac gagaagctac actaacagtt cctgtgaagt ttactaatac tactgttact  93840
acagaaactt ctacagaaga atcgtctact gttgatacga ctacaggaac agaggagtct  93900
tctactacgg atacaaccac tgtagaaagc tctacaacgg attctacgtc ctctacagta  93960
gattctacag aaagtacagt agaaagctct acagagcaaa cagtgaccaa tgaggacact  94020
tctactgatt caggagtagt tgaaactaca gaaacttccc aagtagcagg ctacacagag  94080
tctacttcta gttctacaga gtctaaagaa gttaaggaaa ctcatactag cactacagaa  94140
catgctaaag agttaccatc tacaggcaca gaggtagact atgggcttgt tgggttcggt  94200
ggtgcaacat taacagttgt ggtggcacta gtagttaaaa aattgttgaa taagtaagaa  94260
acacaatatt gcgaccctca ttaattgggg gttgcaaatt atattatttt ttttaaataa  94320
acctattgac atttaacaaa ctataaggta aactaagttc ataagataaa ggggggaaac  94380
aaatgagtca agtaagcaaa catggagaaa aacgtgtacg tgaacgtgta ggagtgaata  94440
agagctctgt agaccgacaa tttgagttag ctttagaacg aggatacaga caaaaagagc  94500
taacaggtcg tctaaagaaa tgggtagtat caagagtatt taactctaag taccctcaaa  94560
catgtatttt atataatggt aaatgcttca ttgttagcag tgaaggtaca ctagttactg  94620
tgttaaacat cccaagtaat ttactaaaag attttgcaaa attatctaag aaaagaggaa  94680
aataaaatgg atattatgga tattgagttt ttagaagaac ataaacaatt agtaaaagaa  94740
catgtagaac aagaattaaa attaatgcac cctcttaaga agttacaagt aatgacagac  94800
tggttaggag atacagaaga caagctttct caaggagact tagattactt caatgactta  94860
acagaaacag agctaataga ggcaatggat gctagtgaaa ttgtagagtc ttattcagat  94920
gtcttgttag attttattga ctactacaat attgatttaa ctggtttaga ggaacagcta  94980
ggtgtgtaac catggataag gctgaaaagg tagataacat tgtaagacag gtcacagggg  95040
ctgttattaa gacaactgca aaagtagctt ttattgtttt tgttttaacc tttgcaggtg  95100
ttttagtagg ttattatagt tattcatttt taacaagtgc agggtggttt gccttaccta  95160
tgatattatc agtagatttg ctatatgttg cggtactgtt aggcgggcta gcctttatat  95220
ttgcagaggt ctacaaagta gttttagaag tgaaaaagat agttaaacga ggagggcaat  95280
tatgagtaat aaaacattag aacaaagagt aatagatgct aacaaagaga taaacgataa  95340
gcttaacgaa tcatcaatta ttcgtaaaca aattgaagaa ttagaggaac aggaagccat  95400
cttactatca gacgtagagg acttacttga ttacttagaa aatattggag tagacctata  95460
ggagggactt attatgaata aaaaagtaga ggaaatgaca atggaagaaa aagacaaagc  95520
actaattgca atgggactta ttgatgtaac gcaggaggca gactgggtag tattagctac  95580
ttgtgaagaa tgtgagagaag agtacgaagg agaggagtac gaagaagggg actgtgcaga  95640
gtgtgaacat tgtggaggag aatactttat gattgagaca gctctcgagg gtactcgttg  95700
tggacgttgt gatgactact ttgatatgtg ggacgactac tttgagtttg agaatgaagg  95760
taacccatat aaagataaac atatctgtga acattgttat gaagaactag tatctatggg  95820
aatggaagag aaattttaag atactactaa gaaggagact taatcatgaa cgaattagaa  95880
gaacttaaaa atacactgat tagacaaaaa ctttcaatgt tggagagtta cgaaatgaga  95940
gaagcatcat tttggataat gtttaatggg atattacgtg tcatcatgtc agtagctgtc  96000
atagcctttg taaactatgc taagcatgta agaccagata atgtagccac atggtttcta  96060
gctctgattt gggttatttt cctagcagaa ggtattaaag gtgcttatga tgctgttgca  96120
tttggtattc accgcaaaaa atttgctaaa catattaaaa atatgcgtgg gataatcgca  96180
atcacacaat tacttattga agaagacgaa gagaaattaa aaggaggcaa gctagatgag  96240
taaagatgag aaattagttg agtggtttga agttgcctta atggtgatta tgtggttgct  96300
tatcacgttc agtatcttat acacaatagt ttccttacct ttcatggtac acgaagggga  96360
ctggctaggg attgtgcgaa acgtactact ggacattgta gtattggcaa ttggggttgt  96420
cgctacatgg ttgcaattaa gatttaaaaa aggaatggag gaataattaa tgggatattt  96480
agagagtgca attgaagaaa ttgaacgagt actactagga aataaaagtc gtgacaccga  96540
agaagtttat ttaaacaatg caattcggta tatcaaaaaa gagttaaaga aaaaagaggt  96600
agagccaacg tggttaaatg aaccacagac attgttcctt aattggttta acgaattata  96660
cgcagtaggt ggtttaactc atgtaacaga ggcagtaggt tttttagaat ccacaggagg  96720
tagaatgaag tatccagaag catattctgc tttcagtaat ttaagtgaga atgaattgct  96780
tgaggtttac agtaaatttt atacagggtt attcttaaaa gcacaagggg gtgaattaga  96840
atgaactttc atggtaaagt atttcatgat aaagtatttg acattctttc tcgtgattac  96900
cctgattggc agaggtatca gacagagaaa cgaccacatc ccaatgagct tagaaaagac  96960
tttgccattg atagtacaga tagtagatat gaagagtatg ttatgggaga gtttaatgta  97020
gaaacggcta gcggagatgt taaagtatac gcagtaggaa ttagaagagt agttcataaa  97080
aaagctgagg aggagtaaat caagtggagt acacagagaa agacattaaa gaaggtatga  97140
```

-continued

```
agttacgttg cacagataat agtaatgtag gttactggga agttgataag gtttacgagg  97200
taacacgtaa taaagacctt ggcttagtta tcgcagggga aggtgaaagg agtcacagaa  97260
ccgtaaagta tattttaggg gtgttaaatg gtgacagcaa aattaaattt gaagttgtag  97320
aggaaaagcc tgtacgattt gctaaggtaa cttgtgtata ccctcctgat agaggtcttg  97380
tagaggttgg gcattgttat gaagtgctta aagagttccc tacaggaagt gtgcgtatct  97440
accttaatag taaactaggg aaccatgagt tactcccaga ccagtttgtc tttgtagatg  97500
aaccatcaaa tgatggagaa aaagacgtag aagagctaga tgtagaagct aagatactag  97560
ccaagattga acagttaaca gcagaagcag aacaactgtt tgctaaacgt gaccgtgtaa  97620
atgagcaagc acttaactta aatgcaaaag ctcgtaagtt agaagaatct ttagaggtac  97680
taagggagta catgtagcta agtgttttta tgattacatc tattaaggag atgagagaat  97740
gatttattat attaattttt tagaagattt cgcatcaagt tggagtgcag ataagcgtta  97800
tcgtgttcgt agaattatga caactggtag ctacgctatt attgacaact atggtcatgt  97860
cagattcagc agtgacacag cacgaggtgt ccttaagaat atagagcagg agtatgccac  97920
tcataaggtt gagcttacac tagcagaaga agaaacaacg aataagccta ggtttaaagt  97980
aggggaacga gtgaaagtgt ctaatgattt acaggcattc gggatagaat ataagactca  98040
cataacctct aagatgatgg gctgtgcagg taatgaggct actattacac gtgtttgggg  98100
gagtaacgta cgctacttta ttaacatcga tggtatacac caagattggt gttggacgga  98160
ggacatgtta gataagattg aagaagaacc tacactatct attagatgtg ttgaggcagt  98220
tcatcccttt tggacaaaag gtaaagccta cgagataaac cttacatctg atggtcgcta  98280
tcgggtctgg gatgacgagg aagatggtag cagtggcaaa tccataaaag aactactgga  98340
cgttatcaat agtggcggta acaaatttga gctactagat gaaacaccct cagaagcaga  98400
acctaggcta aaccatgcta tatctgactt agagaaaata gaagctaaga ttaccgcttt  98460
atcagaagag tcttttcagc tattcaataa gagtgaagag ttaagtacta gagcaattga  98520
actgcaagat gagtcaatag ctttagaaga agcattgtat actattaaac aatatttata  98580
ggaggagatt taaatgcgta aaaatgtaat ttgtagatta gaatgtgttt caaaagacaa  98640
agacaactta ggtgaatgga ctgtagataa tatttaccct gtgtttgaat cagaactagg  98700
taaagtatat atcctcgatg atgaaggtac cacttgttcc agagatagcg tgtctcttat  98760
tatctctagt atggctagct ttggggtaac atttagggta gcaaaaagata aagcagaaga  98820
ccctatccct agcaatccac aaagcagtac atcattagaa atagttaaag ggtatgaaca  98880
cttagcggag tttatagact cattaagtag caaccaacgt gtagtgtctc actcagtaga  98940
ccctaactct caatggcact atatcattta tgaaactaag tcagctgaat tgggcggagt  99000
aaccctagag gaattactag acacactagt gtataatgta catgttgtag tgatggaacg  99060
tagtaagaga acatatgagc cactagaaaa tcacacgttt aagtgggaat atggaacaaa  99120
gaataccaag gattgggaaa aaattgtacc tttattaggt tgcaaggtgt ttaatactaa  99180
cctcaatagt aacagagggt tccatattac tattttgaaa taaactgttg acaactacta  99240
tagtccatgc tatagtaggt acatagataa aaaacaaaca atattaggag gtagcataga  99300
gtgaaagaaa cagaaaagaa gtatagcaga gagtataagg ggctagaatt tgaaattatt  99360
atcacttatt accctgaaca agacatgtat tttgtaattg taaggaacgg acagcaccgt  99420
acactaacta aggttacagg gaaagagtgg ggaatgagcc ctcatacaga ggaagctgtt  99480
attgaggtag cacttgatac atgctacacc tatattgaaa atcaagaagc gcaaaataac  99540
tagattaagg agggactatg atggtaggag acttcatttt atgggttaaa caagcatgga  99600
aagaaacatt ctgtattcat gactacacgg ttaaaggtgt atataaaaca ttagatagtc  99660
atgggtactt aaagtgtaaa aagtgtggaa gaattaaata ggaggacaac aacatgaacc  99720
agagacagaa gactagacaa gaaaataaat ggtttgagga gcatgggtat gatacacagc  99780
aaccacgaga atgtattgag tgcggggctc ctttaagttg gaaagatgag ttacagaaaa  99840
gtcatggagt gtgtagtgag tattgttata tgagaagtgt tgggctgtcg ttatcagatt  99900
ttatttaagg agatgaaaca ctaatgttta aaaaagataa aaaagaagaa aagacttata  99960
gagaaggaga cctccttaag gctgtagggg gttactaccc agatgctagg ttgagtttag  100020
gaatcacata tccattgtat aaaaccacca atgagggttg gtatattatc aataacgaag  100080
gtagtcgggt aaccttaatc gaaatggatg ctttaggcat tgactacgct gtgatggaag  100140
aacccttatt agaattaaaa gaaggagacc cattgctagt cgtgtccgac cttaagagag  100200
gtgttcgagg cttagcaggt gcagaagtac agtgtttaaa cattaccggt gaaatggctt  100260
cactagcagg tacagttgtt cattatgata aagatatgag ccatattgca aaggggctgt  100320
tcactgttaa agagaacgat tcttattggt gtgtagcgat tgctattcca ctaaataaag  100380
tagctgaccc tgattttgca ttagagcatt tgcttgctac gttaaataaa aaagcctcta  100440
ctaaacgtct ggtattgaat gagataaaat atgatttaaa ccttcttcac gaagagctag  100500
acgaggtgtc caacgaagta gagaagctaa caaaaaacat tgaaacaatc tataataaca  100560
gataggaggt acttagatga gtatgccgag tgatttaggg aaaacattaa agaaacctat  100620
tgcaataaat aagaatcctg atttttatga attagcggta ggtggtaaag ttatctacaa  100680
cgaagaagta atggagattg ctaaagcttt ctctaataag aagaccaagt actacctact  100740
aaacacacga agtaacaaac aagtatgtgt accagtgtat catgtaagac cttatgatac  100800
ccaagtagag ggtcttaaac taggtgatgt cctagatgct atgcacatta tgacaactgt  100860
aacgttaagg gcagtgaaca agcacgggtt tgttgtcgat gaggatatta ttgaatgttt  100920
agtagatgac atcccagaaa atgcgcttat tgttactagt gaggtatccc gtattcagcc  100980
agaggatttt ggtaaggtaa ctattgacta ttttgtttag atatgttagg atagacttaa  101040
gataggatag gataaactta ggatgcgctt ttgtttagga taggcttagg ataagatagg  101100
ataaacttag gatagactta ggatagactt aggatgcact ttggtttagg ataggatggg  101160
ggatataact atgagttacg ttaacgagtt tgaaacaatt ggagattggt tagatagaga  101220
aatttatgat gtgttactaa gagatgagca tgatattgaa gaattagata attggggaat  101280
ggctttgttt gcattaagtg aaggttacgt tctaacagat ggacttgaca aaccattcct  101340
agagttaact agagaagacc tagtagcagg ctacaaccac tttaaagaag agctgaatgg  101400
gtggttacga ggaggtaaac tgctagaagt ctctgataat ttatctacaa ttcaggggtt  101460
cagttttgac catgacgatg ttttattctt agaggataac aacaaagctt atgcaatgct  101520
agtaggtatt atcattgaag caagagacac atataaaaat ggtttctgta agggtcacta  101580
tgtaatacct taccaagatt gagttagcct tatggctagc tttttctttt accctaagta  101640
gcaggctaca aaaatcttct aagtagcagg ttgcaaaatc ttctaagtag caggttgcaa  101700
aatcttctaa gtagcaggct acaaaaatct tctaagtagc aggctacaaa aatcttctaa  101760
gtagcaggct acaaaaatct tctaagtagc aggttgcaaa atcttctaag tagcaggcta  101820
caaaaatctt ctaagtagca ggctacaaaa atcttctaag tagcaggcta caaaaatctt  101880
```

```
ctaagtagca ggctacaaaa atcttctaag tagcaggttg caaaaatctt ctaagtagca 101940
ggctacaaaa atcttctaag tagcaggttg caaaatccgg atgcgcccgg ctagcggtgg 102000
ggagtcaagc catgcgggtt caccttaata gctaccgtcc ccagattgtc ggtttttctt 102060
actatatata gtaagaaaaa taatttaaaa aaaataaact tttctattga caaaaaacaa 102120
aagctagtat aatatagagc gtgtaaggaa caacaataat aaaaaaaata aagataaagg 102180
ggcgctatta aaatgaacaa gtataaattt acctatgcag acattaagaa tttaccagag 102240
gaagaaaaag aaaaagaatt aaaaaatcgg tgtggtgttt tagcggtaga gtgcttaagc 102300
actaaacagc tacaaaagaa aaaacctcga tttatggttt tcttaaatac cgttattttt 102360
gatagtaccg cagaaacagg cggacaatac gcaacggcaa ccgttaaaac cgaaccgata 102420
ggggacggac gttttcgagt gtgtgacggt tggggacagc tttctaatgg aattattgaa 102480
ctgttaaaat aatttataaa aaaaatattg acaaataaca aaagataaac tacaataaac 102540
ttgtcagata aagaaggaa gttatgaaca tgaatgaatt agaagcagtg aaagaatgga 102600
ataataaaat tgaggaacaa caagaagtgc taaacaaggt tattgttgct ttttataaag 102660
aaattgactt aaaggttaaa atggtaaacc gtggcttgct agggcagtta ccagctttta 102720
acgaactaaa aggaatgcta tcaggtatcg agctaacagc aaaggttatt gcacccgata 102780
acgtgctgcc tattacaacc cacaactttt tagaatattt atttctaggg gataacgaac 102840
aacgagcata cgcaaaagaa tacctagacg gcttttaaa atcagtagaa taaggggagg 102900
aaaattttcc tcctttacat aaaaaaaaga ttgacaagtt aaaagaacca tgataacata 102960
taaatgtaga caagggaggg gctttacatg atgaacggac taaaaaaact tgtgaaagct 103020
aggcaataca agaaagaagt aaaaaaaatt atcactatgc aaaagaaagc aataaacgaa 103080
ctagaaacat taaacaaaaa tttaaaatta attaatcaaa actattgaca aataacaaaa 103140
gataaactat aataggttta taagataaag agaggaagtt attgacatga cagaacaaca 103200
atttaaaaaa gagcatttat tagaaccaac agaatggcgt agtgggggct acttagacac 103260
tagtttaatt gaccaatcac aatcttatta tattgagtca cgtccgagag tctacggcgg 103320
gtgttacgtt taccaatatg ttacaatgaa agatggcacg gtttacgagc tttacagcat 103380
gacggcaagc actaggggaa ttgttgcaca taactgccac gctagaaacg tattgcaaag 103440
agatgtaaaa caatacagag atagcgccat tcattattaa ggaggggagg gctttcctcc 103500
tttacataga aaaaaaattg ttttatctat tgacaaataa caaactatag tgtattataa 103560
atttataaga taaagagagg aagttttaaa tatgaaatta tctaatatta ttctagtggg 103620
gttgcttgtt agcgttgtac tactttgggg ctaccttagc attatgattt gcttacaagt 103680
ttttagagcg ttaggcggtt gggatattag aacgttaacg gtttgcagtg gtttgctatt 103740
tgcctatgtt ttcggtttaa aaggaatttg ggaacaaggg acagggaaaa acaaataaaa 103800
aaagtttata aaaaactatt gacaaaaaac aaaatataga gtattatagg cttataaaga 103860
taaagagagg gagttataaa catgaaattg aacgttattc atttactatt ttgcttattt 103920
caagaacaag aaagctattc tattttaagt tacgaatcag tagacgaatt ttattctagg 103980
ttaggttatg acttagagag tgagtggcta cttagggact taggtattaa tggaacaagt 104040
gacttggtag agttgctaac agattacaat aatttattag agaatgagat aacaaaagca 104100
gtcttttctg ataaatggtt ataatttaaa taaaactatt gacaaaaaac aaattaagga 104160
ggaagaatag gggaaacggg gagggaggga cttcctccct ttacatagac taggagggct 104220
taaaatgaca acagaggaga aagcactaaa cattgcagag aatagaggta taacagatta 104280
taaggttagg gggaacgtat taagctatta tactagctac ccgatggaaa aatgcacata 104340
ccttgtaact attgacattg aaacgctaga agaagaaaga aaagaactca aaaaatatta 104400
taaaaaaggc ttgcaaaatg cttgcttata gactataata taaagagggg tggcggttgt 104460
tattaataag agaataaaaa aattacaata tgaaagaatc agaaagctag aaaagagaaa 104520
aagaggtgaa ccacctgaat ttattttcaa cggtaactat tcattggaag aaatagagct 104580
atttttacat tttagaaaaa aaagtgaggg caaaaaatga gcgtggtggc tttgcttggt 104640
ttacttgtaa aaattacatt tatttttaaa ttgttagcag ataaaaaaag ttaatcaaaa 104700
ctattgacaa ataacaaaag ataaactata ataagtctat cagataaaga gaggaatggt 104760
aaacatgaca aaagcagaac tacaatataa aaaagcaata ggagttgcag tctttgcaac 104820
aagtggaaag gataaaaagc aactaggaaa cgtggcaccg tttagcattt atgagatttt 104880
agaaattgac ttaaataaaa atcgggtata ttatgcttta aattgtgggg aacgacatgc 104940
agtatgcttt actaaactac gcaaagaaga agaaacaggg aacgatttta ttttaatcaa 105000
taaacaacca tttttcttaa aagatatgca caaaggttta agttggtcaa aaagtttata 105060
aaaaaactat tgacaaataa caataactaa tatacaatag gtttataaaa taaagagagg 105120
aagtttttaa catgacaaaa gaaaacaacg tatttttaaa tgaaaaagag ctaatgaaag 105180
aagttattga cactttagaa aatggctttg atggttatta ttgcgactta catggtgaga 105240
tttttaatca tggagcaaat gctgacatta aagacttgga agaatatgga atttttaacg 105300
caattggaga aatacaagaa tacgaagaag aaaattttgg ggaggttttg acagacctag 105360
gaaacccgac ggaggttacc aatacgcttt actatattaa aggtcacgag tttttatatg 105420
gtagattaga ctttaatgat gttttagcag atgttgcaga ggggctaaaa ttagataaag 105480
acttatggaa cgaggaagcc accgaggaag tgaacaaggc tattattgag tgtttaaaaa 105540
aagaagtgcc ttatttaata gattagaaaa acagggagga gtttcctccc tttacataga 105600
aaaaaaatat aaaataaggg aagtgctaaa catggaaaca ttagaaaaat tcggttatac 105660
atggcaagga atgaaagaag ttacaaaaga agaagcagag aaaaacatta agaacggggt 105720
cggcactttt ctattatatc cagataacaa caattgaagc agtgaaagaa agaaagcaat 105780
gcaatattag ataaagtatt gagagcttgc aacttgttac caactgaaaa gaacgtgcaa 105840
acagctaaaa actttttaga agaacaaggc tttaaagtag aagctagtaa agagttagcg 105900
ggaaaatacc ttgtaaaatt ttcaatttaa taataaagaa tgaagagggg aagttataaa 105960
aatgaaacta acagaaaagg aactaaacac aatttttaaga gatgatgaaa cagggaacgg 106020
gggaacggct ttcttaggtg aaacactagc cgacttctta gaagaatcag gtattgactt 106080
tacaaaccta actattttag aagtaaatga attactagaa aataatggaa ttgaaccaat 106140
tgaggtagtg ccatgttaaa aaatatcaaa aaatcagata aactcactag aaaagatata 106200
caaggttttt ggggagatga aacaaaaaca ttagaagaat ggtataagtc aatttcaaaa 106260
gaatcagaca ccgaaaaagt agaaactgct aaaatgatta atacattgaa agaatatgca 106320
aataacaacg aatttcattt cgtaaaagga gagcaaggac aatgacaaac acaaacacaa 106380
acaaccaaca atggaatcag aagtttaatg atggtactat gaaccagaac aaccaacaaa 106440
aggaagttat cactttacaa gtcgcagaaa gtttcgtcag tcagatttta acaaaagaat 106500
attcggtgat tggtttagtt attctaatgt tttattttat gtttggcatg tttggcattt 106560
tcgggggtgc aatctatatt gctttcactc acacaaaccg taaaatcggg gcatggcaac 106620
```

-continued

```
aagtaagaag cgtatacact attaaggagg aacaagaaga atggaacaat taaaagggct  106680
aacaattaga gaattgatta agaaactaga agaagtgcca gaagaaaata aggacttgcc  106740
tatttatact tttgaaaatg aaaactcttt gcctattaaa gatatttcat tatatgatga  106800
aaatgctaaa cactcacaag aaaacccgtt aagttttgat gtaatcagat aaggaggggc  106860
aaagatgaat agttttatga ataaacaagc taaacaggta aaaagaagta aagaaataaa  106920
actagtagaa gaagtaagaa gaaaaaacgt aaagaaacgt ttttcagagg aagttagaaa  106980
gtacctagaa aaagggtata taatcaggtt agaaaataaa gtttttccat ttgctttaat  107040
atctattgac ctagaaaaag gggaaaaggt cataagtctt attcttgtga acgaatatga  107100
tggaatagca aactatacag caatgaaaaa ggttacctta agagaaaaag ggaatagagc  107160
tatcctaaaa agaacgttaa cggataaaga tataaaagta gtgagtatgt ggaaaggaat  107220
ataaaagaat gagtgtatac agtttaaaat tactagcaat cttagggata gtattattct  107280
tttcagttat cgggatagtg tacgataata aacaggacga aaagaaataa acatataaag  107340
aggtaaagag ataaggaact atagagctat ataaatgtgt acacttatag gaataagaag  107400
aaaaggaact atatacctat acactcatac actcatattc agatagacac ataataagta  107460
agggtaaagg agagaggagg agggagagaa agaggaaaga ggaaaaaagt tgtttacctg  107520
agattttaaa gaatcgactc catcaaaaac ccgacaaggg ggcgcataag tctatttcaa  107580
aataatctga aataagtata gttattactg tttatagatg gttatcctta aatatctgaa  107640
aataggggcg tttatctgat tatatagtta gctatcttat actattaacc atctagccta  107700
ttactgcatt cattgctatt atattctata tagggggcgc ttatatcgtt tatagtgtaa  107760
ttatgagggg aacgactagg aacgcttata cgggcttata gggggcttta aatgcatagg  107820
ctatttatac atatattaga atacacaagg aggaggggcg gaaagttagt agattagact  107880
gttaaaaaca aacgggggat agatgcacat tgttatttta ctgattgggc taggttaact  107940
agctaaaata agaatgctat tgtagcaacg tttataagaa ataggggtgt actttttcccc  108000
tagggaggtt ttaaaagggt ataaaattct tttgttattt aataaaaaag tccatcttag  108060
ctattgacaa ataacaacaa ctttggtatt ctatatttgt aagataaaga aagggagtta  108120
tagacatgga atatacatta gacgaattgc tagaagagga atatagcaca ctagacgaat  108180
tgctagacag tagagaattt aaaaaacaaa tggacaacct taatcacgtc ccacaaatgc  108240
aaccgcaaag ccataacagc aatacgctag cagatacggg acgttatcct gaaaaataaa  108300
attgaaaaaa ggggttgaca agttcagccc ctagtggtat tctatatttg taagataaag  108360
aaagggagtt tttattatga atcattataa attatatgta gatatgaaag agggaactca  108420
cgattatgtt tcggcaactg tctataatat acttgatgaa aaagttttag ggttgccaga  108480
tattaaaaaa cctgagaacg tagcttacta tactgatgaa tggaaaaacg ggctatattc  108540
ttactatgaa aaactcgcaa tatcagagtt aaacgactac aacgctactt tttcacattt  108600
ataaaaaaat taaaaaaaac tattgacaaa aaacaacaac tagtgtattt tattaagtgt  108660
aaggaggaac aaacctcctt acaccacaca acaggaagga agtttttact atgacagaat  108720
ttgctaatat gaataaagaa gaggtattgg agctacttaa tgattggttt ggtgttagtg  108780
actatgatac agtgatggaa gagttaggag agatgaaaca agttaccttt acaggtagca  108840
caaaccaacc tctattaggt ggtaacggta acttaattag tttacctcaa ttctttaaaa  108900
ataacgaagc agaatcagag ttcccaactt atggagagct actagaggaa ctagagaaag  108960
atacatggaa tctcgaagca gaggacaaca cttacaatta tagtggcttt ttagaaagtg  109020
aatcagattt taaagttatt caggcagaaa attcagacac gactattgca ttctttgcaa  109080
tccatacggg tatagacata agagcgggct actcaaaagc aatcccagtt atttttgaaa  109140
cttactatga tttttatgaa tttctaggta actacttttg tagtcaaggt tactatgctt  109200
ttaaacacga caacaaggaa tacacaatca gtttagacgt ttcggctacc tcagaatatg  109260
tacgaattta tatagctgat gaaaacaacg aggaactaca gcaaggctat gaacaagaaa  109320
cttgtatgga cttagacata gaaagcgtag aaggatactt gaaagaggaa ggaattgagt  109380
ttactgactt aaaacccgca ttgtaaccat ataaggcact agggagctta tacaatagag  109440
ctacaagcct cctagtgtaa ttataaggta aataactaga aacgcttata cgaaagaata  109500
gggggcttta aaatgacaac ggatgaatta aaagagtttt actatgaaaa cgggattgac  109560
ttgtggaatg ataacctata ttttgaacaa gttgtttcta gtggtggatg gtactacgac  109620
aatgaacgcg gtttatggtt taattatgag gattaaaaat ttaaactttt ctattgacaa  109680
aaaacaaaaa ctttggtatt ctatacttgt aagataaata gagaggggaa ctaataaaaa  109740
tgaaactaaa agactttatc aaactagcag aatccaaggg cgctacatta gaagcataca  109800
acgagctagg aggttatgaa ctaactagag gggacacagt agacccgaat ccggttttga  109860
ttgcttacat gcaaggggct tacagcgtag aaataccaaa caaggaacta gaaaacaagg  109920
agttaacaga actagcgttt gtctataaaa atgtaagtct tatttatcca aatgaaaaag  109980
aactattgtc aggactagga ctatagcaca acggcatata aagcccgtag cgaggtttta  110040
gcgggcttta tatataaata ccttaaggag gaaacaaggt gcttacagtg gaaaataagg  110100
gcgttaggtg gctagtgagt aaagaagcat ggaaagcagg ctttgctatg gaggtgctag  110160
gcttgccaga ttgtaaaatt agtacagtat taaaatcggt ctataaaatt attatctaac  110220
tatttaaact aatctattga caaataacaa aaactttggt attctataca tgtaagataa  110280
ataaaacaaa agaaagagag tgacaagaat ggaaacgaac aaagcatatg aaagactatt  110340
gaaagaagta gaaaacttac agaatgattt aatggatatc gaggactatt cagaagaagt  110400
atatcaagcc tttcaaagat taatcgaaga actcgaagag gtaaccgaat agggctagac  110460
cagtcctata ggtatatacc agttgacccg cccccgtggt tttttgaccg tactttgggg  110520
gtggggctat ttgcctaccc cgaccctggg gtataaattt ttttgtagct agaaaatttt  110580
tatatattta taaagtcaac accccacata taaagtcaac ataagggctc accctagggc  110640
tcctatatag gctcacctaa atactcccat ataaaaaaga cccctccccg ttgataagga  110700
taggtctttt ttatttagcc gtctgcccta tgattggtta ttaggttcag gttccgccat  110760
agtctttgcg aagtatgtcc agtatttatg gaagtctgca aagtccaaga agtactcccc  110820
gacaatctct cctgcttgat tgcggtaaag tggtactttc gttttctcgt ctttatggac  110880
tccatactct gtgccattta atgaaatcca tacaatatcc ggagtcacac tagttactgt  110940
tgccttatca caacctagta tcgggtcacg aagttctggt tttgtgaaaa ctgtatcccc  111000
aaccttcaat ttgtctagtc gctctttgtc tattaatgtt gtctccattt gttctccctc  111060
cttatacatt ataaaaaata tttaacgtct aattactgcc ctcaaataaa gaacattact  111120
acccatccaa taagcataaa taacaatgtt gatacagtag cttttgcaaa taccatcaaa  111180
atagaatctt ctgtatttgt agtagtctta gctgtaataa aactaataaa tacatctagc  111240
ccaattgcct gcgcccatgt aagtgttaac accccaaatg ttggggcaat taacccgttc  111300
cacaagaaca tcgtaacata ccctccaata gcaagggtca acaccactag aactaaagtc  111360
```

```
ccaaaaaatt tacctaatgc atttgccaat tcgtcttttg tattcttatc catcgttttc  111420
ctccttaata atagctatat ttacctctta tttttttgtt aattctattt aggcttgcaa  111480
aagtaattat gttcaagata tatgcgccaa ttactgatac tgcctgcatt gtgcaaaaca  111540
cgattgttat ccagtagctt gtagtagctt ccccgctagt tagcccccaa taaatgctat  111600
atgtcaccat gagtgtgttt agcagtatag ctacccctcc taccaataat agtaggtaac  111660
cagatagttt catttagttc ccctccattg aatgattaag taagctcttg ttcagttctt  111720
ttaagtaata gtcacaccta acgtgcacaa gacccatacg ttcccttgta atagggttat  111780
aatgtaatcg tgtaggtact gtgtactcat taggtataga taagtctaat tgggtagtta  111840
aattgactac tctatccgga gggcacatcc atagaggctt attacagtgc caacatgtcc  111900
cactttgtag tacctcgtat tttcgtttaa gttgtttctc ttcttctatt gttaattagt  111960
cgtgatagca ctgtgtcatt gcgtatggct ccctccgctt ttatatttgt tatagtttag  112020
tgttaaacca gtcctatatc ctctcctagc gtttacaata gttgtttaag gtgataatag  112080
gtagaatacc tatcaccgcc ctaagaggca tatagggtac ttataggact ggtgtttagt  112140
taactgtttt aagtggcata aaaaatatgc gcttaagtca acattagttc ttttacttta  112200
gatgatgtca attgcaatat aatgatttgt tttggataca ttagcaattt cataatctaa  112260
gtatggttct agtacttcgt tgttacttcc tatctttgtt ctaactgtta tggtagcccc  112320
tgccgtggga taagtaatga gtacgtccac tccgggcttc attaacttaa ctaaatcttt  112380
taacttcatc tttatctcct ctttaatagc atatgcttaa atctatttta tgtcaactgc  112440
ttaatttttg tgctcgtagt tgcacagata ttgtatcaac aatgactgcc cactgctcct  112500
ccgtaaaatt gaagtcaaac tgtgtatagt cttcctcacc tgttgtagta attgcaatgt  112560
ctccataatc atcaactgag aaatagatag ttgcagtcgc attttcctcc ggattttgag  112620
gaagtgtaat agctaactct ccttgctcta ctttcatcta ttgccccccc ttagctctct  112680
tccttctcaa tcatcttgat acctgtaaag gcatatacag ggagttcttc tgtgtaagtg  112740
tactgattag ctttaaaggt aacttcgtag taactctcca tgccacagtg taacatgtct  112800
acatatctaa tttccttaca aggcatagca tttttctcac tcccacagaa gagccagtct  112860
tctgtacagt attctactct acctgtgtgg atacttctaa ctgctacgta tggtttttcc  112920
atctattctt cctcctgtgt aatctcttct aggtcacaag ggtgtacatc tagtgttcct  112980
gtccttagac tataacgaga gtttcctcgt actgcgtaaa caccatctgg gtatactttt  113040
tcaagatata cagtatcccc aattgtaaac ccatggtcat aacgggtatc cccaataacc  113100
ttaaactgtc tttttatcgt atacccatac atgtaagccc gtgctaatac gtattggtta  113160
ccctcatcaa tccattcaac tagcttgtca tctggtgttt catcgtatgg gtcaaaatac  113220
tcattagcta ataagctcaa cattgaatcg tactttttga ttgctcgtgc aacaaaacta  113280
ggtatctcta ctttttagc catctattct tcctcctatt taatcataat acatacaaaa  113340
tacataaaaa agctaacatc agcaaaacac caccccatcc agctgttaca tatgacatat  113400
agaaaacgta tataaggtat gttactgcta taattgttaa taatacaagt atcgtgttaa  113460
tgagcttttc taaatcaatc attatacaac ctcctagtcc tcacaagtgc gagtctggtt  113520
cttattatac tcttactcct acttatatcc aaagaacttt aagtaatttt ctgcttcttt  113580
ttctaagtgc tcgtttagtt catctagggt aacaacttc ccacagtcct cacaggtgta  113640
ggtctggttc ttcttatctt ctagcagttc accatcacat acaaggttga tacaatgggt  113700
tgtccaactc cctacatcat caggtaagtg ccccattata cgtcacctac ttttacggca  113760
aatgccatga atcgttcatc cattttgcgg atttctttct ctgtaaaggt agggatgtct  113820
tttaggtagt ttgtaaagtc aggagaccct aatcggtcga tatagctata tccccaacca  113880
tctttatctt ttgcaataat gatgtagtac tcgtcttctt cttcctctac cgtatgacct  113940
agtacccatg ctttggcaag tttctcatgg ttttctgggt tattagctaa ccaaaagtac  114000
atcttactag ggtagcttcc tttgtcaatc atgttaataa acgttaagtt ctcttctttg  114060
cacttgtcaa tatatttccc tactttataa ggaataacaa ctttttcagg ttcgtctaaa  114120
tcatatgcta aggagactgc ttttgctatc cctgtattgt agcctagagc atgggggttc  114180
aatgtaccgt cacaccctac ttgagtaaaa acctcgtcac ttagtctact aataaattca  114240
ttcttattca tttagttccc tccttaaaaa tcaagactgt tttcaataag ttctgatagt  114300
cggagcatta cctcatgagg tagctctaat tttgtactct cctgtgagtc tgcggagctg  114360
acttccaaag tatattttac ttctgttttc tcatttacac gggaagcctt cttctcaaca  114420
catactttat aaagtgctga gttattgact gcgataattt tttcttgtgt atttacacta  114480
gtattgctat cataagtaat ttcatagccc attataaaac cctcctattt gtatactggt  114540
acagcaaaag cccagtatct ttcatcaatt tcttttattt cttgttcggt aaatttgctc  114600
ttacccatgt tgggtttatt tgagaagtat acttcattat tgtgggatgt ttcaacccaa  114660
agataacaat cttctccttt attaccaaga ccagtaaaca cgacatggta aagtggttct  114720
ttctccacct catatccatc tttcattcgt attaaagttt caatagggtt attcttactt  114780
tggtctaacc aacaatcgaa ctctgattca tgtgggtagc tgttgccatc taacattcta  114840
atttgtgtaa aaatagctag gtctaatgca tgtttatttt cctcgtacca ttccgcaaca  114900
aactttggca caattacttt tttaggttcg tctagctgtt ttgctaaaga gattgcgcta  114960
ataattgata gatttgacac tatacgataa ggtgttttac tagattcttt tagttcttct  115020
aattttttaa tcaattcttg tttattcatt taatttcttt cctttctttc aatagcccac  115080
tggctgaatg cttgtaagac ttgcaactgc gcaatttctg tcatgtatct ataattttta  115140
taaacagggc tattccgata atctgttttt gtagaattgg ctctcagtct ccaaaatagt  115200
tctataggtt caatatctgt taacgtatat ttttctttta accaacccaa aacaatttgt  115260
tgattctcac ttagttctac ttggtctacc ttatcatcag tgtatttgaa ccagattttc  115320
tcatatgttg tttgtccgcc tgtgattgtt acaaattcgg cgcttggttg ctcatttga  115380
aatttttcta gttgttcttc gtaatgtata tccccaacat caaattcttt aaatttaatc  115440
attgtactcc ccctgttcta aaaaccaatc agtaaatgct tgaataactt gcgcttcctc  115500
cgttactgat aaagagtaat atgcctcttc tgttttaggg tcttcatagg tctccccaat  115560
acgttcgagc gcctcaaata aggaatcttt actacagtaa cctactttta accattcaaa  115620
tacctgtttc tgatttttat tcagttctgg ctttttaact gcctctactg cagtcttata  115680
cgctattttt aaaaggtctc cttcaaaact attagggaaa ttaatttcac catttgcttt  115740
catatacata tagcaaactc tatcaattat ttcgttatat ctttgtctac tcattcacta  115800
tccctcctcg tcctctacgt caccccaacc aaagctacag taggaagaga acacgtctct  115860
agctacttcg tctatctcct cattcgtagc attatcgggt acttctactg tctctatttc  115920
accaatacct gcccaagttg tctcaatata tacatttatt tttcgcatag tttaatacct  115980
aagactacat agtcgtcttt ctgtgcataa tcggtgatat aagtaacttc tactttaata  116040
aactctcctg tatacgaacc acatgtgtac tcatttaata aaagaatatc tcccacatgg  116100
```

```
tattgtctat catttttacg tatttcaaat agttttctac cttccttaac tgctttaaag  116160
tacgtaggtg caatcttgag gttatgagta acttctaatt tactaactaa atcaaaaatg  116220
atagtgttta atttgttacc ctctacctga tgattcaatt tttgtaaagt tgttgatatt  116280
acagtatgcc taccttctct atcaataact gagtttcttc tgttatactt agtaagtctt  116340
tccttttctg cttttgcctg tgctagtcca tttattgttt tagatacttt tacttctcca  116400
tttacaataa cttgtactag gtatctgtcg tcctttgttg caaacttatt atccataatt  116460
agtacctctc tttcataatc ttaattgacc agttatcgtt gttactgaat acccgttcta  116520
ggtcattcaa tgagttggta tttacaattt cttttttag ttttctatct gaattaatat  116580
taccaaatcg tttaaggaat ctttgtttaa agtgggcata acccatatag tcgaaggtaa  116640
taacgtgttc tttaccaaat ataccccgct ctcttaactt aatctctaca ctctcataag  116700
agctatctac tttcataaaa ttatttagaa gagtgtgcaa atcaatacaa atagatgccc  116760
ctgcactacc gcctataagt atatatttag ggcactttat atcggggtaa caaggggcat  116820
ctaattcata ccacatatta tttacgtcta ccccatacca tacactattt acatctactg  116880
aggctctttc tgtcttaaat ggttttatgc aagtatattt cattgtctct cctccaaatc  116940
gtctagtacg tcttctaatg ttgtgacaac cccctgcaaa taaccaagtt catgccaccc  117000
ataccctctc ttatcttgct ctaacaaatt attaattctt tttgttttac gtttaatttg  117060
ccggttatat cttcttttta gtccctcttc aaaggtcact accttttttg cttcctctat  117120
atcttttaat aattggtcta gcccatctcc attagtgcca tagctataca ctagcgcttt  117180
ctcgtcctta taggtagtta cccctaatga ttggtataca tacttcttac tggggacaaa  117240
tacaagagta atgggtctgt acaattgagg taaaagacaa tcttctgaca gcccaccaaa  117300
atctgtttta gaagatacct tctctaccac atacctcata tcttccatac ttaacgactt  117360
aatacataaa atatatctgt taataaccat tttctttagc tccccctaca cccaaaatag  117420
ttttcgattc tctgttggtt taaaagactc caattctcgt gaagtattac tttttccatc  117480
tgttaaacct tctttcactt tatatattaa aaaaaataaa tctagctatc tacaaataca  117540
ttgtatcatc agctagatta aaagtcaaca ctttatattt aattatttta tattacaata  117600
gttctttatc taaaattatt ttagggatag cccatattgt agtgtaacga accccttat  117660
ggttacctgt aactaatacg aacgttgccg tgtctagctt agtaccgagt acagatgcta  117720
gtagttcgtg gtcttctttg ctaattggta cttcaaaatc aagttctcca agctctacca  117780
caaagttatt tgctctaatt cccataaagt attcatcatt acgttttaca tggaatatat  117840
tcttcgtatg aaaactttgc ataacaatat ttgcaaaata actgttatcc ctagctacaa  117900
taaatctatc tacatagata gcctctttac tgagtagttc ttcaatgcag ttactcataa  117960
catattctcc tcctcttcta atagtagctc tgatacgtaa atttccatca ttagactttg  118020
ttcaatcccg tctagtaata aatgcatagc acacaagcca cacaacattt catctaaata  118080
aaaatcacca catgtctcct ctaatggtac ttgacacatt aaacactcta tcattgtaca  118140
gccctcctta atttaagttt tctctaactt ctgttagcac ctctcctaat agattaagtc  118200
cttcccattt actcatatca cgagagcgtg ggtctgattc acgtaaccct attccccata  118260
ctttatcaaa aggtgatgcc tctgcaaact tggttccttt agggatggat agcataaagt  118320
tacgtaaact atcattttgt gtgaatttat aagtatttcc agctaaaacg attgatttac  118380
gatgctttac ccacaagtct tcttcaaaat ttttaacttg tctacctaaa cgtttagcat  118440
cttttgggct ctctgttttt aaaattcttt ttgctgtatc gacatcatta aaaagcattg  118500
ctttacgtac catcatgtag tgctctgctg tcgggaaaat aatagcttcc cctaaaccct  118560
taataggtgc actgaactgt gatgggtacc actgtgacaa gcactctttt cctagtttat  118620
tacgtttgct tggggtatgt ccccaaaata aaatatattt actcatttaa tgttcctccc  118680
aatattcata gtagtttccc ttatgttcaa aaacaaaatg agggctaggt aactcaccat  118740
taacttctat atgctctggg ttattataag aatagtaggg ttcgttacca gtaggactaa  118800
ttgctattac tggtttatct ttaaaaaatg gtggtatttt atctccatca tttaagttta  118860
atttataggt acttaatggc acgcttctac gatgcccttt cagtgttgta tactcctcaa  118920
gactaattat tctaaggaaa cccttagctt ttagaggcgc taaactgtct atcgaaacgt  118980
cttcttgctt ataagtgaca agggcgctat aaatggttga ggggtttttg tatgccactg  119040
aataattaat tgaagtgtgc ttatggtttg ctaaaaattt ctctaattcc ttagataaac  119100
cataaggtgt atcactatca ataactttta ctttaatcat gtgttatcct ccctatatgc  119160
ttctctaact gttcctatac tttggtctgg gtctggttta ctaaatggta agcttgcacg  119220
ctcttcctta ctcaatgttt ttaagcaagc cacatgtact gcaatgaccc ctgacttagc  119280
ttccatacta tccgggagtg taagtatata gtcattatac agtttactta acactagcca  119340
ataacgattg ctactacttt tcatattagc taaaatcatc attttttcat agtaatcttg  119400
ccccatacaa gaaagtcctc ctattgcaga ttggaggagc tcatcttcaa gagctaagat  119460
agtatttgcg taccctttca gctccttgtt aagcccctct atagcaatct caaaacattc  119520
tctttctgga gagcctacag ttaaatcatt aagtggctca tatgctctta cttctctccc  119580
actaggggct tgtcttcgtt tacctatacg ataagagtct ttaaactcat actcggaacg  119640
aaaaatttct tcttgactat ttcttccaga ccttcctcca aaatagcaat cttctactac  119700
tccaccaaga ccattataat gtcctctagt tgtccctatg actttagaat gtctaatatg  119760
ggttagctga cagagctccc ctccgttatc agggtcacct acaatagctg tctcacatac  119820
aggacagata tatccaaaac acatcacttt atctacctcc aattaatata cattaagaaa  119880
aagttacaat tttttcacaa ggaatatcat agtatgcctt taaaccataa tgttccaaca  119940
tgtattcttt agcataatct acaaggtgct cagggcattt aaatgtgtaa gagccactca  120000
tcattacacc actattactt aactcttctc tcgaagcttt agcaaaccac ttagcacact  120060
ctacaggata accaataaca caccctaaaa cttcctcgtc attaaaccct agcttaattg  120120
attcattgta tacttctata ctcatcttat ctgatgttac taggtatata ctaccatata  120180
acctcgtttt atagtaagag cgttccagat ggcttagctc ttcttcccct aatacgattg  120240
ctacacgatg acctaaatta aaatctaaaa taggctttgg aaaaacgtat tctgctttct  120300
caacaaactc cacttagcca cccctttct cattccctaa attatcttaa atgctgtatt  120360
agttagaacg gtaagtcact attgtgttct tcctcttctg ggatatatag gatattttca  120420
atcttttctt caatatgtcc aataatctct gtgtgctctt taattttctc tttatgattt  120480
tctctttgct tatttaactt tgcatattgc tgtaattcat ctggtgttag ctcttctagt  120540
cttttttca tttgttttct ccttctaatg taattttctc tacgtcatca acactaccaa  120600
aagatggggg ctgtgtcaag ttcttatcta accagttagc gataatgtca tgtaactcgt  120660
ctatagcctc atcgcttact tcatccgttg ggtagtagtc ctccgctact tctccatatt  120720
cactgtatag ctgttcccct acagattcta acatacctac tacatctaca ctaataactg  120780
ctttattgaa ctgccctact gcaaagcttg ttgttccctt ttcaggtaat gctccaaata  120840
```

```
tatcctctac gtgcatccct aagctatcta catatgtttt tccttcatta atggacaata  120900
atgcaagttt tcctgcagac actgcctctt ctctcgtaga gaacgtctca cacgctttcc  120960
atacatctgt gtcttcctct agtgctaata catagtcttt atcttccatt gtcttgccct  121020
ctctatcctt ttaatataat catatttgta ttactgtcta gttgccatcc atcaaattct  121080
aagtagtggt cataagggtt aattggttca cctacaacta tatagtcctc tagtgcgtga  121140
ccttggtctt ttagctctag taattcgtct aataaatctt gtgctgtcaa attattcatg  121200
ccatatagta tcctttctct ttagcttctt cccactcatc tacagaaaac aaacgctcat  121260
tccgagacaa agagccataa cagtttactg ttaagtctac cataaggaag tccttaccgt  121320
attgttttgt ccaactctct gtatatggtg ttactgagtg cacttcttta atatattgct  121380
ctaacatatt cattttatgt taccctttct tggtttaaat tttcgtgttt gtgttcggtt  121440
gtttctactt acttctttgt atctacggat tcctaatgcc ttagattctg ggcgagaacg  121500
acctatctgt cttacatata agtctagcgc ttcttttact ttatcatcat acatcttccc  121560
taattctcgg aaatactcaa actcacctaa atacacataa ggcatacgcc agtcatctag  121620
ggtagccgtt accattgttc gtttgtttaa atcataatta tagatatata gaaacactat  121680
ataagcacct gtcatcacag aatagcttgt cctaatttca cttagagtta cgctgtctct  121740
taatgatgtt aaataaccat tccacttttt tttacgttct tctgctaaag tttctatgaa  121800
gtagtttacc tctttttcgt ccctcaccac ttgctacctc cttgttgttt atgtctatat  121860
attatcatct actttgttat atgtcaacac ctttgtaata aaaaagaacc tagtaattta  121920
cttacttagg ctctcttgtt tatacgtgtt tagtaagtta cctttactat cgacaacaac  121980
agcattaagc tgaccaccat atgcacaggc accatcaatg aaaatacttc tatcacctaa  122040
gaagacatcg tagctgttct cttttctcaa attaattgtg ggtgtgtgac ccattacaat  122100
tgtcttatct gttttattct tctgtaacgc tagcggtctc gtccaaatca tttcatcttt  122160
agtggctgtt ttccaatcag gctgacgata aacaggtatc cctgcgtgta cacataaggt  122220
gtctccatgc tcatagtatg gttctaataa actaattact tcaactacat ttgtttttttc  122280
taataacatc tttctagtgg taaacgcatc ctgtaggtgt tcatctaaat ccaatagact  122340
acttattgtt ttatcaccgc cattgtacat ccacattgcg tacatctcac ttaggtcttc  122400
gtagtctgct tctcttatca atggaaatgt taaaaaatct aataacattt ggtcatgatt  122460
tcctaacaaa gcagttcctc cattaataat atgcttataa acgaaaccca gtacttctgc  122520
ggatttgcta cccctatcta cgtagtcacc taaaagtatt aagtcctctt catcactatt  122580
ccaatgttta ttaagaagca ttattagctc atcatagcaa ccatgtatat ctgatacaat  122640
aaatacttta tctttcaatg aataatagcc cctttaacta cttctgctag ccaataagta  122700
gctagtacta gtacagtatt gacaataaat gttattacta taaccagtgc taacttataa  122760
tttttactcc tagcattata gtttatataa ttttttatgt taactctaat atttttaaac  122820
aaagcactcc catatacgtt cagtgctata tatagtaaaa gcaatacgat aaagtagcct  122880
tgagctagaa acacgtcaga ctccctgaac gagttattaa accatatgct aaatatcgca  122940
atcacttggt gaattataag cattgcgcca ttaccaaaaa gaagtatact aaacgctata  123000
ccgactacgt ctctgtactc tgaaagtagt ctatcatata ctattatccc tttagtaaaa  123060
ataaaagcaa caactgccat ctgtataagt aaaaatattg ttacggctaa taagtttctt  123120
gtatgcatag tcataattta gccactcctt tcaaaatggg taaagaaaga ataataggta  123180
tatcgttctt tttctaccct accttcatgt ataaaggtaa actcaacaaa cttaactctt  123240
agcggtatat ctggtgcttt ctcccaagga agtactcttg ggaaatcata gaatactctt  123300
gtggggtaaa cttctttcat aagtatccta gggtatcttt tctttggtat aaatctttta  123360
cctattatac ttgagtagtc aggtttcatt gtaagtcacc atgaatagag tatgctctat  123420
ttgctttgtt aaagtttact tgttttttgt ttactaatct tattgcatct tctaataaaa  123480
gaggttttcc taatttatgg ttatctaatt ctggtgagtc taccccctaca ttcagtaagt  123540
ttggttcggg tctggctaac tcatgaatgt gcccatgtag attaattagg ttatctctat  123600
ctcctaaaat tagtgggtaa tgtgtcatat gcacaacctt atgcattcgt tttaaaataa  123660
taccaacgtc ttcccaatga accctatcat tcagggaagt attgcgttta atctcttttc  123720
gtagaggact attatcgtgg ttacccttta ttagccatat agtgccattt aagcgctcta  123780
agacgttagc tatactattt accttggcac ccattgcaaa gtctcctagg tgatatacaa  123840
tgtcctctgg gcgtactgta gcattccact ctctaattaa gtattcgttc atctcttcca  123900
catctttaaa ttgtttccgt gtgtccataa aagaggcttc cccacaaatg tttctatgga  123960
agaagtgcat atcagatatt acatattctc tccccatact tgctcctcct tagtgtgttg  124020
caaaccatac gaatacagct agttgtagat agtgtactgt ttggtcgata attagttgtg  124080
tctttttatt aggtactgtt tttaagaacc atgcactttg tgcttttaaa tagtccatga  124140
taaaatgtgg aacccataag catactacaa ttagcccaag ttttactggt gttcctaaga  124200
acaatgtagt tgcgacaata atatacgtcc agatgtttac atggatgatt agtagatata  124260
aatcagtctg ctttcctttt gcgatatagt cactttgtaa ggcatagtcc cctactgcat  124320
gagccattgt aaggataatt acatagtata agtaattcaa attaagtcct cctctttgta  124380
tgggtaagga caagtgtcac attcaaatcc atattcgtta ggtgctccct ctaaaatatt  124440
tccgccacat tctgggcaag ttgctagttt cattgttctg cctcctttac atgatttcaa  124500
gatatagccc tgcacttggt gttgtagaaa tcagcataac ttctaggtct aagtgttctc  124560
cgatacottc gtattgttca ataagtggtt ttgtttctga taaagtgaat gttacaattt  124620
cttcatccgt catgtgctct actaatgtga ctgtgcgacc aaattcaata tgttgtaata  124680
aatgtcctag tttaatcatt ataatttccc ccatcaatta ataatagtaa gataccacct  124740
atcacaagta accagaatac tgctaagatt agtaccattt agttgtcctc cttgaacagc  124800
tcatcgtata attcttgaat tgcctcacgc tttactttta acattgcaat ctgtgctgat  124860
atgatattgc ttggttttcc caccaaacgt ccctctaagt gcccaatatc catattgtat  124920
tgaataaggg tttgttgaaa ttttttttcta atctctgtgc gttcattaat tggttgctct  124980
ggttcaatct caaacagttc aaacattgaa cgccagcgcc catttacgtt attcaataat  125040
tcactaggtg tgccccccaat atctactgtg tcatacccat tgtctttaaa gaagtagccc  125100
accgtttcgt tgtgataaac aggatattct ctcccttcta tgaactgtgg ttctagtgca  125160
tctgcttttg tacatttaat tccgtatgtc attttattaa acctcccatt ccttaatgat  125220
gtattggctt ttatagtttg catagaaatc tgagtcactt gagaagtata tatctagttc  125280
ttttactttt tctagtactc cttgaaggga tgtaccaact gccatgttag tacctgtccc  125340
cttatcaatt ccgagataga gtgtaagttt ctttggttct gcaccgagca attcaaactt  125400
agaatgccaa tagttattta attcagctaa tagtagctca ggagtggctc ctgattctat  125460
aatgtctccc tcatcatctc taaggaagta acctctagca tcatcataga atacatcgta  125520
ctctttacct tctgtgaaga tatgctctgt tttaagtgta catctaattt ttactgtcat  125580
```

-continued

```
tctaatttc ctccaattca atttctttta ttgatacaaa gccaagtata ttgcggaaag  125640
tacggtcttc attccagtat ataaattgtg ttagaagtgg tttgtggtca tctgtgtatg  125700
ttgtttttttg tctcgtagta gctttcttca atttgttcat caatattttg taccatttca  125760
ttataatatg tgactgcttt atcatatgag gtgaaagccc tcatttttac cgctctatac  125820
tcaaatttca ctaaccatgc tgagcttaat ttcgtcattt atttcttcct ccacttcttt  125880
gattgacttg attatatatc tatggttctc tctaaatgcg tggtaagcat catcaagtga  125940
atatgcgtat aatcttgttg tttgcattac agttctatat ccgttacgtc caaccattgg  126000
ttcgtcaact tctacttcta actcaaataa tagttgtttt ctaatcattg tttttactcc  126060
ccttttctat gatataatat taccctacta ttatgattct gtcaacaggc aaaaaaaaga  126120
agtagaaaaa tctactccta ttcatcgttt gacaactttt ccataccata tagtaactgt  126180
agtagtacat atagtacaat atcaaatccg tcaagtggct ttccaagtac tataacttta  126240
acaattgtca ataccgctaa aaaaataaat agccacccga ttattttatt tgcatgtttt  126300
ctaattctca taactttcta gtacctcttc aatattcttt ctggtttcgt tagctaactt  126360
accagtccgt tcaagccaac ctctaaccat ttctttttct actttgctat gtttattcgc  126420
atcctccttg ataccttcta cattttccat caagttatct aagtcctcca taacatctaa  126480
taaagtgttt cttagtttta acacatcgat agacaactca tagttccgtt tagacaattt  126540
ttcgttacgg ataaagttct ttttagttc ttgttgtgtt tctagtagct gagtagtttt  126600
aataatatca gcttctaatt tactaattcc gtctagttca ttcatcacat gtcctcctca  126660
tattctacta cttcctcaat aagtttcagt acttcttctg ctgtgcccac tgtgctatag  126720
tccgcaaagt tttctgcagg tttcataata gccactgaat agggtttgtt ctctacataa  126780
atatgcccga atcctttttaa agaatgaatt acctctactg cccatccatt agcgtactct  126840
tctcggtata ctacttgctc actggttgct cttactggtt tattcattgt taaaaccata  126900
gaagtttctt acaatgtttt ctacacgttc catgccctct aagtagctac gtttctcagg  126960
ggagatatag ttcttgtaat gagggacttc cttctcttcc tctacctctt ttgtagtacg  127020
ttcaatcagt ttaataagtt ttacttcgtt ctctagttga gactggataa tgtctaacag  127080
ttcatttttc gagcagttgt ttagtggttt acttccatag tcaataattg tcatagtagt  127140
cctcctattt taatgtgtac tctttatatc ctttatgtgt atcgtgcccg cactttgtac  127200
aaaagcctgc ttgttcaata tctattgaag agtaccctgt ttgtactgca tacgtctcat  127260
aagtatggtc acacgtatct tcttctgatt catctatttt ctctaaacga atagcctctc  127320
cttctgccac ttcgtggtta aagagcaata ctgcagtttt aataggctca tatacctctg  127380
ggtggacggc ttcattcatc ttaaagctat ttccactaaa ttcattgaaa gcatctagcc  127440
attcctgact gttctcataa gatacaattc tgtaattcat acgaaagctc ctctcgtgtt  127500
ttcttaaata accagtaccg ttcatcaatt tcttttatct ctgcctctgt taaatagaag  127560
tcttttaatt tggatagggt atcttgactc aatggctcgt ttctaggtag tatacttact  127620
gctaactgcc cgtccttgcg taatagtaac ccgtagtctc tctcctgttt ctgaggcatt  127680
actacatagt acttaggtaa actagcagtg tttgctactg cttgaataaa agtatctgta  127740
ttagcaaaga accatttact aaactctgac ttggggtact cacatgcgtg tctctgccct  127800
tccaagataa tttgtaactt atccataagt tgttctcgtt gtttatcaat aaactctttt  127860
acctgttttg gtacttctac ctcattattc atagtttgtc tcctttgtta tactttgtca  127920
atagtgatat acacatactt gccctctaac tgcttaacaa tatctagtat gtcatgacca  127980
cctagcttaa atgtgtttgt ctcaaaccct tcgatagtaa aggaagacca accgtaccaa  128040
ccttcttcaa agtccaagac ccccatagat ttaagtacta tatttttagt gatgtcttct  128100
aatgaagtac gttctacagc agagaaaatc tgaatctctg cgttatcaag atgatactta  128160
gaagaaatgc ctccatcgta ctcctcttct gttgtagtgt cctcagctcc taacgcatac  128220
agtgcattac aaataagcat gtttaaggct ctgtgctcat ggtgatactc aatttctttt  128280
acttttctt ttattaagta aggttcgttt gtttctgcac cggggctgtt atcaatagtt  128340
acccaacctt ttaatatctg tttacccatg attgctcatc cttcctttag tacagcctat  128400
cgctgtcacc agtaaatcta aattttcctt tgtcagagtt actgtttgtt catgtacaca  128460
gtccggtcta aatacctcta ctgtacgatt tactacagca atatctacag tatcttccgt  128520
tgtctggctt accttgataa actgtttgga aaactcccca cggctaacac cttctatcat  128580
aagctccatt tttttatagc ctcctctctg gaaagtccat gaaagttgtg gaaagtacgc  128640
tcttgtagtt catctactgt atttggtaat gtacgaaatt cgtctacccc tagtgaaata  128700
cttgaggcta cctcttcata ataacattta acgtctactc ccattttacc ataaggtaac  128760
accattactt ctatatgaaa ctcatatgga gcattctgtg ttaatggttc gtataataac  128820
catgtctcat gatagtttac aggaatatct aatagtaaac tgtttaaatc atctagctgt  128880
tcagataagt atgcaattct tgtcatttta cggtcttctg ctataggcat tgaacaacct  128940
aacgtgtctt ttatttcttt aatttctttg gtaagctcag ccattaattc aattatttta  129000
taaaacattt ctattccctc tcttctatat attccccttc ttctaagaaa aagcaagcag  129060
gttctccctc tccattttca gtatcaccta ggtattcatc atctaagaat gcacagtatc  129120
cagttgagta gagggttaca cagtccttat ggtacatcga atcgtccgtt aaccgcacaa  129180
cctcgtccat ctcactgaac acttcattac acgccccgca tgatactaac tccttactca  129240
taggctgcct cctttatcta ttacgtagtc taccagttct ctaataacct ctgcctcctc  129300
tacactagag aggtctgccc aaacttgaag tgtcgcatcg ttagccttac cagatattaa  129360
attgtgtaag ctatctgcaa tagttagctt tgtacgttca agatagtgaa ttagccagac  129420
taatacaatt agctgtttct cagttagctc agtattagtc tttgtgtaaa cctcatagtt  129480
atctaaggtt aatgggaatg tttcttcatt attaattact tgaaacccgt tatttggttc  129540
gttttcatat tctccataag ttactctctt acctattttt agttttacat agatgtcttt  129600
accttctttg tgtagtttat ctaggtcact attataccac tctcttgttt caattttagt  129660
aagttccata aagctaaccc tccttactga gttccttgat acgttgttg atttctgctt  129720
ctgttttctc tagttgtcgc attttgtttt tatgtcgaga taattcatgt tcctttgcag  129780
tttctgccat tgctaataag ttttctaagc ttgctgtatt tgccattaga ttgccacctc  129840
atagttaaat tttccattat gtttatagtt tactacttta atttctgata gtggggaatc  129900
aaagaagttc ctccccttct cccatggtaa gataagttct ggcacttctt ctgatattgg  129960
tgcattcacc tgttgttcaa taagttctaa atgtcgttcg taaatgtgtg cgttatcact  130020
cgtccaatat aagttaccta actctaaccc tacagtattt gccataacca attgtaatgc  130080
atgatactga ataatattaa atggaagtcc taagcaaaca tccgaagacc gagccttcac  130140
atgtaagttt aatttaccct ctacaactgt ccagtgagtt gtccatacac atggctctaa  130200
tgacatatcg tataaatctt ccacgttcca taaagtagtc ataattctac gagagtttgg  130260
tgtgctctta agttgttcaa taactgcctc tacctgattt agctttaggt atggttgatg  130320
```

```
tgttcctgct atcccaccac ctttttttagg tacgactttt ggaataagtg aacctgcttt  130380
gcgatttttta gctaactcaa catctccact ataaacagga ataaaacgtt ctttgttaaa  130440
taatgcgtaa ccatacgctt ttccaatagt gccatcttct tgctcccatt cgttccaaat  130500
agttacacct cgttctttta accacgaaac ctcgttagac atttcttgcc aaatccactg  130560
caattctgtt agcgcccatt taatacctac atgcttacta cgtaataaag gagcccccat  130620
atctggtgta attgtaaagt ttacaccttc aataaactta gttgttgcag gagttccatc  130680
agcatatact gcacgagtac cttctggtag ctctgttact ccgttcttaa taatatccat  130740
tactaaatct ttataaattt tatcaaaatc catgttgtgc cctcctacat ttcttttccc  130800
tataatagaa atatatcata tctaaattta aaagtcaaca aaatattata aaaaaaatat  130860
gagacatatt ggtatgtctc atatctacta aattctatac taaactggct agcttgtcta  130920
aagcgttata gtccgcatcg gttactggtt ctactttacc taataagtac ccattaccta  130980
cctgagagaa gaagtcatgg ttactagttg ttgtagagat accattcatt acaatagggt  131040
ttacgtctgc acttgttgtt gggaataaag ggttcatccc taagttagct agagctttat  131100
ttaaattgta ctccaaaaat gtattaacat cttttgtcca accaatctca ctatatagtt  131160
cagcagtata ctgtgtttcg ttctcccata atttaaatgc taaatcaatt acccattgtt  131220
ccatttcttt ttgttcagtt tctggtaact ggttaaaccc taactggtat ttatagccga  131280
tataggttcc atgtacagac tcgtcacgaa taattaattt aataatttcg gctgtattaa  131340
ccatttttgc ctcacctaaa tagcgtagtg gtgtgtaaaa acctgagtaa aataggaagc  131400
tctccaatag tacggatgca ctctttttct gtagtggtgt accgtttcga taaatatcgt  131460
taataatgtt agctttatat tgtaaacgtt tatttgtagc tacccattca aagatattgt  131520
caatctctgt aggtgtatta aatgtgctaa aaattgttga ataactttta gcgtgtactg  131580
cttccataaa ggctatgtta tttaaaacag cttcttcatg ctgtgttctt acatcatcaa  131640
gtagtgagtg taccccgat tctgattgaa ctgtgtctag taatgttaac ccaccaaaca  131700
ctttatttat taaatcttgc tccatatcag agagctttgc ccaatcatta acatcgttac  131760
ctacagggac acgtgtgtcc aaccaaaatt gctcagtaag ctttttccat gtggcttggt  131820
caattacatc atcaatctta ttccagttaa ttccttcata cttttcttgc aaattcatgt  131880
gctcatctcc ttaaattgta caactttcac actctgaaac ccctacttcg cttccgtctt  131940
cttcggtgaa tgttctaaca taataaattg tttttatacc ttttttccat gcataatgtc  132000
ttaataaagt taagtcccga gtggatgtag cgccaccctc caccttccaa ggataaagat  132060
tttctggtaa ctctgagcgc ataaacaatg ttaaactcat accttggtca atatgttttt  132120
gtgctgttgc gtacacgttg attacgtcaa tcatacttgt attgtacgct gacttgtaat  132180
atggaattgt cttctcagat aaccggggtg cagggtaata agttttacct gttttcccat  132240
cttgacgttc ttcaatcata gagataattg ggtgcaatga agaagtagtc tcattaacat  132300
aagcaatact accattcgtt tataccgtta ctttcgtaat actttaacac tgctcttagc  132360
agtcggacta gactatacct tatactatcc caaaatagta ccaactatta tagtcgttgg  132420
acgtccctca ttttacagag gtttcgatgc tgatttccca ttgtattacc cttagcacct  132480
gtaacaaggc ttttatttca gcataggcta tctaactaat tttttctgct ttcgcaacat  132540
tcacgctcac cgtttccagt cacgttgtag tttagttagc tttagggggt tccagcaatt  132600
taagttgttt ttgactcata ttcacatatg agaaagccca atattattta ggcgccacag  132660
ctaaacggtt ttgatggtat agaccacctt caataatact gtttcttaat gtttcccaat  132720
cttttacatt aggtagtacc actccatcaa atacttccgc caccttacta gagatttcct  132780
gatttagtgt tggtacatat tcatcaaagt aagaaccgtc tgcgtattta gagttctcaa  132840
agttatggaa tgttgtgcca cgctctttag caatcttatt acttgccacc aaagtagcat  132900
agttaattaa ttcaaacaga gcatccgtca tttcaataga ttcaggtgag ccatattcta  132960
cttggttact tgcgaaccac gcatgtagcc ccattgcccc taaaccaatt gtatgggctt  133020
tatcattacc attcttgata gtaggtactg cttttatatt tgacacatct gtaatatatg  133080
ttagagctct taccatcgtc tcaattgatg ccactacatc attagatgtt tctaacaagt  133140
taaggatgtt aattgaacct aaattacagc taatgtctgt acctaactct tcgtatactt  133200
gttcatcatt tagcttagat ggtgtctgta cctgtaatat ttcactgcat aaattactca  133260
taatgatttt gccatcaata ggattggctt tatttacagt actaacattc ataatatatg  133320
ggtaacctga ctcttgttgt aaacggctaa tttcttcttc taaatctcgt gcattcatta  133380
ccttacttct gatatttggg ttctgaatca tgttattgta ttctgaatca atgtctacaa  133440
atgagaatgg tacaccgtat tctttagcaa catcatatgg agaaaataag tgaattacat  133500
ccccagactc agctagctca taaaatttat cgggaacaac tactcccaaa gaaagtgttt  133560
tgatttgctt tgcggattct gcattttctt ttctagttga taaaaagtcc ataatatccg  133620
catggaaaac atttagatag actgcgcctg caccttgtct ttgtcctaac tgatttgcgt  133680
accggaaacc atcttctagc attttcataa cagggacaac cccgctacct gctccctcaa  133740
ttcccttaat agggtctcca agagctctta ggtttgaaag atttaacaag tagtccatgc  133800
tttaacatgg ctcagactat atcttaacta aatttgttac gtttagttct acgcgcttcc  133860
aaaacaagaa tttcacttgt aatgtactct actaggttac tcgctaatat cctcccgaca  133920
atagctaccc gttcgatagt cgttacactt ttacaatttt tctcctcgaa attttctaca  133980
caacttagct ttatctccaa gtttatcttt tcttttaaag tagccggata cgttagctaa  134040
tgaagtagat aggtacctac tagcctctga catatcttta aactcaaaag attcgtttgt  134100
ttcgatattg gttattttta caggaataga cgtagtatgg caaggtttttc tccctagtac  134160
cctaaaacca tgtttagtgt tctctgatat agtacaccat tcaaggttct ccaaacggtt  134220
gtcttgtttg tccccatttt tatgattcac tactggatag ttgttagtgt taggtaagaa  134280
agtcatagca accactctgt ggacaagtag gtacttccta ataccttcct tgttatacat  134340
agctgttttg tagtaaccgt ctttatcagt agacaacttg aagtatctgt cctttttttct  134400
aattctgccg agggttgaaa cctcgtaggc agggaaatca gggactgcct tccagtattc  134460
tttttccata taaccacctc cttaaataag gagaaaaatt gtacttagca cggtattgcc  134520
atatctttcg acttaggttc caccgttagc ctacataaag tagacaccct aggtttctag  134580
gttcacgtag tttatagtga gctatattct ctaacccact ccaccaccaa gtttagatag  134640
ttgaagtgca ctgttcaacg ttctaccaat tgaagacatt gaatcttcta cttgaattag  134700
aaaacagctg acatactccc ctcttctaag cctacctgca tttaaaaaag taggggttgc  134760
aggttggtat ctacggttaa ttagctcatc tgcaatcttc atagcaagct cttcgtcacc  134820
atcacccatt gtgagtgcat taaacgctac tctatcttca taacgctcta ggtatcgttc  134880
cccatcatct gttttcattg cgtattgttt gtagaaacgg taagccccca taaatgtgtc  134940
gaatctgaac tttttactat agatgaactt aaataatttt tttataaatt ccattgagta  135000
cttgtcagta atcactgttt tatcgatgta cccttctcta ataaggtaac taattttctc  135060
```

```
ctctaaagag tagaaaaata ctgtgttctt gtttacatgt tctaaaaaga atgctctaac  135120
agcttcttta tctttgtcta actgaatctt tccgttatta gggatattca attggttatt  135180
aagctcaata tatgtgttca tatctacacc ccaagttctt tttctagttt tttaaccaaa  135240
tcaggtctaa caccattaaa tgagaaacca tcatcagctt ctacatatgg taatgaagac  135300
actccttttt cttttagata agctaaagct tgctcatcat gagagatatt tttctcatca  135360
aatgggatat tctttccatt taacatattt tttaaaaata aacattgacc acacatatct  135420
tttgaatata ctgttacttt tgtcatttac tacattctcc taactttttt atcgtattta  135480
ttaattatac actattttgc attaattgtc aaaaataaag aaccaaaaaa actagagact  135540
acaaaagtta attgtagccc cttttaataa gttacacctt gtcacctaag aaatcttctg  135600
attcctgcga tttattcgta accttatcaa gtagtaaaac agaatagttt ttaccagttt  135660
caacctgcaa cctattaaac actttctgat attcttctgg tgtgtctgta acttctaata  135720
agtattttgc atttaaaaat gatagtaatt caagtagttc tgccttacta cctgccattt  135780
gaactacaac gttaccttca tcgttcgtgt atgttccaat tttatttcta gtagccaaac  135840
aaatcagtcc ttcgtaaatt taatgtattt gttaactgta tacacatttt taacttttttc  135900
ccaaacgtta gggtatacgt tcatcaataa cttagtatct gcgctagcac gtttgtactc  135960
tggcattaat ttaaatgtgc ccccatcaat actaatttta gattccccta actcttccat  136020
atcagaaatg atactacttt ttagctcatc aatctcttct ttaatacttt tttgcaattc  136080
atataatttc ttgtaagagc gtaagtcctt ctctagtagc tcctttttttt gtaaatctgt  136140
tgttttcata catatctctc cctctcttat ttctataata agattatagc atgtcagata  136200
tgtaaagtca acactttttt atacaaaaag aattgcccat tataaaggca attcttgtcc  136260
gttgtcttct tcaaaaagaa tctctacagg tatattatat aatttagcaa gtttttactct  136320
gtttttaaca cgaggttctt ttataccgtt ttcccaataa gagattgatg accagtgaac  136380
tcctatcata ttggctaact ctcgtagaga ttcacccccta gcctctctca ctcttttaag  136440
gactttaggt tttggtacct tttcttccat gactatccct ccttattctt aaaaaataag  136500
agcctatcag gtagacaggc tcagcatcag gaactatgcg aaagccccga tataagttac  136560
tttaccatta catttacgtg caaaagcctc taactcttta cgagcaccta aacggtcagg  136620
ttgcgaagat tgaacagtaa tttctttagg taccgttact tcacgtgtac gaatttcagt  136680
tttaccattt tttaatttct tctcatactc ctctgtacga gttgttgtcg tagaaatgat  136740
tccataaaat tttttcatat taatagctcc ttactgtttt ttttaataaa ttataatagt  136800
ggtaataggg ttttatgaga ctcctactca ttgtaagcct tccttaatag atacttacaa  136860
ctatacgttt atagacctct ctcaaaaagt ctccgtaacg tcttaccttc atcatttaaa  136920
acgtacacag aatttacaaa agttttatac ccttcttttt cagttctgta ctcgtaaggt  136980
gaatttggca cacgagtgat ttcttcatgt ttagagttaa gtaatgaaaa agcattctct  137040
tgctctaaaa gaaactgtac ccccatcaatt aattcaataa aaggcttaac aataggttcc  137100
tctgtactgt ctttacaatc gtattttcgt tctcctaaaa tttgtagtat catgtctatc  137160
tatctcctct gtttaagtat taatttgtga gtttccactc acaatgctga ttgagagagt  137220
cgaactccca ttcccgggtt acaaaaccgg agtaatagcc attatactaa atcagcgtaa  137280
cccctcaata gagggagttt cttatactaa attaccatat ccgtaggtat ttgttttagc  137340
ttgtttaaac atgatactct tgatagctaa gtcattgtac ttttcatcgt cttcgtcatc  137400
aaggtacaca tcaacattaa cgttcttacc taaaaatatcg attgtttcat ctttacctac  137460
ttgtaagtct ttactgttaa atgatacatc aaaatagatg tcgtcttctt ttgtacgact  137520
accgaatgat actctatctt caaataaatt taaacttcga gagttaatta caacaggttg  137580
tagcccacct tcaaattgaa tagtaactgt ataatactga ttttcaatat taagaatgtt  137640
caaatcagca atagcttcac caaatgagat gccaaagctt aattccaacg caattgctcg  137700
taagcaatca tagtttaact taattctacg gctaaactta acaacactgt caatttcccc  137760
atagtaagct ttgtctaact tatcttgcaa gtaagtacga atttcgtctg catcagggta  137820
gtcgaaacgt aaatggtaat ggaaacgtcc cggacgatta agcataaagt cgtttacacg  137880
atttaagtta ttaacagtaa gtgcataaat acgcttgcgt tgtgataacc catcgaataa  137940
gctcaatagt ttttcttgtg attcacgacc gtcacggtca ttgaatactt tttcaaattc  138000
atcgaacaag ataagagact cttggtcaat actgtcaata aattctgcga tacccggata  138060
agcttctgta attaagataa caggcatacc ctcttcaata gctcgttgag ataagatttg  138120
agtaaatagt gatttaccaa tccctttatc ccccacttaaa ataaccccta aactacgatt  138180
gattgtttta aatgtgtgta gtactttctc aattttaact aaacggtcac cataaacttt  138240
agattctttc aatttaaaat cgtctgtaac cgccaatgag aacccagaca ttgggttgaa  138300
tctaacttta taagtttgcg caggcaactt atcataagtt ttcaggtcgt ttgcataaat  138360
ctcataatta ctaccataat tgattacttt catatattct ctccttaata ctttttaata  138420
aattataaat ggagagtgat ggagtcgcac cacccgagcc taagcaacag atttacagtc  138480
tgctccgcta ctacttacgg aataactctc cttgaataac caaccagata ggtacctgac  138540
acacggacag cacctgtgtc tctctgttac tggatgatta attgtgtatt tcgcatcacc  138600
taatatagtt atcaaggtag gacttgacta tactagattt agctaggttc taactataat  138660
ttcctatgat agctcctact actaatcata tttatataca gttaaactac acataactaa  138720
accgattacc ttggttcgca tgttaagagg cgcaggcaac caatggacat tgcaggtctc  138780
gaacctgcga ccgttcggtt atgagccgaa tgctctgacc aactgagcta aacgtccgta  138840
gggtagtagc aacaattaca aatgctactc tcctgatgat tataaactta tcaaatcgga  138900
aagacaggac ttgaacctgc gacatcagac tcccaaagcc tgcactctac caagctgagc  138960
tactttccgt gttacctgtt taatttggtc ttttaaacta ctacacacag gtaaagataa  139020
accctctgcc aaggggagac tatcatcgaa ccgtatgtaa gttgcgatgg gtagtagcca  139080
tattatatta ggttattagg aagttcacct atgcagaagg tgggagtcga acccacatgt  139140
ccattacaga ccgatgtttc taagacaccg ttgtctacca gttccatcac ttctgcggtt  139200
gtactaccaa ggttacctct aaaaggctaa actcgtgtct ggtagggagc cataccttac  139260
atggattgca aggaacctaa cctcagtagc accttttact attaagggtt tctgatttaa  139320
cgttttccct agaccgtacc ttaacagtaa tactggtgag aggatttgaa cccctcttac  139380
ctacaagcct ccgacaagcg ctatgggaaa caagcggtgc attaaccata actatgctaa  139440
ccagtacact actgttttac gcagtcctca tactaataat tcatgtggac tcaaccccat  139500
tcagggaagt gttagtctat tttttggtga gaactggtta actccatgta cgtcaaacat  139560
tccctagact actcacttac attgttattt aatgtcacat gacttatgac agccgtactc  139620
aaaagtttca aggactttta cctcactatc caccgacagt atgctcggca acgtctttct  139680
aataataaat tacccatcac tgttacagta acagaaccat tgaattaacg agcaatatca  139740
gtattactaa aagtagtctg tctgtgtggt acaagcacta gcagtattac aacctatagt  139800
```

```
atgtctgttt gtcaatcgtt aaattctttt acaggagtac ttgttaaact tagggaggta  139860
taacaagtat gtgcacataa cccgagtgct actccctaaa gtagcctata cgggttaacg  139920
tagatggagg gaatcgaacc cccaaccgtc cgcttagaag gcggatgctc tatccgattg  139980
agctacacct acaaattatg gggtaatga gcccccataa taactcatag tagtttcatc  140040
tatcgaggat taaaatgaat atctaacttg aataaagtat aacactattt acatagcatg  140100
tcaacacttt tattaaaata aatttctata cctcactaat gccaatgact atacgtaagg  140160
agagaacgtt gatggcactg gctacttagt tggcgctaag ttagtgaggt atagaaagag  140220
aactacattg accgaatcgt attatacagc cttagtagtt gttaacaatg tttggaactt  140280
agtagcttac tgcaataagc taccccgaag catcggggtg ggactgtggt aagccccaaa  140340
cccttgggta tgctccatcc tgcctccgga gaagtcaggc tcaattctca ttagttaaag  140400
gtttactagt taacggttag ctgattagtc atactacgta aactactagt aaaatatagt  140460
tttccaatta aggctaacaa tcggtagagg atttgaaccc ctattattgg ttttggagac  140520
caacgtgtta ccagttacac taaccgacta tgtaaagaag gaaagcgaag accttcttta  140580
cagtaattaa aaaaaacaaa caaaaaaaat acaatcatgg aatcaaggtg ggatgtaagg  140640
agatgccatg tgtccactta cagtggaata ggtaactaca gatttgcact gttttacatc  140700
ttgtttaatg gttacctgtt aatagctaac ttccagtgat aagtcctctt atatggtagt  140760
tcatgtagta tttgtttgac aatatggtag ctagctaaaa tgacgacagt aacgggactc  140820
gaacccgtgt gttccacgct gacaacgtgt tgggacagcc tctgccctat actgccatta  140880
tttatgccgt agttttttta gaaaggaaag ttttttttata atatacaaca acagttgaag  140940
cgctgatgtt actacggcat aaatatattt tttatgagct tttaataact caaaacttaa  141000
tataataggg cttttactcc tgcttcatgc acactcactg cattcggtca cacacccaga  141060
gaggctgaac tatcgggagc tacccaatag cttctctctg cttttaatgt atggtctagc  141120
acggtggcta acaacgttca cctaaacatt cagcattaaa tagtattgtt ataagttctt  141180
cttatatcat atattttgta agctgactta ggctacttgt accaaggtct cttgttaaac  141240
ccatatttct atggttctcg tcaaagggag tcttttgagg tttctaaggt ctgccaagtt  141300
tctcacgctt ccacctaact tagattcttt tccacaggaa cgtctattat atcccccaag  141360
agtcttgtac cttacaatcc atgtacactc cacataacgc ttaactgata ctagctttta  141420
ctagtagtta ctcttatgtc accataagac atacctgcta cctaaaacac tatcgcactc  141480
taggctacat tcagaatcac gccacgttat cctagcaagc tgttcaaact ttctgcacta  141540
ggttctatta tattaagttt tcaattatca aaagcagttt ttctttacta tttaataata  141600
gcacaacctc tattatttg tcaactactt tttttagag agggtgcccc taattttata  141660
taggggcaag agatattaaa catagctgag ctatgtaaaa gctaatgtag gaattgaacc  141720
tacttaatgt aagcaacacc agtttagctt ataagcattg tttgcaaagt ccatgctatg  141780
cactcagtag gaatcgaacc tattgccgaa ggtaccaaac taccctgagt gctcctatag  141840
atatattata ccacataacg agatattaat tttttttggt gatatagtat atctatattt  141900
tttaaaattt tagaaatacc tttgatacat tccggttatc caacgtatga atatataaata  141960
tcatgttatt ctgattgtgt caataacttt tttacatttt tttataattg tgtaatgtcc  142020
tatttctttt tttctgattc cttatattta taatatatac tatatagtac tatatatata  142080
tattaattac tattagatat tatatataga taataagaat ctaggaaatt taaaatagga  142140
cattctaatg ctgactcagt tacaataaac ttatggtggc taccttttta caaaaatgtc  142200
ctatttcatt ttttctatct ccttatatta ttatttataa tatatagtat taagtattat  142260
atattattat atatatagta tataatataa gaaagacaaa aatttaaaat aggacatttt  142320
acttaaacaa aaaaaaagag agcagttaag ccctcttatc ttaatgagaa atagttatta  142380
attgttccca atctgacttc ctcatcttct ggtgtttcat cctctggttt cgtatacaag  142440
ctagtgattc tttctggaac atctactacg ttctcagtag ctgtctgtat ctggaatgca  142500
tttacataag ttaactcaga atctctatca gctagtttat gaactggaat cattggcaac  142560
tctgcacctt tcattgcacc atttacaatt gacattgcat cattagttgt tacaccgagt  142620
cttctaggga acacagaata tgtcccagat gctaatgaaa cctctacaac tttctctctt  142680
ttagggtaat tcatgatact tctcctttca aaatatgtta taataatact atatactata  142740
ataacacatt ttacaaatta cttaaacatg ctgaacacgt aagtgacaac tgctcctaag  142800
acaatcataa aaacgttctc tacaatatcc ctcttgtggt cgaactcttt atcgtttact  142860
ccttccagtg catctatagt ttcttccaac ttagtaatct ggtaggttag gtgtgcatat  142920
ttttcttcgt gaacagcaag tcgcttatca agactattga caatatctct caactcacta  142980
accgcactat tcagttctac attgtcctgt ttaatgccct tctcggttag ctctccatgt  143040
tggagtttat cttccagtcg ttgtagtctt aaaacaaggt catttacttg gtaatcgttc  143100
atatatgctc ctccctgtaa gttatgttgc tctatattag tcagatgtaa accacagaca  143160
gactagtata cctataatag cgcctaccgt gtagactata ggtatatagt acccattaaa  143220
aaacaagtat agactaccta tactaattcc atagagcacg aaagtgaact tgtatgatgc  143280
caaagggctc agttctgctt gtagtttctt atactgtagt gcacgagtga catagtagga  143340
catcaagtaa acaaacattt gtagtaacag tacacagacc agtgctgttt catacattat  143400
```

```
SEQ ID NO: 3            moltype = DNA  length = 143280
FEATURE                 Location/Qualifiers
misc_feature            1..143280
                        note = Bacteriophage Myoviridae Spounavirinae strain
                         phiEF14H1
source                  1..143280
                        mol_type = other DNA
                        organism = synthetic construct
SEQUENCE: 3
gttgttccct cctctccctt agagctacta ttaatatagt acactgagct gttagcaaac  60
aggtgtgcta aattaatata gagactaaaa atgtagacgg gagagtggta aaaatggata  120
atagcaaacg aattattaaa aaaattattt ttattaccat ctctgcatta gtcatggtta  180
ctttaagtaa gctgttctct aaatatgtta ttgtagaaca aaatgcccca tttcaggcat  240
tagttggcgg tgcctcatgt gcactgttat ctagtattct gtttgactgg tatactaata  300
aaaagaaaaa agagaacgta gagaatcaac ttaaagaagc aatcagtgac ttgcagaaga  360
ttaaagctat cataaaaaga tagcctatta ggaggtggga tgggtgtcta ttaccaataa  420
agacattaag gataaacgta gatatatttt tagtcaatct agtaaaacaa caactataaa  480
aagaggggac aaacgcataa gtagtgcaac aagaatatgt gcagtttgtg gaagaccgct  540
```

-continued

```
atctaagctc gtattaagaa caggcgtacc aacagtagta gtagaccata ttagctgtaa  600
gatttcagac attgttagac taaatgtctg tgaggatata aggtcttgtt atgcgtattc  660
tagtaagaaa ggggaaagct agctaatggg tatggcagat agacttaaag ataatgcaaa  720
acaaaaaaag ttagaaagaa caccagagca acaactaaga gacacattta atcaagcttc  780
aataaagctt atcaatcaat ttatggctaa cgttacatca ggtgctatag aagttgatga  840
tattgcagat ttaacaaggc tatttcagat ttatttacag gttaataata taaatgatgg  900
aatgcaagaa ggtacaggaa ctctacctgc acttacatct gagcataaag acatcatatc  960
tgaaaaggtt agcacagaaa agattattaa ggacggtgaa gaagaggagc taatttctct  1020
tgatgagtta gccagtcttc cagatgacca acttgaggaa gtcttagtta acagagagct  1080
acagatgaac agagagaacg aggcgacctt ctaatgacga caaaagcaca acatatagct  1140
aaaatggcta aagagatgta tggtacagat aaaattacaa cggagcagtt agcttatata  1200
acagatatgc tgaccccatc aacgtaccta ttgagaaatc actctgtgcg taatcaccca  1260
ataactttta ttatatcagg aagggatgca acaaaagcac aggcacatag accataaacc  1320
aacaaagctg tggtctttaa actctactaa acgggcatag taaaataata tacacgtaaa  1380
caatatactg gtaagagaga ctaaatccta gtgtataagg acagggttga cctaccgtgc  1440
taaatcagtt atactataac tgtaaaagcc taacgactaa atttctaggt agctaactaa  1500
aaggagttag tgagaactag ataaaaggca aataaactat gcaagctcaa taaaaataat  1560
aatatacagg aggtgattaa gatagctaag gacagaaaag aaattttcat agaaaagctc  1620
aaaagtgtaa aaggaactga ctttgaactt ataggtgagt ttacaaagca acgagaaaag  1680
actctatttc gtcataacgt gtgtgggcat gtttgggaaa ccactccggt tgtcctactt  1740
aactcaaaaa aaggcggagg gtgccctcat tgtcaataca gaaacaaagc aacttcacca  1800
aaagaatacg aaaaaagagt aacagacaca tttaaaggag aatacgttgt actcaatatt  1860
aatgagtata aaaacaatag tactaaactt aaattcttgc attctaaatg tggtacagaa  1920
ttttatctgc gaccagcaag tttattcatt aatgcaacta gttgtcctaa ctgctctaaa  1980
aataaccgtt gctcaactaa gagaactact aatgagttta gagagttgct tcttaaaaca  2040
aaaggatact cctatgagct aacggaagat gcagagtaca ccggagctaa caaaaaaatt  2100
aaggttaggc atacaacttg tggttatgtt tgggaggcta gagctaacca cctgctacag  2160
ggttcgggtt gtcctagatg taacgaatca aaaggagagc tattagtagc tactattctt  2220
aagctaagca acacctcttt tttgagagag cacacctttg acgattgtag aagtactaga  2280
cccttacctt ttgactttgc attaattagt aataacaaag tgcgtggttt aattgaatat  2340
gatggagaac agcacacgaa accagtaagt tgtttcggag gggaacagaa gtttaaaagt  2400
acagtaagaa atgataacac taagaatgat tattgtactc ataaaaaaat acccttactc  2460
agagtatcat acactaatag tcctgaacag attgagcacc tagttcagca gtttttaaaa  2520
agcatagatt tgttgtaacg tagagcaacc taaaccaaaa agtaggttga tgatatagtc  2580
tagtccccta ataaatatcg ggaaaccgag ggtaaccaaa tggcaaccca aagataataa  2640
atgaccaaca tagagacaag gcaataatta aatcaagaca attagggtta agattagccc  2700
ctttataaag caatttgtaa agaaaactct gttaaacggg catagctgaa taaccaataa  2760
gctgataaga gaacctaagt cctgaaaagg atagaggtaa tcccgtgcta aatcagtgca  2820
aagcactgta aatgcctaac gactaaattt ctaggtagct aaccaaatgg ggttagtgag  2880
aactagataa gaaaacctct taagaggaag taaagcagag caacctaaac caaaaattag  2940
gttgatgata tagtctagtc ccctaataaa tatcgggaaa ccgagggtat aacgtaagtg  3000
agatgggtgt tggttctatg ctacagtttg cagacacgca tagttatgat gctgttaaat  3060
gtctttatac attcccaacg aatgagcaaa tgactaaatt tgtacagaca aggttagacc  3120
ctgttttaca gaatgggtac tacagcacaa ttgtagacca agaagttaac tcattaaaag  3180
ctaaaaaaat aagaaatagt tttttgtatt ttcgttcaag ttcaaaaccg ggcgctgtgg  3240
aaggtgtcga tattgactat ctatctatgg acgagtatga ccgtgtacct gcattagcag  3300
aggcttctgc gttggaatcc atgtcttcct caccttataa gatagttaac agatggagca  3360
ctccatcagc acccgatatg ggaatacatg ggctctttaa agggtcagac caacattggt  3420
atttacataa atgtgagaaa tgtaattatt acaacgaaat gagttatgat gcatataccc  3480
cagaggctcc tgtagagagt agaggtaaca ttctttgtgt taacccaaaa ggggtcgatg  3540
ttgttgctaa aacagtagtt gacggctcat tccagtttgt ttgtcaaaag tgcggagaac  3600
cgttagacag atggtacaac ggtgtatggg tacctaaata tcctgataga acaaaaaatg  3660
gtctaggtac tagaggatat atgatttccc aaatgaacgc agtatgggta actgccgacc  3720
agttaaagac caaagaactt caatcattgt ctaaacaagc cttttataac tatactctgg  3780
gtgaataacg ccccttcaac tggaaacagt tgtcgaaaac tctgttaaac gggcaaagct  3840
gaataaccaa taagctgata agagacccta agtcctgaaa aggatagagg taatcccgtg  3900
ctaaatcagt gcaaagcatt gtaaatgcct aacgactaaa tttctaggta gctaaccaaa  3960
tggggttagt gagaactaga taagaaaacc tcttaggggg aagtaaagca gagcaaccta  4020
aaccaaaaat taggttgatg atatagtcta gtccgactgc caagagcagt aacaaaatac  4080
tacgaaagta gcggtagctc gtatccttac gcagacttga aattaactgt taacgactct  4140
gacgttgata gccataagag aaactattta atagaacctg ctaaagacag aggtgattat  4200
aaatttatat ctgttggtat tgactggggt aacagacatt gggtatctat acatggtgtt  4260
aaaacaaatg gtacggtaga tttgataaaa cttttttctg taggtaagtc caacccgcta  4320
gaccctaatg caatagatgt agacatacag tctataaaat tacagctagc tccttacaat  4380
ccagatataa tcgtagctga cgtaggagac tcaggggata aagttgctaa acttatgcaa  4440
atttatggaa aagaacgagt ttttgggtgc gtttacccat caacccctaa atctacaggt  4500
aacttagtac ctacttggag cccacaagca aataaagtat ccgctgacaa gttaatgcag  4560
aataaacgtt acattaacaa gatgaaagaa ggagaaatag gttactactc aaaaccagat  4620
acagagctta atttatataa agagcactgg aagaatgttg ttatacgtga tattgaggac  4680
gaaaagacat cgacaggttt tagacaaatt atcggcagaa aaggtgatga ccactactca  4740
caagcaagcg tttattccat gttagggtat gagtacctaa tgaatgtatt tacaggagta  4800
aaagagtatg gatttgactc tgattgggtg tcaactcaat tagcacctac gaaacctgat  4860
atatttacag aatttgtata ggtagattgc cttatttagt tttagtcaag ctgaataagg  4920
cattttgtat tgtttgatat atatttttgt ggtataataa atatagttag ggggatagtt  4980
atggtagaca acaatgtaaa aataagtaaa agtacaattg aaggactaat aaataagtct  5040
ttaagttatg agtacgttat aaaaaataac gaattgctga caaacgaata tcaacatatt  5100
gtaaaagcgt atgggtttga caatttttat gacatgtatc tatatgcaga tagctgtgat  5160
tctaaagata tgtatttagt aaaaggtggt caaaaagact tgtctaagct gaaacccgtt  5220
aaaagaaaag ttgttagaaa tggtaaaact atgactacaa ctatttatga agatacaggc  5280
```

```
agttcagaca gtaataacag taacccttta gacaaagaga gtaaaaagaa aaaagagtta  5340
gaaccagtta atgctaagga actacgtaag gtcagcttag gtagtgatga agaagagaag  5400
ttagacccta aaaagatagc aaaattgcta gcagacacta aaaaatttgg aaataatttt  5460
gatacgcagt gtactgatta tcttattctt gaacaagact ctgttacacg aggagtggta  5520
gggtttacta gagaaggttc ttatttaaaa atgtcttttct caatgtcaga tgaggctgtt  5580
gaaggtatga agatgttagc tttttcacag ctcacattaa aggcttggaa attgggtcta  5640
ggggctaaga taagcacaga taatgcacct gatgtagagg aactaattag cttatatgga  5700
tacaaaagaa ataatacaga gtatattgtg tcaatgagct cactgcgtag tcttctaggg  5760
gagccttagt cataagtgct acgttagtca ttatactagt attttcaact attatttttt  5820
taatttttaa tttactagta agtaaggtag ttaaagaatt ttataactta aagatgctag  5880
caaaagaggg actaacagat aaagtaacag atataacaaa tgatataatg catatattga  5940
aaggagaaat aaataatatg gaattaatta tgaataataa gaaactagat gaattaacta  6000
ataaggtagc cactgatgag gactacgata tttttgtaga gaagatgggt aagctagtta  6060
aagatttgta tgagaactac cagtttttac aacaaaaccc accagaagga gactacacat  6120
caggttattt tttagggttc caagtaatca gagcagaata cccagttgag tatgagaatt  6180
tatttagatt agctgtagat aaaaatttaa atgaactaga gataaacaag agatttgtcg  6240
aagctgttaa ggatggtaaa gttttaccac taggtgaggc tatcattgat gaattacaaa  6300
cagggtgtag ctctatacta caggcacaag aagtacgtgt aaatattgta tttggtacaa  6360
aagaatatat ggctaagcaa gaagaagagc gtaaagaacg tcaagctaag ttagaagaag  6420
aacgagaaag agctatggaa gtactaaaaa caaaagatga cgtgcttaac acattaagag  6480
taactgaggc tttggctaat gaattaacag atgaagtcgc agaaaaatat gatttaatgg  6540
agctagttaa cagtatgaga gaggggctga aagctcataa tggaaattaa aaattctttg  6600
gggaaagctc ttataaaaaa tttaagattg cttaaagaaa aaagagatgc aatgcccgat  6660
aacttagaat atacaagtca agttatgatt cctgtgccct actatctaat aaaaaaaggg  6720
gataatgcag tagaatcatt ccttatgtgt gcggggatga taaataggga taaagattta  6780
ggtctgccta tttctttaga gaaaggtaag caacaagtta agcttaacaa tggagaactg  6840
acaactattg tagaatgtgt tgctacttac tcagataaaa ctgatattga cggtgtagag  6900
agattcttag ttgaacatct ataaaaatta aattaacgag ttctattttg tgctatatta  6960
gatatgcatg aaatagaact cgtttctttt tttatgacta actaaggagg tttaatagat  7020
ggcaggagaa gtatttagta gcttgattac aagcgtaaat cctaacccaa tgaacgcagg  7080
tagccgtaat ggtatctcta ttgaccgtat tattctacat cataatgcaa caacaaataa  7140
agatgttgct atgaacacgt ggctattagg tggtggtgca ggtacgtctg cgcactatga  7200
agtcacacca acagaaatta tagggtgtgt tggtgagcag tattcagcat tccatgccgg  7260
aggcacaggt ggtatagatg tccctaagat tgctaaccct aatcaacgct caatcggtat  7320
cgaaaatgta aactcgtcag gagcacctaa ctgggatgta gaccctagaa caattacaaa  7380
ttgtgcccgt ttagtggcag atatttgtaa acgttatggt attccatgtg accgacaaca  7440
cgtgttagga cataacgaag taactgcaac agcatgtccc ggaggtatgg atgtagacga  7500
agttgtacgt caagctcaac aatttatggt agggggctct aacaacgcag ttaaaccaga  7560
gccaagtaaa cctacaccaa gcaaaccaag taacaataaa aataaagaag gagtggcaac  7620
tatgtattgt ttatacgaaa gacctattaa ctcaaaaaca ggagtgttag agtggaatgg  7680
tgatgcatgg acagttatgt tttgtaatgg agtaaattgt cgtagagtat cccacccaga  7740
tgaaatgaaa gtaattgagg atatttacag aaaaaacaac ggaaaagaca tcccgttcta  7800
cagccaaaaa gagtggaata aaaatgcacc atggtataac agattagaga cagtatgtcc  7860
agtaataggt attactaaaa aatcttaata ctagatttaa gaccatctta gggtggtctt  7920
ttttctttct ttgtaatatt cgtaataata tgtaatggct atgtaaccgc ttgttatttt  7980
ggctgtaaca attacatgtt atattagttc ttgtaagcaa cacaaataaa gaaaacattg  8040
aggagaattt tattttgaag aaaactagta ttttaggttt aagtttatta agtttaggtt  8100
tagtagtagg tttaggaacc gaagctaagg cagaagaagt aacagagaat ggtaagacat  8160
attggaaggt agagtcagga gacacactat cagaaattgg agctaagtac aacttagatt  8220
tcactaatat ccacaaagtt aataaaggtg ttgtagctga ccctaatgtt attttcgtag  8280
gtgacaaatt gttattacct ttagatgaaa atggcaagct agtggaacaa gtgaatacca  8340
ctgaaccaga tattgaagta caatataacg aaccagtaac acctgaacaa cctgtagttg  8400
tagaacaaga agttgtagag caacctgtag ttgtagcaga agcccctgcc cctgtagtag  8460
aggtacctgc tgacagtagc tcagcaaaag agtggattgc acaacgtgaa tctagtggtt  8520
cttatgatgc aacaaatggt cagtatattg gtcgttacca actatctgcc tcttatttaa  8580
atggtgacta ttcacctgcc aaccaagaac gagtagctga tgagtatgta gcaggtcgct  8640
atggctcatg ggagaacgca aaatctttct ggttagcaaa tggttggtac taaaattaaa  8700
tagcaataaa gacctcttta ttaaggggtc ttttttttat gctatattaa tatatagtaa  8760
atagtaatat aaaatggtta tgattagtta tgtggtataa tagacttatg ttaaaaccat  8820
ttaaggaggg gaaacatggg ttatattcaa gatgagacat ggcagatggt taaaaaagtt  8880
gctaaaaaga atgggtttgt tggtgactgg attttaatta tccactcata ctatgagtat  8940
ggtggaaatc acgtccagat acatacaaca ataaacggag aaagctatag aattttaaga  9000
ttgttagata gcagagagat acttttatta gatagaaaag gtaaccctgt aatttatgac  9060
tatgaaacag ttaacgatgg tcaaaaaagc ttcttttata atgatatgga agagaaagaa  9120
atcgaaatac ctaatggaag atgcttaaac gataagacaa ggataaaaat ttatgtataa  9180
ggtaggtgta acagttgcca aaatggttag ataaagcact gggtatagaa aaatcgtcca  9240
tagaagaaac taggaatatg gaaaattata agatgcattt aagggaaata gacaccaatg  9300
tggtcaataa cgagccgtac agtatggaaa gtattgaaaa aggtatgaat ggtaagacca  9360
ctgcatatat gcaaccaatt attggagaga tgtcagtaaa ccccgggtat aaaactaaac  9420
cgtctatacg taactctcag gacttacata agacacttaa aaagtttggt aataacataa  9480
tattaaatgc tattattaat acacggtcaa accaagtatc gatgtattgt aagcccgcaa  9540
gaaattctga gacaggtgtt ggttacgaga tacgtttaaa agatattgaa gcagaaccta  9600
cttcacatga cattgctaat attaagcgta ttgaaagttt tttagaaaac acagcacaat  9660
ttagagaccc taatagagat aattttacaa ctttttgtaa aaaacttgtt cgggcaacat  9720
acatgtatga ccaagtaaac tttgaaaagg tatttgataa agatggtaac tttatcaaat  9780
ttgatactgt agacccaact acaattttct tagcaacaaa tggtgaaggg aaactaatta  9840
aaaacggtga aagatttgtt caggttgttg ataacagaat tgttgctaaa tttaatgaga  9900
gagaactagc attcgcagta cgtaacccaa gagcagacat cgaagtaggt cagtatggtt  9960
acccagagtt agaaattgcg ttgaagcagt ttattgccca tgaaaataca gaggtattta  10020
```

-continued

```
acgatagatt cttctcacat ggaggaacta ccagaggtat cttacatgta aaaacagggc  10080
aacagcagtc tcaacaagca ctagacattt tccgtagaga gtggagaagc tcactagcag  10140
ggataaatgg ctcatggcaa atacctgtag tttcagcaga agatgtcaaa ttcgtcaata  10200
tgacaccctc tgccaatgat atgcaatttg aaaaatggct taactactta attaatgtta  10260
tatctgcttt gtatggaatt gaccccgcag agataaactt ccctaacaat ggtggtgcaa  10320
caggctctaa aggaggctcc ctaaatgagg gaaactcaaa agagaaaatg caagcttctc  10380
agaataaagg gctacaaccc cttttaagat ttatagagga caccgttaac acatatattg  10440
ttgcggaatt tggagaaaaa taccaattcc aatttagagg gggagaccta agtgctcaac  10500
tagataagct taaaataatt gagcaagaag gtaaagtatt cagaacagtt aacgagataa  10560
gacatgataa aggtttagaa ccgattaaag gcggagacgt tatactaaat ggtgttcaca  10620
tacaagctat tgggcaagcg ttacaagaag aacagctaga ataccaaaga agccaagacc  10680
gcttaaacag actattagag ctatctggtg gagatgtaga acaaccagaa ccagaagagc  10740
ctaaagacag tcaaaatgat acagatgttt catttcagga tgaacaacaa ggtttaaacg  10800
gtaagtctaa gaaagttaat ggtaaggtag acgacaatgt tggcaaggac ggtcagttaa  10860
aatcggaaga aaacaccaac tcaactaagc atggtactga tggtataaaa aaagaataaa  10920
agataatgga gggggctagc tccccctcaa ctttgtttgt gttactagat agtacatgtt  10980
ctgctatatt aaatacagta aaacgtttag gtggtgaaaa gcaaattgtc agaagttaga  11040
gaaaaatata gtattttcgt accactggat attgaaaatt ctatacagaa gtctgaatct  11100
gtgaatgatg gtgaatggta tgttcaagga tatgcaacta ccccagattt agatttacaa  11160
ggagatatta ttttaccaca gggcattgat atttcttatt ttattgaaaa tggttggata  11220
aactatgagc ataaaaatga tgctgagttt attataggtg ccccaactag caattgttat  11280
gttgatgtgg acaaagggtt attcgtagag gctaagctat taaaggataa caagtacgca  11340
cagtctatgt ggaagctagc taatacaatc cagaaatcag gaatatctcg tcagttaggt  11400
ttttctattg agggtgcagt agttagtaga aatgcacaag ataacagaat catagaaggt  11460
gttaaaatac ataatgttgc attaacgaca catccggcta acccaagagc tacatgggag  11520
acactagtta aatcttggac tacaggatat ggcacagcac cagatgcaca agtagatgca  11580
ggcgcactta gaagagagat gtttaaagag gacatttcta atttgacgta tgcagtaaga  11640
actattgcag gactatataa taaaaaacct gcagagaaag agtttatttt acgtgaagtg  11700
gctaaggata tagaagtaga cacttccgaa aatgaattat ctaaatttat gttacaatta  11760
agtagaggga tttccttgaa agaagcaaca aactttattg aaaaaagaaa ggggtaagaa  11820
atagtggcta aaacattaaa cgatattata gaagattttg atgcacagtt aaatgaaaaa  11880
gtaaaaccta ctacagatga ggaaattaca aagtctgtag aagaacctac tgaaccagaa  11940
aaagttgaag aaggtgctga ggttgagccg gaagaaaagc ctaatgaatc tgaggagact  12000
acaggcaatg acggagaaga atccggagtt actgaaacag ttgaagcaga acaggaagaa  12060
ccagaaactg ttgaagaagt agcagttgag gaacctgttg aggaacctgt tgaagaatca  12120
gcggaaactg ttgaaaaatc tgataaaact aaagaaaata aagatgaaga agaggaggaa  12180
gacgaagaca aaaagaaaga aaaagacaaa aaagacaaag ataaagaaga caaagaagac  12240
atcgagaagt ctaccgaagt cgaacaagtt atcaaatctt ctgaaatctt aggagctatg  12300
gaagctatct ttaaaaatat gttaggtcta agtgaaaagt tagacgaaat tcatagagag  12360
tttaaagaag ctaaagaagc taaagaaaaa gacgaagcgg agtctgttga gaaatcttta  12420
cttgataacc ctgaaattaa aacaggaaaa gaggactcag aaggcaaggc tgttgggttt  12480
gttaataagt ctgtagcagt tgaggaagag gtggctaccg aagaaccaac tgtagaagta  12540
gttgttgatg gtgaacaaga cacagcagaa cctgaaaaag aagtaccgtt ccgtgataga  12600
gtacaggcta ttagaccaga ctttatggaa acatataaac gtgtgtctgt tagcggagta  12660
gctcaacgtg gtgaattaga atcagttaga cacacttggg gaactgctag aacaaatgat  12720
gacctagcta aaattgaagg gtttattaat aaatataaat aaatttacta tatagtgaac  12780
gatttttaat tgtactgcta tattaatagc agaaacaata aaagacctga cattccctcc  12840
tgaacctcca cagggtcagg tcttatattg agaggaatat aaagaaaggt gatttataca  12900
taatgacaga gaaaaagaat acagaacgac aattaacttc cgtacaggaa gaagtaatta  12960
aaggcttcac tacaggatat ggtattacac cagaatctca aactgatgcc gccgctttaa  13020
gacgagagtt tttagacgac caaatcacaa tgctaacttg ggcagacgga gacttatcat  13080
tttaccgtga catcactaaa cgtccggcaa cttcaactgt agctaaatat gacgtatatc  13140
tagcacatgg acgtgtaggt catactcgtt ttactcgtga aatcggtgta gcaccaattt  13200
cagaccctaa cttacgtcaa aaaacagtta acatgaaata cgtttctgat actaaaaata  13260
tgagtatcgc aacaggttta gttaacaaca ttgaagaccc aatgcgtatc ttgacagacg  13320
atgctatctc agttgttgct aaaacaattg aatgggcttc tttctacggt gactctgact  13380
tatcagaaaa cccagatgca ggttcaggtt tagagttcga tggtttagct aaactaattg  13440
acaaacacaa tgtactagat gctaaaggtg ctagcttaac agaggcttta cttaaccaag  13500
catcagtatt agttggtaaa ggttatggta caccaacaga tgcttatatg cctatcggtg  13560
ttcaagcaga cttcgttaac caacaattag accgccaagt tcaagtaatt agcgacaacg  13620
gtcaaaacgc tacaatggga ttcaacgtta aaggttttaa ctctgcacgt ggtttcattc  13680
gtttacatgg ttcaactgta atggaattag aacaaatttt agatgaaaat agaatgcaac  13740
ttcctaatgc tcctcaaaaa gcaactgtta aagctacttt agaagcagga acaaaaggta  13800
aattccgtga tgaagattta acaatcgaca cagaatacaa agttgtagta gtatctgacg  13860
atgcagaatc tgcaccatct gatgttgcat ctgtagtaat tgacgacaag aaaaaacaag  13920
ttaaattaga aatcactatt aataacatgt atcaagctcg tccacaatat gttgcaattt  13980
accgtaaagg tttggaaaca ggattgttct accaaatcgc tagagtacct gcaagtaaag  14040
cagttgaagg agttatcaca tttatcgatg tgaacgatga aattcctgaa acagcggacg  14100
tattcgttgg agaattaact ccatcagtag ttcacttgtt cgagttacta ccaatgatgc  14160
gcttaccatt agcacaagtt aatgcttctg tgacattcgc agtattatgg tatggagctt  14220
tagcattacg tgcacctaag aaatgggctc gcattaagaa cgttaaatat atcgcaacag  14280
gtaacgtgtt taactaacgc taatctttaa aagactaagc aaaattgaat aaaaatggaa  14340
taggggacgg ttaatactgt tccctatttt tattataaaa tacatgtatg gaggaaataa  14400
tatgttaaaa tcagaaatct taataaataa aacagtaaca acagcttttg gtgaggcaac  14460
atttgaccat aatggggaaa ccacagacct aacagtagaa cagcaagaac atttagggac  14520
taaagttcca tatatacaat atataccaga tgcacctaaa gctaaagaaa aagaagctac  14580
tgcagaaaaa gcagacgagg cacctaaaaa ggctaagaaa gcgcctgcta agaaaactac  14640
aaaatctaaa aaagaggaag actaaggagg tatttatatg tacccagact acggatacga  14700
ggaacaaggg gacaatacat accaatacca accatatgca catgggaacc ctaagcatat  14760
```

```
agatttagac aaaattgatg atatacagcc tgctgattat ggttggacac ctgctacgct  14820
gaaacaatac atgtttggtg tagaagttgt taaccctgaa acaggggagc ctttaggaga  14880
tactttctat gaacatatca tagattcagc aatagctaaa gcagagaaac gactagatat  14940
tgctattatg cctagactta taagaggaga acaccatgat taccaccaat cagatttcaa  15000
ctcttacatg tatactcatg tgtttaaaag acctattatt caagcagaaa agcttcaatt  15060
agaagttaat ggtagagggc tatacagata cccgtctaat tggtggaaag tgtatgcact  15120
agcaggtcat atacaaatgt acccaacatc cctcatgcag actggaacac agtttggtta  15180
tgaaatgacg ttctcagggt acccacaatt agcaggaatg cctccatcag gaggacaagt  15240
tgatgctcct caaatgattc atattgacta tgtggcagga atgctaccta ggaaaaatag  15300
aggatacaat gaagactggg agtgccctgc ggacttagaa cagcttgtaa taaaatatgc  15360
gttaaaagag atattccaac aatggggtag acttataatt ggtgcaggta ttgctagtaa  15420
gtcactaaca gtagatggta ttagtgaaag tatacaaaca acacagtctg ctatgtatgg  15480
tggagcttct gcagatattc gacaaattga cgaagacata caagaattag aaaaatcatt  15540
ggtatcttac tttggaatga acttaggtat tatttaaaaa aggggggttaa caaatgggtg  15600
aaaaaccaat tagatttggt ggagcaggtg aaacaggtaa ccctaacaag caattaaata  15660
ctagtagggt tgaatttgaa acaaaaggta tggctagctt cattgaaaat agaggtattg  15720
acgttttgtg ggaaagagca tggctatgta catgccgtaa cccaatgacc ctctcaccta  15780
agtcggattg ccccatctgt aggggaagag ggattgctta ccaacctgca gtaaaattaa  15840
gaatggctat acagagtcaa gagaaaggta tctctaatca agatttagga ctactagaca  15900
caggaaccgc tattggaacg actgagctag attctaagat aacctttagg gacagaataa  15960
cagtccccga agttaaaata tatcaaagct ttatttttaa tgtaaataaa agaagagtag  16020
ctaatggact atttttaagc tatgatgtga acagtataga agatatttat ggtaaagacg  16080
gacgtatctt agttgatgga gtcgatttta gaatggacta tgacacaaat actatttatc  16140
caaatgaatc tttaatagat actaatatat ccataaatat gtctgttaca cttagatata  16200
ttgttataga cctgttaaaa gaaagtagat accagtatac cacattcggt gttaaacaaa  16260
cacaatttga atcactacct aaaaagctct tattgaagcg tgaggacgtg tttattgata  16320
gtgaaccatt ttcattagac atagatacag caagccgtat ggaagagcta gagggcaaaa  16380
aagatacaag tgaagctatg gtagacccta agcgtaaagc tacaaaatca ggaggcttct  16440
ttggaggtaa gttaaatggc tagaaaagga cagagacccg tattatttac tgattcaaaa  16500
gcaatacttg gcaatctgac tcgtgcagtg gttgatgaag tactaagtga tgcgcaagat  16560
gttgctctac gtaatgggtc ttctgtacag agaatgccta gctatttgat agtaacagag  16620
tctaggatgg caaaaaatgg ggttatagat ttgaaacctt tctttgcacg ttctaataaa  16680
aagaaatata ataaaaaagg ggaatggtac ctatacatcc ctattagtat gaaaacacgc  16740
aacatgtcaa gacgattata cgatgagctg agagcagttc cagtaggcac aaaacctgta  16800
actgttaaaa tggactatct gtatgataga cggaagcaga gcccatcagt gtctagtatt  16860
aactataaac ctaaatctac taatgtaact gttataccac agagttgggg taaaggtaca  16920
cgtaacacct atgtagcttt ccgtacagtt aacgctaatt ctcctgcgaa tagttggata  16980
ataaatcgta gaaacgttaa tgatgatgat atgagtaaga caatgctaag aaacatagac  17040
aggctcatga agtggaaact aaagaattta ggaggatagt gtatgatacc aagtttagac  17100
acttacttgt ataaagaatt tgaagaaagg ctaaggataa ttctatcaga gtgctatatt  17160
atagacgaag ctttaaaggg aatggacaaa gaagctttag aatcttttaa aaacacttat  17220
tgctctatag atggtaagcc acctaagaga gaagtagaga tgtcctattc attcccacaa  17280
gaacatctgg attcatttgc tcgatttgta gtaactctcg gtagtagcga agaagatagc  17340
aagtctattg gaggaatcca aggaggctac gagtatcgag aaggtaatgt aattagtgag  17400
gaagccacta ttattagaga aggtgacaag ctgattataa atacatcaaa accagtagcg  17460
gactatctaa acagctcaga cataagtttt gcagaaagcg accattttag gattgaagat  17520
aataaacctg tatttgattt ttcatacaat gaggagttag aaggtatatc cattaatgtg  17580
tcgtatataa gcaaaatatc agatgatgat gttgcaggtg tatacaaagg ataccaatct  17640
aacgataatg ttagtataat tggaataagt tctaatatag atactgctag gtgtttagat  17700
gcaattgcta gaattatact aatcaccatg agagacagtt tagatgaaaa aacagggtat  17760
atgttgcaaa cactacattt tggtgatatg caagttgtca tagaatcagg tgaaacactt  17820
gtgtttggta gaccttgtac tgtaaactac agagttacta attctattgg atttgattta  17880
caacaaagaa tcacagagat tattacaaaa aggaggatga aatcctagtg gctaaagaaa  17940
cagagaaagt agtaaaaaaa gaagttaaaa aggagcaacc taaaaaacct aaaggttatg  18000
tccatgtcga tacattttta gattatgcaa aagtattata tggactaaat aaatatcagg  18060
tagcgggttt cagagcacta atggcaggta gagaatacca acacgaggat gctgattttg  18120
ttccattttt agaaaagtat ataggaaagg aagttaaata ataaatggct gtagaacaat  18180
tcccaagaaa aaaagtatca cgtccacata ctgagattac cgtagacaca agcggtattg  18240
gtgggtcatc aagtagctct gacaaaacat taatgttagt tggctctgct aaaggcggta  18300
aaccagatac tgtttatcgt ttccgtaatt atcaacaagc taaacaagta ctacgtagtg  18360
gagatttgct agatgctatc gagttagcat ggaatgcatc tgacgttaat accgcatcag  18420
caggagacat tttagcagtt cgtgttgaag atgctaaaaa cgcaactctt acaaaaggtg  18480
gtttaacatt tgcttcaaca atttatgggg tagatgcaaa tgaaattcaa gtagcattag  18540
aagacaacaa tttaacacac acaaaaagat taactgttgc attttctaaa gatggttata  18600
agaaagtttt cgataactta ggtaaaattt tctctatcca atataaaggt agtgaagctc  18660
aagccaactt tacaattgca caagatagca ttagtaagaa agcaacaaca ttaactttaa  18720
atgtaggttc tgaaccagaa agtacgacag aagtaatgaa atatgagtta ggtcaagggg  18780
tttactctga gacaaatgtt ttagttagtg caatcaatag tttaccagat tgggaggcta  18840
aattcttccc tataggtgac aaaaacttac ctactgatgc tttagaggca gtaaccaaag  18900
tagatgttaa gacagaggct gtattcgtag gagctttagc aggagatatt gctaaacagc  18960
tagaatacaa tgactatgta actgtagctg tagatgctac aaaacctgta gaagactttg  19020
aattaacaaa cctaacaggt ggttctgacg gaactgctcc tgagtcttgg gctaataaat  19080
tcccattact agctaatgaa ggtggttact acttagtacc attaacagat aaacaagcag  19140
ttcactctga ggctttagct tttgttaaag accgtacaga caatggtgac ccaatgcgta  19200
ttatcgttgg tggaggcact aatgaaacag tagaggaaag cattactcgt gcaacaaact  19260
tacgtgaccc tagagcttct ttagtaggct tctctggaac tcgtaaaatg gatgacggac  19320
gtttgcttaa attaccgggt tacatgatgg cttcacaaat tgcaggtatt gcaagtggtt  19380
tagaagttgg tgaagcaatc actttcaaac acttcaacgt aacatctgta gaccgtgtat  19440
ttgaaagtag ccagttagac atgttaaacg aaagtggagt aatctctatc gagtttgtac  19500
```

-continued

```
gtaaccgtac tttaactgca ttccgtgtag tacaagacgt aactacttac aatgacaaat  19560
ctgacccagt taaaaatgaa atgtctgttg gtgaagcaaa cgacttctta gtttcagaat  19620
tgaaaattga actagataac aacttcatcg gaactaaagt gattgacaca agcgcaagct  19680
taatcaaaaa ctttatccaa tcattcttag ataacaaaaa acgtgctcgt gaaatccaag  19740
attacacacc ggaagaagta caagttgtct tagaaggtga cgtggcatca atcagtatga  19800
ctgtaatgcc tatccgtagc ttgaataaga ttaccgttca gttagtatac aaacaacaaa  19860
tcttaacagc atagagtgta ggggcagttg cccctcctct tacataatga ataaaatata  19920
ggagtgatat atacatggct agtgttggaa atcaaacagt ccacacaggt aacacagttt  19980
acctaatgat tggtaataaa attatcggtc gtgcgcaatc tgcatcaggt gagcgccaat  20040
acggtacaca aggtatctat gaaatcggta gtattatgcc acaagaacac gtatacttga  20100
aatatgaagg tacaattact ttagaacgta tgcgtatgaa aaaagaagac ttagcaagtt  20160
taggaattac agcgttaggt gaagacatct tacaacgtga cattattgac atcgtaatga  20220
tggataattt aactaaagaa atcgtagtag cttatcgtgg ttgctctgca atttcttact  20280
cagagtcatt cacagctaac gaagttacat cagaaagtac gcagtgagat tataaataca  20340
aaatttatat agctgtgcta gttcgtaaag agctagtatc gagagttaat tgctttgaat  20400
ccctaaagct caacgaccca aacagtaact ggaaacggta agctgagagg tgcgaaagca  20460
gaaaaaatag ttgagatggt ataaggttaa atcctaagta ctgatacaat gggtctttag  20520
cagggacagc cctaagtcaa ttgatacggg acaccttcaa cgactatcct ctgacggagg  20580
agtaaagcca caagccaatg gtggaagaaa aattctctac cctaacaagg gtacccatat  20640
agtctgagct aacatgaaag tgttagaggc aaacgcctac ttggaagttg cgttccaagg  20700
taacaaaact gttcacatac ctaacttctg caaaggttaa atagcagacg aactccaccc  20760
agcttgactg ggtggttctt ttacggtaca atacttttat tattgttaga tatttaggag  20820
atacaacatg agaaaaaaat ggacattaca agaaagaaat attcttataa aaaaatgggc  20880
ggagactaac aacgtaaatc tcttaccaga aacagcaacc tttacaggaa ataagagcac  20940
tatatactac gtatggtcag atggggagct tcaaggctta ataggtaaaa cgaactttga  21000
cagtataata tctggaagta aacctacagt taacggtctg acagaagaga gcaaaaatat  21060
tagggctaaa aaacgctttt tggaatatgg gctcgaatta ctagaggagt atcaaggatt  21120
caatacacca cataaggtga gagtgttgga tggagtatac gcagggtatt atggaaaaac  21180
ctcattagcc acagtcaatc aaaaaagtac cagaggtaaa atagcgcagt taaacataac  21240
tattcttaca gaaagtgaga aaagacgata tttcagagaa tatgcagagt ctcggggata  21300
cacaattatt aactaccctg aaaaattagc tgttcgaggt aagtgtactt tgttatctcc  21360
ccaaggtaat gagtgggaga cagtctggta ccattttgct tatcaggaga actgcaattg  21420
tccgttagat gttaaacgta gtattgggga gcgcatggtt agaagtttgc ttaaagagaa  21480
tggtattaac tttgaagaac agaaaaagat agttattgat ggtagaacat tattttttga  21540
tttttactta cctgatgaca atacctatat tgaatataat gggaaacagc actatgaaga  21600
caccggaggt tactataagg gtaaacttca agatttacag gaacgtgaca aactaaagga  21660
gcagtggtgt aatcaagcag gtgttaatct tgttgttatc ccatacactg caaatagcat  21720
aaacgaagta gctaatgttt tatccgagat agtaccaatt aaaaagagac tagtttcagt  21780
tgtttattct gatagtatac ctaatgagga tattattgat tactataaaa cacatacagg  21840
taaggaaact tgtaggaaat atgatttaac acaacgtaga ctgagcttac tttgtaacag  21900
agtcggcttt aataaaagga ggtacctaaa gtgaaatatc catatttagt agaattgtat  21960
gcaaaacatg taattagaga tgcagggtac atagaaaatg taccaccagt tatttatgaa  22020
gacgttgtga aacgtgttga agaaataaaa agagaagaaa acttaacaat agattaacta  22080
gtataagttt aaatagacct aattcagata taggtctatt ttttttgcca ctataaatac  22140
aaataactag atagtgtggt ataataaaga tagtgctata ttaatttatg agtaaactag  22200
gaggaaataa taatgacaga aaataatgaa aaggtattta cacctacacc aaatttatca  22260
cgtgagcaat taatagaaaa gttgcaacgt ggagaaaact tgacggatga agaagtaaat  22320
attttgaaat attacaatga tgcagaagaa cgtaaacagt tagatagaat tatcccgggt  22380
gttaatgatg tattttctaa gcattacaac ttaaaagaat atggtttaga atttgatatt  22440
aaaataaaag cacctaatat tatcgaaaat ggtaaaattc aggcaagaag agaagcctat  22500
ttagaaggca tgggaatggc agttagcaac tttattttcc aaagttacca aatgttagca  22560
actattcgag tatgtggagt agaggtacca aaagtattag ctgatgatga aaaaatttat  22620
aatttatatg tattaggagt aattgcaaag gactatggtg aatggctaaa ctcctttcga  22680
tactagagtt aaagaactag gcggaataaa agcccttgtt agaaatagct atagtagaaa  22740
tctatgggca ataatgaaaa aatttaaggt actaccgagt gaccctgcgt ggcaaaatct  22800
cacaagtgac caagtagagt ggattttata taacatggaa agagacatag aagaacaaga  22860
acgactagct aagggaatgc agttagaaag tgagttccaa gactatgacg attcatggta  22920
tgataaacca catgatgagt tctctccaat tcgtgaaggt gacgatgagg aagaaattgc  22980
tcgtaaactt agtgaaatca caagtgagga agacatggct aaacttaaag ctcgttggga  23040
ggcaagccaa gaagttgatg ctatccgtgc agaaggtgga acaacaattg aagaagatac  23100
gattaacgaa cttattgcta acaatgttaa aaaagcaatg gaagaggcta gacgtattga  23160
gaaacatggt ggaaacaaat ggcaagagaa atcatcaatt gagttagaag aggaacgtaa  23220
gaacctagag tttaactcac agttgaaaca aggagatatt caggaggcta tcgatttgtt  23280
taacaaagat gtcgagccaa catcattaga tgacgaattt caaatttaag ggtagggtat  23340
tccctgccct ttacttgtaa aggaagtgtg gaaatgagca acaattatcg tttttatgtt  23400
gaggcaatga ctggggatgc tgttgcaaaa cttaatgaaa tagacaagtt aatggataaa  23460
attgattcaa agagtgcaaa gggcacccag aattttttcc atacaagtca gaaagacatt  23520
gataaagctg ttgaggaaat gcaaaagctt atcaaggcaa aaaaagaact agatagagct  23580
tttgataatc agaagataaa tgcagaaagc atgggagaca tgacagcata taaacgtgct  23640
gtatcggatg cagaagaact aactagaaga tttaacaagg cacaaaaaga atttcaaaat  23700
catgctagaa tgcaagctaa ccctaattac ataaatgcta gtacactaag gcaacaaaag  23760
gcatttcgtg atgagttaac agaacaagag agagcaataa gaaatatctc tagggcacaa  23820
caggaactaa acagagtgaa ctctagggtt aaccatcgtg caaaccaagc aagcgcaaca  23880
ggaagaatga cttacaatca gtcagagagt atgaagcgtg accttagacg tactggtgta  23940
tttgaaagcc taggttcaga aaataaaagc agacagcaag agctacgaga acgatataaa  24000
cagagacaag aagagctagc agagactaga agtaatacaa atttagatag acaagttcgt  24060
aagaataggg aaactagtat tcaggctgag ataaaagaaa ttgagaaaga aattgaagct  24120
agaaaacgcc tagcagactc tattaaagag actgtagaga acttaaaatc taaggaagct  24180
tcactaaatg catctgacat aaaagtagat gctgatagaa agagtgctcg tggtgttcta  24240
```

```
gctgagcgtg caccttctat atcaatggct atgctaggag gtaccgccgc cgccataggt  24300
ggtttatacg caaaaggagc aactgctaac gcaggtatgc gtgatgcatc tatatcttta  24360
ggacaacgta caggtactag tgacttccgt gcattaagaa aaagtatgca agaaatgggt  24420
attgagaaac agttaggcta taaaggtgct gacatgttac aattccaaga agatgcattg  24480
agtaatattg gttttacaag taaagaggac ttagcaggga gtacaagagc cttagcagag  24540
ggctcaagag cagttccagt agacaatgag actttaagtg acttcatgaa tagtcaaatg  24600
aagagcgggg ctattagtgg tagagaccaa attaagaata ttcaagaagg tttcttaggt  24660
gctatccaac gctcagggat ggcaggtcgt gagaaagaac agctagaagc tcttaaaaca  24720
ttaagtgagc aaagctttac tggtcgtaac ggaagtaatc aagagcttaa agaacaaatg  24780
gcaatgttaa caatgctaaa ccaaacaggt aagcgtgctg ttcaaggtga gcaaggggca  24840
cagttaatgt caagtttatc tgcaggtatt caaggtagtg tatggaacaa taaggcatct  24900
ttacttttag gtaaagggac acaattccaa gggctagcag gaatgtacga cttaaaagct  24960
atgcaagaac aaggagcaac accagagaac ttacagaaaa ttattggcag tgtccaacaa  25020
tcagttcccg gtgacgaaaa gtctcagaag tatgctttcg gtagtgcttt acacgaacta  25080
ttcggtacag atgctaagaa tgaccaaata gatgcaattt gggaggctta tgccaacggt  25140
ggtttaagtc aggataacgt agacagaata atgaatgaaa gccaatctac aggaaaaggc  25200
aaatacgata agaacataga agactatgca aactctaaag aaggaaccgc taaccgttca  25260
gaagctgtta cagagaaaca agcttcacag attaatgata tgggggacat cttaagagaa  25320
actaactcta aattaggagc acttcctcct gcgttatatg cgttaggagc aggcttagga  25380
gctatggctg tttcactagc cacatcaggc tctattggtg gtttatctag tttaatcaaa  25440
aaaggaactc gttctacttt tagtacaggt ggaggggtaa ctgcaggggg cggatttta  25500
aaatcagcta aagaagcatt ctctgcaggt aaaggctctg gcggatggtt ccaaggtatt  25560
aaaaatgtag gtagtgtagc taaggactcc gcaatgggtg tcggagctaa ggctgttgaa  25620
ggagcaaaag gactaaaagg tgccggaatg ggcagtaagg ttcttggtgg cttaggaaaa  25680
gcaggtaaat tcctaggcaa agttgcaacc cctctagcga taggttcctc tctactagat  25740
attgcaaccg cagatgataa aacaaaggcg gtaggggaga gtgttggagc tattggtgga  25800
ggtatcggag gagctaagtt aggggcaatg attggtacat ttattgcacc cggtcttggt  25860
acaggtatcg gaggagctat tggtggaggt atcggcgcca taggaggtac tctagcaggt  25920
tctaaactag gcggtaaatt tgttgatggt gttcgtaaat tcttcggagg agaagaagct  25980
catgcggaag aagcagactt aactgcaggg caagatgttg cttctgggca agagagtaaa  26040
tcaggagtac aagaagccag agacacggct aacaaacgag tcctatctga gaaaacacgt  26100
gcagagaata acgcagaaga gtccgccaat ctctctatct attctaagtt attagataga  26160
gcccaacgta tactaaacca agcaaaaaat caaaacggta tattcggtaa ctcaggtagc  26220
tctaaagatt cttctgacgg aatgggttca gatgcttcta gtaaagactt tggaggagac  26280
tgggagaaag ccattagaca agcatctaag aaaatgggag tagatgtttc tgacgatgaa  26340
atagatacaa tacttagatt gattcaggcg gagtctagtg gtgacgagag cgccgttcaa  26400
cagataattg atgagaacaa cttcaatggc aatggtggag ctaaaggttt gctacagtat  26460
gtccaaagta cttttgatgc atacaaagta gacggtcatg acaacataat gagcgggtat  26520
gaccaattgc tagctttctt taataatagt aattggaaaa atgacctaaa ttcttgggat  26580
agccgttatc aaaacggtag tacaggatgg ggtcctactg gtaataaaac tagagcgatg  26640
ggtgggcaca taactagccc agagtatgcg ctactgggag aggtagcagg tcaagatgag  26700
tatgttataa atcctagtca gccaacagct ccacgtttat tagcagaagc tactagaaaa  26760
acagcccaaa acttccgatt aacaggtaat ggttctggtc atgattgggg agcttcaatt  26820
tctaaaataa atgcaacagg aggagctcaa tcaggttcag ctcctacgat gacaaataca  26880
aatgaggtat cagttaatgt caccatacaa ggtggaggaa caagtgatag tatagctaga  26940
gaaattggtg ataagtcagc aggaattatc agcaaaacac tcgatgctac cttcacagat  27000
ttcttcgcaa aagaatacag gagagtgtag aggcttaatg tctctacttt tctctaagga  27060
ggtttataat gtcagtagag ttaagatacc cgagatttga tttaactttt tttacagaga  27120
cagacaacta ccatatagtt tatgatgcaa aagatgggct tactggacgt aataacaata  27180
acggtgaagc agagaaggta agcaataatt ttatggcaga gtctgtaatt agtttaacta  27240
caaaaaatgc tttagaggat gatagtgcag tcttctcatt cgtattagca ggggacgtgt  27300
attgggatag agtactaaat gctaatgatg cagttattct taaaatagac ccagatactt  27360
cctccactaa aaaatcagat aaccctgtac tactagttgg tttaatatct gaggttagac  27420
tagagggtga ctatggggaa aactctaaga tgtacaggat aacaggacag tctttcgcaa  27480
aggcgctaat gcagtttgac ttaggtgtta ttcaggaagt aagtgtagtt ttgacagatt  27540
taggttggtt gcctgacgat gcacaagaag gtataaaaat gtctggtagt agtgcaagtc  27600
aaatagcaga aagcttaatg aaaagatttt tacaatatat gaaatttaat tttaatggtc  27660
aaggtataga taagttctta gagtgggagc tagatagttg gacagaggcg gagagactaa  27720
tagatagtac cccttacata aactatgaag gttctttaaa gcaacttata gatgatgtaa  27780
ccgctaaacc gtttaacgaa ttatatttcg atgcaacacc agagggtaaa tgcagaatga  27840
ttatgcgtag aaccccattt gataaatctg attgggaaaa attacaaacc tacacagtaa  27900
catctgcaga agtaatatct gaatctgtag cagttaacga tacagaagct tactctatat  27960
ttaacatatc tattaataac ttgtatggga ctgactctat gatgttaggt tctaaaccac  28020
aagtattccc tgatttagtt tctaaatatg gttataagaa actagaagta cctaataggt  28080
atttagaagg agcaattata gataagagta acagtggaga taaagctaac acaaaacccg  28140
aaagtgataa tgatagtaaa gagagcgatg gctcaacagc taaacagatg tttgacagag  28200
agtacgctct tgtcttaaac tatctaaaag ggtatcctgt tgatgtgcta agagttaaaa  28260
aaagtaatgt aagaacatca ataacacagg tagacagacg tataacagat aacgaagcag  28320
ataaaattat agaccactat attacaaatc aagcattaag taaagaagac ttttctaaat  28380
ttacaggaat aaccgaagaa aatatagaag agggtaacgg taaagtagaa cctacatata  28440
ccgcagttag ggacttcctt aatgggttag ataaaaacct aggagtatct agcataaaag  28500
agaaattaat gaactacttc aatttgatac ctaaccaagc cacatctatt gctagtgaat  28560
acaaagcaca aggtaactta ggtaaactaa aatatgaaga aataatggag aataacccaa  28620
gtgatagctc aaccgtcact ggttcagata aacgatttgt ttctgagttc actaaaagac  28680
tagcaaattg gtactgtgaa aacgctaatt tctacagtgg ggatattgta gttaaaggtg  28740
accctaaata tagattaggt aaccgtttgt ttgttcaaga tgagcaaaat ggtgagttgt  28800
gggaatacta catagaatca gtagaacact cgttctccta tacacaaggg tatatcacta  28860
ctcttggggt cactagaggt ttacaaaatg gaggaaacga tagattcact catttatggg  28920
gtaaatctga ggacttctcc ggaggtatgc taggtgagaa aaccttgcaa gcactactag  28980
```

```
acgaacaagc agaagcaaac agtaaaaatg atggaggctc tgatagtgga ggtagctcag  29040
gtaaagagta tacagcaggt gcaggaactc agctagcggt attcccatta gacgtaatta  29100
atgtaactca gggagaaaat ggtggataca gccacatggg agcacttgca atagactttt  29160
cagatggtac tcctcataaa ccttactatg caccatttga ctgtgaatgt gtgtacactg  29220
actcttactc aggggttgca tggcaatctc aaaagcctgt taaatgtgta gatggtagcg  29280
ttacttacgt aacactatta tgtgtacacg acaacaactg ggcaagcaac aaagtagggg  29340
ataagaaagc taaaggggaa gtgatagggc actcaggaac tgcaggacaa gcatcaggag  29400
accatgccca cttcgaggtg tctaaaggta aatggcaagg ttggagcaca agcagtgcgg  29460
gagtttactt tataaaaaac ccttctcatt tatacgatgt attttctata aaaaataatg  29520
taactggaaa aacaactaaa attatgaatg gtggagggta caattggcgt agtatagact  29580
gggacgataa atctggctca ggttctggaa agaaaaagac agttggtgct agagccatgg  29640
ctactccatt cggattacgt atgatgcgta gcgctcctgt agaaccagaa gaaccaaaag  29700
ttgttaaaca agtagaaact aaaacagttg ttgaaaagaa accaaaagta gaagttaaaa  29760
agctcccaat actttatggg aataacattg ccacagaagc aactaaatgg ggaagagctc  29820
actcgaaaac agagtccaca ttccaatctg ccttcaattt tggagctaat acagataaag  29880
acccatttga ggaagacatt atagcaacag acagtgcagg atttgtttgg tggtgtttct  29940
accatgcggg catatcacta tctggtggag ctagaatggt taccactcgt tcactactct  30000
atgataacca attacaaact atctctacta gaggtcagaa gtctttagag ctatttgata  30060
agatgaaggt aggagattta gtttggttta acagagctag tcatgtaggg atatattgtg  30120
gtgagggcaa gatggtctct tgtaatggaa aaggtaacat ggatgagtcc ccaaaaacag  30180
gtattgttat tgtcgacatg tctaaaggtt attggtggaa cgcttttgac ggaaatgtac  30240
gtagatataa ataaccctat tttttagggt tattttttt tgtataggta gtttttagtt  30300
attgtgctat aatagataat gaggacacat gatgagagga tgaataaatt ggtaaaacgc  30360
agatttcaag caggtctagg ctcagaaatt aaaagagtat ataaagaagg acaacaaatt  30420
aacacgctac tattagcaca agtaattcaa gtaaactata aatataatac agtagaccta  30480
ctagctttac agcataaaga agtatttcaa aattcctatg caaatgaggg acgtttctct  30540
gcaagacttc ctatggaatt tggcggtaga aatatcgttg gacagcctta tgggcaggtt  30600
aacccgatag cagtaggaac agtagtatta gttggtttta ttaattccga taaagacatg  30660
cctattgtaa ttagtgttta taataataac gatgtaagca agcaactttc aagaacacaa  30720
ttttcaaatt cagaccctaa agatttagag ttaattgggg atatgcacca aaaatttagt  30780
ttataccctt cattgacata tgatagcgtt gatggagaag gaggacgtgt cgttactttt  30840
tctggtaaat catttattgc ttttgataca aaagaagtag ctaactcctc tacaactgat  30900
gcaggttatg gtactaaata tgaggactta gagacatcat actataataa tggtgaccta  30960
atagagccta tgaaaggtag agcaccaaat gtactgttta agcatcaagg ggtacttgac  31020
gatgatggca aaccagattt gcacgatttg ctaattcata ttaacccaga tggtacttat  31080
agaacttcta tgatgaacaa agaagaggat tggcgcacac tatttgaaat gacaccagat  31140
ggcagagtta aattaagaaa acaagactct attaatattg atggtggcat agaaataagt  31200
gagctaggaa tcaacaatga ggggttcgtt tatttacgta atggggatat ggatttagaa  31260
gtacgaaaag acggtatcta ttcacaaggg aaactgttta cagccgatgt agacctatcc  31320
gatgtatatg acaaactaaa tggttgtctc atacagatta aggaaacaaa tggtcaatta  31380
gagattatag ctaatggtgt agaagaacaa aatggaaaaa tatcagaact ttctacagaa  31440
ataacaattg tagcaggtaa agttgaatca aaagtaacaa agacagaagt tcaggatatg  31500
attgacagtt cttttgtaga tatgtctgat gcgattaaaa aagcacaaga agatgctgac  31560
aaagcaaata aagtgattgc agatatgtct agtgataata gactgactcc gagtgaaaaa  31620
atagatttat taaaagaatg ggatattata aaaaatgaat atccaagcta tctcgaacaa  31680
gcagaaacct acgaggttga cagtaaagac tacactgcta agtacaattc attagagcta  31740
tttgttaccc ctatattggc tgacatggag tcaactagct cggtagacgg agcaacactt  31800
cgcaaaacgt ttaattctta ctatacagca agaatagctt tactaaactc tattagtaaa  31860
aaactaaaag acggtatcac agaggctatg aaaaaagcat cccaagcatc actagatgca  31920
acacaagcaa tggcagatgc ctcacaagct aagattgatg cagataatgc taacaaactt  31980
atatctgata tagcaagtga taacaagcta acaccttctg aaaaatacca acttaaaaag  32040
gaatgggatg taattgttaa ggaataccct acaacaattg cacaagcaga gaagtacgca  32100
gtagacacag cagagtatac agctaaatat aaagccctag agctgtttgt agagcctttg  32160
tttaaagaca tggatgaaac tagtatagta gacggagaac gccttagagc gacattctcg  32220
gactattacg caagtaagat tgctttacta aaagaagtaa cggactcagc taaaacagag  32280
ctagatgcct atggtaataa aatatctgta atggaaacaa acattactca aacgtcagaa  32340
gctattactt tactagctac tagagtacaa actgtagaag acggtgtaca atcaaataag  32400
gcacaaatcg aaatacaagc tgaacaaatt agtcaaaaag taactgctag tgaggttaaa  32460
ggaattgtag acgattctat taacaatcta acattaggtg gaactaactt atttgttata  32520
aagacacaga cagcaggttt gctaaacgag aatgatggaa ctgtaggtac tgcagtagac  32580
aactcagtag tgtcagacta cattaaagtt aatcaaaaaa caccatatat tgctacactt  32640
tacggtaaca ctggcacaaa catgattata acagactggt acgataaaaa tagaacattt  32700
atttctgggg aagctgtggc agactctggg gattttagta aaaagtatgt gtcacctgag  32760
aatgcagtct atgctaggt aagttataag aaagcaaact ctgtgaatat caaattcgag  32820
gcaggtacaa aggctactga ttacagccct tcatgggaag acataaaagg tgaccaaact  32880
gctttagagg aatacattaa aaaagtagaa gaacaagcca agaaagctca acaagatgct  32940
gaaaatgcta aaaatgatgc tgaaaatgca aataacgcaa tagctgatat gtcaaatgac  33000
aatatgttag caccgaatga gaaaaaacaa atactcttac aatgggaaca gattaaaaca  33060
gagtatccaa taaacttaga ccaagcaact aaatttgggg tgtcttctca acagtataca  33120
acagcgtata acgcactaga cgagtactta aaaccaatac tagctgacat gacaacaact  33180
tctgtagtag ttggttctac tttaagaaat acgtttaaca attactatga caaaagaact  33240
actttactaa acagaatatc tgacgtagca aaaaatgtag cagacaaggc acaagaaact  33300
gcagatacta tcaatgataa tttacaaaat attggtgggt acaactatgt agggttctct  33360
tccggagaca atatgttgcc tagactgatg attaaaaacg ttggttacta cacattaggt  33420
tcgtcaacca cagagttcat tgacagcatg gtagctgtaa aaggtgatgc aacgacccaa  33480
cctttcgatt atactgtagg tacttctgat aaagaaattg ctggtggcgg tttagctgat  33540
tatcgtatga aagaaataaa agaaggtcag tggctaacag cttctgcgaa tgtgcaggta  33600
ataggtggtg gctccgctag gttagctatc tacactttag aaggggataa ctgggtaggt  33660
tctaacagta cacctataca agtaagtgat ggtttgaaac gtgttgtggc tcaaagaaaa  33720
```

```
gtaacaggct taacaaaagg tgtgttaata cgtattgagt cagccgacac taatgttaaa  33780
gagtttcgat ttggtaatgt tcaactagaa gtgggtatca tcccaactcc ttggaaaaag  33840
tctgatatag atattcaaga ggacataaac aatgttgttc agaatatcaa aacatacact  33900
gcttgggcta acgatttaca gggtcttgat tttacaagag aaaaggttga aggaaaaact  33960
tacatgtatg taggtacctc tatgaaagat agtgataact attcagatta tacatggagg  34020
ctaactgatg aacatataga aggtcagatt aatggtaagg aaggcgcatg gatttactct  34080
ccaacagccc ctgctaaccc atcgcaagga cttatatggg tagacttgtc aaaagtcccc  34140
aaccaaccta agcgttgggt agattcagaa actgggtggg ttgcattaac accagaagag  34200
gttaaagatt tgccttgggg tgaagatggc acaagcttag ccgactgggt gtcacaggca  34260
gagcaaagaa tatcttctga tagcattata aatactgtac taggttctga ggatttcact  34320
agtgtgttcg atacaaaagc taacacttct gacctaggta acttggctac ctatgaagac  34380
ttagactcaa taaaagagga ctataaccgg ctaatcaaag aaggcataaa tggtattgat  34440
tttactcctt atgtgactaa ctccgaacta caacagctta aagacagctt taacttctct  34500
gttcaacaag ccggaggggt taacatgctt aaaaactctt taggattctc tgggttagac  34560
ttctggaatg gtacagtagg gaagaactta ctacctaact ctacttggaa tttaggtttt  34620
ggtagatggg gtggtacttc aatcactagt tttgaaatat taccaccaga agatgacaag  34680
cctacgagta acatattagc ctcaatgcca cttcgctctt ctactaaaga aataggtaac  34740
agacctcacc cattaaaagt taactcgggt gaaacgtaca cagtaagctt cgactataaa  34800
gaagaagcat tatcttacaa caaggacaga cctatccttg ttgtaagaaa ctaccctgat  34860
aagaacacag accaatggat ggagtactca atagaaggtt gggcagtaat ggctaacgga  34920
agcactactg acttaactgt ttggagacgt tttacaaaaa catttacaat aggtactagt  34980
ggctacttag atattttacc gaaaaccata atagaatcgt gggaacacag gtctttttgg  35040
agagagctaa aaatagagaa agggacacaa gccactactt gggtacctaa caaggaagac  35100
ggggcgttta ctggtgatat tgttgagact attcaaacag aagaattagc caacctcggg  35160
tttggttccg gatttattag ttctaaaaga cctagctctt cattaacaca atctgtagaa  35220
ctacctgaaa taggtgctaa ccttgagtat tcactatctt tttatatgaa ggtaactaca  35280
gataaccctg tagctgactt taaatgcggt attcgggttt atgatggagg tactctaact  35340
tatacattag gcatagaaga tgcaacacag ccaataccac tagggttcca acaatacaag  35400
cttgtgttca ctcccacaag tacctctact aaaatagaaa tgtttgtaga aaatgggcaa  35460
gaggcatctg ttattatatc aggtattatg tataaatatcg ggagtatacc tcttaaatgg  35520
caaccatatc caagtgagat atacaatacg aatgttaaga ttgatattaa tggggtaacc  35580
gttaaaaaca atcaaacaga tgggtataca atgattactc cccaagagtt ttcaggatac  35640
tctcgtattg atggtaacat agaacgtatt ttcactttaa atggacaggt aacagaagtt  35700
aaaatgctaa aggctgaaaa acgtataact atggaaccag tatctgtatt cgctatgaac  35760
acagtaacgg atacaaaaag aattagaggt tgggcatttg tgccatcatt tgaataaata  35820
attcaacttt ttaaccgaaa acctcactta caagttgttt tcggttaatt tgtgttatac  35880
tatatagaga aggacacgaa aggacgatga gactatatgg ctttaaacgg aacaaagtat  35940
acagcctttg cccgacatag attagtttta gagtggcgcg caaatcaaaa cattgcaggg  36000
aactactcaa caatcagcgt atggctatat ctacaatcta tggataaatg ggggagactt  36060
gatgctcccg ctattggtga tgccaaagtt accgtagaag gaactacaca gacagaaaaa  36120
gcttcctcta tgttaaatgc tttccaaaag aaactattac tagctaaaga gtggagagtt  36180
aaccataata atgacggttc taaaagaata actattgggg gtagctactt tgtaaacgtt  36240
acttttactg ataatggtgt accaacatat tacggtacga taactatacc taactttca  36300
gtagacctga atagaatacc tagaagaagt tcattaaacc ctgtccctac attaaattta  36360
ccggggaact taccaataac aataaatagg cagagctcca cattcaaaca taatctaact  36420
gcttgggtgg ctaacagaga taaccccaca ttaagtaatg atgcccattg gacgtacttg  36480
acaaatctta ataatgtaga cactagtggg tcatttagtt ttacagtagc aaataacaaa  36540
actattttta ctgcattaaa caataggact agttggcaag gcaaggttaa actatggact  36600
atagggttag atgatgtagt tagtcaggag agaacataca agattgtccc cccaatgaat  36660
gcacaagcat cgggaggtaa gataacctta aatgtgggag agaaaatcaa tgtatcacta  36720
agtaactatc ggtctgatgc aaactttact tatgatgggg tatttaacat tagtgggctc  36780
aacataccca ttgctacaaa ttcagcaggg aacacaatgt cgtatacact aactcaaaca  36840
gatgtagaca atatattgaa gaaaatacca aatgcggatt cctcgtgggg tcaagtaact  36900
gtaacaagta agtatagtgg agtacaatac aggactccat ggacaggaca gagaatagat  36960
ataactatac ctaaaaacaa gtatgtacca agcattaatg gtacccctac ttatgaagat  37020
acaagtagtg tctctgtcgg gcttacaggt gacaatcagg tagctcttca aggtaagtct  37080
aatatcaaag tgactatccc tgctaacttt gcaacggcta atggttactc tactttgaaa  37140
acaattgatg tgtctttagg cggtacatca aaaacagtca actattcaaa tgcagaaaca  37200
gttgtagagt taggggctcc cgctaaccat acatcagaca ccttaatagt cacagtaact  37260
gacagtcgtg ggtttaagtc taactggaca aagcatgtag acatttaccc ctacgaaaac  37320
ccaaatatgt actttacagt cacacgtaga aataactttg agacaactac agatattaat  37380
gttaatagta catggtctcc tatcactata ggtggtgtaa acaaaaatgc tgtccaatca  37440
gtaacctacg caacaaaagt agcaggtgtt ggtacttatg gagcagaaac tgctttaaat  37500
tttacagcta atggtagtat ggtaacagta aaaaatacac caatagaatt agataatacc  37560
aatacatacg aagttaggtt gagtgtaact gataagttta gtacgtttac tagaacagct  37620
actgttaaac cgggtaaccc tatcatgttt attgatgccg ataatcgaag tctgttttta  37680
ggtaatgcct ttgttgacaa taacaataat gagctaagag gcttattaga gatagaaaga  37740
gataagtggc aggagaatgg tttagtagga atatccttaa acaacagtga tatatcagca  37800
gtcaatggca tatggttctc gacagataca tcaaataacg gaggtgaagg gctccacttt  37860
attaaatcag gtaaatcaag aaattcattg acttgggatg actatgatta cttttatatg  37920
agggacaatg gattctatgt taacaatgac tctaacccta tatttactgt gactgatggt  37980
ggggatttaa ggttccctaa actggataac ttatgggatg gggcggctta catgcacaaa  38040
gaccagataa tagtaccacg taaaaaactc agtgaatgta gaaatggttg ggctttaacg  38100
ttcagttctt acgataaaag tacaggtaag ctgtccttat gggatataat tacattcttt  38160
attcacaaga ccgcaccgga ttctccttta agtggtacag gtcacaggtt cttcttacca  38220
gatggtaggg atgctacatc tcaaaagaca aaatatatat acgtcaatga ctatcagtta  38280
aggggtcacg aagaaaatga tgacaaaggc ggaacagcta gcacaaataa cagaaataag  38340
gttcttatga gggtggatga atggtaaata tgagaacaat atacgtagaa gtaaatgatg  38400
aaggttatgt agaaggttgg ggcagtaacc tgtcaggtaa taataacatt catagtgtaa  38460
```

-continued

```
caatagagga taacgaccag tttttttata aaaactcctt aaattttaag tattcaaatg  38520
gctctctagt attcgatgaa gataaggcac tgcacagtgc taaactagcc aaaaaagatg  38580
aaatgttaac tgcatgtaac tatgaaaaaa atctaccttt gacttttaaa ctagacaacg  38640
aaaattactt tgctcaaccg ttaactgcgg aagaacttaa tgaaacaata ttgcctctgt  38700
tgtcaggttt aacagagact gttcctcttg aattagttaa agtaagtgac gatgtacaag  38760
taacattaca agttggatac agtgtaatta aaaatttata tgattataca aatctaataa  38820
atgaatactt aaataaaaag ttagaagtag atgtgtttaa gatgatagat gaggctacta  38880
cttttgaaga agttgaggaa gtatcatgga aaactacaac tagtgatgag ttacctaatc  38940
aacctaaaat agaagacctc cctataaata acaaccaaga aatcgtagat aagttaaaac  39000
aagagaataa agagctaaaa caaagagtag aatttaacga actagcttta atggatgcaa  39060
taaacatgtt ttctgaaatg aacaagtaag ttattattaa ctaaaggagg tgatatttct  39120
atgtacccat acttatcaat gttatatgca tcttatgtaa tcaaagaccc tgagaactat  39180
cctttagaga aggttccggc actaattaga gaagatgtgg agaaaatcgt ggaagagatg  39240
gcaaaaaaga acgaaaaaca aggatagtta atttagtaat tggagtaaca ataggtttaa  39300
tcatagggct actaatttaa actaatataa atgagggtag tttgtgctac cctctttttt  39360
atactatatt gtactatatt aaggaacgaa aggagcggtt actatgggac aatcagatgg  39420
tatgggcggt acattaaaac gtattgcgat tcaagtaggt aacgacccga ataaaggttg  39480
gtatcgattt caagtaaacc caactcaata taaatataat aagccacatc gtgttactat  39540
atttaaaact aaatcaaaca ttataacaga agactttggt aaagatatag aaactatcca  39600
attttctggt acaacaggat tcagggtaga tagcagaggt aaaaatgggg cggacagact  39660
aaaagaatta gaagaaataa tagataatta cgcaaaacag ggcggtaatg gtaataggtc  39720
tagtgtagag atgaaatttt ataatttcac agacgataaa tattttgttg ttcatttagc  39780
accagaaggg ctatccattg aacgttctgc agaacagcca ttattattta attacacctt  39840
aagtttagtc gtgttaagag aggcaggaca gccctctgag agagctcaag taagccctca  39900
gataggtaat gtaagtccta gcattggacg gacatacaat gcacaacagg acactagaac  39960
acctgctcaa atacttcatg atgaatatag gagaagtgtt atgctaaata cagcagtaaa  40020
tcctgcagta acatcgggag cctataacta tggtgtaaat gagttaaaaa aaataatcgg  40080
atatggaggg tagctcatgg aaaaagtaga acaatcagca gatttgctaa gattttttag  40140
atatttaaat gtcgatatta acggtgaagt tgtagccaat gttattgacg accaaccaaa  40200
ctttatatca aggttctaca cccctcatac acgagttaat aaaatatcta gtacactatt  40260
agatattgtt cgagataatg atatagggga aacaaataag gctttgtcta aagactcctt  40320
aacttataaa tttttaaaaa gtggacttaa gctttcatct ccacgtattt acgagctagc  40380
acaaattgta gtactagaat cttttgctct tatatatgct atcgaagaag aaccagagat  40440
gtttaaaatg attaacgaat cagatgtaaa gcagactaga gagaatgtta aatacttaat  40500
tgattgttta ggaggagcaa aagattatac agacatagtg atggacttac aatctatgga  40560
tgtcgctcta ggatatattc aggagcaagt tcctctaata caaggaggtt taccagtaaa  40620
tggcacgata taaaaaacat ttaattgtat atggggatac aatgcaatcc atagcacaaa  40680
aagaaacagg ctctgtagat aattgggtaa aaattgcgga gtacaatgac ttagtttacc  40740
cttacatagt agatactatg caagaaaaaa tgagcaactt agaacatcta gctacacttg  40800
gggacaccct ttttatacct gatgaaggta acttattgga cattaataca agctcattaa  40860
accaaagaga tatggatttc ttattaggct tagctttagg taaagacttg gatatgacaa  40920
gtgatacaga ttactacgag aatcatggaa caagtgatga agtgtttgca ataacacata  40980
atgggcatgg ggacttgaag atagctagtg gggcagacaa tattaagcaa gccactatat  41040
caagattgat gacagctaag ggtctcttta tgttgcaccc agagtatggt agtgacttgc  41100
acttaatgtt cggtaaaaca acaattgaac aaatgaagat aattagtata gaagtatgcg  41160
atacagtact taaagataca cgagtagcag aatgcgttct agtgaaccat tatattgaag  41220
aagaccgata tgttggtaac tatagagcaa ccttaaagtc tactagagag caatttgagt  41280
ttgttgttca aaacgataac tcaggggctc taattattgt atagaaagga taaggtttaa  41340
tgagactaaa gaaaatttca gagatactag gtagactaat tgatgtaact atgataaaca  41400
cacatgagat aaacgatttt tcagttggtt ctactattcg ttctatttat gaagctgttt  41460
ctatggagtt agaacagtac tatattttag gtagagagaa tattttatgg ggaattgaac  41520
aaggagtcct aaatgctttt gactttagga aaagagaagc aaaaagagcg tatggtatgg  41580
taacactaga gttccatacg gttactcaga cccctgtgta tgtgccaaca ggaacaacat  41640
tcgactctag cttgtctggt gcccctagca cgttaacatt ccaaacgatg caagactaca  41700
taattccaga aggtgttata acagcaaagg tagaagttta ttgtacaact gtaggtacaa  41760
aagggaacat acctaaagga agaatcaatc gggtaattaa caatatatca aacttaaaaa  41820
ccgtgtataa tgagtttgat tttttaacag gtactgatga ggaaagtata gaatccgtta  41880
aaaaaagatt tcatgcattt gtggaatcac gtggtagagc aacgataaaa gccttagatt  41940
acggtacacg tcaagtagag gaagttgcag gagtttatat caaagaagaa gtaggctacg  42000
ttagaatata tgcacatgac ttaaacggtg atttaaaaca agaaacacta gataaaataa  42060
aagtagctat tgaggactac agacctgcag gcattaaact ggatgtattc cctgtaataa  42120
aatccaatgt acaagtgagt gcaactgtta ctataagtga caaatcgaga ataaatagta  42180
aattagaaga aagagtggag cttacaataa gaaactactt aaatagtcaa gttgtttcac  42240
aaccattaat cttagctgac ctaattcagg ttataatgaa tattgacgat gttttaatct  42300
atgactgtaa aattaacaac atggaaggga acatggctgt tagggacgaa gagataattc  42360
gtgcaggaga ggttattgta gaactgatat aaattaggag gaatataatg tgagtaactt  42420
ttataaaaat atccaccctc tgttgagacg tggtaagaaa cctaacaagt atgatgatac  42480
taactttgca gtgcttaatg cgttgaacta tgaattaact caggcagagc aggagaccat  42540
tgctagtaag attcattctt cattagaaac agctacaggt gagtacctag atacttgggg  42600
ggactggttt ggtgtatatc gtaaagatga ttggaatgac gaatattata gaaaaagaat  42660
tataagagaa cttttactaa aaagagccac aattcctgct atcattgatg cgttattgga  42720
tttccttaac gacaatgatg cagtcatcca aatatatgaa ccttggagaa acattttcta  42780
tacaaataag tcaaaattaa acggtgacga ccatttaatg ggttactact accgttttgc  42840
aattatcgat atttcaattg atagaccgtt tcctcctgaa attgtagaga ttattaaggc  42900
tttcaaacct gcgggagttc tattttatct aaggctagac acaagcttaa ataagaataa  42960
aacaactgta gaaagcccat atgtatacct agacgtgacg aataagacag aattagagtt  43020
ccttaacggt ttatactatg acctacgagg taacattaac ctgtctgacc aacgtacaca  43080
agtagtagag agtaatatct tccatacgaa taactctatg ctaaacgggg aagatgtgct  43140
tgcaggagca tttgaccacg gaagaggcta cattcactta gcaagtacaa cattgcttga  43200
```

-continued

```
ttacacacca aaacctactg actctatgag tgacttaaaa acagctctag gagaatcagg  43260
tgctgatatg tataatcaaa caaaagaaaa ggacggaaga acagcttcta ttcaagtacc  43320
tgcaacaaag aatgttcaca ccttgtactc aaacagcatt gactttggtg gctatgatta  43380
ttcggggaat ccgaatgtta tgactaagcc ttatattgct gacaatataa ccggcggtac  43440
aacaggagta gttgtaacac caattgatga tggcgcaaga ctagaaaaaa cacgagttga  43500
tatatctgga acgtttaact tagcattggg taatcttttg aataatacag attatataat  43560
ttcatatgat gtacttgtgg aaaatggata tgtaggagat ttaaaaactt gtaatgttgc  43620
attagaagga cagtttgaag gaaagcctaa ctattttggt attttttata tgaatagtgt  43680
aacatcaaca gatgtatggc aaaaggtttc tgtaaaattc aatagtggtg ccaacatgga  43740
aaaattaagt ggttttaagt ttagagtata tttatctcaa cgtgttcaag cagcattaaa  43800
aataaaaaat gtgaaaattg aacgtggttc aacagccacc ccataccagc caaatttact  43860
cgatgcacca tattatctgg gtaaggtggc tttgggtgag aatattgcta ataagtccgt  43920
tgagtttcca ataaaatcta gcaattatct cttatataac gctagaatgg tagagccttt  43980
tgttgtagga gaaccttata caattaccat aaaagcaata aaaccagcca gtcaaacgtt  44040
tatggtatat aacattgggg aaggaactac ttattacgga aaactaaatc cagttgaggg  44100
attgacagac gtatggtcac taacattcac accaagaaat gtttcgtcaa ctaatcctag  44160
cgatttacgt atttttcagt acccatcatc aacattaggc acatgtcaaa ttgattggtt  44220
aaaaattgaa aaaggtgaca ccagaactcc taacattgat tcctacgact acgtaggttc  44280
tctgatagaa gatacagaaa cacctacgtt agacccgact aagtatacat ggacagtaaa  44340
tggggatata acaaataaaa aggcatatat ggtgtttgat attaagacat ttatcgaaga  44400
aaattatgct atagaatttg aaaaacttat tactgaccta ggagaagacc aagcattaaa  44460
taccgtgttt gaaaacttta acatctctac aacacttaag gctctagtaa gtccaagttc  44520
accaatcagt ttctcggttg aactatacga tttttctacg agtgcatggc acaagttaaa  44580
cacggatagc ttagacttac gtatgcgtac attcaactta gtagcaaacc gtatcacaga  44640
ctatctaaat gattacaagc tattatttgt tcgttacgtg tttgataacg aaacagataa  44700
agatgtaaca gttgaactag acatgctaaa tgtactattc aagtatcgtt taggtgaggg  44760
gtacagtata ggactacaat catctgtgga atcactaacg gaactcgttc ctatagaagg  44820
gtaatagcaa ataatatgtt ataatataaa tagggcacct agttgtgtcc tatttttttaa  44880
taaacatgct atattaacaa ttgaatgata aagaaaagag gtaaataatg tggctattgc  44940
aactaacaat tcacgagtgt atgcctcact ccaattaaaa aataaacaag acagtatgta  45000
cctagcaatt ggtaaaacca ctccttggac taatgaagat gcccccccctg caccagaccc  45060
tactacggct actctaacag aggttatcgg ttataaaaag gtagcaagag tatctttatg  45120
tagagaatat ctaccaagtg acgattctaa ataccctgtg gtgtcctatg gttcaagaaa  45180
atttacgcta attccagatg aggacggcta taaagagcaa gcgtggatgg tgtatgtaga  45240
agcagaaatt acaggagatg aactaccaat aggaacattt aggcaagtag gtattcatac  45300
tgacttagtg tctaaggcaa gttcagaaaa gaaagctttg ttacctacag atgtaacaga  45360
tgcaggtatt ttgcaatttt ttgaaaatag acagcaacaa aatagaacaa gtgatgtaat  45420
tttaaaagag aagtttatta ttacaatgga aaataagaag tcagttaaac aataggaagg  45480
gtgacataga tggctaaaaa tattacaaat gatgatttag gtaaagagcc ttataacaat  45540
agatattacc aaggcaaacg attttcaggt ttactattta aaccagataa gccgttacaa  45600
caagccgagt taaacgagtt acagtcaatt attcaaggag atttaggcaa tgtggctgaa  45660
tccatattta gtgacggtga catccagact ggtatggaat atgtactaca agataagaag  45720
cttactatta aaaaaggtaa agtattctta ggcggtaaaa tgcgtaactt tgacgaacag  45780
agtatcgata ttaccggaga gggtacggag tatgtaggtg ttaaacttgt acaaaaagtt  45840
attacagcag aagacgaccc atcactgtta gaccaaacaa gtggtgttcc tagccatttc  45900
tcagaagggg ctgaccgatt agacgaagat gtagtactag cagttaatga tgattctgca  45960
tcaaacattt accactttgt taacggtgag ttatacatta acccagatac tcctgagatg  46020
gataagatta ataaaatact agcagaaaga acttatgatg aatctggttc atatcgtgtt  46080
cgtggttttg atatgtacac agaagttcac ccaacagacc ctaacaataa aattcagtta  46140
gttgtcgatt caggtcgggc atatgtttta ggttttaaag tagataaacc tacaactact  46200
cgtattgata ttgaaaaatc aagagagtta gaaacaatca ataacgaagg tttctactat  46260
agcaatgcaa ctcgtaaaaa taaattaggt aattccccag tatcttctgt agaccgtgta  46320
actgcacaag ttgaagttgc taaagaacag gtttctcgtg gggtcgtagg tggaggtacc  46380
gattacctta aaaacacctc tgtaacaaaa gttattcgtg tatggactga gggttcagga  46440
gcacaggagt acaaacaagg tgaagacttc caattagtaa acggtcaagc aatatcttgg  46500
gcacctacag ggcaagaacc tcctgcaggg ggaacctact tcgttcaata tgtttataat  46560
aaaacaatga ttgaaaatac agattacaaa gttgtaatta ctggtgaagg tgatgctagg  46620
gaatggtata tcgactttaa cgagatgaca ggttctaaac cagtcgatga atcacttgtt  46680
aacgtagact ataaatactt cttagctcgt aaagacctaa ttgtattaga ccataacggg  46740
aatttcactg tccataaagg acaacctaac gctttaagac tagtagaggc acctaaccat  46800
gtagacccat tagttttagc tattggtaca gtagtagttt acccagactc aaatactgct  46860
gatgctaaac aatggacaat cacacgtcta acaatggaag agctacagaa gttatctgtt  46920
cgtgtggaaa acatggagta taaccaagca gtgttctact tagaccaacc ggcaatggca  46980
ggagaaaacc ctatctatct acgtggagta ttctcggatg cgtttatctc actagataaa  47040
tatgacgtta gtcacccaga tgccacaatt gcttttgact ttgacacagc agaaataaca  47100
ttaccttatg cagaaattaa taaaacagtt ccaacaatta tcgaaggttc tagtgaagca  47160
catgtgtggg gcagactagt aacagcaccg tttaccgaag aagtgggtat tagacaacca  47220
tttgctacgg aagcaatgaa cgttaaccca tacaacacct ttaacaaaca gggtgcctta  47280
aagctaaacc cttctgcaga taactggatt gaagatgagc gtatcacagt taccaaagaa  47340
gaaacatcta ctatgactgt tcgtcaatgg tggagacatg gtggagcatc ttggacaaac  47400
gatgagatga acatggtatc taacatcacg cttgaccccg gacaatcgtg gggaggtgcc  47460
tctggtacag aagaccaacg taaacaaggg ctatccggtt ctactttaac cagtggtggt  47520
cagcaaacca aagaatcaat gattgagttt atgagacaaa ttgatgttga ggtttacgca  47580
gagaacttgc aacctaatgc taacaactta tacgtaacat tcgatggctt gagagtacct  47640
gttaccccat cttctggtta ccgtaaaggt gccacagaag gcactggtat ggcaaatgca  47700
gacggaacat ttaaaggggt atttaaaata cctgcaggag ttcgttgtgg tactcgtgaa  47760
gtatctgtta gaaacgatac aaacttagca agtactacgt tcactgcgca aggtacgcta  47820
aaaacaactg aggatattat cataaaaacc catgttacta ttaacttggt tgaccctctg  47880
gcacaatcat tcagttttaa cactaacaga gttgcaacaa gttttgacgt attctttgca  47940
```

-continued

```
tctaaggata acagtacaaa tattatttgt caagtacgtg gaatatcaga aggtgggcaa  48000
cctaataaaa ctgtgtatgc tgaaagagtg ttaaaacctt ctgaaatcaa agtatcagat  48060
gatgcaagtg ttcctacgaa aatcagcttt gatgacccac taatgtgtaa agcaggtcaa  48120
gaatactgtt tagtattcat tactgactct gataaataca caatgtggat tgcaactatg  48180
ggtcaaaata gagtagacga accaacacaa acagtaacat caaatcctta cttggaaggt  48240
gtcctatata gttcatctaa cgcaagtgca tggtctattc accaactgtc tgatttgaag  48300
ttcactgtat acacggctaa atttaacgaa gaagctgtac ttgagttcga tgttatgaag  48360
aacgttaatg tagaccgcat agtgttaatg tctacctacc taacacctgc aaacactggt  48420
tgtagatggg atatgaaact agtccttgat aatgagcctg caggtacaac agtagatgac  48480
aaaccttggt tacctattgc taactacgta gacttagatg ttaaccagtt agctcgtgag  48540
gctaagctta gagcaacatt taaagctaac caatacatct caccaatgct atccttggac  48600
gacattatgt tcgcaggatt tttaacagca ttgaaaggta gctatgtatc tcgtacaata  48660
gatttaacag aggctccata caacacggtt aaaatgtcat atgaacaatt tacacctgcc  48720
ggaactgttg tgactgctaa atatagtaca gatgaaggta aaacatggaa gacatttaca  48780
gtacagccta caacaacaca acgtacacaa gactttgttc gtgtagacta tgttgaaaag  48840
attaatacgg gtgggacatt taagtccatt aaattccgtc ttgatatgac gacccagaat  48900
tcatttttgc gcccgcgcgt aagacgctta ctcactaata tgaccgacaa atagaagatg  48960
taactgtaat gtaacatttc tatgcctcct actgtggtat acttactgta tacaaaatag  49020
taggaggttt tttaatgggt aaagcattac aattagcagg tactacattt ggtaaatggt  49080
acgtaaaaga gcgagatact tctaagaaag gtagagcata ctggatttgt gagtgctctt  49140
gtggaagaac agttcaatct attccgagcg gtactcttac tacaggctca tctgtgatgt  49200
gtaaacaatg tgcaaatgag aaatctttag tgggtaagac ttttggtagg ttgaccgtca  49260
ttaaggattc aggtgaacga gcaactaatg gtagtatcct ttgggagtgt aaatgttcct  49320
gtgggaaaac aagccttgtc aggggttcag agttgacagg gggtcgcaca aagagttgtg  49380
gttgttactc cacggatgta ctcaaaaaag tagccactaa gcatggattg tctaaagtga  49440
acggaaaacc cacaaaatta ttccgggcat gggcttcgat gaaacaacgg tgttacaaca  49500
agaaccatgc gagttataaa gattacggtg gaagaggtat aaccatatgt tctgaatggc  49560
gtgaagactt tgaaactttc catgattggt ctatagctaa cggattttcc gatgacttgt  49620
ctattgatag aattgacaat gacaaaggct attcaccaga caattgtcga tgggtagatg  49680
ctaaaaccca gattcgaaat agacgaaata ccattactta caactggaag ggttcagagt  49740
acaccttagc tgaactggga gaactaacag gtataaacaa gatgactata aaatctaggc  49800
tgaactccgg agccactctt gaagaagcac tagacccaaa agtgaatacg tcagttttga  49860
ctatgagtta caagggagaa actaagcctg tcaaacaatg gtgtaaagaa ctgggattga  49920
attacgcaac tgtacgtagc agacactata aaggttggac tgatgaagaa gccttaactg  49980
gtatacgtaa caaatagcaa cagaataagt ataatagact ctatatgtta taatagacat  50040
atagagtcta tttttttgt taggaggaat aaaattgcca gaaacacaca gacaaacaag  50100
ctcaggtgcg cttatattta aaccaactat agctgaacaa gagcataaaa atgctatgga  50160
atctataaaa caagagagaa cagagctaga gaaagaacta gctaatgtta aagctatcaa  50220
agatgagttg tcaaaagagc tagcagatat taaacaactg aaagatgaat tatcaaaata  50280
gtttctaaat tgtcttattt aggatttctg gttcccttat actattaact aatatattta  50340
aataactata tataaaatat ataatatata aataatatat aataagacta cgaaaaatat  50400
aaaataggac aaatcaactc tgtatacacc ttgacaatta cctactatgt gatataatga  50460
atatattgat tatactaagg tgggtatgtc aaggagcatg tatactaatc taacttaaag  50520
gagatttatt aataaatgag actagtagta gatattatgc atactcagat aaggtatgaa  50580
gattcggaaa attatcttag accagaaatt cataaggtaa tgcattcaga attaggagtt  50640
aaagcagatg gttatcaatt tagtcctgca tataaagcag gttactggga tggtattatt  50700
gatttttcg ataaagaaaa tgacacgttc cccacagggt tactacctca tgtagaaaca  50760
atactaggga accttcaatc aactttatca aagtcaggtt acatttttca gtttgagata  50820
attgatgata gacctgatga gttcatgtca gtagatgaca tggataagga gatagtgctt  50880
aatggggata acaatgacaa gataacatta agagactatc aatatgaatc tgtggagcaa  50940
gttattaaga acagaatagg tattgtaaac gttagtactg gtgggggtaa atgcgtagta  51000
gcatctacga acctactgac ttacgataaa gggtacaaaa catttgaaca actgttcaag  51060
gaacacaaca ttgatttaac acaatcagag gcaactatcc ctaacacatt tggggttaca  51120
ttagtgaatg aaaagggaga accagaaacg cctagtcatt taactattaa tggagttaga  51180
catgtaaaca aggtaacaac tgagcatgga tggactgaaa caattactga caaccatcca  51240
ttactaactg tatcagaatc tggtagcttt aaatgggtag aagctaaaga cttgaatgta  51300
ggtgattgga ttgttggacg taaaggtgat aatttatttg gaacgaatac tacatgtacc  51360
gtggagagcg catatagctt aggtttatta acagcagacg gctattgtgg gcaaccaacc  51420
cagattacat taaccaataa ccaaccggag atactagcgg acattcaaga tttctttact  51480
aaagaagggc tgtccactaa ggtagaccct aacaaagact ctaaagatag taagatagtt  51540
aggggtaccg caggagctag agaactttat aataaatatg gcttatcaca aggattagcc  51600
aaggataagt caatcccaga gtgtatcatg gaagcaccga aggaagtaca gttagcttat  51660
ataagtgggt atttagagtg tgaactgagt atggaggtac ctaaatgttc aatagaggta  51720
atttctgcct ccgagaagtt acttcaccaa ttacaactct tattaggaaa catgggagtt  51780
tcctcaagat tagctaagaa ggtagttaaa gggtacgagg ctaattggta tggtagatta  51840
actatcggag tgactgactc agtttaccta ctaaaacaat taacatttaa aacagcacaa  51900
cggaacgaaa gaagagcctt atttattgaa acagcagagt cccgtaatag taaccaccaa  51960
ggacaacctg taccttttgg taaggagtta gttaaacgat actgcgataa ctacctaggg  52020
gacactaaag gacttagtaa ggcattcaaa gtaccaagaa caattagctt acatcggctt  52080
aaaaatttaa ttcatgagtt ccctaatgga aacccgacag attttgctaa cctgacaaga  52140
ttaactgatg gtagatatgt ctattcacaa gtaacaagta ttgaagatat gggatatgaa  52200
ccaacttatg atttacacat gcccgaaaca catagtttta ttgcaaatgg tatgataaac  52260
cataacactg aaatagcatc aggacttata cagcaaataa ccccttactt agagtcagga  52320
gaacgtattg catttttac gaatagttct tctatttttt cacagtcaat tgaccgtatt  52380
gagaaaagac ttggaataaa agtaggtgct tttggtgcag gtaagaagga cattcagcaa  52440
gttacttttg taatgatacc tacgattgta tctgcaatat ctgcagaccc agaggctaag  52500
cttaagctga ctgctaaaga aagaatgtac aagaaaattg ctaaggatat agctccaaaa  52560
tttgaaagag ggtttaacca aaggagtttg cttgaaggat acctaaataa ctttcaagtt  52620
aagacaaaag cagacctgca gttgaaacat gaactagaag aaatttttta ttcatgtggt  52680
```

```
acgaacaaac aggttattat gaaaatgaaa gggtatcaag cagaatacca aaagattgtt 52740
gaaaagaaaa atggtaaagt tcttaagaag tacaacgagg ctatggagtt tttagattcc 52800
atatctgtaa tgattgtgga tgaggctcac catacaagtt cagatacttg gtataaagtg 52860
ctaacatctt gtaataacgc tcagtataga atggcactta ctggttcgat tgaccgtaca 52920
aatcatgtgc tttggcaaag acttcaagct atattcgggg agattacgac taaggtgtct 52980
aacaacacac ttattgagtt aggtcactca gccaaaccta aaataacaat attccctatt 53040
atagctcctg tagatattca aaccactacg tatatggatg cctatcaaaa aggtatagta 53100
gacaatgaat atagaaattc tcttattgca aagttgacta agaagatgta tgataaaggt 53160
aatgggattt taattataat taatcgtata gagcacggag aggctattag taacttacta 53220
aaagaagagg gagtagctca ctactttatc aatggacaac ttgaaaatga tttaagggat 53280
gaaaaaattc aggacatgcg tgatggagca cttaaagtaa tgatttcttc tacgattata 53340
gatgaaggtg tcgacatttc agggattgac acattaattc ttggtgcagg aggtaagtcc 53400
ttaaggcaga cactacaacg tgttggtcgg ggcttacgta agaaaaaaac aggagaaaac 53460
aaagtagaag tattcgattt ttatgattta acaaacaaac atttgaaaaa acattcagag 53520
cagagaagaa aaatatatga agatgagcaa tttgaaattg ttgatattcc tattcctaaa 53580
taactataat aaagaaaggg tggcatacaa ttgcaaagtc catgcctaaa tattgaatta 53640
aaagaaaaat ttaaattaaa caaaggtata acagactttt tagagagagt tgcagataaa 53700
tctcagagat ggggtgaaac agtagcctcc cctatccgta aaacggatat ggcaaaagag 53760
actggaaaaa accctagaac aattacaaga tatattaatc aattagagga actaggttta 53820
ataaaaaccg aaacaaaaag aggaatgaat ggagggactt tagtcgtgtt taacacagat 53880
atgcttaatt ttgagccaaa ggaaaaccct atcacgtctg atactaaaca agcaaaggag 53940
attagagaac aagttttccc taaagcccca accaaagtac caaaacgcag atacagaaca 54000
aaagcggaga tagctgaggc acgtatactt agtgaaaaac ttaaaaaacg tgaagacatt 54060
ttaaatgata aaattgagtt taacgttgtt actagaagtt ttttcgatag ttttgacgaa 54120
ccagaagcgt actttaaagg ctatttaatt tcaagaatgt ataatgctta tgtgacaatc 54180
attccttatg aaaaatataa tagactgaaa aatttagatg agaaaaaggc taaacaacaa 54240
ctacgagcat acgaaagctc ttacaattac gatgtgttgc ctagaagatt tgttgggaca 54300
cctcagtaca aaaaatttgt agagctagct aaatattgtg aagagaacaa tatcaatcct 54360
ttagtttatt taacagtgca atttgataga acagagtttt tgatttctgt aggtaaagca 54420
cgagtagggg ctacacccta tgtaaatact ttgttatgtg cagaggctaa agaggcttac 54480
acaaatagaa aactgttcta cagaatgtta cagaaccaat atggattgta tacgtctatc 54540
aattcagaag ctacttatta tggtgcaact tatccaatta tttcaggact attgaatgct 54600
tacaatatgc cacagaaaga cttgtcacag ttagatactg tgatttgtga cttagaatat 54660
aaaaaagata ttgacaaaaa agcaggtacg ttgtactctt attatacagc aacacttaaa 54720
tcgttaggtg aatctgacgt atctagtgaa gctaaagaaa gtattgctaa cttcttgaaa 54780
gaacaagttg caaacttttc tagtaaacgt gggctaactt caacacagta tgccttagcg 54840
ttccctattc agataaactc tgcacgcagt ttattaatga atgaggaaga cgaagaacta 54900
ctttatttat tgttaggtaa ccagtcacga ttatctaatg taacaaatga tgaagctgaa 54960
atgtttatta aacaaggtag aaaattaagt atgtcttggt ggggctcaca gaacttctca 55020
agaacaatgt tcatgttagc ggactactat gggtttaaaa caaatatatc taagttaggt 55080
atgtacatta aagaatttgg tgaggagaaa attcctttag attctgtagg tatgttagat 55140
gtaaatagaa tctatgatgt cttaatgact gaacaagaga ttttagagat tgacaaaagt 55200
aactgggaga accaaaaaga tatgcgtgac gacaaataag aaatataaat gggagaggga 55260
cggatagtaa gatgagtcaa attcaaaaac aagttattta tagagcatta agtgagccat 55320
tctttgcaaa ggaaatccta agtaaaattc caatggatga gtttaaagat tctggatatg 55380
agatgattgt ttctacaatc aacttatatt acagaacaca tgatgagagc ttagaggaac 55440
agagtttatt aacactagta gaagataaga tgttaaaaca aaacaaaagt ttggaagctc 55500
aaaacaaagt ctttgaggta gttagcgact tatacgaact agagaacgaa gatgtagact 55560
cagaagttat cagtgagaac attcagaact acgttcgtaa ggtactaaca cgagaagcaa 55620
tcatgaaatc tgtaacaaat gaaggcacac taggctctga tagtaatatt caacagctaa 55680
tggatgactt gagagacatt cttactatcg agacagcagg caataattca gaattgctag 55740
acttcttcga tgacgtagat aaaaagatgg agttacttgc aaacttgcaa caaaacaaat 55800
acccaactgg tttcacagct atcgatgcta tttccgatgg tgggctagct cgtggagaag 55860
tcgggatggt tgttgcacct actggtggtg gtaaaactac ttgggcagtt aaccaagcta 55920
gaaactatgt tgtacgtggt ttaaatgttc tttatgttcc tttagaggaa aaagtagacc 55980
gtatgattgt tcgttttgaa caattattat cacaacaaag taagaagaac atcttagttg 56040
atggtgaatt gaataaagac ttgtataccc aaatccaaca agcgtatgga gcgggtaaag 56100
aacagatgaa ttggggtaac ctttggattc gtaaatataa accacaagag ctaacaccta 56160
gcggtttatc tcagttaatc tccgatgtaa tgattcgtaa aggacagcaa attgatgttg 56220
tcattattga ctacccagat ttaatgaaaa atcctcatgc aagtggaagt aatggtgaat 56280
cagatgcagg aggtaaactg tatgaagata ttcgtgcgat tgcacaagaa tatgattttg 56340
tttgttggac gttatctcag ttgaaccgag caagctatgg tcaagatatt aaaaatgcag 56400
gagctatcga aggctctaaa cgtaaaatga acgcagtaga gcttattttt acattaaacc 56460
aaacatcaga ggagtttagt aacggatatt tgagagctta cgtagataag ttacgtaata 56520
atagtgggat tgcctatgat aaaatgttgt attttaaagt actcccagaa actatgacta 56580
ttagagatga aacaccagaa gaacgagcag aacatgaagc actgttagca gataatgcga 56640
tgaatagagc aagtagccac tctgatgaga ataactacac agcaaacgat gttaataaaa 56700
agataagtaa tttgaataat acccttttcag gaggttggaa ttaatgaaac atattattaa 56760
tttttcagat tttcatatgc actttttaa agatttttca aaaccagacc cagagtatgg 56820
aactgatagg gcaaaagagc aaattactat attagacaac ttgatgaact atgcacgaaa 56880
caaaaatggg gatgttttat ttaatggaga catgttccat aaacgagtat ctattgatgt 56940
tagaatattc aatatgttat ttcaagtaat tagtagctac cctgatgttg atgttatcat 57000
ggtcagtggt aatcatgata aggtaactaa ctctctatat tcagatagtg ctttagcacc 57060
atttagtgct ttaccaaatg ttacagtttg ttctacgtta aacaagattg ttaaagatga 57120
ttatacgttg tatgctgtta gttatgggga agaggtcgaa gagatgaaag cttggataaa 57180
agaacaagct gacaatttag accatgaaac agttaatatt ctaagtgcac acattggtgt 57240
agatggttca tctactggga agtactccca tacacttggt ggtgctttta aagtagctga 57300
tttataccct gacaagtttg acatagttac attgggtcac tatcataaac gacaattttt 57360
aggaaaccta tctaatgtgt tttatgtggg caataccttta cagacttctt ttgcggatga 57420
```

```
aggtcaagaa aaaggttttt atgatattac tatagagggt aagaagtggg aacaaaaatt  57480
tattaaaact gactatactc cgtttgaaac agtaacagct gataacccat caacaacagg  57540
ttctatggag aaatcttata tccagtttat cggtaatgtg gatgaggttg aggctgtaaa  57600
gagaataaaa gaagagaata acttaagcaa tattagaata aaagttcaga aggactacca  57660
tgttgagcca cgtataaaca taacagcagg ttcgacacct aatgaagttg tcaatgcatt  57720
tattagtaaa aagtacccta acgcaaaaat aattaaagaa aaagctctcg actgtttgag  57780
agaagcaatg gaagtataat aattgtttag cctagatata tctaggcttt tttgcgttgt  57840
actattgact ttattagtat tttgaagtat aatatgttta ttgaaataat taatattttg  57900
ggaggaaaag atgttaaagt ttaaacgagt tagcgcagag aactatatgt ccattggctc  57960
tgtatctatt gatttagaca accaaggact cgtacttatc gaaggtataa atgatacaaa  58020
cgaaacattt cagagtaatg gctcaggtaa aagtacttta ctgtctaccg ttacttatgc  58080
attgtatgga gctaccccta gtggtttgaa agctgatgct gtaattaata aacaagcaaa  58140
gaaaaatatg tcagtgattt tagaatttga aaaagatggg gtaccatatc gtatcgaacg  58200
ttatcgtaaa cactctaaac ataaaaatac tactagattt ttccaaggaa caaatgatat  58260
aactcagaaa tctgtagcag acactgataa aaagattcaa gatgtgttcg gtattgatta  58320
cctgacttat gctaatagta tcatgtatgg tcaaggtaac gtagaaatat ttgctacagc  58380
aactgataag ggtaagaaac aaatcttaga gaatttagcc gatattggtg tttaccgata  58440
tgcacaggat gttgctaaag aaagagcaca aaaagcacta gctcttgcag aagagctgaa  58500
cagacagtac attgctaaga catatgaaaa agatgggtta actcaatctt acaatagtgc  58560
tttacaacaa tatgagaata cagaaaagct gattcaacaa aaagagagtg agttagctaa  58620
tgcagaatta gctattaaac aaagtgagaa gaatctgtca gagggaagag cgctacgtga  58680
acccgaatta gaaaagctaa gagagcagat ggcacaacta acttcccctg cagacgttcg  58740
tgaaattgat gtagaagttg aaacacagta ttctaacgtt agtagattat ctagtgcaaa  58800
aacacagaat gatactgcta ttgagaaatt aaaaaaagaa ctagaagatg ttaaaacaaa  58860
tacaaattgc tacctatgtg gtgctttatt gagcccacag catagagaac aagaaattca  58920
acgcattcaa agagaaatag cggataaaga agcgtttatc gaaaagctta atagtgcatt  58980
agcagtgtat tctcctctgt tagagcaagc aagagctaaa caagaggaag caagaaaagc  59040
tattcaagaa catactaata tttatcataa acttaatggt gaaatgaatg cgttgtatca  59100
tgagatagat acattagaga acacattgaa cacatctatt aataataggg acagcattaa  59160
ggatatgtta gcaagactac aagaaatacc taaacctcaa tatgactatg acaaagaccg  59220
ggaaatagaa gatgagctaa ataaaattaa ccaattaaaa ttagatgccg aagaagaagc  59280
tagtcaatat aaaactattg cacaagaaat tttctctaat aaaggcatac gctctgaggt  59340
acttgaccta gttacacctt tcttaaatga aagagcaaac cattacttat ctaccctttc  59400
aggttcagat attgaaataa actttagtac ccaaacagag aaagcagatg gtagtttagc  59460
tgataagttt gacttagagg tagtgaatgg ctccggtgga aacacatatc aagcaaactc  59520
cgagggagag aagaagagaa ttgatttagc aatatctttt gctattcaag atttagttca  59580
gtcaaaagca aacattgctg ttaatttagg tttgtatgat gagtgttttg atggtttaga  59640
tgcaattggt tgtgagaacg ttattaaaat attgaaagaa cgccaaaaga acattagtag  59700
tattttcgta ataactcact cggagaactt gaagccattg tttgagaacg taatcactat  59760
gaaaaaagtt caaggtcgtt cttaccttga agaaagtaaa taggtgatta catgaagatt  59820
tatacattaa gtagagagtt aaacgaaggt actatatttg tacctacaag tagtagtaat  59880
gaagggagac tatttagctt cccgctagag acactattcg attggtaccc ttgttgccca  59940
agatatgagt atcagtacag cacttctcga aaaaaactat atttgagatt gttagactca  60000
gacaaaacat tagtagctag atacggtgtt ggggataata aaaagagagt tatttcaaaa  60060
atagcttgct ttaatgagaa tgaatggtat aatgaagaag tggcaaatga gaatgcagag  60120
ttgtttaact ttgctaaaca atatgacatt gttacacctt taaaagaaga ttacacctta  60180
aaagaagtag ataatagtat ctctaaagta ctggacattc ttgatttact ttacacaaat  60240
caaaaagtta aagtagaaga agagcttata aataaagtgg atactctaca attgagtaaa  60300
ccagactcgg atgaacttaa acaagcgtat aaggatatat ctgagtatat gaggttagac  60360
agagaggaaa aagctactta tgtattaagc aggtcactag actctttaaa tagtgtttat  60420
gaaaaatttg gtaatgtgta tacaatgtta aatattatga ggaaagtagt ggcttaaatg  60480
tttacagact tgttatctaa cgaattaggt tcacctaaat atgcagtaag ggactacagg  60540
tataattgcc ctttttgcga ctacgatact aagtataagt tttatgttag ggtagaagaa  60600
ggacacccaa agaataactt atggcattgt tttaagtgtg gtagttcagg taacccagta  60660
tcttttgtaa tgaagtatta caacgtgtct tttaaagaag cgctagagat attagaagaa  60720
tacggctata ggtttaataa taaaaattat gtgcctaaat cagataagtt aactgatgag  60780
gaatacttat tacttcttct aggttcgtta ggtaagccaa aagaagaaac taaacaagct  60840
aaaaaagagt tagtagcacc cccattgcca gatggtttta aactactaag tcagaacctg  60900
agagagccag aagcgtaccc tttcttatta tactgtaata agagggggtt tacattgaat  60960
gatatttata tgcacaatat tggatatgta aaagattctt gggtaccctt agaaaatggt  61020
aagtcagtta gactcaaaga ccacttagtt tttttaactc atggaaaaga tggtaagtat  61080
caatattgga atactagggc tattggggaa agctttatta agtctttgaa cgccccaagt  61140
aaagagggtg agcattcaaa aaaggatact atatttaata ttaatagagc tagtcaaacc  61200
cctcagatag ttataacaga aggtgttcca gatgcattaa cagttggtga gtctggtgta  61260
ggtacttttg gtaaacaagt gactgacgag caagttgaac ttattttaga tagtgtgaat  61320
gaagagcaaa aaatatttat ctatttagat aaagatgcta aaaaagaaat taagaagtta  61380
gcagagaaac tatataagag acataacgag acttatgtag ttataagccc aacaactcaa  61440
gatgcaaata gtctagggag agaagaggct tggaatatta taaataacta ctctgtaaaa  61500
gcagatggag tagggttaat aaaattaatg ttatagatag gagagggaaa aaaatgaagt  61560
atacactaga agatttacat gcaggtatga aattacgttg cacggacaat aaaaactaca  61620
gtttttggac tacgaataaa atctatgaag taactaaaaa agagtcaggt tcactatgta  61680
tttttgatga ttatggaatt gagagcctag atgaggacat cttagtacgt ttaaatggta  61740
atacaggaaa cgcagaattt gaggttgttt ctaaggtgat gaaggatgca gattacacag  61800
aagaagacct tgaagaaggg atgttacttc actgcaaaga tgatatgagc tttccatggt  61860
gggctacagg acaaacctat gaaatctata agggtgaaaa aggaatttta tttaccaagt  61920
caggagacgg taaccaatac tgtgctaaag aaatagtagc tcgattaaat ggtagtgcaa  61980
gcgggtcttt tgaattacta gaaagaccac ataaaacaga gttagaaaag aaagtagaag  62040
caagaattaa ggaactaaaa ggaaagaaac tttgtttatt ctacaagcaa caacaaatta  62100
agatagaaga aaacgaaata tctatagaaa tcagtaagct aagtgaagca ttaaaagcga  62160
```

```
ttgacgtatt aagagaattt gaataagaat aactatagga ggacaacaaa caagatggaa  62220
agagtatcag tatactttct aaatagcaga aatattatgg atgaggatga gacaaagcgt  62280
acttatcatg gaacatttaa ttcaatgaaa gaagcagagc agtcagttcg tgactggtgg  62340
aaagcaaatg actttaagtg tggtaccctt agaattattg aaggtactga ggatgggatt  62400
gttcgttggg actacggaaa ccatactggg ttctatctat ttgtaccaga aggtgctgta  62460
gtaaaataca caatccgtga aggcgctaag aaaccaaaac gaggaagaga aaatgatgta  62520
gcacatgact tgttcacagc agacgatgga gtagttattc ccgggagatt aggttcaaat  62580
gttatttcta ctggaataaa aacatcgttt gaccccaaac aatatggttt attcattaac  62640
cctcgaggtg gtatgatgaa atacccaatc actttaggaa acacacaagg tgtagtggaa  62700
ggggaatatc gtggagaggt tggtttacca cttaaaaata cgttctcttt acaattagat  62760
gcaagagctg tttctaagaa cgttttaaca atcaatgaag aaggtaaact tattaacatc  62820
ccagtaacag tagctcggtc aatgtatcca agctttaatg ctctttatga aaaacagcta  62880
gagaagctaa gtgaggagct acagctagtc tatggaggag aagttagaat atctaatgct  62940
gatgagtatg tggttgcggg aacactattt atcccaaaag gcactcgttt atgtcaagct  63000
ttcttactac cacgatacga cacacagttt gttgaagtat cagcgttagg tacaactgaa  63060
cgaggagaag gcgcatatgg ctcatctggg gtggtatagc tatgctcatc ccagaattta  63120
agccaccatt attgtacgtt atgggtagct tttctgttat gttagaaaaa caccagtgca  63180
gtgtaacttt tgatttaaga gagccttatt taggtacctc ttacgataaa atagtgaagc  63240
ttattaaaat gacttaccca aactatagct taacttatgt agggatgaca gataataaat  63300
ataagttcac attaaagaat aaggaggact agcatgtaca ccaagaaaga ggaagtagtg  63360
acagttaaac acctagttga taaagagcaa attagagtag gggacatagt aggttacaaa  63420
aagactatta gagggttcga tgcaaaaaga gtaaaagaca cactctcagt aacaaatcaa  63480
ataggtgtag tttctcgtgt atgtgacgag tacattactg ttcatgactt ttttgataag  63540
tgctcacgag aaatatgggc aaagacattt gaaaatttag aagttcgcaa aatagaggat  63600
ggtaacagcc tactacggag gtatgaaaat gaatttcgtt gattatttta atcagatgca  63660
gaatttagtg attgaagaaa aaacagatga gtatgtttta ctagagaaag aacatggtca  63720
aaagtatgtg acatatcaag agctagaagg agcgttaagt acagtagcac gcaacactgc  63780
atttatggta gaaaattata accttatgca agatattaat ttaaaaattg tattgaaaaa  63840
attaaaagac agtggtacaa ttacagaaga gcttgaaaaa gagattctta aagagttcaa  63900
aaatattgaa agtttaatgg aggacgaaac atatgagtaa agagagtaaa cgcaacaaac  63960
gtatcgggga gttatcggaa gcagacatga gagtgtgggc tgagtggtta gccacagggc  64020
aggttcatga taaaaaccac caaaaacagt tagaacgctt aagtaaacgt tcagtatcat  64080
tatctgatgt aactactatt gtcgaattta tgggcaaacg gaatgatggt tatatttctt  64140
ctttaattga acagcaggct gtatttgaca atttattaac aaaactaggt gtaacggaag  64200
agaaccgctt agaggctaaa gcagagtacg aaaaagagtt aagccttatt caagaaaaaa  64260
tccaaaaaga gttagagtct attaaagaaa ataaagaaaa ataatatgaa agaggttagc  64320
tgaatgacag actacagcgc agtaggcaag aaaagtcgta acaaaggcgg acgttttgaa  64380
cgtcaaatgg ctaaagaact cacagagtgg tggggatatg agtttaaccg agtacctgct  64440
tctgggggc ttcactgggc ttctagtaat aacgttgccg gggacattgt agtccctagc  64500
gatgctaact tcccatttgt tatagaatgt aaaaatcgtg aagactggac gattgagaac  64560
ttattcttaa ataacaaaga aattaagaac tggtgggcac aagttgtggg ggatgcaaaa  64620
gaaacgaaaa atatcccact acttatattt actagaaaca gagcaaagaa ttttgttact  64680
atggcatata atgaaaaact tgttaatgag attgaaaaaa gaggttaccc tttgatggtc  64740
tctaacataa catatgtaga cgactacaag gatactcatt gttacaagac atttactaca  64800
gttttagatg caataactag ctttaagcct tatggtagca aagataaaga ctacttttta  64860
ttttattttc ctagtgacta tgactgggaa gatagcctag tttatgaaac aaccataatg  64920
gatgatgcta aacaaatgga tgcagaggat tcactagatg cactagttaa ttcttattta  64980
ggaggagaat agtatggcta aaacatatca ggaagctcta gcaacggtac agtcgtatct  65040
cgaatcagat agtgtaatga aagaaacctc aagtatatct gttagtttct cagctaactg  65100
gacaggtgag cgggaagact acgttattga tacattgaca tacgacattg atttacgagt  65160
attcagctta gaaactgcac atgttgtagc tatagggaag aaactacctc aagatagcaa  65220
tgagcatgct gaactcctta aaaaacttaa aaaagaattt aaacaagctt ctaaaaaact  65280
acgggaggac tagagtagat gatagacaac gttaatagtc ctagtcatta tacgcaagga  65340
gaaatagagg taatagaggt tatagaatat attactgcta agtaccctgc ggaaattaga  65400
taccatttag gaaatgttat taagtatatt tgtcgagcac ctttcaaggg aaagctacaa  65460
gaagacctta acaaaagttc ttggtacttg aaacgagcac aactggtttt aacacagtca  65520
ccaagtagct atataggtaa atgtaagaaa tttttagaga atttcctatt taagaatagc  65580
catatcagag atgctcagct aatagaaatt ccagaagaac ctattattga gaaattttta  65640
tttcaaacag cacagagtta caataaagaa cagcaaaact atattatttc agccttaatg  65700
gaactaaaca gtagttcagg tgatgtgaaa actgttcttg aaaatacaga aaactattta  65760
aaatttatta caacttagta caatataatg ctctttctac gaaaagctat cttttatatt  65820
tatggtataa tagagatagg gaaattaaaa agtagaagga gcattttata atgacaaaag  65880
cacccagagt gaaaagactt aatatttata acactgaccg gtactttaat attaatttaa  65940
tgaaaaaaga agatatagca aaaaaaatta aagttaaccg attgaatgaa gaagagatag  66000
agagggaaat ggacgaacta gcaagcaacc cattgaagac ccctataggc tacatggata  66060
gaacaaatga aaaatcttat atactttatc aagagaagta tacgaacgac agacttattc  66120
agaaattatt taaacatgca gggtctgtgt cttattacac agatacaatt gtaccatact  66180
acataattga gcaaatatct aagaatttaa caagtgaagt aatctatcct acaaaaaata  66240
gctatgagaa cagagagatt gaaaatgttc aactagcttt cactgcttgc cctgtaacga  66300
ttgactgccc agtagtacta cctgatgtta gcccgtatga tgtgttattt gcactacatc  66360
ctctaaaaac aaatgtagac aagattcaaa tatcgttccc ttgtcttaca gaagaagagt  66420
tcgatactag acatgaagaa tactatcata aagtaggtag ccactatgag gttaaatcag  66480
agtacaaata taaattcttt aagtatgtac aaacttcctt atctatttgg gctatgaaca  66540
tttggctagt gtgtgatagt gatgaggact acaataaaat agacagatat attcagaaag  66600
aaaaaattaa acgtaatgct aacagagagc gtgcattaaa gagaaagggt aatcaggatg  66660
agtaaagata aaacgattaa ccgaacagac atagctcgaa caatctctca ccatactggt  66720
tatcgaatga aagatatatt gaagatttta gaagtagaag atgaagtagt agctcaagca  66780
gtatcacaag gtatttctgt aaagaatcac aaattatgga aactaaacat taaaaaaaag  66840
ccagagaagg tagcatggga tggtataaac tctaaaagtt ttatacaacc tgaaaaatat  66900
```

-continued

```
gtagttaaat ttgtaccatt atctaagttg aaagagtcaa tagacactta taataaagag  66960
agcaaataaa gctctctttt ttgctctttc tatattgaca aataacataa tacaaagtat  67020
actagtgtca tagagcaaca gagaggagaa aagtgtaatt gaaaattcta ttcttacaag  67080
agtacattag agaaaatcat gtccataatg gaaagaacgg acaaacagtt gattttaaaa  67140
gaacagaaat gggtaaaaaa cttacaggtc tgttaaatac aataggactg acaggtaggg  67200
actatgctgt agactatgtg tacgacatga ttccggaagt acagaaagtc aaccctagaa  67260
caggtaaacc aattaagtat aagacaccta cgttaagaca gcgtaaagaa ccagaggaac  67320
ggttactcag acgtttaatg aaatacaaac cagatattat catcccaatg gggagatgg  67380
gttgtaaaaa tttattagga agtacttcta tcacaaagaa tagaggagta ccaactaaga  67440
aaacaattac gaatgagaac atactgagaa cggctgatga gcaagggctt gaggtagacg  67500
aagtagtaga ctcttttgaa acttgggtac tacctatgtt tagtatggaa tactggacag  67560
ctaacccaaa cattgagaac tttatcatgg cggatattga tacattgggt aagtttgttc  67620
aagaagggga acaagcattt atccctaaaa aagtagatta cgaatttgtt gataacattg  67680
aacgtgtaag acaaattttt ggttttttag acaaaacgaa gccagtaact gcatgggact  67740
tggagacaaa tagtttacgt ggtgacttat taggggctaa gcctcttgta atgtctatga  67800
gttggctaga gggacaaggt gtgactatac cgttagaaca ccatgaagct aaatggagcc  67860
cagaagaact taacgaaata tatgacttat ttgagaagtt tttagcggac agacagcaac  67920
caaaagtagg acaaaatatc cagttcgata ttagattctt aatgaacaca aaaggattta  67980
cagagtttga agacaacaga gatacaaaaa ttgcttacta tctaattgtt tctcagaaag  68040
tagacacttc aaaacggcta tccgatattg catatgaatt aacagatatg ggaggctatg  68100
acgaaccgtt agagcagtat aaaaaacaat ataaagagga ctatattgct cgtaagaaag  68160
cagagattga tgctttcaaa gaagctgaaa aagaacgagt agagtgtgag ttcaagatag  68220
caatggatag atataagcaa gaagttaaag aagctaagct tattggtaaa cctactaagt  68280
ccattattaa accagtaaaa gaaaaagttg tagtacctaa gaaatcagat attaaactta  68340
ttaatgagat tgacggtggt aactttaact acgactggat tccattagag attatgcacc  68400
catatgctag tggagatgtc gattgctgtc tacgtatcta taacgttcta tataaacgaa  68460
ttgaggaaca tcctaagatg ttggaattat ggttgggctt ttatcctaga ctaacagcaa  68520
cattagcaca catcgaggct tctggtgttc tattagactc tgaatacgca gaattagtag  68580
agaacatcta tacagaagaa gaacatcggt tgcttaatga aattagaaag ctaccagaag  68640
taaaagaagt agaggatgaa catatgatgt tctacaaaga ggggcttaaa gaaatgacaa  68700
agcctgtcaa agatagagat gcctctgttg ccagactacg agataaatat aaaattactg  68760
atagtgagaa caaagtacat tttaaaccaa gttcgtctga acataaaggt agactgctat  68820
ttaaagtaat gggacttaca ctaccttatg ataaagaatc tattaaaaaa gaaacttttg  68880
acaatggggt accagaacat cagctaacat ggagagatta taaaacagat aaacatgcac  68940
tagcttatat tgcagaaaat tatccagagg ctaaacatgt tgctgaactt ttgctagagt  69000
attctaaagt aaacacacta aaaaataact ttgctcaaaa gttacctaaa ttagcatcta  69060
acaaggatgg catgattcat ggttcatata acagtacagg tacagaatct acacgattga  69120
gtgcaaacaa cccgaatatg caacaattaa gtagtaaggt tggagaccct agacgttttg  69180
actataaata tccaattaaa cgtttattta gaacaagatt tgagggaggt ggaatgctac  69240
aactagacta ctccgcccta gaaatgcgta ttttaggttt gattgcaaaa gataaagcaa  69300
tgacacaagc atttattaat ggtgaagata tgcatgaggc aactgcatct cttgtatgga  69360
agttacctaa agataatgta ccaaaagata tgcgacaacg tgcgaagagt gtcaacttcg  69420
gcatcgctta cggtaagcac aattgccgtc ttgtagcgta agctactcga ttaaacttac  69480
ctaaacgggc atagctgaat aaccaataag ctgataagag aacctaagtc ctgaaaagga  69540
tagaggcaat cccgtagtaa agacgattta ataaactcca ctaaaggagt ggtattatgg  69600
aaattggaac aagaacagac aacaaccctt tatatagaaa attaagaact gtgcataaag  69660
acatgcgcag acgatgtctc aataaaaatg ctaaatcata tgagttatac ggaggtagag  69720
gtgtaactat tagtaaggag tgggagacct taaatgggtt cctagcaact gtagatttag  69780
tagatggttg ggacaaagat acattcctca caacagggct atccttagat aaagacttaa  69840
aaggaggagc cgagtatagt atagctaact gtacatggat gccacttaat gataacaaaa  69900
gcctactatc aatgaactac aagaatgtct gtgctattga cccaaatggt caatattatg  69960
ttatagacaa cattgacaag ttttgcagag agcacaacct taatcattcc aatatagttc  70020
aagtaattaa tggtagatac aagcatcata agctatgggt attctggtat gaaggtgata  70080
aacctaagaa agggatacaa ccacacatag cgattagccc attgggtgac acctactatt  70140
tctataaagc tcctgacatg gaaaagtatg ggctaaattc taaatgtgta gctagatgct  70200
taagaggaga gagaacaaaa cataaagggt ggaagtttat taaatctgaa aacctctaac  70260
gactatcgaa aagtgagtag ctgtcgagag gacacctaca atataactga gtagagtaca  70320
ccaacaggtg gaaatggtaa ggctcctaga gtaacgacta ggagcgtgat atagtctaag  70380
cccctaataa atatcgggaa accgagggta taactggaaa gtcctttttc aattgcacct  70440
aagttaggtg taactgtaga agaagcagag cgtatttttg aagagtactt tgcaagtaag  70500
ccaagtatta aacaatttat tgaagagaca catcaatttg ctcaacgtta tggctacgta  70560
gaaacactac aaggacatcg tagactattg cgtgactcat tctctaaaga taagaaagta  70620
tttaatggag caatgcgtaa gtcagtaaat acaatcattc aaggaactgg tgcctactta  70680
actaacctat caatggtata cattgacgag tatatcagaa aacacaataa gcgttcacgt  70740
attgttatca ctgtacatga ctcacttgtt atcgattgcc cacgtgatga agtggacgag  70800
atggcaaaag tggctaaata tattatggag aacttgccaa ttgatttctt aatgattgag  70860
tgggaaggta aagagatgcg ttaccctatt gtggcagatg tagagattgg ggagaattac  70920
aatgatatgg ttgattatga tgcagaaatt atcaacgagt ttgcttctta ccgaggatac  70980
gtaaaatact tcaaagacca agctaagatt aaagattact atgataacaa acttatctca  71040
gaagagcaaa aagaccaagg tatcaaagtt atccaagatg caatagagtc atataaacaa  71100
atgacaattt aataaaaaaa tgttaaaaat agcttgacta ttgacgtata gtatgttatt  71160
ataatatggc agacaagttt tctgtattaa tacaagaagg gggagttaga gagtgtgctt  71220
aatttacgag tagacgattt agagttcaaa acaattaaaa ttattgatga taacggagaa  71280
gttgtgacac atgatttaca aacagagtta caagtcaatg aatttaatgt gagaacagca  71340
tttttagagc aacctgctaa gtatacttat tggacttcga tactagagcg cttgcgcatg  71400
tatcaagaaa actatgagtt aaaagcagag aagaagaaag cagaactata tgagccttct  71460
cgggttgcct taatcaatca aggagtagct aaacctacaa aagaccagat tgaggcacag  71520
attatgttag atgaagacta ttacaaactt agacagagta tagttaacct atcatttaac  71580
gtgagacaac tgcaatatat agttaaagct tttgaacaaa gaaaagatat gcttattcag  71640
```

```
tatggagcag accttcgtag ggaatatgag tatagccaaa aggttagtat gccagaccca  71700
atgaaaaata aggtaaataa tggtttctca gactttcaat ggaatttaga acagtaaaat  71760
tagtgataaa aaaaataata taatataaaa aaaatagaaa tggagaaatt taaatgaatt  71820
ttcaagaaca attacaacaa caattaaaac aacaaaatat tggagaacgt gaagcggtag  71880
actacccatc aaatcattta aaacataaag aattatactt ccctaaagca gaaaatggtc  71940
agccatcaac tctatatgta cgtgtgttac ctcctgcagt accgggagaa aactataatg  72000
ttagcgctcg tgaggcattc ttaacaactc gtaatcgtaa tggtaaagat ttaaagagca  72060
actttatctt ttcagaacac cctaatgcag aagacatctt agaacaagct atgattcgtt  72120
ggaacgcaga aaatcgtgta ccaaaccctt atagccgtaa tacaaaacct cgtcaacgtt  72180
actacgttaa tgtagtgcag ttaattatta accaacaaac aggggaagtt agctatgaaa  72240
cagattctaa tggtcagcta atggttcgtt tacttaagtt accacaaaca gcttgcatgg  72300
ctattaatga gagcttaagt aacccaatgt tacgcccaca gttttcacct gatgtaccag  72360
aagaagtagc gcaatacagc tttatttctt ctgcagatgc attccctatt tcaattacaa  72420
aaccaccacg tagtaacaaa cctacttcgt acaatgtaca agtgattagt aatcgtagtt  72480
taggtgcatt accacaaggt tgggaaaact tattagaaga cttgaaatac caagctacac  72540
cttctgtaga gtacaatcgt gagtttattg agtactttat tgatgtagta gacgggaaag  72600
aacctgtgca tcaaggagca caaagtcaag gaacccaagc tccacaattt aatcagcaac  72660
cagtacagcc tcaatttaat caacagcctg tacaaccaca atttaaccaa caacctgtac  72720
aaccaatgca acaaaatact ggttggtcgc cacagcaaag ccaaccacaa cagcctgcta  72780
caggttttaa tgcaacgaac atgggaacac ctccaaacat taatggaggg tttagccaac  72840
aacctgtaca acaacctgta caacagcaac aaccgatggg ttctttcaat gaacaaccag  72900
tgacagaccc ttctaccatt tctgatgcgg atatgccttt caatatgcag tccatgcctg  72960
atgtatcacc acaacaaaat gccgtacctg agcaacctgt gactaataca ccagagccag  73020
taagccaacc agttgttaac caacagccaa ataacacacc tagtgtagac gacctattag  73080
caggtatggt aggcaacgtt taacaataat gaaacagtta ggaggggcat actgcccctt  73140
ttaattctgt gttaactatc caaaatattt agtaggagtg aataatattg gcaagaaaaa  73200
gaaaaagtga agaaatagat tttggaacta ttgatttgac aaaagaggta ggactaacta  73260
catttacgga cacaaagttc tctaatgtat cagacagact accaacaatg attccacagc  73320
ttgattacat tttaggtgga ggattgccat ttggacgtat ggtcgaggtc tttggtaaga  73380
actctagtgg taagtccact ttagcagtcc atctgacaaa ggtagcgcaa atgctagatg  73440
taccaactgt atggattgac gttgaaggta ccgcagaccc agaacgctta gcagaactag  73500
gggtagactt tagtgcaggc ggagtattca tggtagagcc taaacagaac aaagacggta  73560
gtaaagatac aatcacggta gaacgtgtag cagaagagtt acaacgactc ttaccagtat  73620
ttagtaagct tggaaaacct gtattaatta tttgggactc tgtagcgcaa acagcttctg  73680
agaaagagtt agaaaaaggt gtaggtaacc aacaaccggg tttgtaataa agctccgtta  73740
ggtagtaata tctaaaagaa acctatcttt atcatgggaa acctctagga ggcaatcatg  73800
agtgaagctg tagaaataca gaacatgcaa cgactatcga aaggggagtt cttgtcgaga  73860
ggacatgaat gagaaccgag tagagtacac ccaagtgggt ggaaatggta gggctcctag  73920
agtaacgact aggagtaaga tatagtctgt actacatggt gacatgtagc agttcataag  73980
agaacgctat aagcttaacg aacttatagg aacataatag attaaggcaa aagcaatggc  74040
acagtttgct caaatcattg cacctttaat gacaaattca aaagcattat ttattgctat  74100
taaccaagca cgtgacgagc taggtagtat gtttggtgga gtagactctc ccggaggaca  74160
cgctttacac cactgggcta gcttacgatt agaagtagtt aaagcaagtc agattaagaa  74220
taaagagcta aatgcattcg gtgcagagga agagacctat gtaggacata tcctgcgtgt  74280
taaaacagca aaatcaaaag tgtcccgtcc taaccaaaaa gcggaaatgt acttaatgtc  74340
cgacacagga ctgaacttag aggaaaacat ttatcgttca tgttttgcaa ctaataagca  74400
gtatgccttg attagtggag gcacgtggaa gtcttataca acggatgcag ggcaagagat  74460
taaatttaat tcagataaag cttgggtagc ttatttacgt tcagaagagg gaagacctgt  74520
tcgagacgaa ctatttgcta aaatgatggt acgctcattc ccacatcgtt atgctccatt  74580
taataatgag gacgtggatg tatgcaaaat tccattatat gaatttacta aagaatatat  74640
ggaaaatcat aaggaacaac ctaaccaagc tactaaagaa gaagtccccg aaacaggaac  74700
agatgtttca gatttactta aacaggtaga ctaatagata agggggcatt tagccccttt  74760
attagctata aaggagagga acttattttg cgcaaaggac tagcacctaa cccatttttt  74820
gaaatattag aaaaacatca agactcctct aaacgtacta tgactatgaa cagcagtggt  74880
acacctagtt cactacaacc aataagagac atgttcttaa aggcaatgag agaaggtaag  74940
aaagtcctaa tagagaactc tgacttaagt agtgcgaact ctgttgttat agagatagaa  75000
tatgtaggta atcgttggtg tttaggttat caacgagtct tattttatgg tatggagtta  75060
aaaataccac acactatcca cttctgtgat gtatatggag cctatgggca cgatgctcag  75120
aaggttaaga gacaagttaa ggtagtgttt gagggggaca accctttgga gtagagatgt  75180
tcaaaaagag gaaaaagaaa tacgtaatgg taatcggttt attacagaga ctcatggcaa  75240
aggagtgttt cctagagatg tagaccgatt gtaccataag tatagtaatc ttagatataa  75300
agtctataac actcataaag actcgttcaa tagtgaggct tcacgtaagg agctcaagag  75360
ctatattgat gagcaattta taaagttaac aaaagagtat gatataaatg gagaggtaga  75420
ctttccggga tatattaaaa aagctctgaa tttacgagta aggcacagct atgtaaaagg  75480
acggttccga gataccgcta gagaacgtct aggcacccaa gataacgaag tagagttatt  75540
gttagggatt gacgatagct ctcaggcaga tattgaggat gcagaactta ttgaatcgtt  75600
attatcaaaa gccaattttt cagaaattga attagcagta tttcagcagt taattcaagg  75660
aacagtaagg gatgctcgta ttattactga attgtcagaa aactacgggg tgtccaagaa  75720
agccgtaaaa gatgctataa aaaatgttcg tgagtttgtc ttaataaatt taacagatta  75780
gagtaatacc tcctttatgt ctgctatatt agcagtagaa acataaagga ggtatttttt  75840
agtggaacaa aacaacactg gcaagtatgc accatttatt cgtttaattg tgatgggaat  75900
ctcatttgtg gcaactggtt tgactacaat atttggttgg gaacctttac cattcacaga  75960
cgaacaaatg aaccaaggtt taatgttagt actatctgta ggtcttgcca tctacaactg  76020
gtacaaaaac aacgctgtaa cttcttatgg taaagcaaaa gaagaagcag gaaaagaagt  76080
agtcggaact agacaagact tcaaaaacag agactaagta cgaggggtgt aacccctcct  76140
tagttaatac aaaggagctt cgacatgaag atagacgaga taagcaaatt agaattgcct  76200
aatctatttg gaaaattcct tgtggtagag actatttcgg atgggtacac tggaaccgta  76260
tctggtcact ataactacga gatagaccaa aaatctgagg aaacttatat ttaccctgta  76320
ttttggaatg ataagcttaa caaatttatt aggtcagatg aattagttgt atacactaat  76380
```

```
aaaaataaag tatactatgt ttgtaaaaca actatagacc catataatca tgcagtagta  76440
gatgagctca cggtagagga aggcatggac aaagacaagc gtacccttca agcgtttaaa  76500
ctttttgtaa atgacctatt ctcatttggt agctacaata tctttctaac aggtaaccta  76560
tcattagaaa acaaccctga tattgttcta gttagcagtg tatcattaga caaacagacc  76620
gctaaaatgt acacagaacg gacattagaa ctaactgcta cggttttacc agagggagct  76680
acaaacaaaa aagttagttt ctcagtagat aaaccagagc ttttagggtt aacagtctct  76740
gacaataaag caactgtcac aagtaaagat aaggcaggta ctgcaattgt taccgtaact  76800
actgaggatg gagaacacac tgataagtgt acagttcaga tagaagagta cataaaagtt  76860
acaggaatta atgttagtgg agaatctgct ttagaaaaag gtaagacata caaatttact  76920
gctagtattg tacccgataa tgcaacgaat cctaaattta cttggtcttc tagtagtgat  76980
accatagcta gtgttaatgc aagcggtgac gttgtagctt tagcattagg tgaagcagac  77040
attatagcaa caactgagga aggtagccat gtaggtaaag tacatgttac cgtatcagac  77100
ccagaaccag tagaaccaac tgaataacat agaaaagagg aaagaaaatg gctaaagaaa  77160
tattaaatat tgaagacctg ttaaaaccag agacactaga agtagcaata gatggtaaat  77220
accttattgt accaacattg tcggatgggt ttacaggtac agtagcaggc ggatatgcat  77280
atgctgttac aaaaaaagga acagactaca cagttaatga attaatctat aatcaaaagg  77340
ataacacatt taaaccttct gatgaaccaa ttattataac tgatgataat gaaatattct  77400
tcattactcg tacattagaa gacccatata actaccctgt agttgctaca gagaaactta  77460
aaactaaaga tgtaaaagaa aaacaagttt tacaagcgtt cttagcattt gctgatgaca  77520
gatttaagct aggtgtttac aatgtgttcc tagcagatga accatttgta tatggggaca  77580
aaacagaata gtttcattat aagagacccg ttaaggtctc tttttttttg tatatagtgt  77640
tgacaatgtt gtagtttagt tatatactat acttatactg tataaggagg taaccacatg  77700
aacgacaata aggaaaaatg tattaaacaa ggaatacgag atacttataa agggtacgat  77760
attttattag atgaagagaa tggatttttc tatgttagcg tacttgaccc agatggcaaa  77820
gaaatcatta gtgggtttgt agaggcggat aaacctattg aagaatacta taaagagctc  77880
ctaggtaaat gcgaccaaga tatatcgttt aaagaccttt tagggttctt aaatggacgt  77940
agagacactg aacgtacaga catacgtttt ttaaagagag acagtggggt ataattaaat  78000
gacaaagata aaacttatta caaaaaagaa cacccaaggc tatgtcatga acaccctgct  78060
acgtagattt tataaaaata atgtagacgt agaatttctt aataaattca atctacctga  78120
tattcataac cacatagggg agcatgatgc tgttatcata gtagggtttc ctttctttga  78180
aagccaacga ggtgcgttag acacggcact gtcatctatg gacaacccgt ttagcaaggt  78240
gtaccattta gcaacatttg gggacaccta tcgtaatgaa ggtagctttc gttcatttgt  78300
agacgaggtt ataagccccg ttggtcattt tgtagaacta ataattgacc taactaagtt  78360
cactaacaca ggtacaaaag aggatgaaca aaatgtagtg gctcttgcta aagaggcatt  78420
agtgtttgcc aaagatatta tagaagagac agacaactac aatcgttatg aagttacaga  78480
cagaactatc tcttgggttc ttcttgtaga tttgcttgga gagaacctat ataaggtgac  78540
agagcctagt aaagagctag acaccatttt gaaagaacaa gaagtacttg tagatgcctt  78600
gaacataaat atgcaggact atgtgctaag aacaataggg aagatgtctg caaacgtcat  78660
taatggaaca gtggtttgtt tcggttatgc agaacagcat gtcaacgaag tagcccataa  78720
attaattaat ttttataagt cacataacta tcaaaaagtt attgtcttta ttggtaggca  78780
cacaaaaggt gacgacatgt ttagtgtaag gagctatggt gtgaatgccg gagaggttgt  78840
ctataaagtt cataatggta aagggaaaga cacaacggca accgtcttct taggtaaacc  78900
tagtgaagct gtaaataaca cactgctaag tgtgctttct gaaattttat agtttaactt  78960
tgtggtataa taaagataga taaattttga taggagtgta aatttttgaa aaacaacgaa  79020
cctttagaga agttattaga caaattagat gaaccaagaa ttttacaaac aattattata  79080
ggtagtttac aacggagctt taatcgagta cacgttggta aatttaataa actagcacag  79140
gagtttgact tagataagga gaacctgtat agcttaaagg cactagttaa ggaaattgaa  79200
gaagataaag agttacacga actttacgaa gctagtatgg caggcaaaat tacgctagag  79260
gctgttcgta aagtattgtt acaagatgat aagtcatcgt ttgatgtact gtcttcttac  79320
gtagtagaaa atcaagcagt gctagcccgt aaccgagagt tcggtaagtt acaacgtgag  79380
ggagcttatc ttgaccatct aattagtggt ttgaagacat acttattaac tgaactaaaa  79440
gacatgtcta gtttaaaata tatcaataaa aatttaaagg caccgaaagt atcctcagac  79500
cgagagctta ttctgtgcct atctgattgg catattggtg cttttgttaa taacattgac  79560
acaggtggat acaactttga aatctttaaa gaacgacttg aaaagttatt agaagaagta  79620
ttccaagtgg ctatggagca ggatattaag aaaattcatg tttaccatat tggggatatt  79680
attgaacaca ttaatatgcg taatgttaac caagcatttg aagcagagtt tcctgctacg  79740
gagcagattg ctaaaggaat tagagttctt gctgatacac tcaatttact agctaaggca  79800
gaatttgaag tgtctttcgg tatggttggt ggtaaccacg accgtttcca aggtaacaag  79860
aatgataaaa ttcataatga taatgtggct tatcttgtag tagaccaact tcatttctta  79920
caagaattag gggcattaaa caaagatatt aaacttgtag acaacagaag tgacgtttat  79980
agttttaaag atacagttgc aggtaaacgt attaaagtaa ctcatggtga cactgagggc  80040
aaaaaagtgg atgttaaaat ccctaaacat atcaaagatg aagttattga ctatttaatc  80100
atggggcata tccatacaac acgtattatt caagaagact tttcaagatt ccatgtgtat  80160
gtcggctctc ctatgggggc aaacaactac tcagcagaga ataacttgcc aacaacaagt  80220
cctgcacagc taattatggt attagaccct gagcgtgata caccgcagtt catgccagta  80280
ttcttatagg aggtactcgt atggaaggta atttagttta tattttattg gctattgcat  80340
atgtaggtga aggtataact gcctttacta atactaagcg taaagaaaga tacatgattg  80400
aagaaggaga ggctcctttg ccacgtagtt cttatgtatt tttaggcatt aactaccttt  80460
taagaatagc tatagcaatt tctcttatct tcatcatacc aactagcttg caacttaacg  80520
taacaggtat tgctttgttc acactaatgg tatttgtagt tccttttata gcaagaatta  80580
tcgaagttgt tattagaact gcaattgttc gttatgttca aaaacaatat attaagcagt  80640
tagaagaacg aaaaggtaaa agagagacta actagtctct tttttgctat attgaataat  80700
gaggtgacta agtatgaatt ttacagaagt aataagccct aatggggaga catcattaat  80760
agatgtaaac aacccaccaa cattaatcag acgtggggtc ttatctatta aaacaaaggt  80820
taataatgaa gtgaaggaaa ctcctgttta tattgttgaa ctagccgagg agctaacagg  80880
tactgatgta gtatctgtct ataaagtaaa agagattgga gattctatcc aaaaagacta  80940
cattgaagaa aaagtgaccc ctaggttcaa aagcacaaca tatctgggtg agttagcaca  81000
aaagattaaa ggacggtcga taaaggaaca acgaagagtt gaaacaaaac caccattatt  81060
cctagcccca gtagttaatg gaatcgatac attcacagga atcgaaggta aaggtttcta  81120
```

```
cgaacgtgaa gaggacagac atattctatt acctgatgga aaaccgggca tagcctatgg  81180
agataataca ggggttttta tcggtttgag ctcgattaag tgggacaagg catatgtaga  81240
cgtggagtct ataacaaagg gttatttgtc acagaaacag atatggttta acctagatgg  81300
tcaaagacca caatttagaa gtgagacact ataatgacag ataaacaatt ttatgaggca  81360
gatattcaag agttaatttt aaataagcaa agaatattcg gggatatagg aaagagcgct  81420
attgtttttg agaaagcaat catgcaaggt aacacaatat gtgattgcct agtcttcaca  81480
gaaaaacgag ggctcattgg catagaaata aaaactgaac gtgactcgac aaaaagatta  81540
aataaacaat tatctgatta tgaaaaggtg tgcgactacg tatatgtatt atgccacgat  81600
aaccatgtac ctaaagtaga gcaaatactt gctagacata atcataaaca cgtaggtatc  81660
ctagcttaca cagagttcat gggagaggca atgttaggtg agtataaaca acctagccgt  81720
tcccctaaaa aatcagctta tcatatgtta aatatcttgt ggaaagaaga tttaataaga  81780
atgcttggta cattcagacg gtatggtgat agactagaag ctaatggagc taaggttatg  81840
aaaacaaaca gccgttctgg tggagtatct ggactttatg ttaaatctac aactgctaga  81900
agaatgacta aacctgaact cattaataat ttaataaata gagtaggcgg taccgaagag  81960
gctacgagag tgttctgtga tgtgtttatc cataatagga atcacccaga gaaagcaatt  82020
aagttaagac attttaaagc aaaagagaat aggggtgacc tagatggggt ttaaaggtgc  82080
aaaatatggt tcttggaata ctgtagttgg taagaactat gtgggtactg ggggcagaac  82140
aagtggtagt aacacaaaac ggctgtccac aaaaggctac taccaagtag gatttgttaa  82200
agaatatcag aacttgacag aaaaagatat tatgttaaaa ttagagtatg gaaaagactt  82260
agtgtctagc tacactggtg tacctgcaga tatgattaag ctacgtaaaa agaaagagga  82320
gcaaactcta gcatctttag acacagttta ttatgttagc attggtaagg aacctgtagg  82380
taagctgtct atacgagctc agagacgttt tagagaggta gggttaacat ttatatacct  82440
agagaagaac tacgtacaga ggaagcttag aggcggtaat gtacgtagtg taggatatac  82500
taacgcaacc aaatctcaga aacgtaaagc agatagacgg aagggcaata agtctaaaac  82560
aactagatag atggaggact actatgagta tttatgatga gctaattggt aaaagtgtta  82620
tagccctaga atatgcggag gatgggtgtg aggcaagcct tgtactaaat gatgggtcat  82680
gcttaaaagt atcttgtaac ccagagccag actgttgtgg gtataatgat tttgaagtta  82740
ttctcccaga tggttttgat ttcacagata acattattac aaaagttgaa gataatagtg  82800
aagaatgtta tggcggttca acagttagga taggcatttt taccaatgat gcacggatag  82860
ttattgaagg ggactacgga agtggttctg ggtggaacta tggagagtat gtagacgtag  82920
aaattgtaaa ataatttact attagatgga ggtaagctat gcttaaaaaa gggaaagaag  82980
taacactaag aaaattttat aatattatca cagataagga atcagtattg ctaggggcac  83040
gctacacaag ctcaataatg actacagata ttcctattac aacaactttt gaagatgttg  83100
aggtagacct taagaaagaa acagttgcag gaactatttc attcagacca gtaggagaaa  83160
gacagattaa tgcattaagt ttactaaaag aagcaagcac agcttatggg ggttacggag  83220
agttcctaga tgatactatt gagaaacctt taatcaatag tgattttgca gtagatgtta  83280
gcctagcaga ctctgctttc tctaacctac aagagattcc atttaaccta tatatgtcct  83340
ccccaaaagt tttttataca gaagtatcaa ttagagggcg taaacatatg caatatgtat  83400
tagaggatga gtcttctagc ggtgtaacaa gtacattagc actggtattc cgtaaaaaat  83460
tgtatgatgg ggaaacattg ctaggtgtgc atacttacac cgaagcacta gcaagagtag  83520
agggaattaa agtgttacag tttatcgcaa atggctctgt actagaacaa gtaatcggtg  83580
cagtgtctgt tttagggggt agcacaggaa caaccctgtt ccctatgttt gacgatatgg  83640
tgatgcaatt tgtgatgatt gagtctgttc cttgggtgca catttcttgt gatacaggag  83700
caattgcttt taaggaagaa gacatccgca atgtaaccat taagtcagct agaccgggag  83760
aatataaggt gactatctac ttgctagacg aaaaagttac attgttaatt ggataaaatt  83820
ttaaaggaag ttgacaatat atgttgactt cctttttgt atgtgctaag ataactacag  83880
ttggataaaa aaaaataaat ggtatagagg gagagattta acatggacta caaaacaaag  83940
gtatatgtag gagcgcttag ttggttaggt actttaggag agaaacgata tttagggcaa  84000
atgcgtgatg tattagctgt gtacgagcta ggtagtcgat acgcaggtta ctatacagaa  84060
gatagcgact atgactatat ggttgtatac atgccggctc cttatgattt aatgcatcct  84120
acaacaattt ataaacagga aacagagatt gatggaaata aggtagaggt aaaatatatg  84180
tctatcgtgg aatatgttta ccgtattgaa aatggagatt tagaggcttt acaaatgtta  84240
aatgccacaa gctcccaaag tttcttcgga gagcctattg aaggtattga caataagcgt  84300
actcgtttag ttacgtatat gaaagaacta gaatacagaa gagaaacatt tacttattta  84360
gcaccagaga agttgtttag aggaattaat ggtcgtatta aagccacaaa aacacgtatg  84420
gataaggcta ttgagaatga cgatatggaa gtagcggtaa aatgtgctat ccttattcgt  84480
tattttatgg acttattagt tgtgctagcg gacggggaat ctattcgtga aggtctcacg  84540
ttctctccta ttattgcaaa tatcattaga gagtttagga aagactgtga gtcagcacag  84600
gctaagacac ttatcaatac tgcacaagtg ctattagagg cggatagaga agagatttta  84660
aatagtatta aagaccatgg gttatcagat ggttacgctc aatcagttag acaatatagt  84720
ttaacaggtc gattgataga tgtactatta ggaggatatt atgactaagt tagaacaaaa  84780
taaagaaatc ttagatatat ttaatagaaa aggaaaagta acagataaag tagaagaatc  84840
tgccaagatt atgctagaat tagaccacga ttatgacttt ggtacagggg acattgctta  84900
tacagagcgt ggcacagata agaagggacg tttctattta gaaagtcgtt tgtttattca  84960
taaactcatg ccctatgggt tcattttaaa cgctgtagta agtaaagtac actatggaga  85020
ccaagaggag accttagaac gagaggtatc ccgtgtatat gagctagagt acaacctaag  85080
agataaggta gctgtgctaa ttaagaacgg taaaccacta aacttctcag aaaataacat  85140
tagtaacatg ttttctgggc acgtagcaca gaatattctt gaacaattag atacaatgtc  85200
tggttcagat atgtatgtat ctgtgtatga acgagttagt cgagttaagg atgaacaaat  85260
tggtaaagta tctcggttct ttgatagatt gatgaagtac aacaagattg aattaattta  85320
taagagtggc gttcctgaag gctttgcttt ggcttatgct tatcgagtag ttgttgtagg  85380
agaaggcaaa gtccgtaatg aatggtacga acctgtaaag agtgtggact atttagataa  85440
ggaacaaaca aatccggcta aacacctagg tattccaaag tctatcttta agattatttg  85500
tgaaggtggg ttagagtgga cattctacca aaaaatagct agtcgtttcc ataaatcatt  85560
agttaacaga agtactaaca aaactcctaa atcccccact gctatgaaga agatagagaa  85620
agagattgct aagttacaac aagcctatgc tcgttttggc ggggtactgt ataaccttta  85680
tcagtttact aaagagctag atgaacaata tggtatctcc catagtaagg atattatcga  85740
aacagagtgg gaatctatat acgaccatat tattgcagga gtagttaacg ataactataa  85800
tagtacaact gcttatgata tttctatggt tgcaaaccta gatttctaca gaactgttcg  85860
```

```
ttatctatac tatcgagtat atgttgagca agggcttact tcacaagcag aggctagata  85920
cacatacaga gactacttga gagcacacca ttatatgaat gcggtacctg ttaagtaccc  85980
taaagctctt aagactgctc atgacattat tattatgaat taccgaacaa tgaaggataa  86040
ggtattgaat agtaactttg aaagtagtgt agctaaatat aaatatttag aagaagtatc  86100
agttagaggt ggctatattg ttaaggtacc taatagtgtg gaagacttaa ctaaagaagg  86160
ttctagttta caccactgtg ttgctactta tgctcatcaa gtagcagaag gttctactcg  86220
tatcctgttt atgcgagata agacagagcc agatactagc ttagttactt ttgaggtaaa  86280
aaataataaa ctagtacaag caagagggct agttaaccgt gacttgacaa ataaggagca  86340
ggagttccta gacaaatggt tagttaaagc agaaattggt aagtattagt ttgcctaaaa  86400
aggcggaata tggagtgtgt atagaccaat tcacaatgaa aaaagtacac taaacagttg  86460
ttatttcatt attaggtaaa acaacttatt ttagatagct gatattgacc aacaaatatt  86520
tcataatgat ttagctatta aagttacaaa aaccctacta atacgtgggg tttttgcttg  86580
tttcaattac atatgaaatt ttacagatgt tctgctatat tagttacaga agctaataaa  86640
acaaagggtt tcgaccctta aaaatgatat ttcatataat taaaagttga aggagtttat  86700
aactaaaatg gctaaaaaag aagtaaacaa cagctcagta ttactgaatc tatacaataa  86760
taaattgctt gtatctaagg tagacgaggc gttagacgag ggtaaaccat acgatttcat  86820
tattgctttt tgtaaagaga agttcgattt tgaaattaat aaacctgcat tatctaggta  86880
caaagagaaa cgtagagagt ctttagaaac aggagtagac ttggaatcac tacttgacaa  86940
acgtagaaaa tcaggtaaaa ttattgatat taagtctaaa gaggtaaccc cacttcctaa  87000
tgaaacatac gataacacat ttggacaagt ggaacagata tacaatgatg tagaggtgtt  87060
agatacaatc atacaaaaag gttttaactc tctaaaagag gtagactatg ttgaagcccc  87120
acttgctatg aaagcaattg aagtaaaagc taagataaca gctaaccagt tccaaggtct  87180
aagtctaaca ggtctaagag agctaagatt aagacagtct gctaaagaac aagcaatgac  87240
tgagattatt ctacaattta ttccagaaga acagcatgaa gaagtattca atgcaattga  87300
atcagcagag aaagagttct atgaaaactt agatttaaca gaggaagacc aaagaatcac  87360
taaagcgttg caagcatcag gtatggatat aatttaggag ggctataatg gttgaaaatt  87420
tgagagaggt aaattataaa acattaacct tagaagaaag tttacatgca ttacttgaag  87480
ggaagaccct tattgtaaaa gggctagaac aaagacgtaa gttagatgtg ctagtaagga  87540
ttttctcaga aggtgttgta cctgttacgc agataagtta tgatacaacc cctgcggatg  87600
gttattggag aacaggatat tggcagatat acgatttgcc aattaatgcc cttagcacat  87660
acccatgttt tatctatgat gatttaaata cggatgaact ccctaaattt atgatagggg  87720
acactgttta ctacacaagt aaagaggact ctatcaaaga ttccgccatt gtaatcagtg  87780
tgtacaaaga cgatgttaac aataagtggt actacaagtt aagtagagac aacgaaatat  87840
atgcagagag tgagattaga agagacaggt tataagcctg cctctttttt ttttaaattt  87900
attgttgaca aatatctata actttgttat agtataaata tcaaggatat tgataataaa  87960
ttttggaggt gccatgatgg caaatatttt agacacatta aagtggttag ataaagggga  88020
caaagttact attgaatttg ataaagagcg gtcgaagtat gcaaaactga ctttgcacga  88080
ttcatcagct aagacaaata ttgtccgtaa cattgttttt tatgatttag acaaaggagt  88140
gtatgcttac actggtgaat acacccctgt atgggataac ttattagatg atatgcgtaa  88200
gacacaaggc gcaggacctg aaattaagac tacaaaagta aatcagttag ctacctatga  88260
agatgcctta aagtttattg aaacaaatgg tacgttttat gtaattggtg aggaagtaat  88320
tgttaaggtt aaagatgcaa aagagctagc attgatgtta atgtacttta gagatgctat  88380
tgaagaacta agaggagaat acgaccctaa aaaacatcat gtagatatga caattgaatt  88440
atcaaaagat gttttgaaaa aaatggcagt acctagacat gaattagact tatctttagg  88500
tggcttaatg agagctgtat cacataatgt tggagaagac ctttttgaaa ctcttgggtt  88560
tgactacatg aagcaagctt gggaagtctt agttaattgc ttgtcactag acactatcca  88620
tgaggtacct ttccgtgtgc tagacgaatt agagaaagta acagatagca tgtctactac  88680
agaccatatt gttaccttgt atgccggtag agaacttaaa aaattctatt cagaggaaga  88740
gtactttgat gtaatcacac acaatttagc tgatgtgatt atggattggt caactatttt  88800
tactacagct gttcttaata atacagaaga tgatgaacac cttaaagagt tacagcttaa  88860
ctttgagaga ttcaagctag atgtagcaga ggttctatta ggtaacgttg caagacattt  88920
actatatgca ggagttaccg atagctttaa cgaagttaac cattatgttg tcggagcagg  88980
taacctgatt agaacagaag gtttgattag aatagaagag ttaactggaa cattagacaa  89040
ccctaaagat gaagatagtt ctgaaacaga taataaagag ttactagatg acatctttac  89100
aaatacaggt gatgatggtg ttgaagactt tacaaaagaa gtagacgagc ttgccatgtt  89160
tgagaacgaa catgctgagg aactttttgga agtcaataac aaattaaaag acaatcaaga  89220
gttattacgt aaaactgtgg aggcgatggg tatggcttct tactctacta ttgattcatc  89280
atttgaacaa gaggaagaaa cagatagcaa ccacacagag acttgtgagg ataccagagc  89340
tttccaaatg ttaagctatg cagtacgttc aggagacaaa ttacttgaac gtgtagagaa  89400
ccacccacaa actgaaaaag ggttgaaaat ggctaaagat tctctaaaag agtttgacca  89460
tacagtgaaa ccagaattag aagcttattt aaaagcagaa gagctagcgg aagacgttga  89520
tagacatgca attgtaacta caattatccg tatcaaggac actatggaag cagatatgga  89580
cggctgtacc gacccaatag agcaaggttt attctacgca ggaagcctaa atatgttaga  89640
agaaatggaa tcattgttac gggctagcaa tagaggttat ggttgggacg taacagctat  89700
ctatcttatc ttgtccattg aactagctta tgggacttac gggttgtctg atttagactt  89760
tacaattaaa aataaagagg aaactcgtaa agaagaacaa gatgcaatta atggtattgt  89820
aaacttctta gccaatcttt taaatacagt actagaagaa gaatcagaat cagaagaaac  89880
acctgtagta gtcgaagagg aagaagagga taaggatgac ttctcactat ctacagaaga  89940
cactgctaag ttattggcag actggtcaaa tggtctacct acgtatgtcg ttactcgtaa  90000
atacggaatt agtatgggag ctttatactc tatcttatat gcaaatgggg cagacgttaa  90060
atcttctaaa gtagcagaac gagtggctca tgtggaaaat gacaaagata tgttaaacgc  90120
agttattcga gactacaaga atggtactcg tttagtagat atttatacta aatacaaatt  90180
atataaaaat ggtttgttct atcttttaga taaatatcga gtgccacgta gaggacgtac  90240
aaagaaataa caatgattaa ggtagtggtg ctcaactact acctaatctt ttattaggga  90300
ggaacttaat tgattctttt tatatttagc attattacaa tgctatccat gttcttacta  90360
tatttgtttg ggatggcttc tgtggctgta atcaaagtag ggtttcttat aggtagtcaa  90420
aacgatatag ctaaaggcat acactcttta cttttcacag gtattgcact tactgtagtc  90480
accggaataa ctagacagtg tttactatta ttttaaaaaa aattggagga tttagcatgt  90540
tgttttttat tgttttagca gtatttatag gcgggcttgc tttatgggga atgtatgata  90600
```

```
gttatgggta cctagactgg acttcatggt tatttagtat tgtggtaggc tctgctgtag  90660
ctactttttt cacactagcg gcggttggaa ttactttcga tgttgtacca agtcatgggg  90720
taacgaaaag tcatgaatta caccctatct atgagaacag taaagtagtt gtagaggcta  90780
aaaaagacca gtttgagatt aacgtagatg gcggtttggt agctattgat gcagaaggta  90840
ctactatcct atctactaaa ggagaggtta agcctaaaat tgtgtttaca gagaactata  90900
taaacaacaa ctggtggact cgtttcctag gtatagcagg taaggtaaaa gacacttcat  90960
cagttcttta tttagactca gataccttag tgtacaataa gccggaaaag aacagtagcg  91020
caccagattt aaaaattaaa taaataattt agaaaaaggg gcttgcataa agtctctttt  91080
tatgttaatg tgtatttata gataggaggg ctactatgga aggtgaagta gtatacttag  91140
atgagtttat gaatttttta actgatagtg gaataaatac tgatgatatt aacgtagtag  91200
atgatagaca ggagggctag tatgtcttat acaaaagaag cattagaagc tagaggctat  91260
cagtttgaca atatgtctat gatagataag atggatgcct tgttagaact gctagaggaa  91320
ccagaatttc gagaaaagat gaaagaagag tacgcagagt tctctaagag gcacaataac  91380
gatgaagaat gaaaagttag agtcttacct tatgaaagag attgcaccta ttttagatga  91440
aatagagatg agtgaagaat tgataaaggg aatggagaac aacaacccat ccgatacggt  91500
tacagtctct ttttccaaag aagaagtaga catactctta gcaatgttag accttgaggt  91560
acctagatta gacagtggtt ctgaattgtt tagccctaat ctggtaaggg aagctaaact  91620
acaattaatt aagaacaagc taacttcaaa atgatttctc actagaatta attagtgaga  91680
aaaaaattaa ataaagctat tgacaaataa caaaacatga tgtaaactaa gtttataaga  91740
taaagaagag gagagataca catgaatgaa caaaagaaag tatatgcaaa attaacagag  91800
gacgaggcag tatttgcttg tgaactagga gataaaatta aacaaattag agagagccaa  91860
gagctatctc gattagaact tgcaaaacga gcaaaagtag accactcaac attaatctta  91920
attgaacaag gtaaacgact accaacattg cgtattatga tgaagttgag caaagcacta  91980
caccgagaat tagctattag ctttacagat taaggaggag gtatcatgag agggagccta  92040
gattattaca actatttgta ccaaacaatc gaaaatcgac ctacggagga gctagatgtc  92100
ctttatgacg gtctttataa aaaagccggt gacctgtttg caatagataa ctttcaagga  92160
gttaaagaag gcagactaat tttaaaaata ttaaaggcta ttagagaaga aattaatagt  92220
agaattgatg aagaaattga cctttacttg tataatatct atgacagtat atcagatgaa  92280
gacaaacgag taaattggct atatgaggtg taggtatgtt tagtgttgtt aaggctgaca  92340
gctatgttaa atcagacata gaaatgtatg aatttaagaa tgtaaaaagt ttggcattga  92400
ctaagaaaga gaaagaacta tggacaggca aaattgctaa atatgttaat gagtttattg  92460
taaatgctta tggagactac catgggaata aaatacctga aataaatgtt gtaatcaatg  92520
gtaagctaag aagaacccta ggttcttttg tccaattcac taacacaaac aaacactgta  92580
tagagataaa tggtaggttt gttaaagaag ttattctatt acaagaaaca cccttagctc  92640
aaagagcgct tgatatttta atggatgtag ccagacatga agctatccac tatacacttt  92700
gttatttaaa tagtttaagt ggaggagacc taccaacgtt caactaccat gacggtgggg  92760
aggactttga aaaagattta tgtttgacag gaacttcacc tagtggtgct acgaaagaag  92820
agtatattta tagttctttt acactaggag ccatcagatg ccgacaccat agtacttgcc  92880
ctgaatgtgg gttggaaaca tacatgtata cacgaggacg gtactattgc tataatgggt  92940
gtgtagggga taacggtaga aaaattatat ttagaccaca aggtgatatt gcaatttata  93000
ttgatgaacc aaaatctaaa gctaaaccaa aagtagagga agctctaaaa gactataaag  93060
gagcgttaaa gctaccttat acaggtacgg aagaaataaa ataaaaaaaa atagttaaat  93120
gtattgacaa ataacaaaac atgatgtaaa ctaagtttat aagataaaga agaggagaga  93180
tttattatgg catacgtaac aaatattgat gtagtagcag atgggttaga tttgtataat  93240
gggaactatg tggtagaacg aggtcaagta gttactttta aactacatgt agcgacatgg  93300
aacaatgagc ctacacccga aaatgcttat gcgattattc gtaataatgg ggtagattat  93360
aagagtaaag ttgatgaatt tggcaatgca gaggttacct tcccagttaa tggtcgtcct  93420
gaccaagtaa caactagcat ctttgcatta acttctggat atgaggggga tatgcctcgt  93480
gtaatgtcag ctatctttag tgacgaaaca gaaattaaac aaactgtaat gaacgttaca  93540
gcatctatta atggggagcc agttagtcgt gaaggtgtat ttttagaacg agaccaagta  93600
gtcactgtag atgttaaagc aacattatct acaggtaagt tctgggaagg tgcacaggta  93660
ggtgtgtaca ataacaacac ggaatactta ggtgacctag atgcagatgg ttatggttca  93720
gtaactttcc aagtaaaagg aaaacaaggg atggacacat cagctatcta cgtattcgtt  93780
aaagaccatg aacgagaagc tacactaaca gttcctgtga agtttactaa tactactgtt  93840
actacagaaa cttctacaga agaatcgtct actgttgata cgactacagg aacagaggag  93900
tcttctacta cggatacaac cactgtagaa agctctacaa cggattctac gtcctctaca  93960
gtagattcta cagaaagtac agtagaaagc tctacagagc aaacagtgac caatgaggac  94020
acttctactg attcaggagt agttgaaact acagaaactt cccaagtagc aggctacaca  94080
gagtctactt ctagttctac agagtctaaa gaagttaagg aaactcatac tagcactaca  94140
gaacatgcta aagagttacc atctacaggc acagaggtag actatgggct tgttgggttc  94200
ggtggtgcaa cattaacagt tgtggtggca ctagtagtta aaaaattgtt gaataagtaa  94260
gaaacacaat attgcgaccc tcattaattg gggttgcaa attatattat ttttttttaaa  94320
taaacctatt gacatttaac aaactataag gtaaactaag ttcataagat aaaggggggga  94380
aacaaatgag tcaagtaagc aaacatggag aaaaacgtgt acgtgaacgt gtaggagtga  94440
ataagagctc tgtagaccga caatttgagt tagctttaga acgaggatac agacaaaaag  94500
agctaacagg tcgtctaaag aaatgggtag tatcaagagt atttaactct aagtaccctc  94560
aaacatgtat tttatataat ggtaaatgct tcattgttag cagtgaaggt acactagtta  94620
ctgtgttaaa catcccaagt aatttactaa aagattttgc aaaattatct aagaaaagag  94680
gaaaataaaa tggatattat ggatattgag tttttagaag aacataaaca attagtaaaa  94740
gaacatgtag aacaagaatt aaaattaatg caccctctta agaagttaca agtaatgaca  94800
gactggttag gagatacaga agacaagctt tctcaaggag acttagatta cttcaatgac  94860
ttaacagaaa cagagctaat agaggcaatg gatgctagtg aaattgtaga gtcttattca  94920
gatgtcttgt tagattttat tgactactac aatattgatt taactggttt agaggaacag  94980
ctaggtgtgt aaccatggat aaggctgaaa aggtagataa cattgtaaga caggtcacag  95040
gggctgttat taagacaact gcaaaagtag cttttattgt ttttgtttta acctttgcag  95100
gtgttttagt aggttattat agttattcat ttttaacaag tgcagggtgg tttgccttac  95160
ctatgatatt atcagtagat ttgctatatg ttgcggtact gttaggcggg ctagccttta  95220
tatttgcaga ggtctacaaa gtagttttag aagtgaaaaa gatagttaaa cgaggagggc  95280
aattatgagt aataaaacat tagaacaaag agtaatagat gctaacaaag agataaacga  95340
```

```
taagcttaac gaatcatcaa ttattcgtaa acaaattgaa gaattagagg aacaggaagc  95400
catcttacta tcagacgtag aggacttact tgattactta gaaaatattg gagtagacct  95460
ataggaggga cttattatga ataaaaaagt agaggaaatg acaatggaag aaaaagacaa  95520
agcactaatt gcaatgggac ttattgatgt aacgcaggag gcagactggg tagtattagc  95580
tacttgtgaa gaatgtagag aagagtacga aggagaggag tacgaagaag ggactgtgc  95640
agagtgtgaa cattgtggag gagaatactt tatgattgag acagctctcg agggtactcg  95700
ttgtggacgt tgtgatgact actttgatat gtgggacgac tactttgagt ttgagaatga  95760
aggtaaccca tataaagata aacatatctg tgaacattgt tatgaagaac tagtatctat  95820
gggaatggaa gagaaatttt aagatactac taagaaggag acttaatcat gaacgaatta  95880
gaagaactta aaaatacact gattagacaa aaactttcaa tgttggagag ttacgaaatg  95940
agagaagcat cattttggat aatgtttaat gggatattac gtgtcatcat gtcagtagct  96000
gtcatagcct ttgtaaacta tgctaagcat gtaagaccag ataatgtagc cacatggttt  96060
ctagctctga tttgggttat tttcctagca gaaggtatta aaggtgctta tgatgctgtt  96120
gcatttggta ttcaccgcaa aaaatttgct aaacatatta aaaatatgcg tgggataatc  96180
gcaatcacac aattacttat tgaagaagac gaagagaaat taaaaggagg caagctagat  96240
gagtaaagat gagaaattag ttgagtggtt tgaagttgcc ttaatggtga ttatgtggtt  96300
gcttatcacg ttcagtatct tatacacaat agtttcctta cctttcatgg tacacgaagg  96360
ggactggcta gggattgtgc gaaacgtact actggacatt gtagtattgg caattggggt  96420
tgtcgctaca tggttgcaat taagatttaa aaaaggaatg gaggaataat taatgggata  96480
tttagagagt gcaattgaag aaattgaacg agtactacta ggaaataaaa gtcgtgacac  96540
cgaagaagtt tatttaaaca atgcaattcg gtatatcaaa aaagagttaa agaaaaaaga  96600
ggtagagcca acgtggttaa atgaaccaca gacattgttc cttaattggt ttaacgaatt  96660
atacgcagta ggtggtttaa ctcatgtaac agaggcagta ggttttttag aatccacagg  96720
aggtagaatg aagtatccag aagcatattc tgctttcagt aatttaagtg agaatgaatt  96780
gcttgaggtt tacagtaaat tttatacagg gttattctta aaagcacaag gggtgaatt  96840
agaatgaact ttcatggtaa agtatttcat gataaagtat ttgacattct ttctcgtgat  96900
taccctgatt ggcagaggta tcagacagag aaacgaccac atcccaatga gcttagaaaa  96960
gactttgcca ttgatagtac agatagtaga tatgaagagt atgttatggg agagtttaat  97020
gtagaaacgg ctagcggaga tgttaaagta tacgcagtag gaattagaag agtagttcat  97080
aaaaaagctg aggaggagta aatcaagtgg agtacacaga gaaagacatt aaagaaggta  97140
tgaagttacg ttgcacagat aatagtaatg taggttactg ggaagttgat aaggtttacg  97200
aggtaacacg taataaagac cttggcttag ttatcgcagg ggaaggtgaa aggagtcaca  97260
gaaccgtaaa gtatatttta ggggtgttaa atggtgacag caaaattaaa tttgaagttg  97320
tagaggaaaa gcctgtacga tttgctaagg taacttgtgt ataccctcct gatagaggtc  97380
ttgtagaggt tgggcattgt tatgaagtgc ttaaagagtt ccctacagga agtgtgcgta  97440
tctaccttaa tagtaaacta gggaaccatg agttactccc agaccagttt gtctttgtag  97500
atgaaccatc aaatgatgga gaaaaagacg tagaagagct agatgtagaa gctaagatac  97560
tagccaagat tgaacagtta acagcagaag cagaacaact gtttgctaaa cgtgaccgtg  97620
taaatgagca agcacttaac ttaaatgcaa aagctcgtaa gttagaagaa tctttagagg  97680
tactaaggga gtacatgtag ctaagtgttt ttatgattac atctattaag gagatgagag  97740
aatgatttat tatattaatt ttttagaaga tttcgcatca agttggagtg cagataagcg  97800
ttatcgtgtt cgtagaatta tgacaactgg tagctacgct attattgaca actatggtca  97860
tgtcagattc agcagtgaca cagcacgagg tgtccttaag aatatagagc aggagtatgc  97920
cactcataag gttgagctta cactagcaga agaagaaaca acgaataagc ctaggtttaa  97980
agtaggggaa cgagtgaaag tgtctaatga tttacaggca ttcgggatag aatataagac  98040
tcacataacc tctaagatga tgggctgtgc aggtaatgag gctactatta cacgtgtttg  98100
ggggagtaac gtacgctact ttattaacat cgatggtata caccaagatt ggtgttggac  98160
ggaggacatg ttagataaga ttgaagaaga acctacacta tctattagat gtgttgaggc  98220
agttcatccc ttttggacaa aaggtaaagc ctacgagata aaccttacat ctgatggtcg  98280
ctatcgggtc tgggatgacg aggaagatgg tagcagtggc aaatccataa aagaactact  98340
ggacgttatc aatagtggcg gtaacaaatt tgagctacta gatgaaacac cctcagaagc  98400
agaacctagg ctaaaccatg ctatatctga cttagagaaa atagaagcta agattaccgc  98460
tttatcagaa gagtcttttc agctattcaa taagagtgaa gagttaagta ctagagcaat  98520
tgaactgcaa gatgagtcaa tagctttaga agaagcattg tatactatta aacaatattt  98580
ataggaggag atttaaatgc gtaaaaaatgt aatttgtaga ttagaatgtg tttcaaaaga  98640
caaagacaac ttaggtgaat ggactgtaga taatatttac cctgtgtttg aatcagaact  98700
aggtaaagta tatatcctcg atgatgaagg taccacttgt tccagagata gcgtgtctct  98760
tattatctct agtatggcta gctttggggt aacatttagg gtagcaaaag ataaagcaga  98820
agaccctatc cctagcaatc cacaaagcag tacatcatta gaaatagtta aagggtatga  98880
acacttagcg gagtttatag actcattaag tagcaaccaa cgtgtagtgt ctcactcagt  98940
agaccctaac tctcaatggc actatatcat ttatgaaact aagtcagctg aattgggcgg  99000
agtaacccta gaggaattac tagacacact agtgtataat gtacatgttg tagtgatgga  99060
acgtagtaag agaacatatg agccactaga aaatcacacg tttaagtggg aatatggaac  99120
aaagaatacc aaggattggg aaaaaattgt acctttatta ggttgcaagg tgtttaatac  99180
taacctcaat agtaacagag ggttccatat tactattttg aaataaactg ttgacaacta  99240
ctatagtcca tgctatagta ggtacataga taaaaaacaa acaatattag gaggtagcat  99300
agagtgaaag aaacagaaaa gaagtatagc agagagtata aggggctaga atttgaaatt  99360
attatcactt attaccctga acaagacatg tattttgtaa ttgtaaggaa cggacagcac  99420
cgtacactaa ctaaggttac agggaaagag tggggaatga gccctcatac agaggaagct  99480
gttattgagg tagcacttga tacatgctac acctatattg aaaatcaaga agcgcaaaat  99540
aactagatta aggagggact atgatggtag gagacttcat tttatgggtt aaacaagcat  99600
ggaaagaaac attctgtatt catgactaca cggttaaagg tgtatataaa acattagata  99660
gtcatgggta cttaaagtgt aaaaagtgtg gaagaattaa ataggaggac aacaacatga  99720
accagagaca gaagactaga caagaaaata aatggtttga ggagcatggg tatgatacac  99780
agcaaccacg agaatgtatt gagtgcgggg ctcctttaag ttggaaagat gagttacaga  99840
aaagtcatgg agtgtgtagt gagtattgtt atatgagaag tgttgggctg tcgttatcag  99900
attttattta aggagatgaa acactaatgt ttaaaaaaga taaaaaagaa gaaaagactt  99960
atagagaagg agacctcctt aaggctgtag gggttacta cccagatgct aggttgagtt  100020
taggaatcac atatccattg tataaaacca ccaatgaggg ttggtatatt atcaataacg  100080
```

```
aaggtagtcg ggtaacctta atcgaaatgg atgctttagg cattgactac gctgtgatgg  100140
aagaaccctt attagaatta aaagaaggag acccattgct agtcgtgtcc gaccttaaga  100200
gaggtgttcg aggcttagca ggtgcagaag tacagtgttt aaacattacc ggtgaaatgg  100260
cttcactagc aggtacagtt gttcattatg ataaagatat gagccatatt gcaaaggggc  100320
tgttcactgt taaagagaac gattcttatt ggtgtgtagc gattgctatt ccactaaata  100380
aagtagctga ccctgatttt gcattagagc atttgcttgc tacgttaaat aaaaaagcct  100440
ctactaaacg tctggtattg aatgagataa aatatgattt aaaccttctt cacgaagagc  100500
tagacgaggt gtccaacgaa gtagagaagc taacaaaaaa cattgaaaca atctataata  100560
acagatagga ggtacttaga tgagtatgcc gagtgattta gggaaaacat taaagaaacc  100620
tattgcaata aataagaatc ctgattttta tgaattagcg gtaggtggta aagttatcta  100680
caacgaagaa gtaatggaga ttgctaaagc tttctctaat aagaagacca agtactacct  100740
actaaacaca cgaagtaaca aacaagtatg tgtaccagtg tatcatgtaa gaccttatga  100800
tacccaagta gagggtctta aactaggtga tgtcctagat gctatgcaca ttatgacaac  100860
tgtaacgtta agggcagtga acaagcacgg gtttgttgtc gatgaggata ttattgaatg  100920
tttagtagat gacatcccag aaaatgcgct tattgttact agtgaggtat cccgtattca  100980
gccagaggat tttggtaagg taactattga ctattttgtt tagatatgtt aggatagact  101040
taagatagga taggataaac ttaggatgcg cttttgttta ggataggctt aggataagat  101100
aggataaact taggatagac ttaggataga cttaggatgc actttggttt aggataggat  101160
gggggatata actatgagtt acgttaacga gtttgaaaca attggagatt ggttagatag  101220
agaaatttat gatgtgttac taagagatga gcatgatatt gaagaattag ataattgggg  101280
aatggctttg tttgcattaa gtgaaggtta cgttctaaca gatggacttg acaaaccatt  101340
cctagagtta actagagaag acctagtagc aggctacaac cactttaaag aagagctgaa  101400
tgggtggtta cgaggaggta aactgctaga agtctctgat aatttatcta caattcaggg  101460
gttcagtttt gaccatgacg atgtttttatt cttagaggat aacaacaaag cttatgcaat  101520
gctagtaggt attatcattg aagcaagaga cacatataaa aatggtttct gtaagggtca  101580
ctatgtaata ccttaccaag attgagttag ccttatggct agctttttct tttaccctaa  101640
gtagcaggct acaaaaatct tctaagtagc aggttgcaaa atcttctaag tagcaggcta  101700
caaaaatctt ctaagtagca ggttgcaaaa tcttctaagt agcaggctac aaaaatcttc  101760
taagtagcag gctacaaaaa tcttctaagt agcaggctac aaaaatcttc taagtagcag  101820
gctacaaaaa tcttctaagt agcaggttgc aaaatccgga tgcgcccggc tagcggtggg  101880
gagtcaagcc atgcgggttc accttaatag ctaccgtccc cagattgtcg gtttttctta  101940
ctatatatag taagaaaaat aatttaaaaa aaataaactt ttctattgac aaaaaacaaa  102000
agctagtata atatagagcg tgtaaggaac aacaataata aaaaaaataa agataaaggg  102060
gcgctattaa aatgaacaag tataaattta cctatgcaga cattaagaat ttaccagagg  102120
aagaaaaaga aaaagaatta aaaaatcggt gtggtgtttt agcggtagag tgcttaagca  102180
ctaaacagct acaaaagaaa aaacctcgat ttatggtttt cttaaatacc gttatttttg  102240
atagtaccgc agaaacaggc ggacaatacg caacggcaac cgttaaaacc gaaccgatag  102300
gggacggacg ttttcgagtg tgtgacggtt ggggacagct ttctaatgga attattgaac  102360
tgttaaaata atttataaaa aaaatattga caaataacaa aagataaact acaataaact  102420
tgtcagataa agaagggaag ttatgaacat gaatgaatta gaagcagtga aagaatggaa  102480
taataaaatt gaggaacaac aagaagtgct aaacaaggtt attgttgctt tttataaaga  102540
aattgactta aaggttaaaa tggtaaaccg tggcttgcta gggcagttac cagcttttaa  102600
cgaactaaaa ggaatgctat caggtatcga gctaacagca aaggttattg cacccgataa  102660
cgtgctgcct attacaaccc acaacttttt agaatattta tttctagggg ataacgaaca  102720
acgagcatac gcaaaagaat acctagacgg ctttttaaaa tcagtagaat aaggggagga  102780
aaattttcct cctttacata aaaaaaagat tgacaagtta aaagaaccat gataacatat  102840
aaatgtagac aagggagggg ctttacatga tgaacggact aaaaaaactt gtgaaagcta  102900
ggcaatacaa gaaagaagta aaaaaaatta tcactatgca aaagaaagca ataaacgaac  102960
tagaaacatt aaacaaaaat ttaaaattaa ttaatcaaaa ctattgacaa ataacaaaag  103020
ataaactata ataggtttat aagataaaga gaggaagtta ttgacatgac agaacaacaa  103080
tttaaaaaag agcatttatt agaaccaaca gaatggcgta gtgggggcta cttagacact  103140
agtttaattg accaatcaca atcttattat attgagtcac gtccgagagt ctacggcggg  103200
tgttacgttt accaatatgt tacaatgaaa gatggcacgg tttacgagct ttacagcatg  103260
acggcaagca ctaggggaat tgttgcacat aactgccacg ctagaaacgt attgcaaaga  103320
gatgtaaaac aatacagaga tagcgccatt cattattaag gaggggaggg ctttcctcct  103380
ttacatagaa aaaaaattgt tttatctatt gacaaataac aaactatagt gtattataaa  103440
tttataagat aaagagagga agttttaaat atgaaattat ctaatattat tctagtgggg  103500
ttgcttgtta gcgttgtact actttggggc taccttagca ttatgatttg cttacaagtt  103560
tttagagcgt taggcggttg ggatattaga acgttaacgg tttgcagtgg tttgctattt  103620
gcctatgttt tcggtttaaa aggaatttgg gaacaaggga cagggaaaaa caaataaaaa  103680
aagtttataa aaaactattg acaaaaaaca aaatatagag tattataggc ttataaagat  103740
aaagagaggg agttataaac atgaaattga acgttattca tttactattt tgcttatttc  103800
aagaacaaga aagctattct attttaagtt acgaatcagt agacgaattt tattctaggt  103860
taggttatga cttagagagt gagtggctac ttagggactt aggtattaat ggaacaagtg  103920
acttggtaga gttgctaaca gattacaata atttattaga gaatgagata acaaaagcag  103980
tcttttctga taaatggtta taatttaaat aaaactattg acaaaaaaca aattaaggag  104040
gaagaatagg ggaaacgggg agggagggac ttcctccctt tacatagact aggagggctt  104100
aaaatgacaa cagaggagaa agcactaaac attgcagaga atagaggtat aacagattat  104160
aaggttaggg ggaacgtatt aagctattat actagctacc cgatggaaaa atgcacatac  104220
cttgtaacta ttgacattga aacgctagaa gaagaaagaa aagaactcaa aaaatattat  104280
aaaaaaggct tgcaaaatgc ttgcttatag actataaatat aaagaggggt ggcggttgtt  104340
attaataaga gaataaaaaa attacaatat gaaagaatca gaaagctaga aaagagaaaa  104400
agaggtgaac cacctgaatt tattttcaac ggtaactatt cattggaaga aatagagcta  104460
tttttacatt ttagaaaaaa aagtgagggc aaaaaatgag cgtggtggct ttgcttggtt  104520
tacttgtaaa aattacattt atttttaaat tgttagcaga taaaaaaagt taatcaaaac  104580
tattgacaaa taacaaaaga taaactataa taagtctatc agataaagag aggaatggta  104640
aacatgacaa aagcagaact acaatataaa aaagcaatag gagttgcagt ctttgcaaca  104700
agtggaaagg ataaaaagca actaggaaac gtggcaccgt ttagcattta tgagatttta  104760
gaaattgact taaataaaaa tcgggtatat tatgctttaa attgtgggga acgacatgca  104820
```

```
gtatgcttta ctaaactacg caaagaagaa gaaacaggga acgattttat tttaatcaat  104880
aaacaaccat ttttcttaaa agatatgcac aaaggtttaa gttggtcaaa aagtttataa  104940
aaaaactatt gacaaataac aataactaat atacaatagg tttataaaat aaagagagga  105000
agtttttaac atgacaaaag aaaacaacgt atttttaaat gaaaaagagc taatgaaaga  105060
agttattgac actttagaaa atggctttga tggttattat tgcgacttac atggtgagat  105120
ttttaatcat ggagcaaatg ctgacattaa agacttggaa gaatatggaa tttttaacgc  105180
aattggagaa atacaagaat acgaagaaga aaattttggg gaggttttga cagacctagg  105240
aaacccgacg gaggttacca atacgcttta ctatattaaa ggtcacgagt ttttatatgg  105300
tagattagac tttaatgatg ttttagcaga tgttgcagag gggctaaaat tagataaaga  105360
cttatggaac gaggaagcca ccgaggaagt gaacaaggct attattgagt gtttaaaaaa  105420
agaagtgcct tatttaatag attagaaaaa cagggaggag tttcctccct ttacatagaa  105480
aaaaaatata aaataaggga agtgctaaac atggaaacat tagaaaaatt cggttataca  105540
tggcaaggaa tgaaagaagt tacaaaagaa gaagcagaga aaaacattaa gaacggggtc  105600
ggcacttttc tattatatcc agataacaac aattgaagca gtgaaagaaa gaaagcaatg  105660
caatattaga taaagtattg agagcttgca acttgttacc aactgaaaag aacgtgcaaa  105720
cagctaaaaa ctttttagaa gaacaaggct ttaaagtaga agctagtaaa gagttagcgg  105780
gaaaatacct tgtaaaattt tcaatttaat aataaagaat gaagagggga agttataaaa  105840
atgaaactaa cagaaaagga actaaacaca attttaagag atgatgaaac agggaacggg  105900
ggaacggctt tcttaggtga aacactagcc gacttcttag aagaatcagg tattgacttt  105960
acaaacctaa ctattttaga agtaaatgaa ttactagaaa ataatggaat tgaaccaatt  106020
gaggtagtgc catgttaaaa aatatcaaaa aatcagataa actcactaga aaagatatac  106080
aaggtttttg gggagatgaa acaaaaacat tagaagaatg gtataagtca atttcaaaag  106140
aatcagacac cgaaaaagta gaaactgcta aaatgattaa tacattgaaa gaatatgcaa  106200
ataacaacga atttcatttc gtaaaaggag agcaaggaca atgacaaaca caaacacaaa  106260
caaccaacaa tggaatcaga agtttaatga tggtactatg aaccagaaca accaacaaaa  106320
ggaagttatc actttacaag tcgcagaaag tttcgtcagt cagattttaa caaaagaata  106380
ttcggtgatt ggtttagtta ttctaatgtt ttattttatg tttggcatgt ttggcatttt  106440
cgggggtgca atctatattg ctttcactca cacaaaccgt aaaatcgggg catggcaaca  106500
agtaagaagc gtatacacta ttaaggagga acaagaagaa tggaacaatt aaaagggcta  106560
acaattagag aattgattaa gaaactagaa gaagtgccag aagaaaataa ggacttgcct  106620
atttatactt ttgaaaatga aaactctttg cctattaaag atatttcatt atatgatgaa  106680
aatgctaaac actcacaaga aaacccgtta agttttgatg taatcagata aggaggggca  106740
aagatgaata gttttatgaa taaacaagct aaacaggtaa aaagaagtaa agaaataaaa  106800
ctagtagaag aagtaagaag aaaaaacgta aagaaacgtt tttcagagga agttagaaag  106860
tacctagaaa aagggtatat aatcaggtta gaaaataaag tttttccatt tgctttaata  106920
tctattgacc tagaaaaagg ggaaaaggtc ataagtctta ttcttgtgaa cgaatatgat  106980
ggaatagcaa actatacagc aatgaaaaag gttaccttaa gagaaaaagg gaatagagct  107040
atcctaaaaa gaacgttaac ggataaagat ataaaagtag tgagtatgtg gaaaggaata  107100
taaaagaatg agtgtataca gtttaaaatt actagcaatc ttagggatag tattattctt  107160
ttcagttatc gggatagtgt acgataataa acaggacgaa aagaaataaa catataaaga  107220
ggtaaagaga taaggaacta tagagctata taaatgtgta cacttatagg aataagaaga  107280
aaaggaacta tatacctata cactcataca ctcatattca gatagacaca taataagtaa  107340
gggtaaagga gagaggagga gggagagaaa gaggaaagag gaaaaaagtt gtttacctga  107400
gattttaaag aatcgactcc atcaaaaacc cgacaagggg gcgcataagt ctatttcaaa  107460
ataatctgaa ataagtatag ttattactgt ttatagatgg ttatccttaa atatctgaaa  107520
ataggggcgt ttatctgatt atatagttag ctatcttata ctattaacca tctagcctat  107580
tactgcattc attgctatta tattctatat agggggcgct tatatcgttt atagtgtaat  107640
tatgagggga acgactagga acgcttatac gggcttatag gggcctttaa atgcataggc  107700
tatttataca tatattagaa tacacaagga ggaggggcgg aaagttagta gattagactg  107760
ttaaaaacaa acgggggata gatgcacatt gttattttac tgattgggct aggttaacta  107820
gctaaaataa gaatgctatt gtagcaacgt ttataagaaa taggggtgta cttttcccct  107880
agggaggttt taaaagggta taaaattctt ttgttattta ataaaaaagt ccatcttagc  107940
tattgacaaa taacaacaac tttggtattc tatatttgta agataaagaa agggagttat  108000
agacatggaa tatacattag acgaattgct agaagaggaa tatagcacac tagacgaatt  108060
gctagacagt agagaattta aaaaacaaat ggacaacctt aatcacgtcc cacaaatgca  108120
accgcaaagc cataacagca atacgctagc agatacggga cgttatcctg aaaaataaaa  108180
ttgaaaaaag gggttgacaa gttcagcccc tagtggtatt ctatatttgt aagataaaga  108240
aagggagttt ttattatgaa tcattataaa ttatatgtag atatgaaaga gggaactcac  108300
gattatgttt cggcaactgt ctataatata cttgatgaaa aagttttagg gttgccagat  108360
attaaaaaac ctgagaacgt agcttactat actgatgaat ggaaaaacgg gctatattct  108420
tactatgaaa aactcgcaat atcagagtta aacgactaca acgctacttt ttcacattta  108480
taaaaaaatt aaaaaaaact attgacaaaa aacaacaact agtgtatttt attaagtgta  108540
aggaggaaca aacctcctta caccacacaa caggaaggaa gtttttacta tgacagaatt  108600
tgctaatatg aataaagaag aggtattgga gctacttaat gattggtttg gtgttagtga  108660
ctatgataca gtgatggaag agttaggaga gatgaaacaa gttaccttta caggtagcac  108720
aaaccaacct ctattaggtg gtaacggtaa cttaattagt ttacctcaat tctttaaaaa  108780
taacgaagca gaatcagagt tcccaactta tggagagcta ctagaggaac tagagaaaga  108840
tacatggaat ctcgaagcag aggacaacac ttacaattat agtggctttt tagaaagtga  108900
atcagatttt aaagttattc aggcagaaaa ttcagacacg actattgcat tctttgcaat  108960
ccatacgggt atagacataa gagcgggcta ctcaaaagca atcccagtta tttttgaaac  109020
ttactatgat ttttatgaat ttctaggtaa ctacttttgt agtcaaggtt actatgcttt  109080
taaacacgac aacaaggaat acacaatcag tttagacgtt tcggctacct cagaatatgt  109140
acgaatttat atagctgatg aaaacaacga ggaactacag caaggctatg aacaagaaac  109200
ttgtatggac ttagacatag aaagcgtaga aggatacttg aaagaggaag gaattgagtt  109260
tactgactta aaacccgcat tgtaaccata taaggcacta gggagcttat acaatagagc  109320
tacaagcctc ctagtgtaat tataaggtaa ataactagaa acgcttatac gaaagaatag  109380
ggggctttaa aatgacaacg gatgaattaa aagagtttta ctatgaaaac gggattgact  109440
tgtggaatga taacctatat tttgaacaag ttgtttctag tggtggatgg tactacgaca  109500
atgaacgcgg tttatggttt aattatgagg attaaaaatt taaacttttc tattgacaaa  109560
```

```
aaacaaaaac tttggtattc tatacttgta agataaatag agaggggaac taataaaaat  109620
gaaactaaaa gactttatca aactagcaga atccaagggc gctacattag aagcatacaa  109680
cgagctagga ggttatgaac taactagagg ggacacagta gacccgaatc cggttttgat  109740
tgcttacatg caaggggctt acagcgtaga aataccaaac aaggaactag aaaacaagga  109800
gttaacagaa ctagcgtttg tctataaaaa tgtaagtctt atttatccaa atgaaaaaga  109860
actattgtca ggactaggac tatagcacaa cggcatataa agcccgtagc gaggttttag  109920
cgggctttat atataaatac cttaaggagg aaacaaggtg cttacagtgg aaaataaggg  109980
cgttaggtgg ctagtgagta aagaagcatg gaaagcaggc tttgctatgg aggtgctagg  110040
cttgccagat tgtaaaatta gtacagtatt aaaatcggtc tataaaatta ttatctaact  110100
atttaaacta atctattgac aaataacaaa aactttggta ttctatacat gtaagataaa  110160
taaaacaaaa gaaagagagt gacaagaatg gaaacgaaca aagcatatga aagactattg  110220
aaagaagtag aaaacttaca gaatgattta atggatatcg aggactattc agaagaagta  110280
tatcaagcct ttcaaagatt aatcgaagaa ctcgaagagg taaccgaata gggctagacc  110340
agtcctatag gtatatacca gttgacccgc ccccgtggtt ttttgaccgt actttggggg  110400
tggggctatt tgcctacccc gaccctgggg tataaatttt tttgtagcta gaaaattttt  110460
atatatttat aaagtcaaca ccccacatat aaagtcaaca taagggctca ccctagggct  110520
cctatatagg ctcacctaaa tactcccata taaaaaagac ccctccccgt tgataaggat  110580
aggtcttttt tatttagccg tctgccctat gattggttat taggttcagg ttccgccata  110640
gtctttgcga agtatgtcca gtatttatgg aagtctgcaa agtccaagaa gtactccccg  110700
acaatctctc ctgcttgatt gcggtaaagt ggtactttcg ttttctcgtc tttatggact  110760
ccatactctg tgccatttaa tgaaatccat acaatatccg gagtcacact agttactgtt  110820
gccttatcac aacctagtat cgggtcacga agttctggtt ttgtgaaaac tgtatcccca  110880
accttcaatt tgtctagtcg ctctttgtct attaatgttg tctccatttg ttctccctcc  110940
ttatacatta taaaaaatat ttaacgtcta attactgccc tcaaataaag aacattacta  111000
cccatccaat aagcataaat aacaatgttg atacagtagc ttttgcaaat accatcaaaa  111060
tagaatcttc tgtatttgta gtagtcttag ctgtaataaa actaataaat acatctagcc  111120
caattgcctg cgcccatgta agtgttaaca ccccaaatgt tggggcaatt aacccgttcc  111180
acaagaacat cgtaacatac cctccaatag caagggtcaa caccactaga actaaagtcc  111240
caaaaaattt acctaatgca tttgccaatt cgtcttttgt attcttatcc atcgttttcc  111300
tccttaataa tagctatatt tacctcttat ttttttgtta attctattta ggcttgcaaa  111360
agtaattatg ttcaagatat atgcgccaat tactgatact gcctgcattg tgcaaaacac  111420
gattgttatc cagtagcttg tagtagcttc cccgctagtt agcccccaat aaatgctata  111480
tgtcaccatg agtgtgttta gcagtatagc taccctcct accaataata gtaggtaacc  111540
agatagtttc atttagttcc cctccattga atgattaagt aagctcttgt tcagttcttt  111600
taagtaatag tcacacctaa cgtgcacaag acccatacgt tcccttgtaa tagggttata  111660
atgtaatcgt gtaggtactg tgtactcatt aggtatagat aagtctaatt gggtagttaa  111720
attgactact ctatccggag ggcacatcca tagaggctta ttacagtgcc aacatgtccc  111780
actttgtagt acctcgtatt ttcgtttaag ttgtttctct tcttctattg ttaattagtc  111840
gtgatagcac tgtgtcattg cgtatggctc cctccgcttt tatatttgtt atagtttagt  111900
gttaaaccag tcctatatcc tctcctagcg tttacaatag ttgtttaagg tgataatagg  111960
tagaatacct atcaccgccc taagaggcat atagggtact tataggactg gtgtttagtt  112020
aactgtttta agtggcataa aaaatatgcg cttaagtcaa cattagttct tttactttag  112080
atgatgtcaa ttgcaatata atgatttgtt ttggatacat tagcaatttc ataatctaag  112140
tatggttcta gtacttcgtt gttacttcct atctttgttc taactgttat ggtagcccct  112200
gccgtgggat aagtaatgag tacgtccact ccgggcttca ttaacttaac taaatctttt  112260
aacttcatct ttatctcctc tttaatagca tatgcttaaa tctattttat gtcaactgct  112320
taatttttgt gctcgtagtt gcacagatat tgtatcaaca atgactgccc actgctcctc  112380
cgtaaaattg aagtcaaact gtgtatagtc ttcctcacct gttgtagtaa ttgcaatgtc  112440
tccataatca tcaactgaga aatagatagt tgcagtcgca ttttcctccg gattttgagg  112500
aagtgtaata gctaactctc cttgctctac tttcatctat tgcccccccct tagctctctt  112560
ccttctcaat catcttgata cctgtaaagg catatacagg gagttcttct gtgtaagtgt  112620
actgattagc tttaaaggta acttcgtagt aactctccat gccacagtgt aacatgtcta  112680
catatctaat ttccttacaa ggcatagcat ttttctcact cccacagaag agccagtctt  112740
ctgtacagta ttctactcta cctgtgtgga tacttctaac tgctacgtat ggtttttcca  112800
tctattcttc ctcctgtgta atctcttcta ggtcacaagg gtgtacatct agtgttcctg  112860
tccttagact ataacgagag tttcctcgta ctgcgtaaac accatctggg tatacttttt  112920
caagatatac agtatcccca attgtaaacc catggtcata acgggtatcc ccaataacct  112980
taaactgtct ttttatcgta tacccataca tgtaagcccg tgctaatacg tattggttac  113040
cctcatcaat ccattcaact agcttgtcat ctggtgtttc atcgtatggg tcaaaatact  113100
cattagctaa taagctcaac attgaatcgt actttttgat tgctcgtgca acaaaactag  113160
gtatctctac ttttttagcc atctattctt cctcctattt aatcataata catacaaaat  113220
acataaaaaa gctaacatca gcaaaacacc accccatcca gctgttacat atgacatata  113280
gaaaacgtat ataaggtatg ttactgctat aattgttaat aatacaagta tcgtgttaat  113340
gagcttttct aaatcaatca ttatacaacc tcctagtcct cacaagtgcg agtctggttc  113400
ttattatact cttactccta cttatatcca aagaacttta agtaattttc tgcttctttt  113460
tctaagtgct cgtttagttc atctagggta acaactttcc cacagtcctc acaggtgtag  113520
gtctggttct tcttatcttc tagcagttca ccatcacata caaggttgat acaatgggtt  113580
gtccaactcc ctacatcatc aggtaagtgc cccattatac gtcacctact tttacggcaa  113640
atgccatgaa tcgttcatcc attttgcgga tttctttctc tgtaaaggta gggatgtctt  113700
ttaggtagtt tgtaaagtca ggagacccta atcggtcgat atagctatat ccccaaccat  113760
ctttatcttt tgcaataatg atgtagtact cgtcttcttc ttcctctacc gtatgaccta  113820
gtacccatgc tttggcaagt ttctcatggt tttctgggtt attagctaac caaaagtaca  113880
tcttactagg gtagcttcct ttgtcaatca tgttaataaa cgttaagttc tcttctttgc  113940
acttgtcaat atatttccct actttataag gaataacaac tttttcaggt tcgtctaaat  114000
catatgctaa ggagactgct tttgctatcc ctgtattgta gcctagagca tgggggttca  114060
atgtaccgtc acaccctact tgagtaaaaa cctcgtcact tagtctacta ataaattcat  114120
tcttattcat ttagttccct ccttaaaaat caagactgtt ttcaataagt tctgatagtc  114180
ggagcattac ctcatgaggt agctctaatt ttgtactctc ctgtgagtct gcggagctga  114240
cttccaaagt atattttact tctgttttct catttacacg ggaagccttc ttctcaacac  114300
```

```
atactttata aagtgctgag ttattgactg cgataatttt ttcttgtgta tttacactag  114360
tattgctatc ataagtaatt tcatagccca ttataaaacc ctcctatttg tatactggta  114420
cagcaaaagc ccagtatctt tcatcaattt cttttatttc ttgttcggta aatttgctct  114480
tacccatgtt gggtttattt gagaagtata cttcattatt gtgggatgtt tcaaccccaaa  114540
gataacaatc ttctccttta ttaccaagac cagtaaacac gacatggtaa agtggttctt  114600
tctccacctc atatccatct ttcattcgta ttaaagtttc aatagggtta ttcttacttt  114660
ggtctaacca acaatcgaac tctgattcat gtgggtagct gttgccatct aacattctaa  114720
tttgtgtaaa aatagctagg tctaatgcat gtttattttc ctcgtaccat tccgcaacaa  114780
actttggcac aattactttt ttaggttcgt ctagctgttt tgctaaagag attgcgctaa  114840
taattgatag atttgacact atacgataag gtgttttact agattctttt agttcttcta  114900
attttttaat caattcttgt ttattcattt aatttctttc ctttctttca atagcccact  114960
ggctgaatgc ttgtaagact tgcaactgcg caatttctgt catgtatcta taatttttat  115020
aaacagggct attccgataa tctgtttttg tagaattggc tctcagtctc caaaatagtt  115080
ctataggttc aatatctgtt aacgtatatt tttcttttaa ccaacccaaa acaatttgtt  115140
gattctcact tagttctact tggtctacct tatcatcagt gtatttgaac cagatttct  115200
catatgttgt ttgtccgcct gtgattgtta caaattcggc gcttggttgc tcattttgaa  115260
atttttctag ttgttcttcg taatgtatat ccccaacatc aaattcttta aatttaatca  115320
ttgtactccc cctgttctaa aaaccaatca gtaaatgctt gaataacttg cgcttcctcc  115380
gttactgata aagagtaata tgcctcttct gttttagggt cttcataggt ctccccaata  115440
cgttcgagcg cctcaaataa ggaatcttta ctacagtaac ctacttttaa ccattcaaat  115500
acctgtttct gatttttatt cagttctggc tttttaactg cctctactgc agtcttatac  115560
gctattttta aaaggtctcc ttcaaaacta ttagggaaat taatttcacc atttgctttc  115620
atatacatat agcaaactct atcaattatt tcgttatatc tttgtctact cattcactat  115680
ccctcctcgt cctctacgtc accccaacca aagctacagt aggaagagaa cacgtctcta  115740
gctacttcgt ctatctcctc attcgtagca ttatcgggta cttctactgt ctctatttca  115800
ccaatacctg cccaagttgt ctcaatatat acatttattt ttcgcatagt ttaataccta  115860
agactacata gtcgtctttc tgtgcataat cggtgatata agtaacttct actttaataa  115920
actctcctgt atacgaacca catgtgtact catttaataa aagaatatct cccacatggt  115980
attgtctatc atttttacgt atttcaaata gttttctacc ttccttaact gctttaaagt  116040
acgtaggtgc aatcttgagg ttatgagtaa cttctaattt actaactaaa tcaaaaatga  116100
tagtgtttaa tttgttaccc tctacctgat gattcaattt ttgtaaagtt gttgatatta  116160
cagtatgcct accttctcta tcaataactg agtttcttct gttatactta gtaagtcttt  116220
ccttttctgc ttttgcctgt gctagtccat ttattgtttt agatactttt acttctccat  116280
ttacaataac ttgtactagg tatctgtcgt cctttgttgc aaacttatta tccataatta  116340
gtacctctct ttcataatct taattgacca gttatcgttg ttactgaata cccgttctag  116400
gtcattcaat gagttggtat ttacaatttc ttttttagt tttctatctg aattaatatt  116460
accaaatcgt ttaaggaatc tttgtttaaa gtgggcataa cccatatagt cgaaggtaat  116520
aacgtgttct ttaccaaata taccccgctc tcttaactta atctctacac tctcataaga  116580
gctatctact ttcataaaat tatttagaag agtgtgcaaa tcaatacaaa tagatgcccc  116640
tgcactaccg cctataagta tatatttagg gcactttata tcggggtaac aaggggcatc  116700
taattcatac cacatattat ttacgtctac cccataccat acactattta catctactga  116760
ggctctttct gtcttaaatg gttttatgca agtatatttc attgtctctc ctccaaatcg  116820
tctagtacgt cttctaatgt tgtgacaacc ccctgcaaat aaccaagttc atgccaccca  116880
taccctctct tatcttgctc taacaaatta ttaattcttt ttgttttacg tttaatttgc  116940
cggttatatc ttctttttag tccctcttca aaggtcacta cctttttttgc ttcctctata  117000
tcttttaata attggtctag cccatctcca ttagtgccat agctatacac tagcgctttc  117060
tcgtccttat aggtagttac ccctaatgat tggtatacat acttcttact ggggacaaat  117120
acaagagtaa tgggtctgta caattgaggt aaaagacaat cttctgacag cccaccaaaa  117180
tctgttttag aagatacctt ctctaccaca tacctcatat cttccatact taacgactta  117240
atacataaaa tatatctgtt aataaccatt ttctttagct cccccctacac ccaaaatagt  117300
tttcgattct ctgttggttt aaaagactcc aattctcgtg aagtattact ttttccatct  117360
gttaaacctt ctttcacttt atatattaaa aaaaataaat ctagctatct acaaatacat  117420
tgtatcatca gctagattaa aagtcaacac tttatattta attattttat attacaatag  117480
ttctttatct aaaattattt tagggatagc ccatattgta gtgtaacgaa cccctttatg  117540
gttacctgta actaatacga acgttgccgt gtctagctta gtaccgagta cagatgctag  117600
tagttcgtgg tcttctttgc taattggtac ttcaaaatca agttctccaa gctctaccac  117660
aaagttattt gctctaattc ccataaagta ttcatcatta cgttttacat ggaatatatt  117720
cttcgtatga aaactttgca taacaatatt tgcaaaataa ctgttatccc tagctacaat  117780
aaatctatct acatagatag cctctttact gagtagttct tcaatgcagt tactcataac  117840
atattctcct cctcttctaa tagtagctct gatacgtaaa tttccatcat tagactttgt  117900
tcaatcccgt ctagtaataa atgcatagca cacaagccac acaacatttc atctaaataa  117960
aaatcaccac atgtctcctc taatggtact tgacacatta aacactctat cattgtacag  118020
ccctccttaa tttaagtttt ctctaacttc tgttagcacc tctcctaata gattaagtcc  118080
ttcccattta ctcatatcac gagagcgtgg gtctgattca cgtaacccta ttccccatac  118140
tttatcaaaa ggtgatgcct ctgcaaactt ggttccttta gggatggata gcataaagtt  118200
acgtaaacta tcattttgtg tgaatttata agtatttcca gctaaaacga ttgatttacg  118260
atgctttacc cacaagtctt cttcaaaatt tttaacttgt ctacctaaac gtttagcatc  118320
ttttgggctc tctgttttta aaattctttt tgctgtatcg acatcattaa aaagcattgc  118380
tttacgtacc atcatgtagt gctctgctgt cgggaaaata atagcttccc ctaaaccctt  118440
aataggtgca ctgaactgtg atgggtacca ctgtgacaag cactcttttc ctagtttatt  118500
acgtttgctt ggggtatgtc cccaaaataa aatatattta ctcatttaat gttcctccca  118560
atattcatag tagtttccct tatgttcaaa aacaaaatga gggctaggta actcaccatt  118620
aacttctata tgctctgggt tattataaga atagtagggt tcgttaccag taggactaat  118680
tgctattact ggtttatctt taaaaaatgg tggtatttta tctccatcat ttaagtttaa  118740
tttataggta cttaatggca cgcttctacg atgccctttc agtgttgtat actcctcaag  118800
actaattatt ctaaggaaac ccttagcttt tagaggcgct aaactgtcta tcgaaacgtc  118860
ttcttgctta taagtgacaa gggcgctata aatggttgag gggtttttgt atgccactga  118920
ataattaatt gaagtgtgct tatggtttgc taaaaatttc tctaattcct tagataaacc  118980
ataaggtgta tcactatcaa taactttac tttaatcatg tgttatcctc cctatatgct  119040
```

```
tctctaactg ttcctatact ttggtctggg tctggtttac taaatggtaa gcttgcacgc  119100
tcttccttac tcaatgtttt taagcaagcc acatgtactg caatgacccc tgacttagct  119160
tccatactat ccgggagtgt aagtatatag tcattataca gtttacttaa cactagccaa  119220
taacgattgc tactactttt catattagct aaaatcatca ttttttcata gtaatcttgc  119280
cccatacaag aaagtcctcc tattgcagat tggaggagct catcttcaag agctaagata  119340
gtatttgcgt accctttcag ctccttgtta agcccctcta tagcaatctc aaaacattct  119400
ctttctggag agcctacagt taaatcatta agtggctcat atgctcttac ttctctccca  119460
ctaggggctt gtcttcgttt acctatacga taagagtctt taaactcata ctcggaacga  119520
aaaatttctt cttgactatt tcttccagac cttcctccaa aatagcaatc ttctactact  119580
ccaccaagac cattataatg tcctctagtt gtccctatga ctttagaatg tctaatatgg  119640
gttagctgac agagctcccc tccgttatca gggtcaccta caatagctgt ctcacataca  119700
ggacagatat atccaaaaca catcacttta tctacctcca attaatatac attaagaaaa  119760
agttacaatt ttttcacaag gaatatcata gtatgccttt aaaccataat gttccaacat  119820
gtattcttta gcataatcta caaggtgctc agggcattta aatgtgtaag agccactcat  119880
cattacacca ctattactta actcttctct cgaagcttta gcaaaccact tagcacactc  119940
tacaggataa ccaataacac accctaaaac ttcctcgtca ttaaacccta gcttaattga  120000
ttcattgtat acttctatac tcatcttatc tgatgttact aggtatatac taccatataa  120060
cctcgtttta tagtaagagc gttccagatg gcttagctct tcttccccta atacgattgc  120120
tacacgatga cctaaattaa aatctaaaat aggctttgga aaaacgtatt ctgctttctc  120180
aacaaactcc acttagccac ccctttttctc attccctaaa ttatcttaaa tgctgtatta  120240
gttagaacgg taagtcacta ttgtgttctt cctcttctgg gatatatagg atattttcaa  120300
tcttttcttc aatatgtcca ataatctctg tgtgctcttt aattttctct ttatgatttt  120360
ctctttgctt atttaacttt gcatattgct gtaattcatc tggtgttagc tcttctagtc  120420
ttttttttcat ttgttttctc cttctaatgt aattttctct acgtcatcaa cactaccaaa  120480
agatgggggc tgtgtcaagt tcttatctaa ccagttagcg ataatgtcat gtaactcgtc  120540
tatagcctca tcgcttactt catccgttgg gtagtagtcc tccgctactt ctccatattc  120600
actgtatagc tgttccccta cagattctaa catacctact acatctacac taataactgc  120660
tttattgaac tgccctactg caaagcttgt tgttcccttt tcaggtaatg ctccaaatat  120720
atcctctacg tgcatcccta agctatctac atatgttttt ccttcattaa tggacaataa  120780
tgcaagtttt cctgcagaca ctgcctcttc tctcgtagag aacgtctcac acgctttcca  120840
tacatctgtg tcttcctcta gtgctaatac atagtcttta tcttccattg tcttgccctc  120900
tctatccttt taatataatc atatttgtat tactgtctag ttgccatcca tcaaattcta  120960
agtagtggtc ataagggtta attggttcac ctacaactat atagtcctct agtgcgtgac  121020
cttggtcttt tagctctagt aattcgtcta ataaatcttg tgctgtcaaa ttattcatgc  121080
catatagtat cctttctctt tagcttcttc ccactcatct acagaaaaca aacgctcatt  121140
ccgagacaaa gagccataac agtttactgt taagtctacc ataaggaagt ccttaccgta  121200
ttgttttgtc caactctctg tatatggtgt tactgagtgc acttctttaa tatattgctc  121260
taacatattc attttatgtt accctttctt ggtttaaatt ttcgtgtttg tgttcggttg  121320
tttctactta cttctttgta tctacggatt cctaatgcct tagattctgg gcgagaacga  121380
cctatctgtc ttacatataa gtctagcgct tcttttactt tatcatcata catcttccct  121440
aattctcgga aatactcaaa ctcacctaaa tacacataag gcatacgcca gtcatctagg  121500
gtagccgtta ccattgttcg tttgtttaaa tcataattat agatatatag aaacactata  121560
taagcacctg tcatcacaga atagcttgtc ctaatttcac ttagagttac gctgtctctt  121620
aatgatgtta aataaccatt ccactttttt ttacgttctt ctgctaaagt ttctatgaag  121680
tagtttacct ctttttcgtc cctcaccact tgctacctcc ttgttgttta tgtctatata  121740
ttatcatcta ctttgttata tgtcaacacc tttgtaataa aaaagaacct agtaatttac  121800
ttacttaggc tctcttgttt atacgtgttt agtaagttac ctttactatc gacaacaaca  121860
gcattaagct gaccaccata tgcacaggca ccatcaatga aaatacttct atcacctaag  121920
aagacatcgt agctgttctc ttttctcaaa ttaattgtgg gtgtgtgacc cattacaatt  121980
gtcttatctg ttttattctt ctgtaacgct agcggtctcg tccaaatcat ttcatcttta  122040
gtggctgttt tccaatcagg ctgacgataa acaggtatcc ctgcgtgtac acataaggtg  122100
tctccatgct catagtatgg ttctaataaa ctaattactt caactacatt tgttttttct  122160
aataacatct ttctagtggt aaacgcatcc tgtaggtgtt catctaaatc caatagacta  122220
cttattgttt tatcaccgcc attgtacatc cacattgcgt acatctcact taggtcttcg  122280
tagtctgctt ctcttatcaa tggaaatgtt aaaaaatcta ataacatttg gtcatgattt  122340
cctaacaaag cagttcctcc attaataata tgcttataaa cgaaacccag tacttctgcg  122400
gatttgctac ccctatctac gtagtcacct aaaagtatta agtcctcttc atcactattc  122460
caatgtttat taagaagcat tattagctca tcatagcaac catgtatatc tgatacaata  122520
aatactttat ctttcaatga ataatagccc ctttaactac ttctgctagc caataagtag  122580
ctagtactag tacagtattg acaataaatg ttattactat aaccagtgct aacttataat  122640
ttttactcct agcattatag tttatataat tttttatgtt aactctaata tttttaaaca  122700
aagcactccc atatacgttc agtgctatat atagtaaaag caatacgata aagtagcctt  122760
gagctagaaa cacgtcagac tccctgaacg agttattaaa ccatatgcta aatatcgcaa  122820
tcacttggtg aattataagc attgcgccat taccaaaaag aagtatacta aacgctatac  122880
cgactacgtc tctgtactct gaaagtagtc tatcatatac tattatccct ttagtaaaaa  122940
taaaagcaac aactgccatc tgtataagta aaaatattgt tacggctaat aagttttctg  123000
tatgcatagt cataatttag ccactccttt caaaatgggt aaagaaagaa taataggtat  123060
atcgttcttt ttctacccta ccttcatgta taaaggtaaa ctcaacaaac ttaactctta  123120
gcggtatatc tggtgctttc tcccaaggaa gtactcttgg gaaatcatag aatactcttg  123180
tggggtaaac ttctttcata agtatcctag ggtatctttt ctttggtata aatcttttac  123240
ctattatact tgagtagtca ggtttcattg taagtcacca tgaatagagt atgctctatt  123300
tgctttgtta aagtttactt gttttttgtt tactaatctt attgcatctt ctaataaaag  123360
aggttttcct aatttatggt tatctaattc tggtgagtct acccctacat tcagtaagtt  123420
tggttcgggt ctggctaact catgaatgtg cccatgtaga ttaattaggt tatctctatc  123480
tcctaaaatt agtgggtaat gtgtcatatg cacaacctta tgcattcgtt ttaaaataat  123540
accaacgtct tcccaatgaa ccctatcatt cagggaagta ttgcgtttaa tctcttttcg  123600
tagaggacta ttatcgtggt taccctttat tagccatata gtgccattta agcgctctaa  123660
gacgttagct atactattta ccttggcacc cattgcaaag tctcctaggt gatatacaat  123720
gtcctctggg cgtactgtag cattccactc tctaattaag tattcgttca tctcttccac  123780
```

```
atctttaaat tgtttccgtg tgtccataaa agaggcttcc ccacaaatgt ttctatggaa  123840
gaagtgcata tcagatatta catattctct ccccatactt gctcctcctt agtgtgttgc  123900
aaaccatacg aatacagcta gttgtagata gtgtactgtt tggtcgataa ttagttgtgt  123960
ctttttatta ggtactgttt ttaagaacca tgcactttgt gcttttaaat agtccatgat  124020
aaaatgtgga acccataagc atactacaat tagcccaagt tttactggtg ttcctaagaa  124080
caatgtagtt gcgacaataa tatacgtcca gatgtttaca tggatgatta gtagatataa  124140
atcagtctgc tttcctttg cgatatagtc actttgtaag gcatagtccc ctactgcatg  124200
agccattgta aggataatta catagtataa gtaattcaaa ttaagtcctc ctctttgtat  124260
gggtaaggac aagtgtcaca ttcaaatcca tattcgttag gtgctccctc taaaatattt  124320
ccgccacatt ctgggcaagt tgctagtttc attgttctgc ctcctttaca tgatttcaag  124380
atatagccct gcacttggtg ttgtagaaat cagcataact tctaggtcta agtgttctcc  124440
gataccttcg tattgttcaa taagtggttt tgtttctgat aaagtgaatg ttacaatttc  124500
ttcatccgtc atgtgctcta ctaatgtgac tgtgcgacca aattcaatat gttgtaataa  124560
atgtcctagt ttaatcatta taatttcccc catcaattaa taatagtaag ataccaccta  124620
tcacaagtaa ccagaatact gctaagatta gtaccattta gttgtcctcc ttgaacagct  124680
catcgtataa ttcttgaatt gcctcacgct ttacttttaa cattgcaatc tgtgctgata  124740
tgatattgct tggttttccc accaaacgtc cctctaagtg cccaatatcc atattgtatt  124800
gaataagggt ttgttgaaat ttttttctaa tctctgtgcg ttcattaatt ggttgctctg  124860
gttcaatctc aaacagttca aacattgaac gccagcgccc atttacgtta ttcaataatt  124920
cactaggtgt gcccccaata tctactgtgt catacccatt gtctttaaag aagtagccca  124980
ccgtttcgtt gtgataaaca ggatattctc tcccttctat gaactgtggt tctagtgcat  125040
ctgcttttgt acatttaatt ccgtatgtca ttttattaaa cctcccattc cttaatgatg  125100
tattggcttt tatagtttgc atagaaatct gagtcacttg agaagtatat atctagttct  125160
tttacttttt ctagtactcc ttgaagggat gtaccaactg ccatgttagt acctgtcccc  125220
ttatcaattc cgagatagag tgtaagtttc tttggttctg caccgagcaa ttcaaactta  125280
gaatgccaat agttatttaa ttcagctaat agtagctcag gagtggctcc tgattctata  125340
atgtctccct catcatctct aaggaagtaa cctctagcat catcatagaa tacatcgtac  125400
tctttacctt ctgtgaagat atgctctgtt ttaagtgtac atctaatttt tactgtcatt  125460
ctaattttcc tccaattcaa tttcttttat tgatacaaag ccaagtatat tgcggaaagt  125520
acggtcttca ttccagtata taaattgtgt tagaagtggt ttgtggtcat ctgtgtatgt  125580
tgttttttgt ctcgtagtag ctttcttcaa tttgttcatc aatattttgt accatttcat  125640
tataatatgt gactgcttta tcatatgagg tgaaagccct catttttacc gctctatact  125700
caaatttcac taaccatgct gagcttaatt tcgtcattta tttcttcctc cacttctttg  125760
attgacttga ttatatatct atggttctct ctaaatgcgt ggtaagcatc atcaagtgaa  125820
tatgcgtata atcttgttgt ttgcattaca gttctatatc cgttacgtcc aaccattggt  125880
tcgtcaactt ctacttctaa ctcaaataat agttgttttc taatcattgt ttttactccc  125940
cttttctatg atataatatt accctactat tatgattctg tcaacaggca aaaaaaagaa  126000
gtagaaaaat ctactcctat tcatcgtttg acaacttttc cataccatat agtaactgta  126060
gtagtacata tagtacaata tcaaatccgt caagtggctt tccaagtact ataactttaa  126120
caattgtcaa taccgctaaa aaaataaata gccacccgat tattttattt gcatgttttc  126180
taattctcat aactttctag tacctcttca atattctttc tggtttcgtt agctaactta  126240
ccagtccgtt caagccaacc tctaaccatt tctttttcta ctttgctatg tttattcgca  126300
tcctccttga taccttctac attttccatc aagttatcta agtcctccat aacatctaat  126360
aaagtgtttc ttagttttaa cacatcgata gacaactcat agttccgttt agacaatttt  126420
tcgttacgga taaagttctt ttttagttct tgttgtgttt ctagtagctg agtagtttta  126480
ataatatcag cttctaattt actaattccg tctagttcat tcatcacatg tcctcctcat  126540
attctactac ttcctcaata agtttcagta cttcttctgc tgtgcccact gtgctatagt  126600
ccgcaaagtt ttctgcaggt ttcataatag ccactgaata gggtttgttc tctacataaa  126660
tatgcccgaa tccttttaaa gaatgaatta cctctactgc ccatccatta gcgtactctt  126720
ctcggtatac tacttgctca ctggttgctc ttactggttt attcattgtt aaaaccatag  126780
aagtttctta caatgttttc tacacgttcc atgccctcta agtagctacg tttctcaggg  126840
gagatatagt tcttgtaatg agggacttcc ttctcttcct ctacctcttt tgtagtacgt  126900
tcaatcagtt taataagttt tacttcgttc tctagttgag actggataat gtctaacagt  126960
tcatttttcg agcagttgtt tagtggttta cttccatagt caataattgt catagtagtc  127020
ctcctatttt aatgtgtact ctttatatcc tttatgtgta tcgtgcccgc actttgtaca  127080
aaagcctgct tgttcaatat ctattgaaga gtaccctgtt tgtactgcat acgtctcata  127140
agtatggtca cacgtatctt cttctgattc atctattttc tctaaacgaa tagcctctcc  127200
ttctgccact tcgtggttaa agagcaatac tgcagtttta ataggctcat atacctctgg  127260
gtggacggct tcattcatct taaagctatt tccactaaat tcattgaaag catctagcca  127320
ttcctgactg ttctcataag atacaattct gtaattcata cgaaagctcc tctcgtgttt  127380
tcttaaataa ccagtaccgt tcatcaattt cttttatctc tgcctctgtt aaatagaagt  127440
cttttaattt ggatagggta tcttgactca atggctcgtt tctaggtagt atacttactg  127500
ctaactgccc gtccttgcgt aatagtaacc cgtagtctct ctcctgtttc tgaggcatta  127560
ctacatagta cttaggtaaa ctagcagtgt ttgctactgc ttgaataaaa gtatctgtat  127620
tagcaaagaa ccatttacta aactctgact tggggtactc acatgcgtgt ctctgccctt  127680
ccaagataat ttgtaactta tccataagtt gttctcgttg tttatcaata aactctttta  127740
cctgttttgg tacttctacc tcattattca tagtttgtct cctttgttat actttgtcaa  127800
tagtgatata cacatacttg ccctctaact gcttaacaat atctagtatg tcatgaccac  127860
ctagcttaaa tgtgtttgtc tcaaaccctt cgatagtaaa ggaagaccaa ccgtaccaac  127920
cttcttcaaa gtccaagacc cccatagatt taagtactat atttttagtg atgtcttcta  127980
atgaagtacg ttctacagca gagaaaatct gaatctctgc gttatcaaga tgatacttag  128040
aagaaatgcc tccatcgtac tcctcttctg ttgtagtgtc ctcagctcct aacgcataca  128100
gtgcattaca aataagcatg tttaaggctc tgtgctcatg gtgatactca atttctttta  128160
ctttttcttt tattaagtaa ggttcgtttg tttctgcacc ggggctgtta tcaatagtta  128220
cccaaccttt taatatctgt ttacccatga ttgctcatcc ttcctttagt acagcctatc  128280
gctgtcacca gtaaatctaa attttccttt gtcagagtta ctgtttgttc atgtacacag  128340
tccggtctaa atacctctac tgtacgattt actacagcaa tatctacagt atcttccgtt  128400
gtctggctta ccttgataaa ctgtttggaa aactccccac ggctaacacc ttctatcata  128460
agctccattt ttttatagcc tcctctctgg aaagtccatg aaagttgtgg aaagtacgct  128520
```

```
cttgtagttc atctactgta tttggtaatg tacgaaattc gtctacccct agtgaaatac  128580
ttgaggctac ctcttcataa taacatttaa cgtctactcc cattttacca taaggtaaca  128640
ccattacttc tatatgaaac tcatatggag cattctgtgt taatggttcg tataataacc  128700
atgtctcatg atagtttaca ggaatatcta atagtaaact gtttaaatca tctagctgtt  128760
cagataagta tgcaattctt gtcattttac ggtcttctgc tataggcatt gaacaaccta  128820
acgtgtcttt tatttcttta atttctttgg taagctcagc cattaattca attattttat  128880
aaaacatttc tattccctct cttctatata ttccccttct tctaagaaaa agcaagcagg  128940
ttctccctct ccattttcag tatcacctag gtattcatca tctaagaatg cacagtatcc  129000
agttgagtag agggttacac agtccttatg gtacatcgaa tcgtccgtta accgcacaac  129060
ctcgtccatc tcactgaaca cttcattaca cgccccgcat gatactaact ccttactcat  129120
aggctgcctc ctttatctat tacgtagtct accagttctc taataacctc tgcctcctct  129180
acactagaga ggtctgccca aacttgaagt gtcgcatcgt tagccttacc agatattaaa  129240
ttgtgtaagc tatctgcaat agttagcttt gtacgttcaa gatagtgaat tagccagact  129300
aatacaatta gctgtttctc agttagctca gtattagtct ttgtgtaaac ctcatagtta  129360
tctaaggtta atgggaatgt ttcttcatta ttaattactt gaaacccgtt atttggttcg  129420
ttttcatatt ctccataagt tactctctta cctattttta gtttacata gatgtcttta  129480
ccttctttgt gtagtttatc taggtcacta ttataccact ctcttgtttc aattttagta  129540
agttccataa agctaaccct ccttactgag ttccttgata cgttgtttga tttctgcttc  129600
tgttttctct agttgtcgca ttttgttttt atgtcgagat aattcatgtt cctttgcagt  129660
ttctgccatt gctaataagt tttctaagct tgctgtattt gccattagat tgccacctca  129720
tagttaaatt ttccattatg tttatagttt actactttaa tttctgatag tggggaatca  129780
aagaagttcc tcccttctc ccatggtaag ataagttctg gcacttcttc tgatattggt  129840
gcattcacct gttgttcaat aagttctaaa tgtcgttcgt aaatgtgtgc gttatcactc  129900
gtccaatata agttacctaa ctctaaccct acagtatttg ccataaccaa ttgtaatgca  129960
tgatactgaa taatattaaa tggaagtcct aagcaaacat ccgaagaccg agccttcaca  130020
tgtaagttta atttaccctc tacaactgtc cagtgagttg tccatacaca tggctctaat  130080
gacatatcgt ataaatcttc cacgttccat aaagtagtca taattctacg agagtttggt  130140
gtgctcttaa gttgttcaat aactgcctct acctgattta gctttaggta tggttgatgt  130200
gttcctgcta tcccaccacc ttttttaggt acgacttttg gaataagtga acctgctttg  130260
cgatttttag ctaactcaac atctccacta taaacaggaa taaaacgttc tttgttaaat  130320
aatgcgtaac catacgcttt tccaatagtg ccatcttctt gctcccattc gttccaaata  130380
gttacacctc gttcttttaa ccacgaaacc tcgttagaca tttcttgcca aatccactgc  130440
aattctgtta gcgcccattt aatacctaca tgcttactac gtaataaagg agcccccata  130500
tctggtgtaa ttgtaaagtt tacaccttca ataaacttag ttgttgcagg agttccatca  130560
gcatatactg cacgagtacc ttctggtagc tctgttactc cgttcttaat aatatccatt  130620
actaaatctt tataaatttt atcaaaatcc atgttgtgcc ctcctacatt tcttttccct  130680
ataatagaaa tatatcatat ctaaatttaa aagtcaacaa aatattataa aaaaaatatg  130740
agacatattg gtatgtctca tatctactaa attctatact aaactggcta gcttgtctaa  130800
agcgttatag tccgcatcgg ttactggttc tactttacct aataagtacc cattacctac  130860
ctgagagaag aagtcatggt tactagttgt tgtagagata ccattcatta caatagggtt  130920
tacgtctgca cttgttgttg ggaataaagg gttcatccct aagttagcta gagctttatt  130980
taaattgtac tccaaaaatg tattaacatc ttttgtccaa ccaatctcac tatatagttc  131040
agcagtatac tgtgtttcgt tctcccataa tttaaatgct aaatcaatta cccattgttc  131100
catttctttt tgttcagttt ctggtaactg gttaaaccct aactggtatt tatagccgat  131160
ataggttcca tgtacagact cgtcacgaat aattaattta ataatttcgg ctgtattaac  131220
catttttgcc tcacctaaat agcgtagtgg tgtgtaaaaa cctgagtaaa ataggaagct  131280
ctccaatagt acggatgcac tctttttctg tagtggtgta ccgtttcgat aaatatcgtt  131340
aataatgtta gctttatatt gtaaacgttt atttgtagct acccattcaa agatattgtc  131400
aatctctgta ggtgtattaa atgtgctaaa aattgttgaa taacttttag cgtgtactgc  131460
ttccataaag gctatgttat ttaaaacagc ttcttcatgc tgtgttctta catcatcaag  131520
tagtgagtgt acccccgatt ctgattgaac tgtgtctagt aatgttaacc caccaaacac  131580
tttatttatt aaatcttgct ccatatcaga gagctttgcc caatcattaa catcgttacc  131640
tacagggaca cgtgtgtcca accaaaattg ctcagtaagc tttttccatg tggcttggtc  131700
aattacatca tcaatcttat tccagttaat tccttcatac ttttcttgca aattcatgtg  131760
ctcatctcct taaattgtac aactttcaca ctctgaaacc cctacttcgc ttccgtcttc  131820
ttcggtgaat gttctaacat aataaattgt ttttatacct tttttccatg cataatgtct  131880
taataaagtt aagtcccgag tggatgtagc gccaccctcc accttccaag gataaagatt  131940
ttctggtaac tctgagcgca taaacaatgt taaactcata ccttggtcaa tatgtttttg  132000
tgctgttgcg tacacgttga ttacgtcaat catacttgta ttgtacgctg acttgtaata  132060
tggaattgtc ttctcagata accggggtgc agggtaataa gttttacctg ttttcccatc  132120
ttgacgttct tcaatcatag agataattgg gtgcaatgaa gaagtagtct cattaacata  132180
agcaatacta ccattcgttt ataccgttac tttcgtaata ctttaacact gctcttagca  132240
gtcggactag actatacctt atactatccc aaaatagtac caactattat agtcgttgga  132300
cgtccctcat tttacagagg tttcgatgct gatttcccat tgtattaccc ttagcacctg  132360
taacaaggct tttatttcag cataggctat ctaactaatt ttttctgctt tcgcaacatt  132420
cacgctcacc gtttccagtc acgttgtagt ttagttagct ttaggggtt ccagcaattt  132480
aagttgtttt tgactcatat tcacatatga gaaagcccaa tattatttag gcgccacagc  132540
taaacggttt tgatggtata gaccaccttc aataatactg tttcttaatg tttcccaatc  132600
ttttacatta ggtagtacca ctccatcaaa tacttccgcc accttactag agatttcctg  132660
atttagtgtt ggtacatatt catcaaagta agaaccgtct gcgtatttag agttctcaaa  132720
gttatggaat gttgtgccac gctctttagc aatcttatta cttgccacca aagtagcata  132780
gttaattaat tcaaacagag catccgtcat ttcaatagat tcaggtgagc catattctac  132840
ttggttactt gcgaaccacg catgtagccc cattgcccct aaaccaattg tatgggcttt  132900
atcattacca ttcttgatag taggtactgc ttttatattt gacacatctg taatatatgt  132960
tagagctctt accatcgtct caattgatgc cactacatca ttagatgttt ctaacaagtt  133020
aaggatgtta attgaaccta aattacagct aatgtctgta cctaactctt cgtatacttg  133080
ttcatcattt agcttagatg gtgtctgtac ctgtaatatt tcactgcata aattactcat  133140
aatgattttg ccatcaatag gattggcttt atttacagta ctaacattca taatatatgg  133200
gtaacctgac tcttgttgta aacggctaat ttcttcttct aaatctcgtg cattcattac  133260
```

-continued

```
cttacttctg atatttgggt tctgaatcat gttattgtat tctgaatcaa tgtctacaaa  133320
tgagaatggt acaccgtatt ctttagcaac atcatatgga gaaaataagt gaattacatc  133380
cccagactca gctagctcat aaaatttatc gggaacaact actcccaaag aaagtgtttt  133440
gatttgcttt gcggattctg cattttcttt tctagttgat aaaaagtcca taatatccgc  133500
atggaaaaca tttagataga ctgcgcctgc accttgtctt tgtcctaact gatttgcgta  133560
ccggaaacca tcttctagca ttttcataac agggacaacc ccgctacctg ctccctcaat  133620
tcccttaata gggtctccaa gagctcttag gtttgaaaga tttaacaagt agtccatgct  133680
ttaacatggc tcagactata tcttaactaa atttgttacg tttagttcta cgcgcttcca  133740
aaacaagaat ttcacttgta atgtactcta ctaggttact cgctaatatc ctcccgacaa  133800
tagctacccg ttcgatagtc gttacacttt tacaattttt ctcctcgaaa ttttctacac  133860
aacttagctt tatctccaag tttatctttt cttttaaagt agccggatac gttagctaat  133920
gaagtagata ggtacctact agcctctgac atatctttaa actcaaaaga ttcgtttgtt  133980
tcgatattgg ttatttttac aggaatagac gtagtatggc aaggttttct ccctagtacc  134040
ctaaaaccat gtttagtgtt ctctgatata gtacaccatt caaggttctc caaacggttg  134100
tcttgtttgt ccccattttt atgattcact actggatagt tgttagtgtt aggtaagaaa  134160
gtcatagcaa ccactctgtg gacaagtagg tacttcctaa taccttcctt gttatacata  134220
gctgttttgt agtaaccgtc tttatcagta gacaacttga agtatctgtc ctttttttcta  134280
attctgccga gggttgaaac ctcgtaggca gggaaatcag ggactgcctt ccagtattct  134340
ttttccatat aaccacctcc ttaaataagg agaaaaattg tacttagcac ggtattgcca  134400
tatctttcga cttaggttcc accgttagcc tacataaagt agacacccta ggtttctagg  134460
ttcacgtagt ttatagtgag ctatattctc taacccactc caccaccaag tttagatagt  134520
tgaagtgcac tgttcaacgt tctaccaatt gaagacattg aatcttctac ttgaattaga  134580
aaacagctga catactcccc tcttctaagc ctacctgcat ttaaaaaagt aggggttgca  134640
ggttggtatc tacggttaat tagctcatct gcaatcttca tagcaagctc ttcgtcacca  134700
tcacccattg tgagtgcatt aaacgctact ctatcttcat aacgctctag gtatcgttcc  134760
ccatcatctg ttttcattgc gtattgtttg tagaaacggt aagcccccat aaatgtgtcg  134820
aatctgaact ttttactata gatgaactta aataattttt ttataaattc cattgagtac  134880
ttgtcagtaa tcactgtttt atcgatgtac ccttctctaa taaggtaact aattttctcc  134940
tctaaagagt agaaaaatac tgtgttcttg tttacatgtt ctaaaaagaa tgctctaaca  135000
gcttctttat ctttgtctaa ctgaatcttt ccgttattag ggatattcaa ttggttatta  135060
agctcaatat atgtgttcat atctacaccc caagttcttt ttctagtttt ttaaccaaat  135120
caggtctaac accattaaat gagaaaccat catcagcttc tacatatggt aatgaagaca  135180
ctccttttttc ttttagataa gctaaagctt gctcatcatg agagatattt ttctcatcaa  135240
atgggatatt ctttccattt aacatatttt ttaaaaataa acattgacca cacatatctt  135300
ttgaatatac tgttactttt gtcatttact acattctcct aactttttta tcgtatttat  135360
taattataca ctattttgca ttaattgtca aaaataaaga accaaaaaaa ctagagacta  135420
caaaagttaa ttgtagcccc ttttaataag ttacaccttg tcacctaaga aatcttctga  135480
ttcctgcgat ttattcgtaa ccttatcaag tagtaaaaca gaatagtttt taccagtttc  135540
aacctgcaac ctattaaaca ctttctgata ttcttctggt gtgtctgtaa cttctaataa  135600
gtattttgca tttaaaaatg atagtaattc aagtagttct gccttactac ctgccatttg  135660
aactacaacg ttaccttcat cgttcgtgta tgttccaatt ttatttctag tagccaaaca  135720
aatcagtcct tcgtaaattt aatgtatttg ttaactgtat acacattttt aactttttcc  135780
caaacgttag ggtatacgtt catcaataac ttagtatctg cgctagcacg tttgtactct  135840
ggcattaatt taaatgtgcc cccatcaata ctaattttag attcccctaa ctcttccata  135900
tcagaaatga tactactttt tagctcatca atctcttctt taatactttt ttgcaattca  135960
tataatttct tgtaagagcg taagtccttc tctagtagct cctttttttg taaatctgtt  136020
gttttcatac atatctctcc ctctcttatt tctataataa gattatagca tgtcagatat  136080
gtaaagtcaa cactttttta tacaaaaaga attgcccatt ataaaggcaa ttcttgtccg  136140
ttgtcttctt caaaaagaat ctctacaggt atattatata atttagcaag ttttactctg  136200
tttttaacac gaggttcttt tataccgttt tcccaataag agattgatga ccagtgaact  136260
cctatcatat tggctaactc tcgtagagat tcacccctag cctctctcac tcttttaagg  136320
actttaggtt ttggtacctt ttcttccatg actatccctc cttattctta aaaaataaga  136380
gcctatcagg tagacaggct cagcatcagg aactatgcga aagccccgat ataagttact  136440
ttaccattac atttacgtgc aaaagcctct aactctttac gagcacctaa acggtcaggt  136500
tgcgaagatt gaacagtaat ttctttaggt accgttactt cacgtgtacg aatttcagtt  136560
ttaccatttt ttaatttctt ctcatactcc tctgtacgag ttgttgtcgt agaaatgatt  136620
ccataaaatt ttttcatatt aatagctcct tactgttttt tttaataaat tataatagtg  136680
gtaatagggt tttatgagac tcctactcat tgtaagcctt ccttaataga tacttacaac  136740
tatacgttta tagacctctc tcaaaaagtc tccgtaacgt cttaccttca tcatttaaaa  136800
cgtacacaga atttacaaaa gttttatacc cttcttttttc agttctgtac tcgtaaggtg  136860
aatttggcac acgagtgatt tcttcatgtt tagagttaag taatgaaaaa gcattctctt  136920
gctctaaaag aaactgtacc ccatcaatta attcaataaa aggcttaaca ataggttcct  136980
ctgtactgtc tttacaatcg tattttcgtt ctcctaaaat ttgtagtatc atgtctatct  137040
atctcctctg tttaagtatt aatttgtgag tttccactca caatgctgat tgagagagtc  137100
gaactcccat tcccgggtta caaaaccgga gtaatagcca ttatactaaa tcagcgtaac  137160
ccctcaatag agggagtttc ttatactaaa ttaccatatc cgtaggtatt tgttttagct  137220
tgtttaaaca tgatactctt gatagctaag tcattgtact tttcatcgtc ttcgtcatca  137280
aggtacacat caacattaac gttcttacct aaaatatcga ttgtttcatc tttacctact  137340
tgtaagtctt tactgttaaa tgatacatca aaatagatgt cgtcttcttt tgtacgacta  137400
ccgaatgata ctctatcttc aaataaattt aaacttcgag agttaattac aacaggttgt  137460
agcccacctt caaattgaat agtaactgta taatactgat tttcaatatt aagaatgttc  137520
aaatcagcaa tagcttcacc aaatgagatg ccaaagctta attccaacgc aattgctcgt  137580
aagcaatcat agtttaactt aattctacgg ctaaacttaa caacactgtc aatttcccca  137640
tagtaagctt tgtctaactt atcttgcaag taagtacgaa tttcgtctgc atcagggtag  137700
tcgaaacgta aatggtaatg gaaacgtccc ggacgattaa gcataaagtc gtttacacga  137760
tttaagttat taacagtaag tgcataaata cgcttgcgtt gtgataaccc atcgaataag  137820
ctcaatagtt tttcttgtga ttcacgaccg tcacggtcat tgaatacttt ttcaaattca  137880
tcgaacaaga taagagactc ttggtcaata ctgtcaataa attctgcgat acccggataa  137940
gcttctgtaa ttaagataac aggcataccc tcttcaatag ctcgttgaga taagatttga  138000
```

```
gtaaatagtg atttaccaat ccctttatcc ccacttaaaa taacccctaa actacgattg  138060
attgttttaa atgtgtgtag tactttctca attttaacta aacggtcacc ataaacttta  138120
gattctttca atttaaaatc gtctgtaacc gccaatgaga acccagacat tgggttgaat  138180
ctaactttat aagtttgcgc aggcaactta tcataagttt tcaggtcgtt tgcataaatc  138240
tcataattac taccataatt gattactttc atatattctc tccttaatac tttttaataa  138300
attataaatg gagagtgatg gagtcgcacc acccgagcct aagcaacaga tttacagtct  138360
gctccgctac tacttacgga ataactctcc ttgaataacc aaccagatag gtacctgaca  138420
cacggacagc acctgtgtct ctctgttact ggatgattaa ttgtgtattt cgcatcacct  138480
aatatagtta tcaaggtagg acttgactat actagattta gctaggttct aactataatt  138540
tcctatgata gctcctacta ctaatcatat ttatatacag ttaaactaca cataactaaa  138600
ccgattacct tggttcgcat gttaagaggc gcaggcaacc aatggacatt gcaggtctcg  138660
aacctgcgac cgttcggtta tgagccgaat gctctgacca actgagctaa acgtccgtag  138720
ggtagtagca acaattacaa atgctactct cctgatgatt ataaacttat caaatcggaa  138780
agacaggact tgaacctgcg acatcagact cccaaagcct gcactctacc aagctgagct  138840
actttccgtg ttacctgttt aatttggtct tttaaactac tacacacagg taaagataaa  138900
ccctctgcca aggggagact atcatcgaac cgtatgtaag ttgcgatggg tagtagccat  138960
attatattag gttattagga agttcaccta tgcagaaggt gggagtcgaa cccacatgtc  139020
cattacagac cgatgtttct aagacaccgt tgtctaccag ttccatcact tctgcggttg  139080
tactaccaag gttacctcta aaaggctaaa ctcgtgtctg gtagggagcc ataccttaca  139140
tggattgcaa ggaacctaac ctcagtagca ccttttacta ttaagggttt ctgatttaac  139200
gttttcccta gaccgtacct taacagtaat actggtgaga ggatttgaac ccctcttacc  139260
tacaagcctc cgacaagcgc tatgggaaac aagcggtgca ttaaccataa ctatgctaac  139320
cagtacacta ctgttttacg cagtcctcat actaataatt catgtggact caaccccatt  139380
cagggaagtg ttagtctatt ttttggtgag aactggttaa ctccatgtac gtcaaacatt  139440
ccctagacta ctcacttaca ttgttattta atgtcacatg acttatgaca gccgtactca  139500
aaagtttcaa ggacttttac ctcactatcc accgacagta tgctcggcaa cgtctttcta  139560
ataataaatt acccatcact gttacagtaa cagaaccatt gaattaacga gcaatatcag  139620
tattactaaa agtagtctgt ctgtgtggta caagcactag cagtattaca acctatagta  139680
tgtctgtttg tcaatcgtta aattctttta caggagtact tgttaaactt agggaggtat  139740
aacaagtatg tgcacataac ccgagtgcta ctccctaaag tagcctatac gggttaacgt  139800
agatggaggg aatcgaaccc ccaaccgtcc gcttagaagg cggatgctct atccgattga  139860
gctacaccta caaattatgg gggtaatgag cccccataat aactcatagt agtttcatct  139920
atcgaggatt aaaatgaata tctaacttga ataaagtata acactattta catagcatgt  139980
caacactttt attaaaataa atttctatac ctcactaatg ccaatgacta tacgtaagga  140040
gagaacgttg atggcactgg ctacttagtt ggcgctaagt tagtgaggta tagaaagaga  140100
actacattga ccgaatcgta ttatacagcc ttagtagttg ttaacaatgt ttggaactta  140160
gtagcttact gcaataagct accccgaagc atcggggtgg gactgtggta agccccaaac  140220
ccttgggtat gctccatcct gcctccggag aagtcaggct caattctcat tagttaaagg  140280
tttactagtt aacggttagc tgattagtca tactacgtaa actactagta aaatatagtt  140340
ttccaattaa ggctaacaat cggtagagga tttgaacccc tattattggt tttggagacc  140400
aacgtgttac cagttacact aaccgactat gtaaagaagg aaagcgaaga ccttctttac  140460
agtaattaaa aaaaacaaac aaaaaaaata caatcatgga atcaaggtgg gatgtaagga  140520
gatgccatgt gtccacttac agtggaatag gtaactacag atttgcactg ttttacatct  140580
tgtttaatgg ttacctgtta atagctaact tccagtgata agtcctctta tatggtagtt  140640
catgtagtat ttgtttgaca atatggtagc tagctaaaat gacgacagta acgggactcg  140700
aacccgtgtg ttccacgctg acaacgtgtt gggacagcct ctgccctata ctgccattat  140760
ttatgccgta gttttttttag aaaggaaagt ttttttataa tatacaacaa cagttgaagc  140820
gctgatgtta ctacggcata aatatatttt ttatgagctt ttaataactc aaaacttaat  140880
ataatagggc ttttactcct gcttcatgca cactcactgc attcggtcac acacccagag  140940
aggctgaact atcgggagct acccaatagc ttctctctgc ttttaatgta tggtctagca  141000
cggtggctaa caacgttcac ctaaacattc agcattaaat agtattgtta taagttcttc  141060
ttatatcata tattttgtaa gctgacttag gctacttgta ccaaggtctc ttgttaaacc  141120
catatttcta tggttctcgt caaagggagt cttttgaggt ttctaaggtc tgccaagttt  141180
ctcacgcttc cacctaactt agattctttt ccacaggaac gtctattata tcccccaaga  141240
gtcttgtacc ttacaatcca tgtacactcc acataacgct taactgatac tagcttttac  141300
tagtagttac tcttatgtca ccataagaca tacctgctac ctaaaacact atcgcactct  141360
aggctacatt cagaatcacg ccacgttatc ctagcaagct gttcaaactt tctgcactag  141420
gttctattat attaagtttt caattatcaa aagcagtttt tctttactat ttaataatag  141480
cacaacctct attattttgt caactacttt tttttagaga gggtgcccct aattttatat  141540
aggggcaaga gatattaaac atagctgagc tatgtaaaag ctaatgtagg aattgaacct  141600
acttaatgta agcaacacca gtttagctta taagcattgt ttgcaaagtc catgctatgc  141660
actcagtagg aatcgaacct attgccgaag gtaccaaact accctgagtg ctcctataga  141720
tatattatac cacataacga gatattaatt ttttttggtg atatagtata tctatatttt  141780
ttaaaatttt agaaatacct ttgatacatt ccggttatcc aacgtatgaa tatataatat  141840
catgttattc tgattgtgtc aataactttt ttacattttt tttataattg tgtaatgtcc  141900
tatttctttt tttctgattc cttatattta taatatatac tatatagtac tatatatata  141960
tattaattac tattagatat tatatataga taataagaat ctaggaaatt taaaatagga  142020
cattctaatg ctgactcagt tacaataaac ttatggtggc taccttttta caaaaatgtc  142080
ctatttcatt ttttctatct ccttatatta ttatttataa tatatagtat taagtattat  142140
atattattat atatatagta tataatataa gaaagacaaa aatttaaaat aggacatttt  142200
acttaaacaa aaaaaaagag agcagttaag ccctcttatc ttaatgagaa atagttatta  142260
attgttccca atctgacttc ctcatcttct ggtgtttcat cctctggttt cgtatacaag  142320
ctagtgattc tttctggaac atctactacg ttctcagtag ctgtctgtat ctggaatgca  142380
tttacataag ttaactcaga atctctatca gctagtttat gaactggaat cattggcaac  142440
tctgcacctt tcattgcacc atttacaatt gacattgcat cattagttgt tacaccgagt  142500
cttctaggga acacagaata tgtcccagat gctaatgaaa cctctacaac tttctctctt  142560
ttagggtaat tcatgatact tctcctttca aaatatgtta taataatact atatactata  142620
ataacacatt ttacaaatta cttaaacatg ctgaacacgt aagtgacaac tgctcctaag  142680
acaatcataa aaacgttctc tacaatatcc ctcttgtggt cgaactcttt atcgtttact  142740
```

-continued

```
ccttccagtg catctatagt ttcttccaac ttagtaatct ggtaggttag gtgtgcatat  142800
ttttcttcgt gaacagcaag tcgcttatca agactattga caatatctct caactcacta  142860
accgcactat tcagttctac attgtcctgt ttaatgccct tctcggttag ctctccatgt  142920
tggagtttat cttccagtcg ttgtagtctt aaaacaaggt catttacttg gtaatcgttc  142980
atatatgctc ctccctgtaa gttatgttgc tctatattag tcagatgtaa accacagaca  143040
gactagtata cctataatag cgcctaccgt gtagactata ggtatatagt acccattaaa  143100
aaacaagtat agactaccta tactaattcc atagagcacg aaagtgaact tgtatgatgc  143160
caaagggctc agttctgctt gtagtttctt atactgtagt gcacgagtga catagtagga  143220
catcaagtaa acaaacattt gtagtaacag tacacagacc agtgctgttt catacattat  143280
```